United States Patent
Levin et al.

(10) Patent No.: US 11,913,944 B2
(45) Date of Patent: Feb. 27, 2024

(54) PHOTOAFFINITY PROBES

(71) Applicant: Promega Corporation, Madison, WI (US)

(72) Inventors: Sergiy Levin, Madison, WI (US); Rachel Friedman Ohana, Madison, WI (US); Robin Hurst, Madison, WI (US); Thomas Kirkland, Madison, WI (US); Keith Wood, Madison, WI (US)

(73) Assignee: Promega Corporation, Madison, WI (US)

( * ) Notice: Subject to any disclaimer, the term of this patent is extended or adjusted under 35 U.S.C. 154(b) by 657 days.

(21) Appl. No.: 16/825,802

(22) Filed: Mar. 20, 2020

(65) Prior Publication Data

US 2020/0340982 A1 Oct. 29, 2020

Related U.S. Application Data

(60) Provisional application No. 62/821,147, filed on Mar. 20, 2019.

(51) Int. Cl.
| | | |
|---|---|---|
| *G01N 33/533* | (2006.01) | |
| *G01N 21/64* | (2006.01) | |
| *G01N 21/76* | (2006.01) | |
| *G01N 33/542* | (2006.01) | |

(52) U.S. Cl.
CPC ....... *G01N 33/533* (2013.01); *G01N 21/6428* (2013.01); *G01N 21/645* (2013.01); *G01N 21/763* (2013.01); *G01N 33/542* (2013.01); *G01N 2021/6439* (2013.01)

(58) Field of Classification Search
CPC .. G01N 33/582; G01N 21/6428; G01N 33/58; G01N 33/542; G01N 21/645; G01N 33/533; G01N 21/763; G01N 2021/6439
See application file for complete search history.

(56) References Cited

U.S. PATENT DOCUMENTS

| | | |
|---|---|---|
| 4,946,778 A | 8/1990 | Ladner et al. |
| 5,260,203 A | 11/1993 | Ladner et al. |
| 7,425,436 B2 | 9/2008 | Darzins et al. |
| 7,429,472 B2 | 9/2008 | Darzins et al. |
| 7,867,726 B2 | 1/2011 | Wood et al. |
| 7,888,086 B2 | 2/2011 | Darzins et al. |

(Continued)

FOREIGN PATENT DOCUMENTS

| | | |
|---|---|---|
| WO | WO 88/01649 | 3/1988 |
| WO | WO 93/06868 | 4/1993 |

(Continued)

OTHER PUBLICATIONS

Rotili et al. A photoreactive small-molecule probe for 2-oxoglutarate oxygenases. Chemistry & Biology 2011, vol. 18, pp. 642-654. (Year: 2011).*

(Continued)

*Primary Examiner* — Shafiqul Haq
(74) *Attorney, Agent, or Firm* — David W. Staple

(57) ABSTRACT

Provided herein are compositions and methods for photoaffinity labeling of molecular targets. In particular, probes that specifically interact with cellular targets based on their affinity and are then covalently linked to the cellular target via a photoreactive group (PRG) on the probe.

10 Claims, 47 Drawing Sheets
(33 of 47 Drawing Sheet(s) Filed in Color)
Specification includes a Sequence Listing.

(56) References Cited

U.S. PATENT DOCUMENTS

| | | |
|---|---|---|
| 7,935,803 B2 | 5/2011 | Darzins et al. |
| RE42,931 E | 11/2011 | Wood et al. |
| 8,168,405 B2 | 5/2012 | Darzins et al. |
| 8,202,700 B2 | 6/2012 | Darzins et al. |
| 8,257,939 B2 | 9/2012 | Wood et al. |
| 8,309,350 B2 | 11/2012 | Isacoff et al. |
| 8,557,970 B2 | 10/2013 | Encell et al. |
| 8,669,103 B2 | 3/2014 | Binkowski et al. |
| 9,056,885 B2 | 6/2015 | Kirkland et al. |
| 9,551,705 B2 | 1/2017 | Hitko et al. |
| 9,797,889 B2 | 10/2017 | Dixon et al. |
| 10,024,862 B2 | 7/2018 | Hitko et al. |
| 10,067,149 B2 | 9/2018 | Hitko et al. |
| 10,168,323 B2 | 1/2019 | Hitko et al. |
| 2009/0253131 A1 | 10/2009 | Wigdal et al. |
| 2011/0172190 A1 | 7/2011 | Marks et al. |
| 2014/0322794 A1 | 10/2014 | Hitko et al. |
| 2016/0355523 A1 | 12/2016 | Levin et al. |
| 2020/0270586 A1 | 8/2020 | Hall et al. |
| 2021/0262941 A1 | 8/2021 | Kincaid et al. |

FOREIGN PATENT DOCUMENTS

| | | |
|---|---|---|
| WO | WO 94/08629 | 4/1994 |
| WO | WO 94/09056 | 4/1994 |
| WO | WO 96/26754 | 9/1996 |
| WO | WO 2010/127368 | 11/2010 |
| WO | WO 2012/061530 | 5/2012 |
| WO | WO 2014/093671 | 6/2014 |
| WO | WO 2014/093677 | 6/2014 |
| WO | WO 2014/145654 | 9/2014 |
| WO | WO 2014/151736 | 9/2014 |
| WO | WO 2016/123480 | 8/2016 |

OTHER PUBLICATIONS

Ohana et al. Deciphering the cellular targets of bioactive compounds using a chloroalkane capture tag. ACS Chem. Biol. 2015, vol. 10, pp. 2316-2324 (Year: 2015).*

Jorg et al. Guidelines for the Synthesis of Small-Molecule Irreversible Probes Targeting G Protein-Coupled Receptors. ChemMedChem 2016, vol. 11, pp. 1488-1498. (Year: 2016).*

Murale et al. Photo-affinity labeling (PAL) in chemical proteomics: a handy tool to investigate protein-protein interactions (PPIs). Proteome Science 2017, vol. 15, No. 14, pp. 1-34 (Year: 2017).*

Ma et al. Affinity-Based Protein Profiling Reveals Cellular Targets of Photoreactive Anticancer Inhibitors. ACS Chem. Biol. 2019, vol. 14, pp. 2546-2552. (Year: 2019).*

International Search Report and Written Opinion for PCT/US2020/023973, dated Aug. 14, 2020. 18 pages.

Carruthers. Some Modern Methods of Organic Synthesis, 3rd Edition, Cambridge University Press, Cambridge, 1987. TOC only. 6 pages.

Dwight et al., Scalable Regioselective Synthesis of Rhodamine Dyes. Org Lett. Oct. 21, 2016;18(20):5316-5319.

Feldman et al., Intramolecular [3 +2] cyclocondensations of alkenes with indolidenes and indolidenium cations. J Am Chem Soc. Oct. 29, 2014;136(43):15138-41.

Fleming. Chemical Reagents in Photoaffinity Labeling. Tetrahedron 1995, 51, 12479-12520.

Hatanaka et al., Development and leading-edge application of innovative photoaffinity labeling. Chem Pharm Bull (Tokyo). 2015;63(1):1-12.

Hudson et al., Engineered antibodies. Nat Med. Jan. 2003;9(1):129-34.

Kambe et al., Mapping the protein interaction landscape for fully functionalized small-molecule probes in human cells. J Am Chem Soc. Jul. 30, 2014;136(30):10777-82.

Klunder et al., Arenesulfonate derivatives of homochiral glycidol: versatile chiral building blocks for organic synthesis. J. Org. Chem. 1989, 54, 1295-1304.

Lapinsky et al., Recent developments and applications of clickable photoprobes in medicinal chemistry and chemical biology. Future Med Chem. 2015;7(16):2143-71.

Larock. Comprehensive Organic Transformations, 3rd Edition, John Wiley & Sons, Inc., New York, 2018. TOC only. 24 pages.

Leriche et al., Cleavable linkers in chemical biology. Bioorg Med Chem. Jan. 15, 2012;20(2):571-82.

Merrifield. Solid-Phase peptide synthesis. 3. An improved synthesis of Bradykinin. Biochemistry. Sep. 1964;3:1385-90.

Ohana et al., Deciphering the Cellular Targets of Bioactive Compounds Using a Chloroalkane Capture Tag. ACS Chem Biol. Oct. 16, 2015;10(10):2316-24.

Ohana et al., Improved Deconvolution of Protein Targets for Bioactive Compounds Using a Palladium Cleavable Chloroalkane Capture Tag. ACS Chem Biol. Sep. 16, 2016;11(9):2608-17.

Pan et al., Target identification of natural products and bioactive compounds using affinity-based probes. Nat Prod Rep. May 4, 2016;33(5):612-20.

Preston et al., Photo-induced covalent cross-linking for the analysis of biomolecular interactions. Chem Soc Rev. Apr. 21, 2013;42(8):3289-301.

Rudolf et al., Chemical proteomics: ligation and cleavage of protein modifications. Curr Opin Chem Biol. Feb. 2013;17(1):110-7.

Sakurai et al., Comparison of the reactivity of carbohydrate photoaffinity probes with different photoreactive groups. Chembiochem. Jul. 7, 2014;15(10):1399-403.

Smith et al., Photoaffinity labeling in target- and binding-site identification. Future Med Chem. 2015;7(2):159-83.

Sorrell. Organic Chemistry, 2nd edition, University Science Books, Sausalito, 2006. TOC only. 18 pages.

Szychowski et al., Cleavable biotin probes for labeling of biomolecules via azide-alkyne cycloaddition. J Am Chem Soc. Dec. 29, 2010;132(51):18351-60.

Tomalia et al., Starburst Dendrimers: Molecular-Level Control of Size, Shape, Surface Chemistry, Topology, and Flexibility from Atoms to Macroscopic Matter. Angew. Chem. Int. Ed. Engl. 1990. 29:138-175.

Vasta et al., Quantitative, Wide-Spectrum Kinase Profiling in Live Cells for Assessing the Effect of Cellular ATP on Target Engagement. Cell Chem Biol. Feb. 15, 2018;25(2):206-214.e11. 21 pages.

Wright et al., Chemical proteomics approaches for identifying the cellular targets of natural products. Nat Prod Rep. May 4, 2016;33(5):681-708.

Extended European Search Report for 20773701.6, dated Feb. 16, 2023. 5 pages.

Damen et al. Synthesis of novel paclitaxel prodrugs designed for bioreductive activation in hypoxic tumour tissue, Bioorganic & Medicinal Chemistry, 2002:10(1):71-77.

Krishnamurty et al. Active site profiling reveals coupling between domains in SRC-family kinases, Nature Chemical Biology, 2012:9(1):43-50.

Matikonda et al. Mechanistic Evaluation of Bioorthogonal Decaging with trans-Cyclooctene: The Effect of Fluorine Substituents on Aryl Azide Reactivity and Decaging from the 1,2,3-Triazoline, Bioconjugate Chemistry, 2018:29(2):324-334.

Meguro et al. Staudinger reaction using 2,6-dichlorophenyl azide derivatives for robust aza-ylide formation applicable to bioconjugation in living cells, Chemical Communications, 2018:54(57):7904-7907.

Murale et al: Photo-affinity labeling (PAL) in chemical proteomics: a handy tool to investigate protein-protein interactions (PPis), Proteome Science, 2016:15(1).

Sumranjit et al. Recent Advances in Target Characterization and Identification by Photoaffinity Probes, Molecules, 2013:18(9):10425-10451.

Yoshida et al. Supporting Information—Convergent synthesis of trifunctional molecules by three sequential azido-type-selective cycloadditions Contents, Chemical Communications, 2018:54(30).

Yoshida et al. Convergent synthesis of trifunctional molecules by three sequential azido-type-selective cycloadditions, Chemical Communications, 2018:54(30):3705-3708.

* cited by examiner

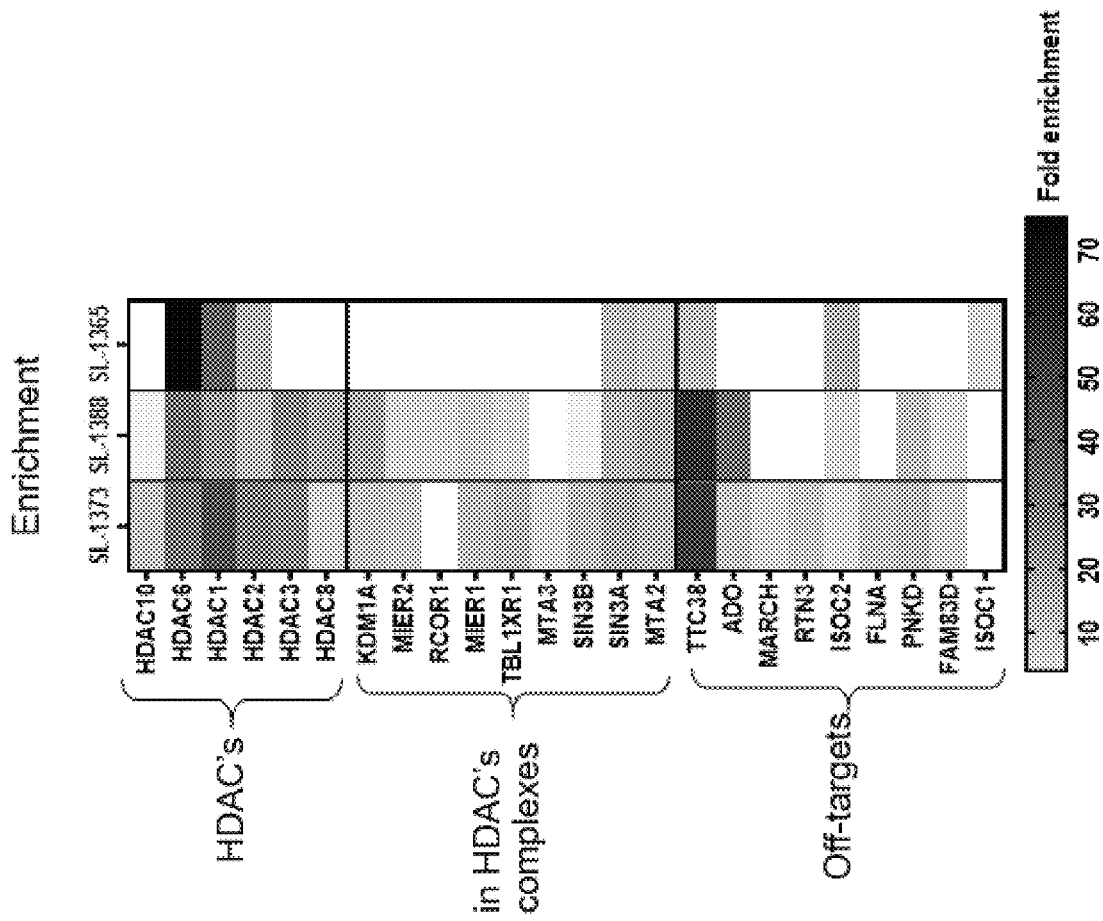

dasatinib

PHOTOAFFINITY PROBES

CROSS-REFERENCE TO RELATED APPLICATION

The present application claims priority to U.S. Provisional Patent Application Ser. No. 62/821,147, filed Mar. 20, 2019, which is hereby incorporated by reference in its entirety.

FIELD

Provided herein are compositions and methods for photoaffinity labeling of molecular targets. In particular, probes that specifically interact with cellular targets based on their affinity and are then covalently linked to the cellular target via a photoreactive group (PRG) on the probe.

BACKGROUND

Isolation and enrichment of cellular targets of bioactive compounds is essential for both target identification and target profiling. It is well recognized that engagement of targets by biologically active molecules in a live cell environment often differs from engagement of targets in biochemical settings; thus, enrichment tools compatible with target engagement within the cellular environment are needed. Furthermore, chemoproteomic technologies are traditionally biased toward abundant and soluble protein targets. Targets with low expression levels and/or low affinity as well as membrane proteins, particularly those with multiple transmembrane domains, remain challenging to identify with chemoproteomic approaches.

SUMMARY

Provided herein are compositions and methods for photoaffinity labeling of molecular targets. In particular, probes that specifically interact with cellular targets based on their affinity and are then covalently linked to the cellular target via a photoreactive group (e.g., UV-activated photoreactive group) on the probe.

In some embodiments, provided herein are compositions comprising a PRG/HA probe comprising: a bioactive agent, a photoreactive group (PRG), a linker, and a haloalkane (HA) covalently connected in a single compound of the general structure:

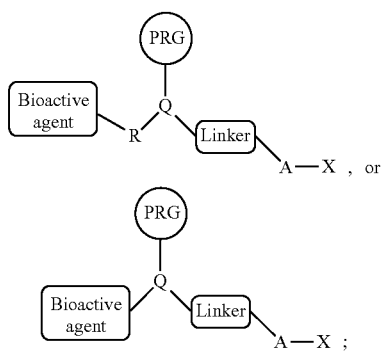

wherein R is a covalent linkage, wherein A is $(CH_2)_n$ and n=4-10, wherein X is a halogen, wherein -A-X is a substrate for a dehalogenase, and wherein Q is CH or N. In some embodiments, the bioactive agent is a small molecule or peptide. In some embodiments, R comprises —NH—, —C(O)NH—, —OC(O)NH—, N, C(O)N, OC(O)N, or —O—. In some embodiments, R is a covalent linkage resulting from the reaction of two reactive moieties (R' and R"). In some embodiments, R comprises —$(CH_2)_{0-2}$NH$(CH_2)_{0-2}$—, —$(CH_2)_{0-2}$C(O)NH$(CH_2)_{0-2}$—, —$(CH_2)_{0-2}$OC(O)NH$(CH_2)_{0-2}$—, $(CH_2)_{0-2}$N$(CH_2)_{0-2}$—, —$(CH_2)_{0-2}$C(O)N$(CH_2)_{0-2}$—, —$(CH_2)_{0-2}$OC(O)N$(CH_2)_{0-2}$—, or —$(CH_2)_{0-2}(CH_2)_{0-2}$—. In some embodiments, the PRG is a photoreactive group such as an aryl azide, alkylaryl azide (e.g., methylaryl azide), substituted aryl azide, or substituted alkylaryl azide (e.g., substituted methylaryl azide). In some embodiments, the PRG is covalently connected to the rest of the compound by a PRG linker moiety. In some embodiments, the PRG linker moiety is $(CH_2)_{0-4}$. In some embodiments, the linker is a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O)OCH$_2$CH=CHCH$_2$OC(O)—. In some embodiments, the cleavable linker comprises the cleavable moiety flanked on one or both sides by alkylene or heteroalkylene chains. In some embodiments, the alkylene or heteroalkylene chains comprise any suitable combination of $C_{1-6}$-alkylene, —O—, —$(CH_2)_2$O—, and —OC(O)NH— groups. In some embodiments, X is Cl. In some embodiments, -A-X is —$(CH_2)_6$Cl.

In some embodiments, the general structure of a PRG/HA probe is:

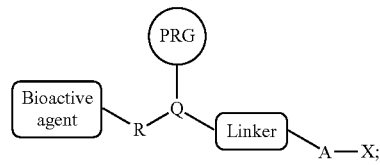

Q comprises CH or N; and R comprises —NH—, —C(O)NH—, —OC(O)NH—, —O—, —$(CH_2)_{0-2}$NH$(CH_2)_{0-2}$—, —$(CH_2)_{0-2}$C(O)NH$(CH_2)_{0-2}$—, —$(CH_2)_{0-2}$OC(O)NH$(CH_2)_{0-2}$—, or —$(CH_2)_{0-2}(CH_2)_{0-2}$—. In other embodiments, the general structure of a PRG/HA probe is:

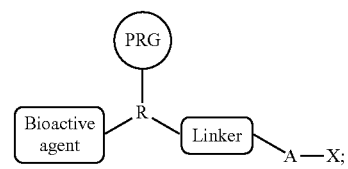

and R is N, C(O)N, OC(O)N, $(CH_2)_{0-2}$N$(CH_2)_{0-2}$—, —$(CH_2)_{0-2}$C(O)N$(CH_2)_{0-2}$—, or —$(CH_2)_{0-2}$OC(O)N$(CH_2)_{0-2}$—.

In some embodiments, the PRG is an aryl azide, alkylaryl azide (e.g., methylaryl azide), substituted aryl azide, or substituted alkylaryl azide (e.g., substituted methylaryl azide). In some embodiments, the PRG comprises the structure:

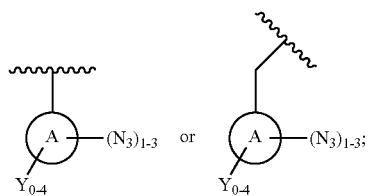

wherein A is an aromatic hydrocarbon ring (e.g., 6-member ring), aromatic heterocyclic ring (e.g., 5- or 6-member ring), an aromatic ring system, or a heteroaromatic ring system; wherein $N_3$ group(s) are present at any suitable position on the A ring; and wherein any Y groups, when present on the A ring, are independently selected from, halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, A is selected from furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, naphthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), and thiadiazole. In some embodiments, the PRG is a substituted phenyl or benzyl azide. In some embodiments, the PRG is a substituted phenyl or benzyl azide such as:

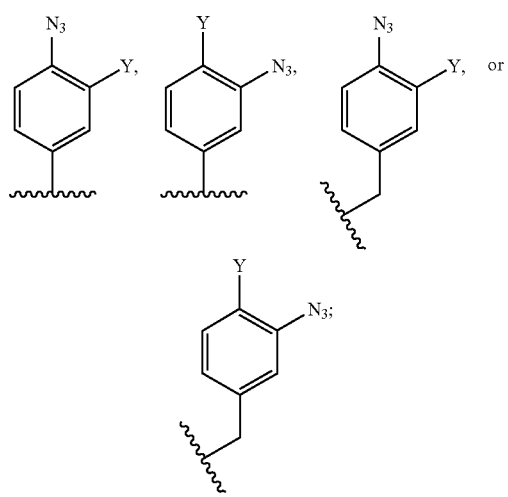

wherein Y is selected from halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, the A ring is a fused ring system such as:

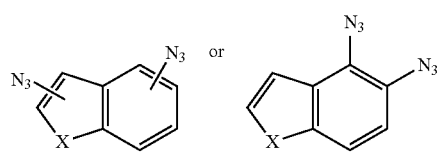

wherein X is O, NH, or S. In some embodiments, the PRG is selected from the group consisting of:

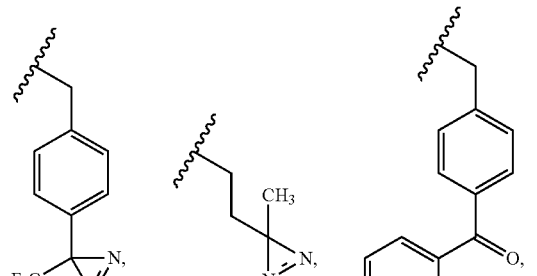

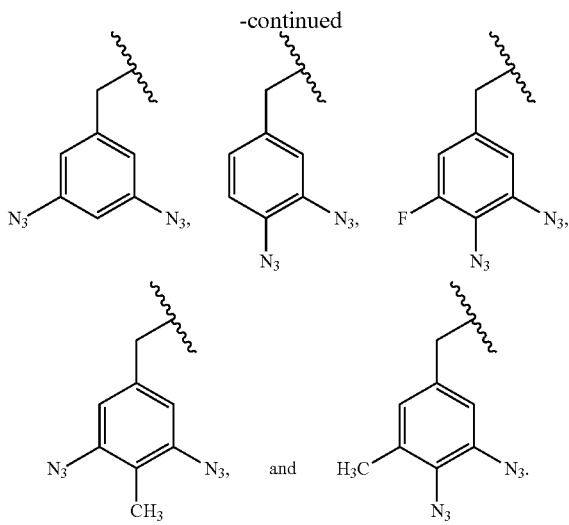

Other exemplary PRGs and A-ring structures are depicted in FIG. 34.

In some embodiments, provided herein are compositions comprising a reactive PRG/HA reagent comprising: a photoreactive group (PRG), linker, and haloalkane covalently connected in a single compound of the general structure:

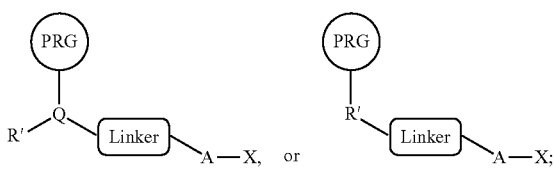

wherein R' is a first reactive moiety capable for forming a covalent bond upon reaction with a second reactive moiety (R"), wherein A is $(CH_2)_n$ and n=4-1, wherein X is a halogen, wherein -A-X is a substrate for a dehalogenase, and wherein Q is CH or N. In some embodiments, R' comprises —$NH_2$, NH, —C(O)OH, OC(O)O-phenyl, C(O)O-phenyl, OH, C=O, aldehyde, difluorosulfinate, sulfonyl fluoride, sulfonyl chloride or halogen. In some embodiments, R' comprises —$(CH_2)_{0-2}NH_2$, —$(CH_2)_{0-2}C(O)OH$, $(CH_2)_{0-2}OC(O)O$-phenyl, $(CH_2)_{0-2}C(O)O$-phenyl, $(CH_2)_{0-2}OH$, $(CH_2)_{0-2}C=O$, $(CH_2)_{0-2}C$, or $(CH_2)_{0-2}Br$. In some embodiments, the PRG is a photoreactive group such as an aryl azide, alkylaryl azide (e.g., methylaryl azide), substituted aryl azide, or substituted alkylaryl azide (e.g., substituted methylaryl azide) moiety. In some embodiments, the PRG is covalently connected to the rest of the compound by a PRG linker moiety. In some embodiments, the PRG linker moiety is $(CH_2)_{0-4}$. In some embodiments, the linker is a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O)OCH$_2$CH=CHCH$_2$OC(O)—. In some embodiments, the cleavable linker comprises the cleavable moiety flanked on one or both sides by alkylene or heteroalkylene chains. In some embodiments, the alkylene or heteroalkylene chains comprise any suitable combination of $C_{1-6}$-alkylene, —O—, —(CH$_2$)$_2$O—, and —OC(O)NH— groups. In some embodiments, X is Cl. In some embodiments, -A-X is —(CH$_2$)$_6$Cl.

In some embodiments, the PRG/HA reagent has the general structure:

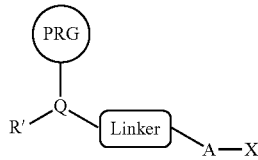

wherein R' comprises —NH$_2$, —C(O)OH, OC(O)O-phenyl, C(O)O-phenyl, OH, aldehyde, difluorosulfinate, sulfonyl fluoride, sulfonyl chloride or halogen. In other embodiments, the PRG/HA reagent has the general structure:

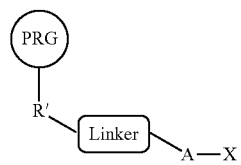

wherein R' comprises NH or C=O.

In some embodiments, the PRG is an aryl azide, alkylaryl azide (e.g., methylaryl azide), substituted aryl azide, or substituted alkylaryl azide (e.g., substituted methylaryl azide) moiety. In some embodiments, the PRG comprises the structure:

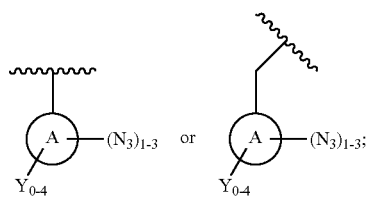

wherein A is an aromatic hydrocarbon ring (e.g., 6-member ring), aromatic heterocyclic ring (e.g., 5- or 6-member ring), an aromatic ring system, or a heteroaromatic ring system; wherein N$_3$ group(s) are present at any suitable position on the A ring; and wherein any Y groups, when present on the A ring, are independently selected from, halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, CH$_2$Cl$_3$, and CN. In some embodiments, A is selected from furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, naphthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), and thiadiazole. In some embodiments, the PRG is a substituted phenyl or benzyl azide. In some embodiments, the PRG is a substituted phenyl or benzyl azide, such as:

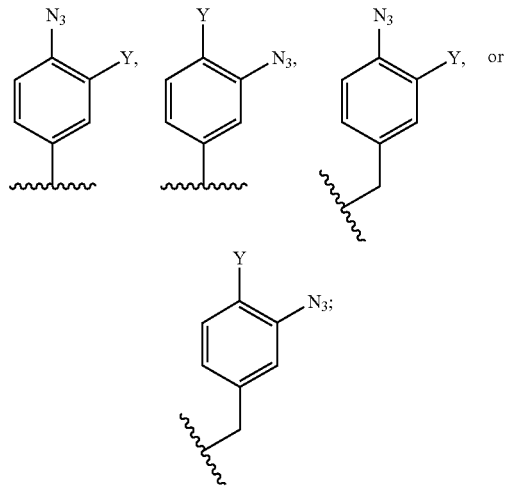

wherein Y is selected from halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, CH$_2$Cl$_3$, and CN. In some embodiments, the A ring is a fused ring system such as:

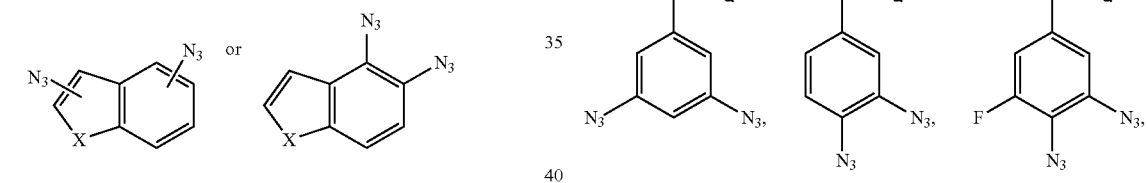

wherein X is O, NH, or S. In some embodiments, the PRG is selected from the group consisting of:

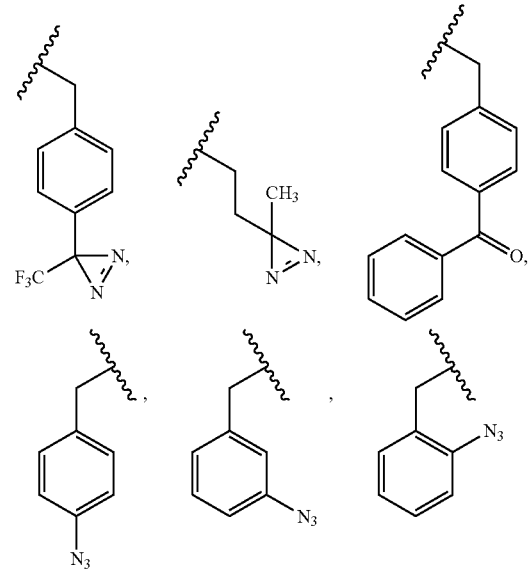

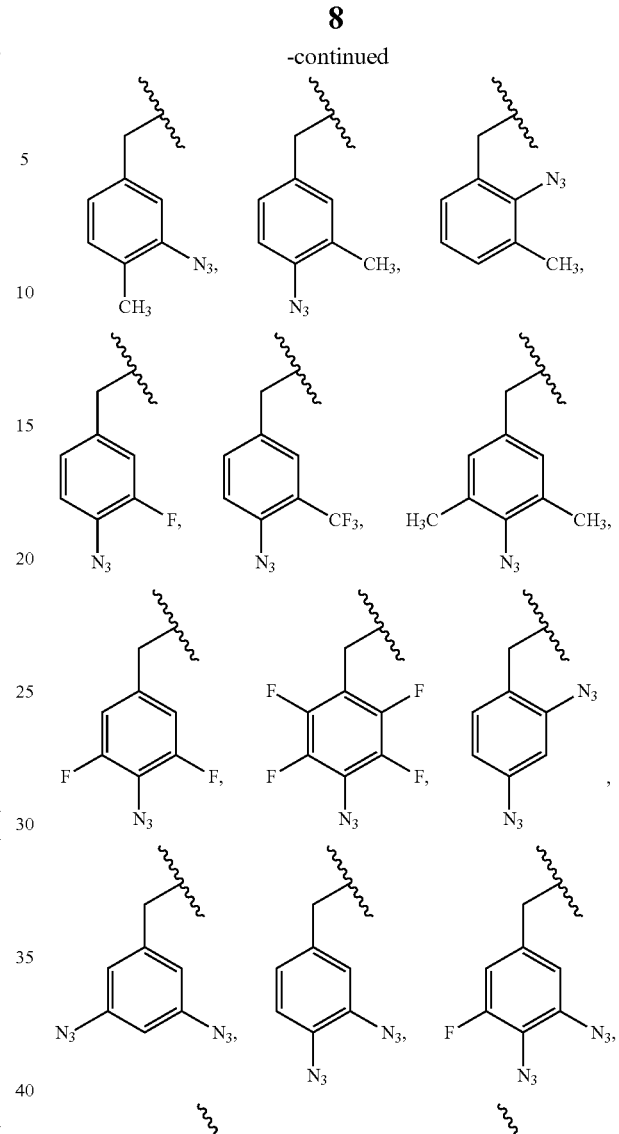

Other exemplary PRGs and A-ring structures are depicted in FIG. 34.

In some embodiments, provided herein are systems, kits, and reaction mixtures comprising: (i) a PRG/HA reagent described herein, and (ii) a bioactive agent displaying the second reactive moiety R". In some embodiments, the bioactive agent is a small molecule or peptide. In some embodiments, the bioactive agent comprises a drug or natural compound modified to display the R". In some embodiments, R" comprises —NH$_2$, —OC(O)O— nitrophenyl, —OH, —C=O, -aldehyde, -difluorosulfinate, -sulfonyl fluoride, sulfonyl chloride or -halogen. In some embodiments, R" comprises —(CH$_2$)$_{0-2}$NH$_2$, —(CH$_2$)$_{0-2}$OC(O)O-nitrophenyl, —(CH$_2$)$_{0-2}$OH, —(CH$_2$)$_{0-2}$C=O, —(CH$_2$)$_{0-2}$Cl, or —(CH$_2$)$_{0-2}$Br.

In some embodiments, provided herein are methods of generating a PRG/HA probe comprising contacting (i) a PRG/HA reagent described herein with (ii) a bioactive agent the second reactive moiety R". In some embodiments, provided herein are PRG/HA probes produced by the methods described herein.

In some embodiments, provided therein are compositions comprising a PRG/fluorophore probe comprising: a bioactive agent, a photoreactive group (PRG), and a fluorophore covalently connected in a single compound of the general structure:

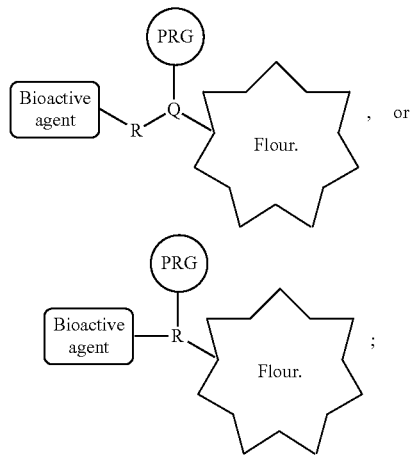

wherein R is a covalent linkage, and wherein Q is CH or N. In some embodiments, the bioactive agent is a small molecule. In some embodiments, R comprises —NH—, —C(O)NH—, —OC(O)NH—, N, C(O)N, OC(O)N, or —O—. In some embodiments, R is a covalent linkage resulting from the reaction of two reactive moieties (R' and R"). In some embodiments, R comprises —(CH$_2$)$_{0-2}$NH(CH$_2$)$_{0-2}$—, —(CH$_2$)$_{0-2}$C(O)NH(CH$_2$)$_{0-2}$—, —(CH$_2$)$_{0-2}$OC(O)NH(CH$_2$)$_{0-2}$—, (CH$_2$)$_{0-2}$N(CH$_2$)$_{0-2}$—, —(CH$_2$)$_{0-2}$C(O)N(CH$_2$)$_{0-2}$—, —(CH$_2$)$_{0-2}$OC(O)N(CH$_2$)$_{0-2}$—, or —(CH$_2$)$_{0-2}$O(CH$_2$)$_{0-2}$—. In some embodiments, the PRG is a photoreactive group such as an aryl azide, alkylaryl azide (e.g., methylaryl azide), substituted aryl azide, or substituted alkylaryl azide (e.g., substituted methylaryl azide) moiety. In some embodiments, the PRG is covalently connected to the rest of the compound by a PRG linker moiety. In some embodiments, the PRG linker moiety is (CH$_2$)$_{0-4}$. In some embodiments, the fluorophore is covalently connected to the rest of the compound by a fluorophore linker moiety. In some embodiments, the fluorophore linker moiety comprises a cleavable linker. In some embodiments, the general structure of a PRG/fluorophore probe is:

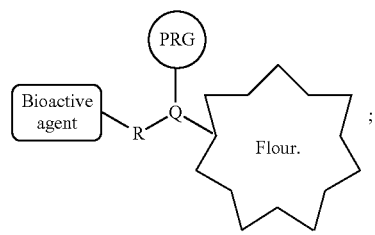

Q comprises CH or N; and R comprises —NH—, —C(O)NH—, —OC(O)NH—, —O—, —(CH$_2$)$_{0-2}$NH(CH$_2$)$_{0-2}$—, —(CH$_2$)$_{0-2}$C(O)NH(CH$_2$)$_{0-2}$—, —(CH$_2$)$_{0-2}$OC(O)NH(CH$_2$)$_{0-2}$—, or —(CH$_2$)$_{0-2}$(CH$_2$)$_{0-2}$—. In other embodiments, the general structure of a PRG/fluorophore probe is:

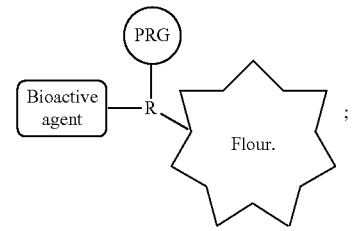

and R is N, C(O)N, OC(O)N, (CH$_2$)$_{0-2}$N(CH$_2$)$_{0-2}$—, —(CH$_2$)$_{0-2}$C(O)N(CH$_2$)$_{0-2}$—, or —(CH$_2$)$_{0-2}$OC(O)N(CH$_2$)$_{0-2}$—.

In some embodiments, the PRG is an aryl azide, alkylaryl azide (e.g., methylaryl azide), substituted aryl azide, or substituted alkylaryl azide (e.g., substituted methylaryl azide) moiety. In some embodiments, the PRG comprises the structure:

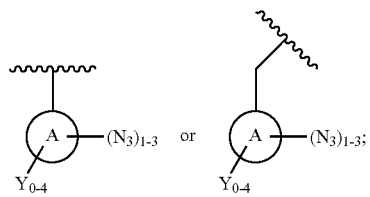

wherein A is an aromatic hydrocarbon ring (e.g., 6-member ring), aromatic heterocyclic ring (e.g., 5- or 6-member ring), an aromatic ring system, or a heteroaromatic ring system; wherein N$_3$ group(s) are present at any suitable position on the A ring; and wherein any Y groups, when present on the A ring, are independently selected from, halogen (e.g., Cl, F, Br, I), CH$_3$, OH, SH, NH$_2$, CN, CF$_3$, CCl$_3$, —CH$_2$—CH$_3$, —CH$_2$—OH, —CH$_2$NH$_2$, CH$_3$SH, CH$_2$Cl, CH$_2$Br, CH$_2$F, CHF$_2$, CH$_2$CN, CH$_2$CF$_3$, CH$_2$Cl$_3$, and CN. In some embodiments, A is selected from furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, naphthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), and thiadiazole. In some embodiments, the PRG is a substituted phenyl or benzyl azide. In some embodiments, the PRG is a substituted phenyl or benzyl azide, such as:

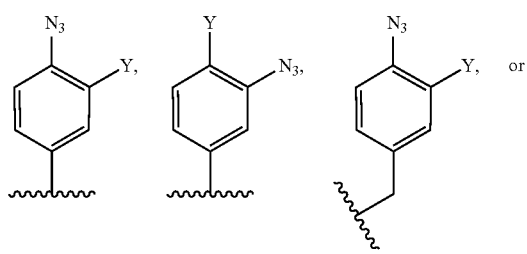

wherein Y is selected from halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, the A ring is a fused ring system such as:

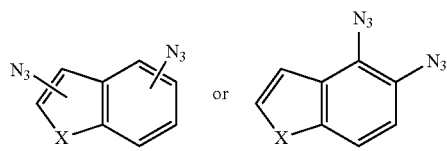

wherein X is O, NH, or S. In some embodiments, the PRG is selected from the group consisting of:

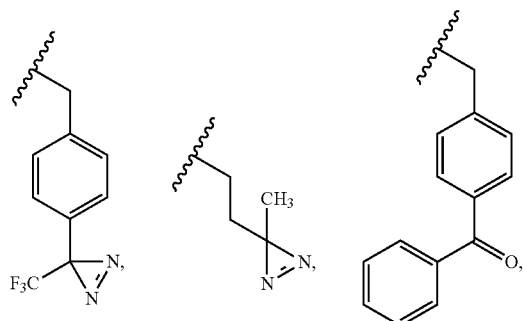

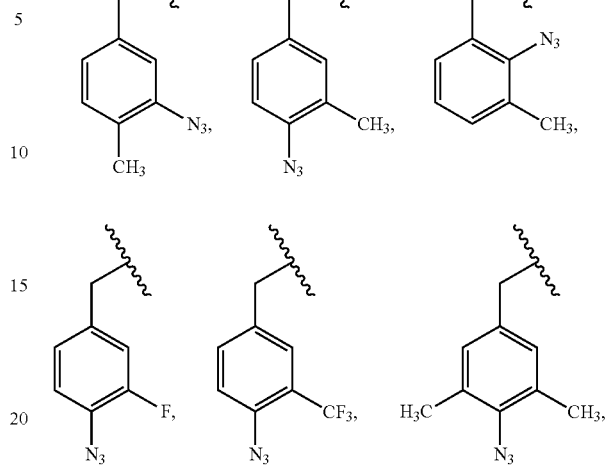

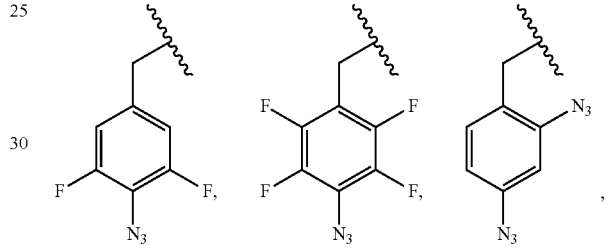

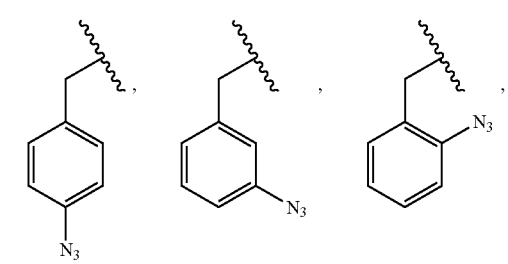

Other exemplary PRGs and A-ring structures are depicted in FIG. 34.

In some embodiments, provided herein are reactive PRG/fluorophore reagents comprising: a photoreactive group (PRG) and a fluorophore connected in a single compound of the general structure:

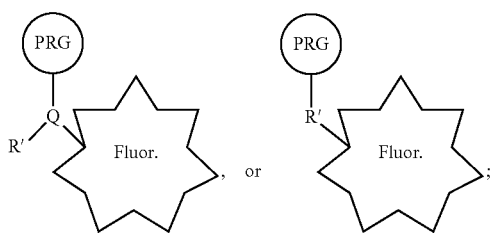

wherein R' is a first reactive moiety capable for forming a covalent bond upon reaction with a second reactive moiety (R''), and wherein Q is CH or N. In some embodiments, R' comprises —$NH_2$, NH, —C(O)OH, OC(O)O-phenyl, C(O)O-phenyl, OH, C=O, aldehyde, difluorosulfinate, sulfonyl fluoride, sulfonyl chloride, or halogen. In some embodiments, R' comprises —$(CH_2)_{0-2}NH_2$, —$(CH_2)_{0-2}C(O)OH$, $(CH_2)_{0-2}OC(O)$O-phenyl, $(CH_2)_{0-2}C(O)O$-phenyl, $(CH_2)_{0-2}OH$, $(CH_2)_{0-2}C=O$, $(CH_2)_{0-2}C$, or $(CH_2)_{0-2}Br$. In some embodiments, the PRG is a photoreactive group such as an aryl azide, alkylaryl azide (e.g., methylaryl azide), substituted aryl azide, or substituted alkylaryl azide (e.g., substituted methylaryl azide) moiety. In some embodiments, the PRG is covalently connected to the rest of the compound by a PRG linker moiety. In some embodiments, the PRG linker moiety is $(CH_2)_{0-4}$. In some embodiments, the fluorophore is covalently connected to the rest of the compound by a fluorophore linker moiety. In some embodiments, the fluorophore linker moiety comprises a cleavable linker.

In some embodiments, the PRG/fluorophore reagent has the general structure:

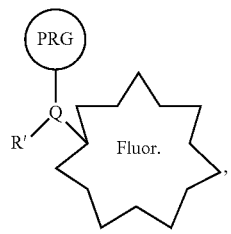

wherein R' comprises —$NH_2$, —C(O)OH, OC(O)O-phenyl, C(O)O— phenyl, OH, aldehyde, difluorosulfinate, sulfonyl fluoride, sulfonyl chloride, or halogen. In other embodiments, the PRG/fluorophore reagent has the general structure:

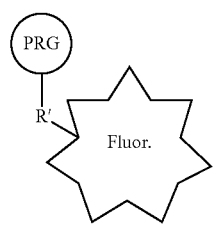

wherein R' comprises —NH— or CO.

In some embodiments, the PRG is an aryl azide, alkylaryl azide (e.g., methylaryl azide), substituted aryl azide, or substituted alkylaryl azide (e.g., substituted methylaryl azide) moiety. In some embodiments, the PRG comprises the structure:

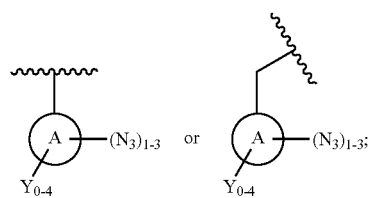

wherein A is an aromatic hydrocarbon ring (e.g., 6-member ring), aromatic heterocyclic ring (e.g., 5- or 6-member ring), an aromatic ring system, or a heteroaromatic ring system; wherein $N_3$ group(s) are present at any suitable position on the A ring; and wherein any Y groups, when present on the A ring, are independently selected from, halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, A is selected from furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, naphthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), and thiadiazole. In some embodiments, the PRG is a substituted phenyl or benzyl azide. In some embodiments, the PRG is a substituted phenyl or benzyl azide, such as:

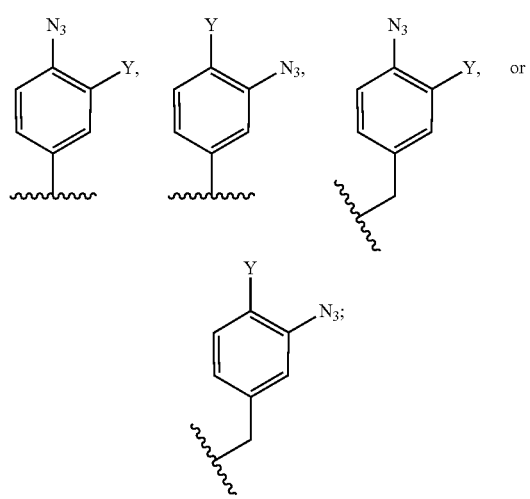

wherein Y is selected from halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, the A ring is a fused ring system such as:

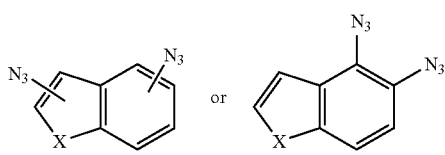

wherein X is O, NH, or S. In some embodiments, the PRG is selected from the group consisting of:

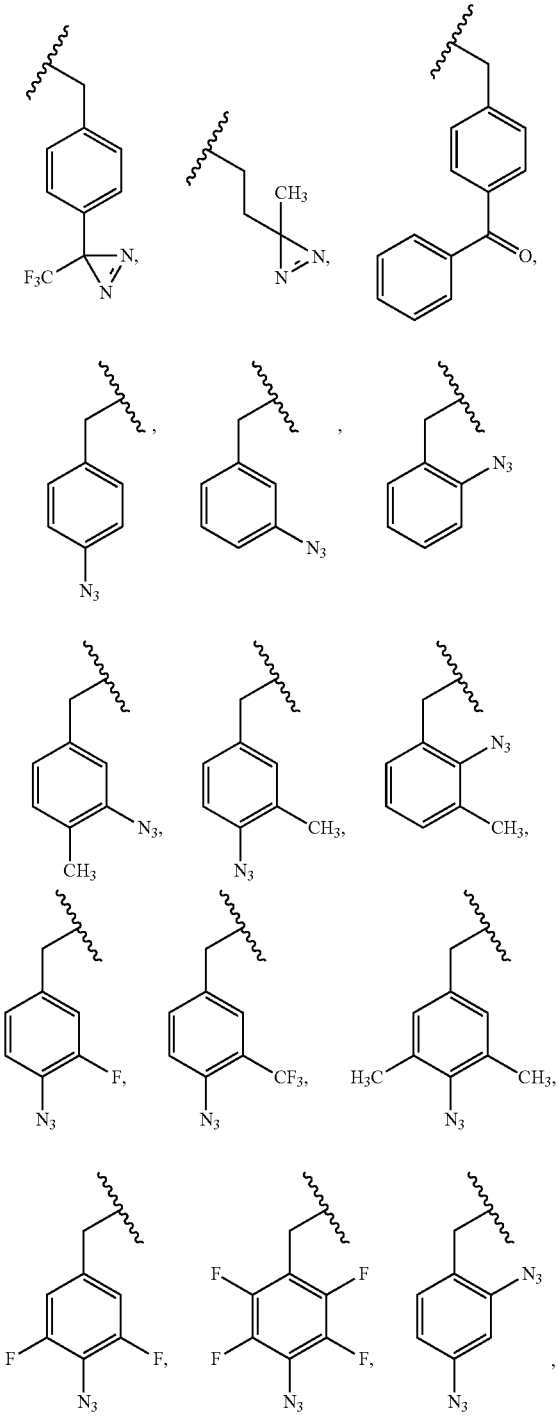

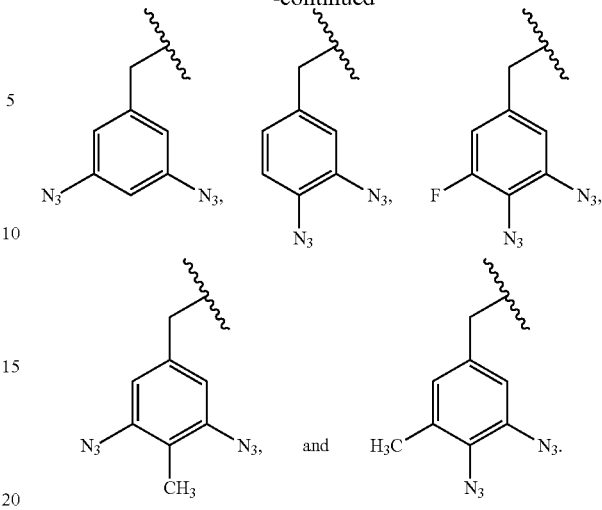

Other exemplary PRGs and A-ring structures are depicted in FIG. 34.

In some embodiments, provided herein are systems, kits, and reaction mixtures comprising: (i) a reactive PRG/fluorophore reagent described herein and (ii) a bioactive agent displaying the second reactive moiety R". In some embodiments, the bioactive agent is a small molecule or peptide. In some embodiments, the bioactive agent comprises a drug or natural compound modified to display the R". In some embodiments, R" comprises —NH$_2$, —OC(O)O-nitrophenyl, —OH, —C═O, -aldehyde, -difluorosulfinate, -sulfonyl fluoride, sulfonyl chloride or -halogen. In some embodiments, R" comprises —(CH$_2$)$_{0-2}$NH$_2$, —(CH$_2$)$_{0-2}$OC(O)O— nitrophenyl, —(CH$_2$)$_{0-2}$OH, —(CH$_2$)$_{0-2}$C═O, —(CH$_2$)$_{0-2}$Cl, or —(CH$_2$)$_{0-2}$Br.

In some embodiments, provided herein are methods of generating a PRG/fluorophore probe comprising contacting (i) a reactive PRG/fluorophore reagent described herein with (ii) a bioactive agent displaying the second reactive moiety R". In some embodiments, provided herein is a PRG/fluorophore probe produced by the method described herein.

In some embodiments, provided herein are methods of capturing a target molecule comprising: contacting a sample comprising the target molecule with a PRG/HA probe described herein, wherein the bioactive agent of the PRG/HA probe is capable of associating with the target molecule; allowing the PRG/HA probe to associate with the target molecule; and irradiating the sample with a wavelength of light that converts the PRG into a reactive form of the PRG, wherein the reactive form of the PRG forms a covalent bond with the target molecule. In some embodiments, methods further comprise contacting the sample with a modified dehalogenase enzyme that forms a covalent bond with a haloalkane substrate upon association therewith; and allowing the modified dehalogenase enzyme to covalently bind the haloalkane of the PRG/HA probe. In some embodiments, the modified dehalogenase enzyme is immobilized on a solid surface, and upon binding of the modified dehalogenase enzyme to the haloalkane of the PRG/HA probe, the target molecule is immobilized on the solid surface. In some embodiments, methods further comprise: (i) removing the solid surface from the sample; and/or (ii) washing non-immobilized components of the sample from the solid surface. In some embodiments, the solid surface is a bead, particle, chip, tube, plate, or membrane. In some embodiments, the solid surface is a paramagnetic particle. In some embodiments, methods further comprise cleaving the linker of the PRG/HA probe to release the PRG- and bioactive agent-bound target molecule from the solid surface. In some embodiments, methods further comprise detection and/or quantitation of the target molecule. In some embodiments, the target molecule is detected and/or quantitated by mass spectrometry. In some embodiments, the sample comprises a cell, and the target molecule is located within or on the surface of the cell. In some embodiments, contacting the sample comprising the target molecule with the PRG/HA probe further comprises allowing the PRG/HA probe to enter the cell. In some embodiments, methods further comprise lysing the cell after the PRG forms a covalent bond with the target molecule. In some embodiments, the bioactive agent of the PRG/HA probe is capable of non-covalently binding to the target molecule upon associating of the bioactive agent with the target molecule. In some embodiments, the bioactive agent is a small molecule or peptide. In some embodiments, the target molecule is a target protein. In some embodiments, the target protein is a cell-surface protein, transmembrane protein, cytoplasmic protein, nuclear protein, or mitochondrial protein. In some embodiments, the wavelength of light that converts the PRG into a reactive form of the PRG is ultraviolet (UV) light (e.g., 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, or ranges therebetween (e.g., 10-400 nm, 320-380 nm, etc.).

In some embodiments, provided herein are methods of capturing a cellular target protein comprising: contacting a cell containing the target protein with a PRG/HA probe described herein, wherein the bioactive agent of the PRG/HA probe is capable of binding the target protein; allowing the PRG/HA probe to enter the cell; allowing the PRG/HA probe to bind the target protein; irradiating the cell with a wavelength of UV light that converts the PRG into a reactive form of the PRG, wherein the reactive form of the PRG forms a covalent bond with the target protein; lysing the cell to form a lysate; contacting the lysate with a solid-surface-immobilized modified dehalogenase enzyme that forms a covalent bond with a haloalkane substrate upon association therewith; allowing the modified dehalogenase enzyme to covalently bind the haloalkane of the PRG/HA probe; and removing the solid surface from the lysate and/or washing non-immobilized components of the lysate from the solid surface. In some embodiments, methods further comprise cleaving the linker of the PRG/HA probe to release the PRG- and bioactive agent-bound target protein from the solid surface. In some embodiments, methods further comprise detection and/or quantitation of the target molecule. In some embodiments, the target protein is a cell-surface protein, transmembrane protein, cytoplasmic protein, nuclear protein, or mitochondrial protein.

In some embodiments, provided herein are methods of measuring photocrosslinking efficiency of a bioagent-linked PRG, comprising: contacting sample comprising a target molecule with a PRG/fluorophore probe described herein, wherein the target molecule is tethered to a bioluminescent reporter, and wherein the emission spectrum of the bioluminescent reporter overlaps with the excitation spectrum of the fluorophore; allowing the bioactive agent of the PRG/fluorophore probe to bind the target molecule; irradiating the sample with a wavelength of light that converts the PRG into a reactive form of the PRG, wherein the reactive form of the PRG is capable of forming a covalent bond with the target molecule; contacting the sample with a bioluminescent reporter substrate; detecting light emission within emission spectra of the bioluminescent reporter and the fluorophore, wherein light emission from the fluorophore is the result of bioluminescence resonance energy transfer (BRET) from the bioluminescent reporter to the fluorophore, and wherein the amount of light emission from the fluorophore correlates with the amount of PRG/fluorophore probe bound to target molecules; further contacting the sample with untagged bioactive agent to competitively displace PRG/fluorophore probe that is not covalently attached to the target; and contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore, and wherein the amount of light emission from the fluorophore correlates with the amount of PRG/fluorophore probe covalently attached to the target molecule. In some embodiments, methods further comprise calculating the percent crosslinking by normalizing the amount of PRG/fluorophore probe covalently attached to the target molecule to the amount of PRG/fluorophore probe bound to the target molecules before addition of the untagged bioactive agent. In some embodiments, methods further comprise detecting light emission within emission spectra of the bioluminescent reporter. In some embodiments, the bioluminescent reporter is a bioluminescent protein or a peptide or polypeptide that is component of a bioluminescent complex. In some embodiments, the concentration of the untagged bioactive agent in the sample is greater than the concentration of PRG/fluorophore probe in the sample.

In some embodiments, provided herein are methods of measuring photocrosslinking efficiency of a bioagent-linked PRG, comprising: contacting sample comprising a target molecule with a PRG/HA probe described herein, wherein the target molecule is tethered to a bioluminescent reporter; allowing the bioactive agent of the PRG/HA probe to bind the target molecule; irradiating the sample with a wavelength of light that converts the PRG into a reactive form of the PRG, wherein the reactive form of the PRG is capable of forming a covalent bond with the target molecule; contacting the sample with an excess BRET reagent comprising the bioactive agent covalently tethered to a fluorophore, wherein the emission spectrum of the bioluminescent reporter overlaps with the excitation spectrum of the fluorophore; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore and wherein the amount of light emission from the fluorophore correlates with the amount of BRET reagent bound to target molecules. In some embodiments, the amount of BRET reagent bound to target molecules correlates to the amount of target molecules not bound by and/or not covalently crosslinked to the PRG/HA probe. In some embodiments, methods further comprise: not contacting the sample comprising a target molecule with a PRG/HA probe described herein, wherein the target molecule is tethered to a bioluminescent reporter; irradiating the sample and then contacting the sample with an excess BRET reagent comprising the bioactive agent covalently tethered to a fluorophore, wherein the emission spectrum of the bioluminescent reporter overlaps with the excitation spectrum of the fluorophore; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore. In some embodiments, methods further comprise comparing (i) the emission spectra collected from a sample treated with a BRET reagent (e.g., bioactive agent and fluorophore) and a PRG/HA probe and irradiated with a wavelength of light that converts the PRG into a reactive form of the PRG with (ii) the emission spectra collected from a sample treated with a BRET reagent (e.g., bioactive agent and fluorophore), but not treated with the PRG/HA, and irradiated with the same wavelength of light that converts the PRG into a reactive form of the PRG; wherein a decrease in BRET due to prior treatment with the PRG/HA inversely correlates with the photocrosslinking efficiency of the PRG (photocrosslinking of the PRG/HA probe to the target prevents displacement of the probe by the excess BRET reagent and thereby results in reduced BRET signal). In some embodiments, methods further comprise: contacting the sample comprising a target molecule with a PRG/HA probe described herein, wherein the target molecule is tethered to a bioluminescent reporter; not irradiating the sample and then contacting the sample with an excess BRET reagent comprising the bioactive agent covalently tethered to a fluorophore, wherein the emission spectrum of the bioluminescent reporter overlaps with the excitation spectrum of the fluorophore; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore. In some embodiments, methods further comprise comparing (i) the emission spectra collected from the irradiated sample with (ii) the emission spectra collected from the non-irradiated sample; wherein a decrease in BRET due to irradiation inversely correlates with the photocrosslinking efficiency of the PRG (photocrosslinking of the PRG/HA probe to the target prevents displacement of the probe by the excess BRET reagent and thereby results in reduced BRET signal).

In some embodiments, provided herein are compositions comprising a photoreactive group (PRG) linked to a bioactive agent, wherein the PRG is selected from:

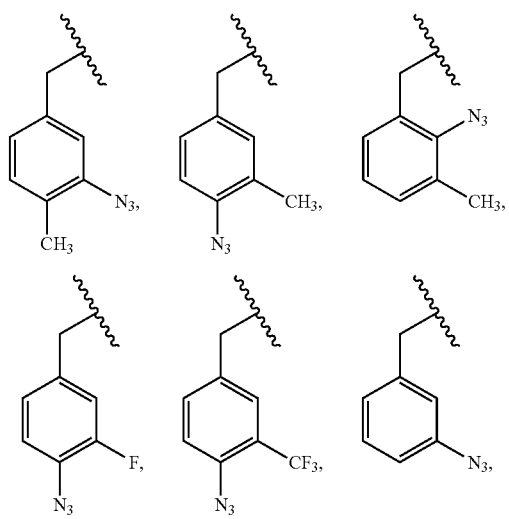

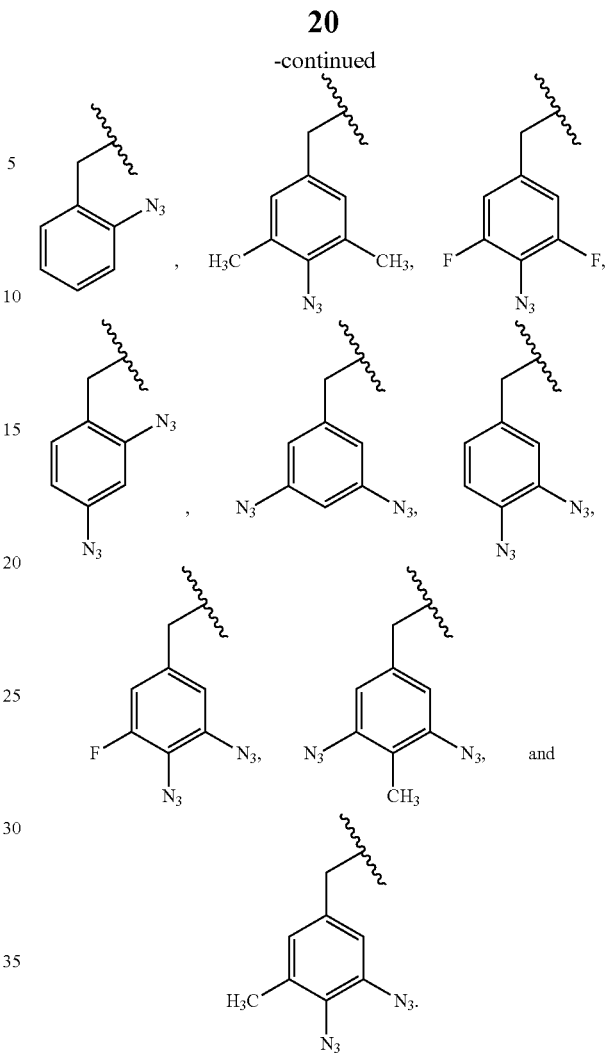

In some embodiments, provided herein are methods of covalently attaching a bioactive agent to a target protein comprising: contacting the target molecule with a bioactive agent linked to a photoreactive group (PRG), wherein the bioactive agent is capable of associating with the target molecule; allowing the bioactive agent to associate with the target molecule; and irradiating with a wavelength of light that converts the PRG into a reactive form of the PRG, wherein the reactive form of the PRG forms a covalent bond with the target molecule.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 35A-C. (FIG. 35A) Molecular structure of SAHA (Vorinostat). (FIG. 35B) Molecular structures of 4-phenylazide, 4-Me-3-phenylazide, and diazirine chloroalkane probes. (FIG. 35C) LC-MS/MS analysis for enrichment of SAHA targets from K-562 cells with 4-phenylazide, 4-Me-3-phenylazide, and diazirine chloroalkane probes.

(FIG. 36A) Molecular structure of dasatinib. (FIG. 36B) Molecular structures of 4-phenylazide, 4-Me-3-phenylazide, and diazirine chloroalkane probes. (FIG. 36C) LC-MS/MS analysis for enrichment of dasatinib targets from K-562 cells with 4-phenylazide, 4-Me-3-phenylazide, and diazirine chloroalkane probes.

FIG. 37A) Molecular structure of propranolol. (FIG. 37B) Molecular structures of diazirine and 4-phenylazide chloroalkane probes. (FIG. 37C) Bioluminescence blot analysis for enrichment of propranolol targets from genome-edited PC3 cells expressing a HiBiT-tagged β2-AR with diazirine and 4-phenylazide chloroalkane probes. (FIG. 37D) LC-MS/MS analysis for enrichment of propranolol targets from PC3 cells with 4-phenylazide chloroalkane probe.

DEFINITIONS

Figure 1:
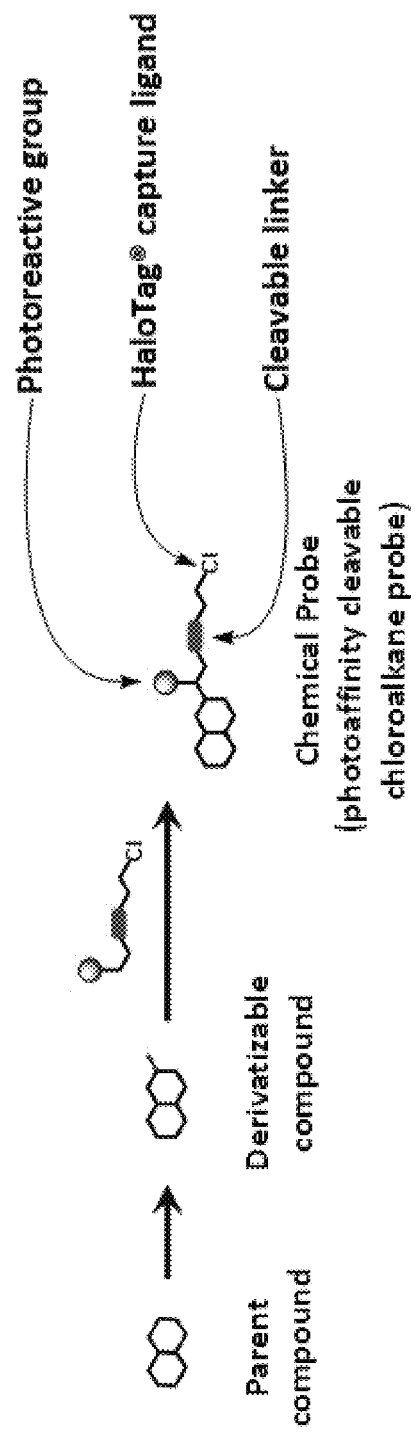
FIG. 1. Schematic representation of a generic photoaffinity cleavable chloroalkane probe.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies, or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an", and "the" include plural reference unless the context clearly dictates otherwise. Thus, for example, reference to "a peptide" is a reference to one or more peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially" means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic.

As used herein, the term "photoreactive group", refers to a functional moiety, which, upon exposure to light (e.g., a specific wavelength or wavelength range of light, UV light, etc.), forms a covalent linkage with a molecule within its immediate vicinity.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products such as plasma, serum, and the like. Sample may also refer to cell lysates or purified forms of the enzymes, peptides, and/or polypeptides described herein. Cell lysates may include cells that have been lysed with a lysing agent or lysates such as rabbit reticulocyte or wheat germ lysates. Sample may also include cell-free expression systems. Environmental samples include environmental material such as surface matter, soil, water, crystals, and industrial samples. Such examples are not however to be construed as limiting the sample types applicable to the present invention.

As used herein, the term "physiological conditions" encompasses any conditions compatible with living cells, e.g., predominantly aqueous conditions of a temperature, pH, salinity, chemical makeup, etc., that are compatible with living cells.

As used herein, the terms "conjugated" and "conjugation" refer to the covalent attachment of two molecular entities (e.g., post-synthesis and/or during synthetic production). The attachment of a peptide or small molecule tag to a protein or small molecule, chemically (e.g., "chemically" conjugated), or enzymatically, is an example of conjugation. The reaction of a SE-peptide with an amine on a biomolecule results in conjugation of the peptide with the biomolecule.

The term "binding moiety" refers to a domain that specifically binds an antigen or epitope independently of a different epitope or antigen binding domain. A binding moiety may be an antibody, antibody fragment, a receptor domain that binds a target ligand, proteins that bind to immunoglobulins (e.g., protein A, protein G, protein A/G, protein L, protein M), a binding domain of a proteins that bind to immunoglobulins (e.g., protein A, protein G, protein A/G, protein L, protein M), oligonucleotide probe, peptide nucleic acid, DARPin, aptamer, affimer, a purified protein (either the analyte itself or a protein that binds to the analyte), analyte binding domain(s) of proteins, etc. Table A provides a list of exemplary binding moieties that could be used singly or in various combinations in methods, systems, and assays (e.g., immunoassays) herein.

TABLE A

| Exemplary binding moieties |
| --- |
| Protein A |
| Ig Binding domain of protein A |
| Protein G |
| Ig Binding domain of protein G |
| Protein L |
| Ig Binding domain of protein L |
| Protein M |
| Ig Binding domain of protein M |
| polyclonal antibody against analyte X |
| monoclonal antibody |
| recombinant antibody |
| scFv |
| variable light chain ($V_L$) of antibody (monoclonal, recombinant, polyclonal) recognizing target analyte X |
| protein (e.g. receptor) binding domain that binds to analyte X |
| (Fab) fragment |
| Fab' fragment |
| Fv fragment |
| F(ab')2 fragment |
| oligonucleotide probe |
| DARPins and other synthetic binding scaffolds |

TABLE A-continued

Exemplary binding moieties (ex: Bicycles)
peptide nucleic acid
aptamer
affimer

As used herein, the term "antibody" refers to a whole antibody molecule or a fragment thereof (e.g., fragments such as Fab, Fab', and F(ab')$_2$, variable light chain, variable heavy chain, Fv). The antibody may be a polyclonal or monoclonal or recombinant antibody, a chimeric antibody, a humanized antibody, a human antibody, etc. As used herein, when an antibody or other entity "specifically recognizes" or "specifically binds" an antigen or epitope, it preferentially recognizes the antigen in a complex mixture of proteins and/or macromolecules and binds the antigen or epitope with affinity, which is substantially higher than to other entities not displaying the antigen or epitope. In this regard, "affinity which is substantially higher" means affinity that is high enough to enable detection of an antigen or epitope, which is distinguished from entities using a desired assay or measurement apparatus. Typically, it means binding affinity having a binding constant ($K_a$) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M$^{-1}$, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion of the antigen binding region or a variable region. Antibody fragments include, but are not limited to, Fab, Fab', F(ab')$_2$, Fv, scFv, Fd, variable light chain, variable heavy chain, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody), produced by recombinant DNA techniques, or produced by chemical polypeptide synthesis. For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises an additional constant region extending between the $C_{H1}$ and $C_{H2}$ domains. An interchain disulfide bond can be formed between two heavy chains of a Fab' fragment to form a "F(ab')$_2$" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen. Other antibody fragments will be understood by skilled artisans.

As used herein, the term "biomolecule" or "biological molecule" refers to molecules and ions that are present in organisms and are essential to a biological process(es) such as cell division, morphogenesis, or development. Biomolecules include large macromolecules (or polyanions) such as proteins, carbohydrates, lipids, and nucleic acids as well as small molecules such as primary metabolites, secondary metabolites, and natural products. A more general name for this class of material is biological materials. Biomolecules are usually endogenous, but may also be exogenous. For example, pharmaceutical drugs may be natural products or semisynthetic (biopharmaceuticals), or they may be totally synthetic.

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light. As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent". In some embodiments, an entity is considered "non-luminescent" if any light emission is sufficiently minimal so as not to create interfering background for a particular assay.

As used herein, the term "an Oplophorus luciferase" ("an OgLuc") refers to a luminescent polypeptide having significant sequence identity, structural conservation, and/or the functional activity of the luciferase produce by and derived from the deep-sea shrimp Oplophorus gracilirostris. In particular, an OgLuc polypeptide refers to a luminescent polypeptide having significant sequence identity, structural conservation, and/or the functional activity of the mature 19 kDa subunit of the Oplophorus luciferase protein complex (e.g., without a signal sequence) such as SEQ ID NOs: 1 (WT OgLuc) and 5 (NANOLUC), which comprises 10β strands (β1, β2, β3, β4, β5, β6, β7, β8, β9, β10) and utilize substrates such as coelenterazine or a coelenterazine derivative or analog to produce luminescence.

As used herein, the term "complex" refers to an assemblage or aggregate of molecules (e.g., peptides, polypeptides, etc.) in direct and/or indirect contact with one another. In one aspect, "contact", or more particularly "direct contact", means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules (e.g., peptides and polypeptide) is formed under assay conditions such that the complex is thermodynamically favored (e.g., compared to a non-aggregated, or non-complexed, state of its component molecules). As used herein the term "complex", unless described as otherwise, refers to the assemblage of two or more molecules (e.g., peptides, polypeptides or a combination thereof).

As used herein, the term "capture protein" refers to a protein that forms a stable covalent bond with its substrate and/or ligand upon interaction therewith. A capture protein may be a receptor that forms a covalent bond upon binding its ligand or an enzyme that forms a covalent bond with its substrate. An example of a suitable capture protein for use in embodiments of the present invention is the HALOTAG protein described in U.S. Pat. No. 7,425,436 (herein incorporated by reference in its entirety).

As used herein, the terms "capture ligand" or "capture moiety" refers to a ligand, substrate, etc., that forms a covalent bond with a capture protein upon interaction therewith. An example of a suitable capture ligand for use in embodiments of the present invention is the HALOTAG ligand described, for example, in U.S. Pat. No. 7,425,436 (herein incorporated by reference in its entirety). Moieties that find use as HALOTAG ligands include haloalkane (HA) groups (e.g., chloroalkane (CA) groups). In embodiments described herein that specify an HA or CA capture ligand, other suitable capture ligands may be substituted unless otherwise specified.

As used herein, the term "cellular target" refers to a protein, polypeptide, nucleic acid (e.g., DNA or RNA), polysaccharide, or a complex comprising any of these with a polypeptide(s). A cellular target could be composed of more than one component, subunit, or polypeptide, e.g., the cellular target is a protein complex. Examples of a cellular target may include a receptor or an enzyme.

As used herein, the term "bioactive agent" refers generally to any physiologically or pharmacologically active substance or a substance suitable for detection. In some embodiments, a bioactive agent is a potential therapeutic compound (e.g., small molecule, peptide, nucleic acid, etc.) or drug-like molecule. Bioactive agents for use in embodiments described herein are not limited by size or structure.

As used herein, the term "small molecule" refers to a low molecular weight (e.g., <2000 daltons, <1000 daltons, <500 daltons) organic compound with dimensions (e.g., length, width, diameter, etc.) on the order of 1 nm. Larger structures, such as peptides, proteins, and nucleic acids, are not small molecules, although their constituent monomers (ribo- or deoxyribonucleotides, amino acids, etc.) are considered small molecules.

As used herein, the term "cell permeable" refers to a compound or moiety that is capable of effectively crossing a cell membrane that has not been synthetically permeabilized.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Sorrell, Organic Chemistry, 2$^{nd}$ edition, University Science Books, Sausalito, 2006; Smith, March's Advanced Organic Chemistry: Reactions, Mechanism, and Structure, 7$^{th}$ Edition, John Wiley & Sons, Inc., New York, 2013; Larock, Comprehensive Organic Transformations, 3$^{rd}$ Edition, John Wiley & Sons, Inc., New York, 2018; Carruthers, Some Modern Methods of Organic Synthesis, 3$^{rd}$ Edition, Cambridge University Press, Cambridge, 1987; the entire contents of each of which are incorporated herein by reference.

The term "alkoxy", as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, and tert-butoxy.

The term "alkyl", as used herein, means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_1$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl", as used herein, refers to a straight or branched hydrocarbon chain containing from 2 to 30 carbon atoms and containing at least one carbon-carbon double bond. For example, an alkenyl group may include 2 to 16 carbon atoms ($C_2$-$C_{16}$ alkenyl), 2 to 14 carbon atoms ($C_2$-$C_{14}$ alkenyl), 2 to 12 carbon atoms ($C_2$-$C_{12}$ alkenyl), 2 to 10 carbon atoms ($C_2$-$C_{10}$ alkenyl), 2 to 8 carbon atoms ($C_2$-$C_8$ alkenyl), 2 to 6 carbon atoms ($C_2$-$C_6$ alkenyl), or 2 to 4 carbon atoms ($C_2$-$C_4$ alkenyl). Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl", as used herein, refers to a straight or branched hydrocarbon chain containing from 2 to 30 carbon atoms and containing at least one carbon-carbon triple bond. For example, an alkynyl group may include 2 to 16 carbon atoms ($C_2$-$C_{16}$ alkynyl), 2 to 14 carbon atoms ($C_2$-$C_{14}$ alkynyl), 2 to 12 carbon atoms ($C_2$-$C_{12}$ alkynyl), 2 to 10 carbon atoms ($C_2$-$C_{10}$ alkynyl), 2 to 8 carbon atoms ($C_2$-$C_8$ alkynyl), 2 to 6 carbon atoms ($C_2$-$C_6$ alkynyl), or 2 to 4 carbon atoms ($C_2$-$C_4$ alkynyl). Representative examples of alkynyl include, but are not limited to, ethynyl, propynyl, and butynyl.

The term "alkylene", as used herein, refers to a divalent group derived from a straight or branched chain hydrocarbon of 1 to 30 carbon atoms, for example, 1 to 16 carbon atoms ($C_1$-$C_{16}$ alkylene), 1 to 14 carbon atoms ($C_1$-$C_{14}$ alkylene), 1 to 12 carbon atoms ($C_1$-$C_{12}$ alkylene), 1 to 10 carbon atoms ($C_1$-$C_{10}$ alkylene), 1 to 8 carbon atoms ($C_1$-$C_8$ alky alkylene 1), 1 to 6 carbon atoms ($C_1$-$C_6$ alkylene), or 1 to 4 carbon atoms ($C_1$-$C_4$ alkylene).

Representative examples of alkylene include, but are not limited to, —$CH_2$—, —$CH_2CH_2$—, —$CH_2CH_2CH_2$—, —$CH_2CH_2CH_2CH_2$—, —$CH_2CH(CH_3)CH_2$—, and —$CH_2CH_2CH_2CH_2CH_2$—.

The term "aryl", as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl.

The term "cycloalkyl", as used herein, refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

The term "cycloalkenyl", as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, or cycloheptenyl.

The term "halogen" or "halo", as used herein, means F, Cl, Br, or I.

The term "haloalkyl", as used herein, means an alkyl group, as defined herein, in which one, two, three, four, five, six, seven, or eight hydrogen atoms are replaced by a halogen.

The term "heteroalkyl", as used herein, means an alkyl group, as defined herein, in which one or more of the carbon atoms has been replaced by a heteroatom selected from S, O, P, and N. Representative examples of heteroalkyls include, but are not limited to, alkyl ethers, secondary and tertiary alkyl amines, and alkyl sulfides.

The term "heteroalkylene", as used herein, means an alkylene group, as defined herein, in which one or more of the carbon atoms has been replaced by a heteroatom selected from S, O, P and N. Representative examples of heteroalkylene include, but are not limited to, —O—CH$_2$—, —NH—CH$_2$—, —S—CH$_2$—, —O—CH$_2$—CH$_2$—, —S—CH$_2$—CH$_2$—, —NH—CH$_2$—CH$_2$—, —CH$_2$—O—CH$_2$—, —CH$_2$—S—CH$_2$—, and —CH$_2$—NH—CH$_2$—.

The term "heteroaryl", as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five-membered aromatic monocyclic rings have two double bonds, and the six membered six membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, or a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl, and dibenzothienyl. The monocyclic, bicyclic, and tricyclic heteroaryls are connected to the parent molecular moiety through any carbon atom or any nitrogen atom contained within the rings.

The term "heterocycle" or "heterocyclic", as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The term "hydroxy", as used herein, means an —OH group.

In some instances, the number of carbon atoms in a group (e.g., alkyl, alkoxy, or cycloalkyl) is indicated by the prefix "$C_x$-$C_y$-", wherein x is the minimum and y is the maximum number of carbon atoms in the group. Thus, for example, "$C_1$-$C_3$-alkyl" refers to an alkyl group containing from 1 to 3 carbon atoms.

The term "substituent" refers to a group substituted on an atom of the indicated group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents such that the selections and substitutions result in a stable compound, e.g., which does not spontaneously undergo transformation such as by rearrangement, cyclization, elimination, etc.

DETAILED DESCRIPTION

Provided herein are compositions and methods for photoaffinity labeling of molecular targets. In particular, probes that specifically interact with cellular targets based on their affinity and are then covalently linked to the cellular target via a photoreactive group (PRG) on the probe.

Provided herein is a chemoproteomics platform for both target identification and compound selectivity profiling. This platform is based on the generation of photoreactive chemical probe(s) derived from biologically active compounds (bioactive agents). In some embodiments, the probes are generated via chemical tagging of the bioactive agent with a (i) cell-permeable, (ii) photoreactive, and (iii) cleavable chloroalkane (FIG. 1). Probes are designed/synthesized using a modular assembly of component parts (e.g., bioactive agent, PRG, cleavable linker, and capture moiety). Assembling PRGs with cleavable chloroalkane in a single reagent (e.g., to be attached to a bioactive agent(s)) allows the development of a library of PRG/HA labeled bioactive agents. This modular generic approach makes use of the robust photo-reactivity of the PRGs described herein, which allow for efficient photocrosslinking to the target(s) without customizing the attachment of the PRG onto each bioactive compound. Furthermore, the minimal influence of the PRG/HA probes on the cellular permeability of a bioactive compound allows for efficient photocrosslinking of the probe to the target protein(s) in a cellular environment. In addition, the built-in capture moiety of the PRG/HA probe (e.g. cleavable chloroalkane) allows for straightforward enrichment of interacting targets through capture onto HALOTAG resin without an additional click ligation of a capture moiety that is required in other systems (See, e.g., ACS Chem. Biol., 2015, 10 (10), pp 2316-2324; ACS Chem. Biol., 2016, 11 (9), pp 2608-2617; U.S. Pub No. 2014/0322794; U.S. Pub No. 2016/0355523; herein incorporated by reference in their entireties). The cleavable moiety of the probes herein allows for efficient release of the enriched targets from the solid support, e.g., for mass-spectrometry identification.

Figure 2:
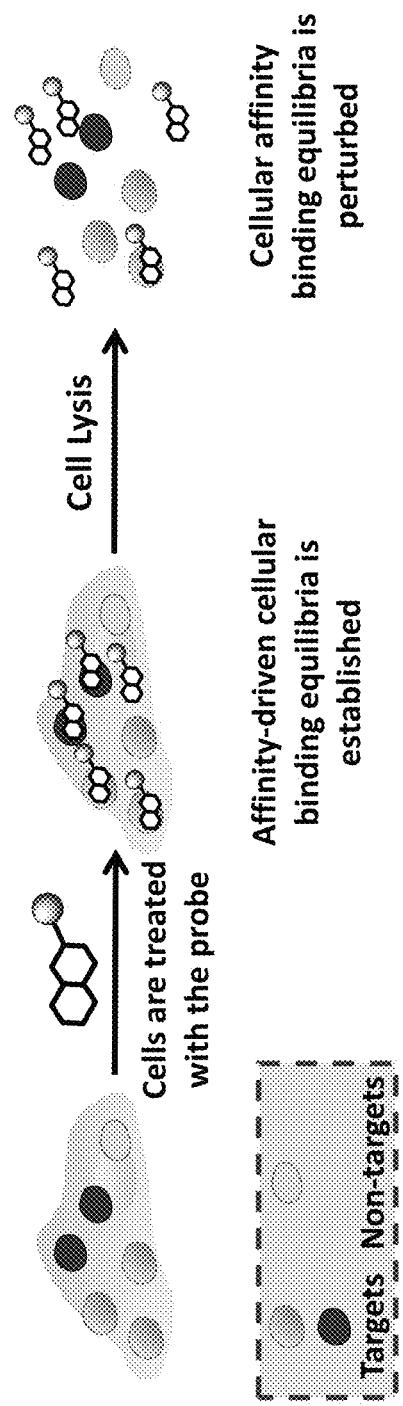
FIG. 2. Schematic representation of the impact of cell lysis on affinity driven binding equilibria with cellular targets.
Figure 3:
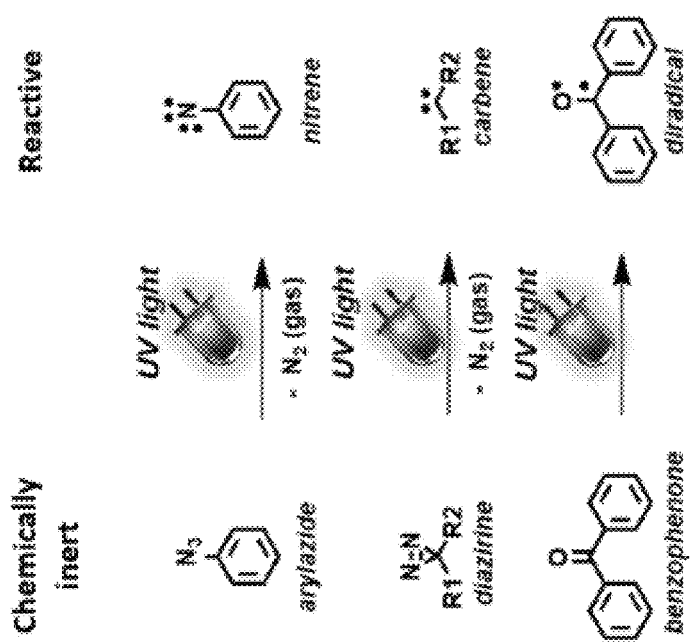
FIG. 3. Common PRGs and their reactive intermediates.
Figure 4:
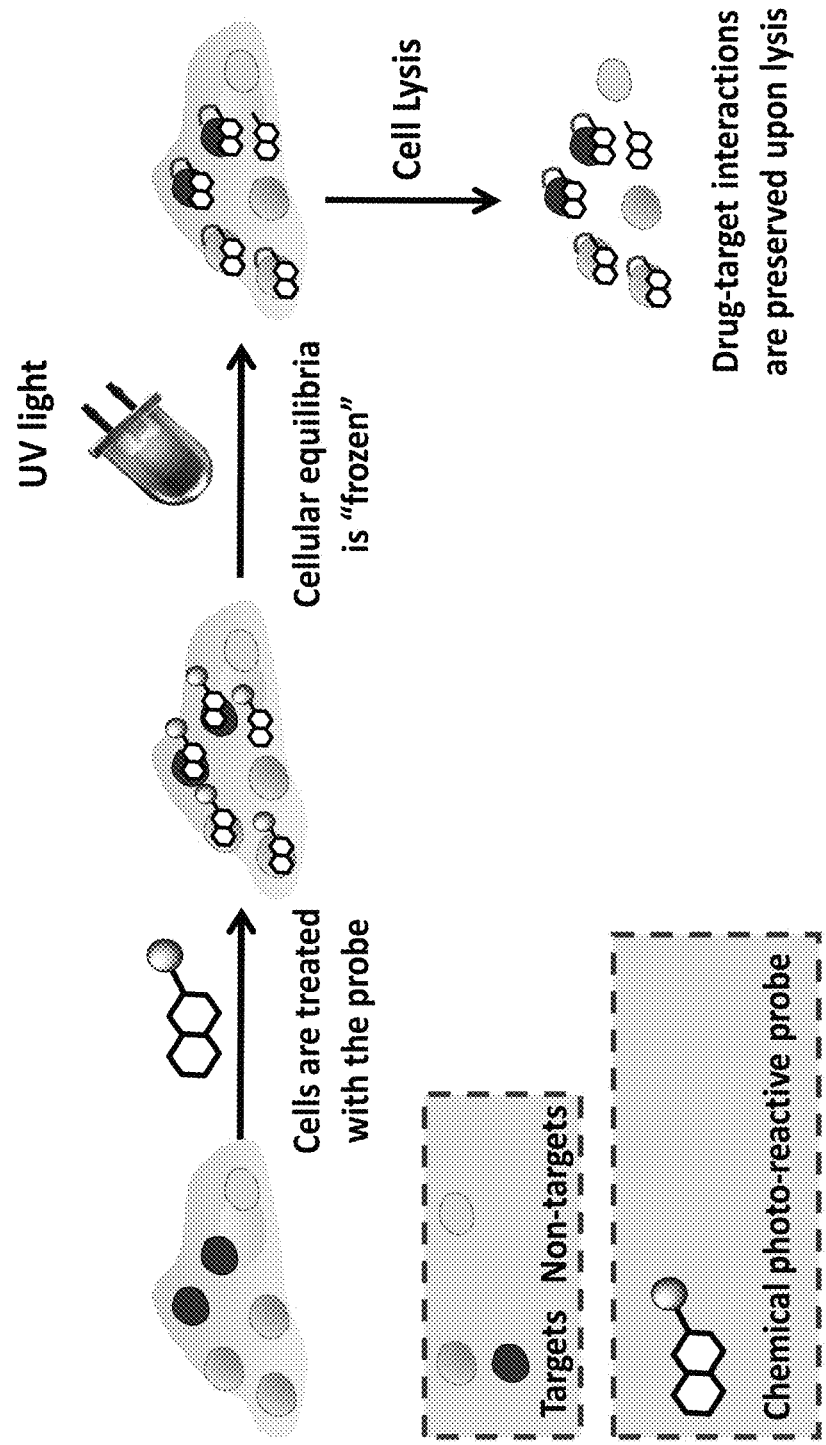
FIG. 4. Schematic representation of UV induced covalent crosslinking of the photo-reactive chemical probe to its associated cellular targets, which "freezes" the affinity driven binding equilibria and preserves them upon cell lysis.

Despite progress in chemoproteomic techniques, challenges still exist for identification of binding interactions established inside live cells. A major methodological issue of chemoproteomic approaches is that the enrichment of the interacting cellular targets requires cell lysis. The cell lysis step disrupts affinity driven drug-target equilibrium established inside live cells and therefore the resulting post-lysis equilibrium may not represent the equilibrium inside intact cells (FIG. 2). The platform, systems, probes, reagents, and methods herein overcome the issues that often confront existing technologies by forming a covalent bond between the probe and the target after the bioactive agent portion of the probe has non-covalently interacted with the target, thus preventing dissociation upon lysis. The covalent bond is formed using photoreactive groups (e.g. arylazides, diazirines, benzophenones, etc; See, e.g., FIG. 3) that are chemically inert until activated by light (photoactivation). Upon photolysis, the photo-reactive group (PRG) generates highly-reactive specie(s) capable of photocrosslinking to a target molecule (e.g., forming a covalent bond with amino acids in target protein). Provided herein is a platform that provides a general tool for labeling any bioactive agent with a photoreactive group, thus allowing for UV induced covalent crosslinking of the bioactive agent to its interacting targets, which "freezes" the intracellular equilibria and preserves them upon lysis (FIG. 4).

Existing photocrosslinking chemistries often suffer from low labeling efficiency and therefore rely on customizing the attachment of the PRG onto the bioactive compound to achieve efficient crosslinking with different protein targets. This is further complicated by the current state of the art employ cell permeable photoreactive clickable probes, which permit biorthogonal click ligation of a capture tag (e.g., biotin) to the probe after the cell are lysed. While these clickable probes address the frequent interference of biotin conjugation with the cellular permeability of a bioactive compound, most click reactions are not compatible with aryl azides, which are useful PRGs. This is because of the inherent reactivity of azide functionality toward common click partners (e.g., strained alkynes, trans-cyclooctene (TCO), etc.). Such cross-reactivity is not an issue for chloroalkane tags, which are fully compatible with aryl azides and encompass a built-in, orthogonally reactive capture moiety that eliminates the need for a click reaction. For example, the HALOTAG ligand (Promega; Madison, WI), a chloroalkane tag, exhibits minimal influence on a small molecule cell permeability and binding interactions. This feature coupled with the unique compatibility of chloroalkanes with a wide array of photoreactive groups and the high reactivity with HALOTAG protein makes the haloalkane capture moiety particularly useful for use in a modular platform employing photoreactive groups with enhanced crosslinking properties.

Figure 9:
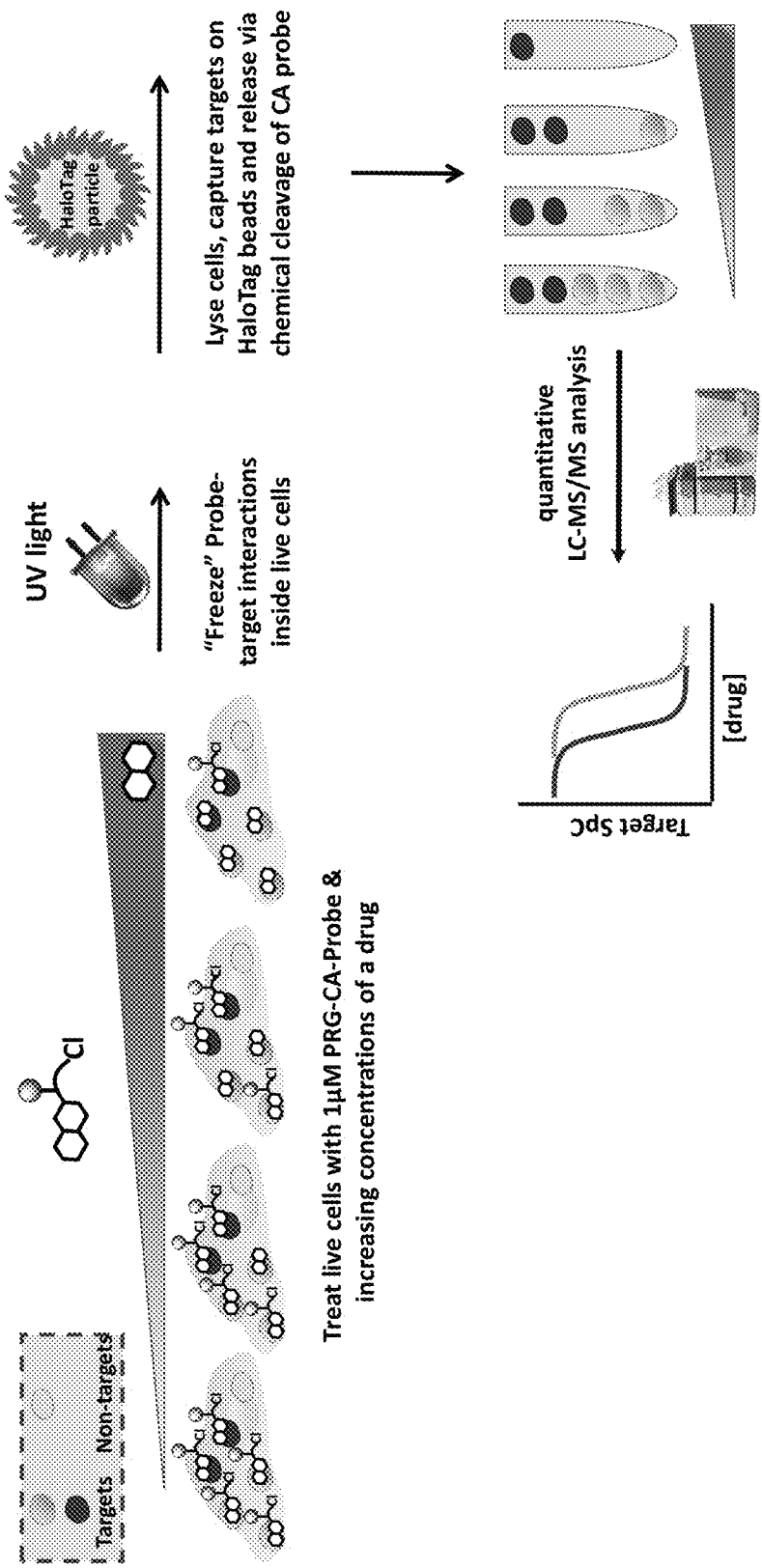
FIG. 9. Schematic representation of utilizing a photoreactive chloroalkane chemical probe to establish a compound selectivity and affinity profiling in live cells.

In some embodiments, provided herein is a chemoproteomic platform for quantitative analysis of a compound's cellular target engagement, selectivity profiling, and target identification. In some embodiments, this platform relies on the chemical inertness of the capture tag (e.g., haloalkane tag, chloroalkane tag, etc.), which permits employment of aryl azides (See, e.g., Table 1). In some embodiments, the platform is based on modularly assembled photoreactive chloroalkane probes (FIG. 1) that incorporate existing and new photo-reactive groups. UV-irradiation induced cross-linking of the photoreactive chloroalkane probe to the targets in live cells, which "freezes" cellular equilibria and preserves it upon cell lysis. Further capture of the interacting targets onto a capture protein (e.g., HALOTAG) resin allows for an entire covalent enrichment of those targets. In some embodiments, the release of captured targets from the solid support by mild chemical cleavage of the photoreactive chloroalkane tag is followed by LC-MS/MS analysis of the enriched targets (FIG. 9).

One of the difficulties encountered by the field is lack of effective assays for estimating photocrosslinking efficiency. The complexity and structural diversity of biological systems coupled with complex reactivity of photo-generated species often results in contradicting literature data on crosslinking efficiencies.

Currently, the state of the art for photocrosslinking chemistries applied in chemoproteomics is dominated by the use of diazirines (both alkyl- and aryl-diazirines) as PRGs. Benzophenones are also used, although, they are bulky and may exhibit low crosslinking efficiency, preventing their general use in many systems. Arylazides are often avoided in chemoproteomics due to their incompatibility with many click-chemistry handles.

Figure 10:
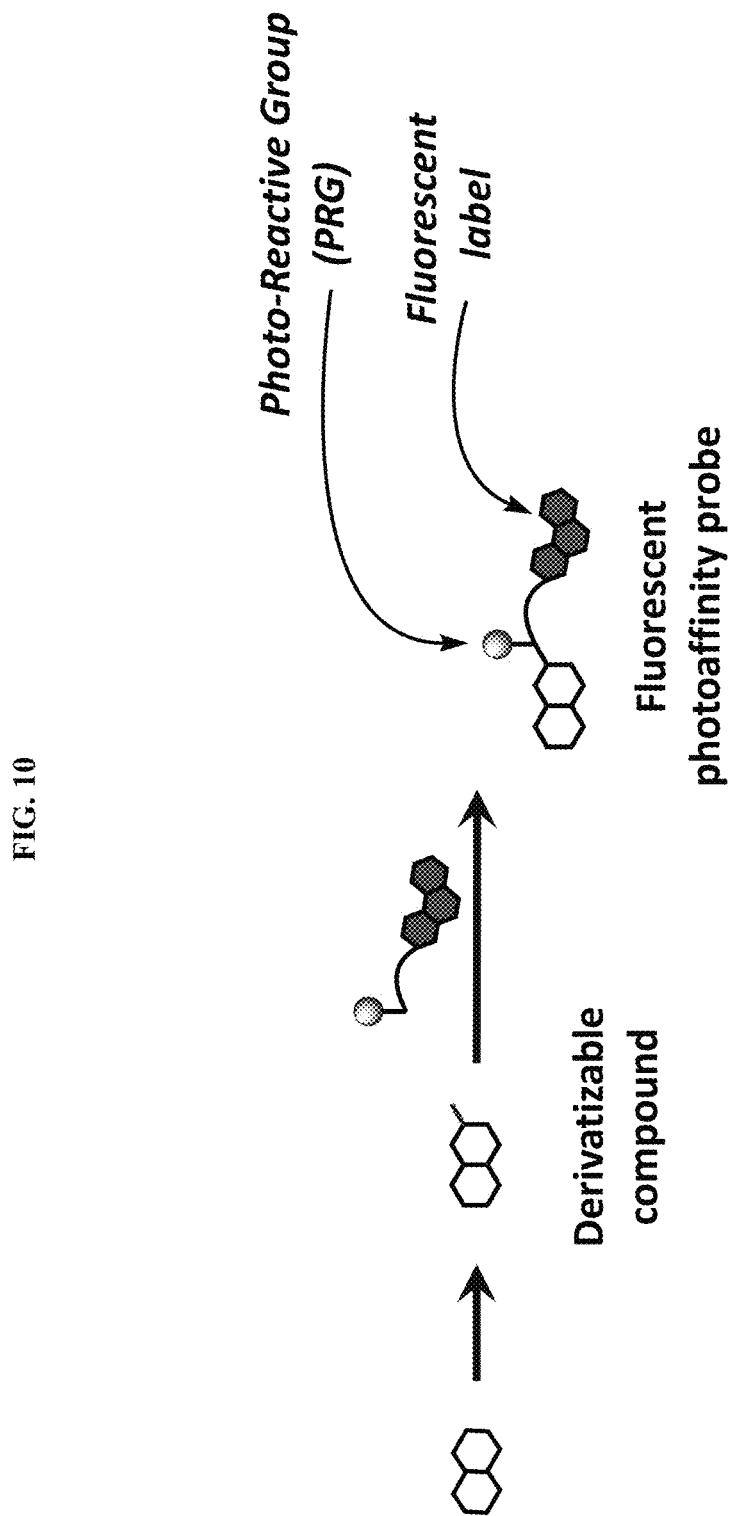
FIG. 10. Schematic representation of a generic fluorescent photoaffinity probe.
Figure 11:
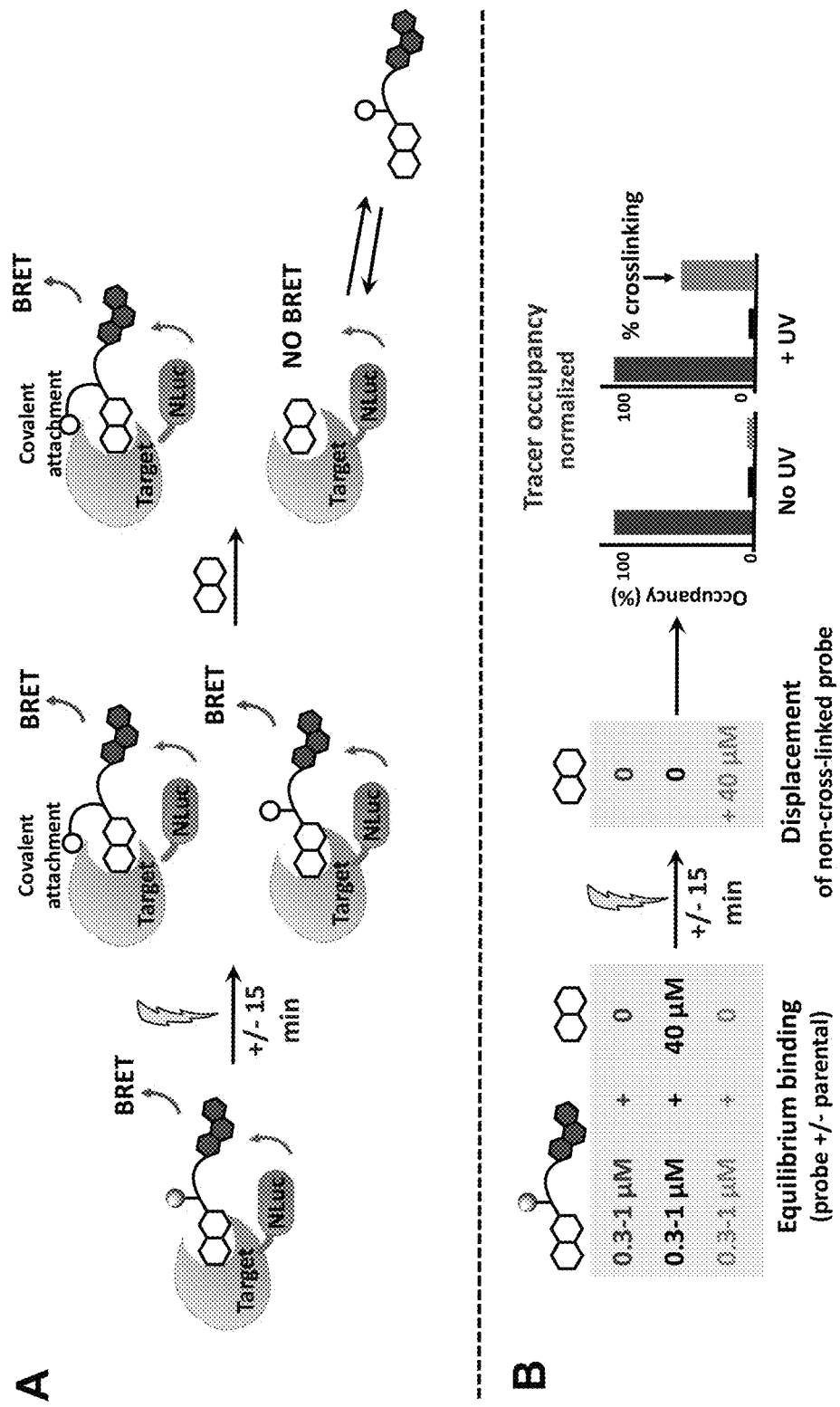
FIG. 11, panels A-B. (Panel A) General scheme of BRET assay for quantifying crosslinking efficiency. Binding of a PRG/fluorophore probe to a target tethered to NANOLUC results with BRET. UV irradiation induces covalent crosslinking of the probe to its target. Treatment with excess parental compound displaces non-covalently bound PRG/fluorophore probe, resulting with a decrease in BRET. (Panel B) Residual BRET, resulting from probe that could not be competed off by excess parental compound, is normalized to maximal BRET from an equivalent sample that was not treated with excess parental compound, and used to derive crosslinking efficiency. Normalized residual BRET correlates with crosslinking efficiency.

To systematically evaluate an array of existing and new photoreactive groups (PRGs), a BRET-based assay estimating photocrosslinking efficiency was developed during development of embodiments herein. This assay format utilizes fluorescent photoaffinity probes that incorporate a PRG and a fluorescent reporter dye (FIG. 10). The fluorescent photoaffinity probes in FIG. 10 differ from the probes in FIG. 1 in their reporter tag, i.e., the chloroalkane capture tag in the probes of FIG. 1 is switched with a fluorescent reporter dye in the probes in FIG. 10. The schematic representation of an assay using the probes from FIG. 10 is shown in FIG. 11. The assay represented in FIG. 11 relies on measuring BRET between a target tethered to a luciferase (e.g., NANOLUC) and a fluorescent photoaffinity probe and has the advantage of estimating photocrosslinking efficiency, independent of other environmental factors. Binding of a fluorescent photoaffinity probe to its target protein fused to NANOLUC results in a BRET ratio for a given probe concentration (e.g., emission from the fluorophore as the result of energy transfer from the luciferase, which is expressed as a BRET ratio). This BRET correlates to maximal probe occupancy at that given probe concentration. Further treatment with excess parent bioactive compound, displaces the bound fluorescent photoaffinity probe, resulting in a decrease in BRET, which correlates to minimal probe occupancy. If following binding of the fluorescent photoaffinity probe, the sample is UV irradiated to crosslink the probe to its target, the subsequent treatment with excess parental bioactive compound would displace only non-covalently bound probe. Residual BRET resulting from probe that could not be displaced that is normalized to maximal and minimal probe occupancy can be used to derive fraction occupancy of covalently bound probe, which reflects photocrosslinking efficiency. Simple fluorescent readout will not necessarily provide reliable information on crosslinking efficiency as dye fluorescence is highly sensitive to its environment and the same dye could provide very different fluorescence readout when attached to a different chemical entity. The fluorescence is not dependent on close association of the probe with the target protein unlike other methods (e.g., BRET).

I. Probes

In some embodiments, provided herein are probes comprising a bioactive agent (e.g., peptide, small molecule, etc.), a PRG, and a functional moiety that allows for detection, capture, monitoring, etc., of the probe before and/or after covalent attachment (e.g., via reaction of the PRG) to a target molecule, protein, etc. Provided herein are platforms that facilitate the use of the capture and detection methods described herein with any bioactive agent of interest.

A. PRG/HA Probe

In some embodiments, provided herein are probes comprising a bioactive agent, a photoreactive group (PRG), and a capture ligand (e.g., haloalkane); reagents and methods for assembling such probes (e.g., for labeling a bioactive agent (e.g., a reactively-derivatized bioactive agent) with a PRG and capture ligand (e.g., haloalkane); methods of using such probes to capture target molecules (e.g., cellular protein targets) in a sample (e.g., complex sample (e.g., cell, cell lysate, etc.)); and compositions (e.g., PRG/fluorophore probes, fusions of cellular targets and bioluminescent reporters, etc.) for determining crosslinking efficiency of the probes herein. In some embodiments, once a capture probe is covalently conjugated to a target (e.g., target molecule, target protein, etc.), a capture protein (e.g., or capture fusion protein) is bound to the capture ligand to allow for isolation, enrichment, etc. of the captured target. In some embodiments, provided herein are systems that allow for attachment of a PRG and capture ligand (e.g., haloalkane) to any bioactive agent (e.g., small molecule, peptide, etc.) upon generating a reactively-derivatized version of the bioactive agent.

In some embodiments, provided herein are compositions comprising a PRG/HA probe comprising: a bioactive agent, a photoreactive group (PRG), a linker, and a capture ligand (e.g., haloalkane) covalently connected in a single compound of the general structure:

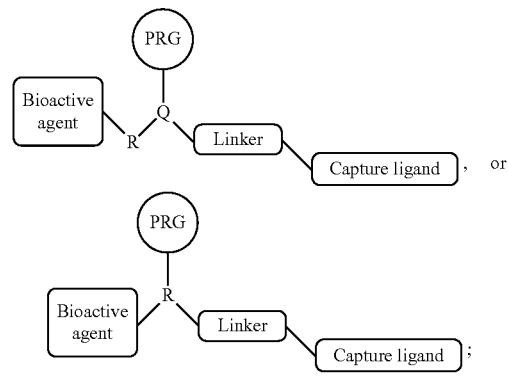

wherein R is a covalent linkage, and wherein Q is CH or N.

In some embodiments, R is a covalent linkage resulting from the reaction of two reactive moieties (R' and R"). In some embodiments, R comprises —NH—, —C(O)NH—, —OC(O)NH—, N, C(O)N, OC(O)N, or —O—. In some embodiments, R comprises —(CH$_2$)$_{0-2}$NH(CH$_2$)$_{0-2}$—, —(CH$_2$)$_{0-2}$C(O)NH(CH$_2$)$_{0-2}$—, —(CH$_2$)$_{0-2}$OC(O)NH (CH$_2$)$_{0-2}$—, (CH$_2$)$_{0-2}$N(CH$_2$)$_{0-2}$—, —(CH$_2$)$_{0-2}$C(O)N (CH$_2$)$_{0-2}$—, —(CH$_2$)$_{0-2}$OC(O)N(CH$_2$)$_{0-2}$—, or —(CH$_2$)$_{0-2}$O(CH$_2$)$_{0-2}$—. In some embodiments, the general structure of a PRG/HA probe is:

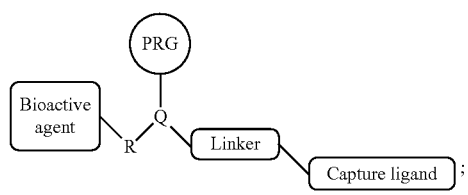

Q comprises CH or N; and R comprises —NH—, —C(O)NH—, —OC(O)NH—, —O—, —(CH$_2$)$_{0-2}$NH(CH$_2$)$_{0-2}$—, —(CH$_2$)$_{0-2}$C(O)NH(CH$_2$)$_{0-2}$—, —(CH$_2$)$_{0-2}$OC(O)NH(CH$_2$)$_{0-2}$—, or —(CH$_2$)$_{0-2}$O(CH$_2$)$_{0-2}$—. In other embodiments, the general structure of a PRG/HA probe is:

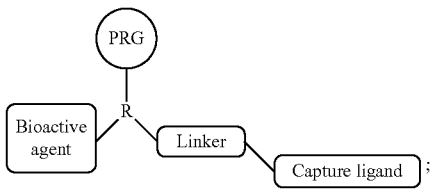

and R is N, C(O)N, OC(O)N, (CH$_2$)$_{0-2}$N(CH$_2$)$_{0-2}$—, —(CH$_2$)$_{0-2}$C(O)N(CH$_2$)$_{0-2}$—, or —(CH$_2$)$_{0-2}$OC(O)N(CH$_2$)$_{0-2}$—.

In some embodiments, the linker is a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O)OCH$_2$CH=CHCH$_2$OC(O)—. In some embodiments, the cleavable linker comprises the cleavable moiety flanked on one or both sides by alkylene or heteroalkylene chains. In some embodiments, the alkylene or heteroalkylene chains comprise any suitable combination of C$_1$-6-alkylene, —O—, —(CH$_2$)$_2$O—, and —OC(O)NH— groups.

In some embodiments, linkers herein (e.g., the linkers of the probes herein (e.g., linking capture ligand to Q/R groups) comprise any suitable moieties to yield the desired structure/function (e.g., length, flexibility/rigidity, solubility, cell permeability, etc.). The probes herein are not limited to any particular linker moieties. Indeed, a variety of linker moieties are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), an oligonucleotide linker, phospholipid derivatives, alkenyl chains, alkynyl chains, disulfide, or a combination thereof. In some embodiments, a linker comprises, or is optionally substituted by, any combination of alkyl, alkenyl, alkynyl, amide, phenyl, benzyl, carbamate, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulfinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention. In some embodiments, a linker comprises a cleavable moiety and one or more of the aforementioned functional groups/moieties.

In some embodiments, the capture ligand is a haloalkane (aka "alkyl halide"). In some embodiments, the capture ligand is a chloroalkane. In some embodiments, the capture ligand is -A-X. In some embodiments, X is Cl. In some embodiments, -A-X is —(CH$_2$)$_6$Cl. When the capture ligand is a haloalkane, the capture protein is typically a dehalogenase enzyme modified to form covalent bonds with its substrate (See, e.g., U.S. Pat. Nos. 7,425,436; 7,429,472; 7,867,726; 7,888,086; 7,935,803; U.S. Pat. No. RE42,931; U.S. Pat. Nos. 8,168,405; 8,202,700; 8,257,939; herein incorporated by reference in their entireties). One such modified dehalogenase is the commercially-available HALOTAG protein. In some embodiments, a capture protein comprises a polypeptide with at least 70% sequence identity (e.g., 75% identity, 80% identity, 85% identity, 90% identity, 95% identity, 98% identity, 99% identity) with SEQ ID NO.: 15. In some embodiments, a capture ligand is a haloalkane comprising a halogen (e.g., Cl, Br, F, I, etc.) covalently attached to the end of an alkyl chain (e.g., (CH$_2$)$_{4-24}$). In some embodiments, the other end of the alkyl chain is attached to a linker or to another portion of the probe (e.g., PRG, bioactive agent, central connecting group, etc.). In some embodiments, the capture ligand (e.g., haloalkane) is attached to the other portions of the probe by a linker. A linker may comprise an alkyl chain or substituted alkyl chain (e.g., C=O, NH, S, O, carbamate, ethylene etc.).

In some embodiments, the bioactive agent is a small molecule or peptide. In some embodiments, a bioactive agent is any molecule that binds or potentially binds to a protein, cellular target, molecule of interest, etc. In some embodiments, a bioactive agent is a small molecule. In some embodiments, a bioactive agent is a peptide. In some embodiments, a bioactive agent is a drug or putative drug. In some embodiments, a suitable bioactive agent is derivatizable for attachment to the other components (e.g., PRG, HA) of the probes herein. In some embodiments, a suitable bioactive agent comprises a functional group for attachment to the other components (e.g., PRG, HA) of the probes herein. In some embodiments, the derivatized group or functional group on the bioactive agent that is used for attachment to the probe does not disturb that activity of the bioactive agent and/or binding of the bioactive agent to a protein, cellular target, molecule of interest, etc. In some embodiments, a bioactive agent comprises a reactive moiety or a reactive moiety is placed on the bioactive agent to produce a bioactive agent capable of being attached to a reactive probe reagent. In some embodiments, the bioactive agent comprises or is modified to comprise a reactive group selected from NH$_2$, NH, —C(O)OH, OC(O)O-phenyl, C(O)O-phenyl, OH, C=O, aldehyde, difluorosulfinate, sulfonyl fluoride, sulfonyl chloride, and halogen. In some embodiments, such reactive groups are suitable for reaction with one or more reactive groups displayed on the reactive probe reagent. In some embodiments, active groups displayed on the reactive probe reagent is selected from —(CH$_2$)$_{0-2}$NH$_2$, —(CH$_2$)$_{0-2}$C(O)OH, (CH$_2$)$_{0-2}$OC(O)O-phenyl, (CH$_2$)$_{0-2}$C(O)O-phenyl, (CH$_2$)$_{0-2}$OH, (CH$_2$)$_{0-2}$C=O, (CH$_2$)$_{0-2}$Cl, and (CH$_2$)$_{0-2}$Br.

In some embodiments, the PRG is selected from any of the PRGs described herein and/or understood in the field. In some embodiments, the PRG is a photoreactive group such as an aryl azide, alkylaryl azide (e.g., methylaryl azide), substituted aryl azide, or substituted alkylaryl azide (e.g., substituted methylaryl azide) moiety. In some embodiments, the PRG is an aryl azide, alkylaryl azide (e.g., methylaryl azide), substituted aryl azide, or substituted alkylaryl azide (e.g., substituted methylaryl azide) moiety. In some embodiments, the PRG comprises the structure:

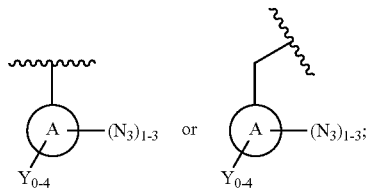

wherein A is an aromatic hydrocarbon ring (e.g., 6-member ring), aromatic heterocyclic ring (e.g., 5- or 6-member ring), an aromatic ring system, or a heteroaromatic ring system; wherein $N_3$ group(s) are present at any suitable position on the A ring; and wherein any Y groups, when present on the A ring, are independently selected from a halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, and CN. In some embodiments, A is selected from furan, benzofuran, isobenzofuran, pyrrole, indole, isoindole, thiophene, benzothiophene, benzo[c]thiophene, imidazole, benzimidazole, purine, pyrazole, indazole, oxazole, benzooxazole, isoxazole, benzisoxazole, thiazole, benzothiazole, benzene, naphthalene, pyridine, quinolone, isoquinoline, pyrazine, quinoxaline, pyrimidine, quinazoline, pyridazine, cinnoline, phthalazine, thalidomide, triazine (e.g., 1,2,3-triazine; 1,2,4-triazine; 1,3,5 triazine), and thiadiazole. In some embodiments, the PRG is a substituted phenyl or benzyl azide. In some embodiments, the PRG is a substituted phenyl or benzyl azide such as:

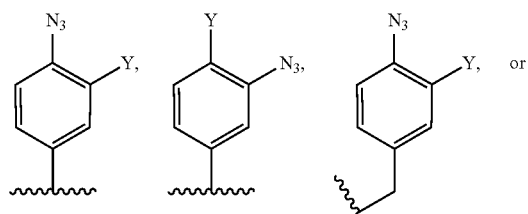

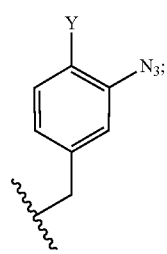

wherein Y is selected from a halogen (e.g., Cl, F, Br, I), $CH_3$, OH, SH, $NH_2$, CN, $CF_3$, $CCl_3$, —$CH_2$—$CH_3$, —$CH_2$—OH, —$CH_2NH_2$, $CH_3SH$, $CH_2Cl$, $CH_2Br$, $CH_2F$, $CHF_2$, $CH_2CN$, $CH_2CF_3$, $CH_2Cl_3$, $CH(CH_3)_2$, $(CH_2)_2CH_3$, and CN. In some embodiments, the A ring is a fused ring system such as:

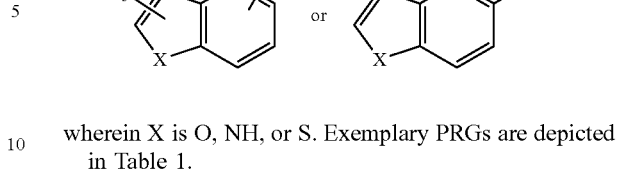

wherein X is O, NH, or S. Exemplary PRGs are depicted in Table 1.

TABLE 1

Exemplary photoreactive groups (PRGs)

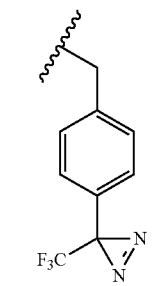

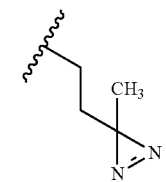 [SMILES: *CCC1(C)N=N1]

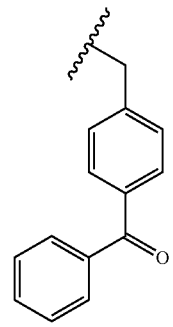 [SMILES: *Cc1ccc(C(=O)c2ccccc2)cc1]

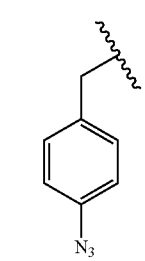 [SMILES: *Cc1ccc(N=[N+]=[N-])cc1]

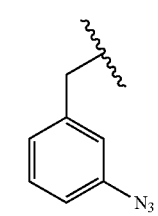

TABLE 1-continued
Exemplary photoreactive groups (PRGs)
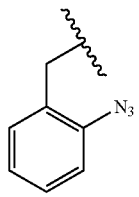 [SMILES: *Cc1ccccc1N=[N+]=[N-]]
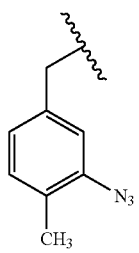
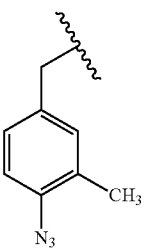 [SMILES: *Cc1ccc(N=[N+]=[N-])c(C)c1]
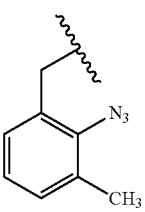 [SMILES: *Cc1cccc(C)c1N=[N+]=[N-]]
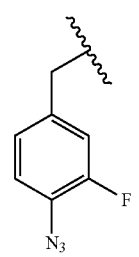 [SMILES: *Cc1ccc(N=[N+]=[N-])c(F)c1]
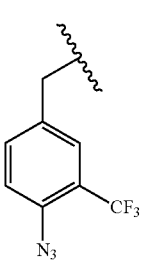
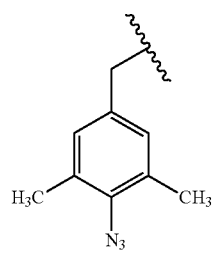
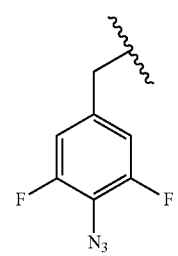 [SMILES: *Cc1cc(F)c(N=[N+]=[N-])c(F)c1]
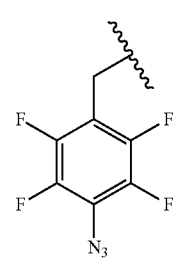
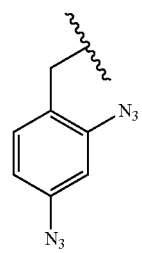 [SMILES: *Cc1ccc(N=[N+]=[N-])cc1N=[N+]=[N-]]
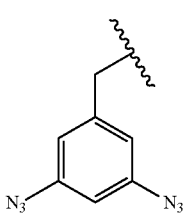 [SMILES: *Cc1cc(N=[N+]=[N-])cc(N=[N+]=[N-])c1]
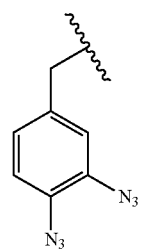 [SMILES: *Cc1ccc(N=[N+]=[N-])c(N=[N+]=[N-])c1]

TABLE 1-continued

Exemplary photoreactive groups (PRGs)

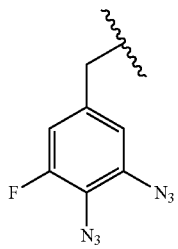

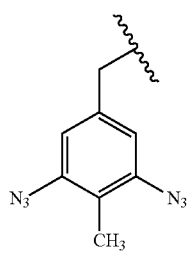 [SMILES: *Cc1cc(N=[N+]=[N-])c(C)c(N=[N+]=[N-])c1]

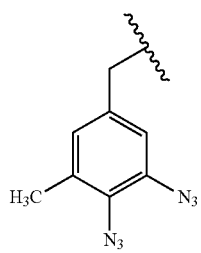 [SMILES: *Cc1cc(C)c(N=[N+]=[N-])c(N=[N+]=[N-])c1]

Figure 34A:
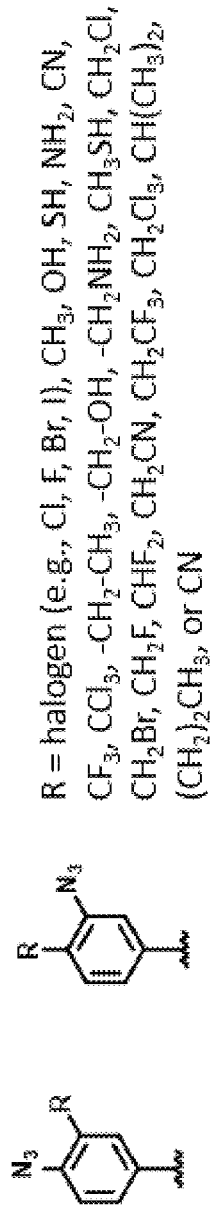
FIG. 34A-B. Exemplary PRGs and A-ring structures.
Figure 34A:
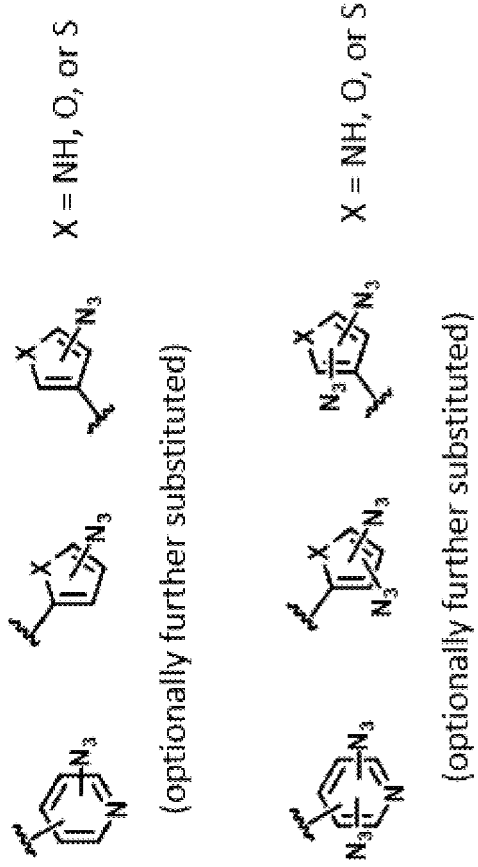
Figure 34B:
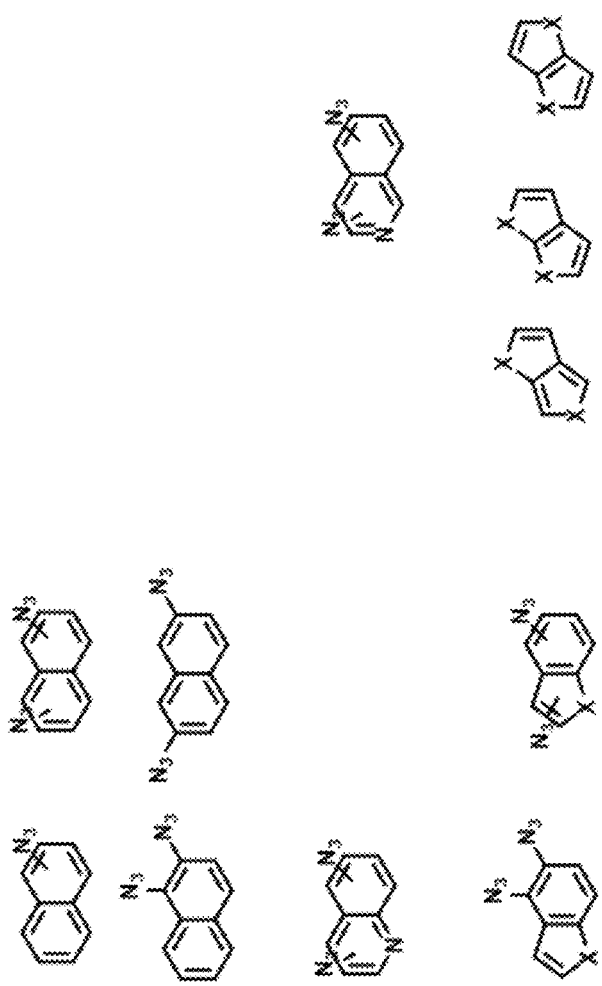

Other exemplary PRGs and A-ring structures are depicted in FIG. 34.

In some embodiments, other photoreactive groups find use at the PRG portion of the probes herein. Suitable PRGs include phenylazides, phenyldiazirines, and benzophenones, where the reactive intermediates formed upon irradiation with specific wavelengths of light are anitrene, acarbene and adiradical, respectively. In some embodiments, the PRG is stable (e.g. non-reactive) in visible light. In some embodiments, the activation energy of the PRG is greater than the absorption wavelength of proteins. Proteins absorb UV light at 280 and 200 nm, where absorbance at 280 nm is due to the aromatic amino acids, tryptophan, tyrosine, and phenylalanine, while peptide bonds are responsible for absorbance at 200 nm. Excess absorption of UV light by proteins leads to the formation of an electronically excited state molecule, which is then capable of undergoing degradative chemical transformations. In some embodiments, a PRG or photoreactive group comprises a diazo group, diazocarbonyl, enone, sulfur radical, halogenated substrate, nitrobenzene, diazonium salt, alkyl derivatives of azides and diazirines, etc. Fleming has comprehensively reviewed the variety of different chemical reagents used in photoaffinity labeling (See, Fleming SA. Chemical reagents in photoaffinity labelling. Tetrahedron. 1995; 51:12479-12520; herein incorporated by reference in its entirety). Sakurai et al. recently reported a study comparing the main photoreactive groups and assessing their reactivity (See Sakurai et al. Comparison of the reactivity of carbohydrate photoaffinity probes with different photoreactive groups. Chem. Bio. Chem. 2014; 15:1399-1403; herein incorporated by reference in its entirety).

In some embodiments, the PRG is covalently connected to the rest of the compound by a PRG linker moiety. In some embodiments, the PRG linker moiety is $(CH_2)_{0-4}$.

B. PRG/Fluorophore Probes

In some embodiments, provided herein are probes comprising a bioactive agent, a photoreactive group (PRG), and a fluorophore; reagents and methods for assembling such probes (e.g., for labeling a bioactive agent (e.g., a reactively-derivatized bioactive agent) with a PRG and fluorophore; methods of using such probes to tag target molecules (e.g., cellular protein targets) in a sample (e.g., complex sample (e.g., cell, cell lysate, etc.)); and compositions (e.g., PRG/fluorophore probes, fusions of cellular targets and bioluminescent reporters, etc.) for determining the target crosslinking efficiency of the probes herein. In some embodiments, provided herein are systems that allow for attachment of a PRG and fluorophore to any bioactive agent (e.g., small molecule, peptide, etc.) upon generating a reactively-derivatized version of the bioactive agent.

In some embodiments, provided therein are compositions comprising a PRG/fluorophore probe comprising: a bioactive agent, a photoreactive group (PRG), and a fluorophore covalently connected in a single compound of the general structure:

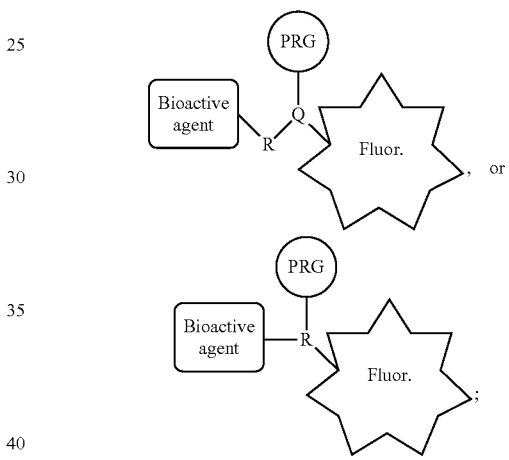

wherein R is a covalent linkage, and wherein Q is CH or N.

In some embodiments, R is a covalent linkage resulting from the reaction of two reactive moieties (R' and R"). In some embodiments, R comprises —NH—, —C(O)NH—, —OC(O)NH—, N, C(O)N, OC(O)N, or —O—. In some embodiments, R comprises —$(CH_2)_{0-2}NH(CH_2)_{0-2}$—, —$(CH_2)_{0-2}C(O)NH(CH_2)_{0-2}$—, —$(CH_2)_{0-2}OC(O)NH(CH_2)_{0-2}$—, —$(CH_2)_{0-2}N(CH_2)_{0-2}$—, —$(CH_2)_{0-2}C(O)N(CH_2)_{0-2}$—, —$(CH_2)_{0-2}OC(O)N(CH_2)_{0-2}$—, or —$(CH_2)_{0-2}O(CH_2)_{0-2}$—.

In some embodiments, the general structure of a PRG/fluorophore probe is:

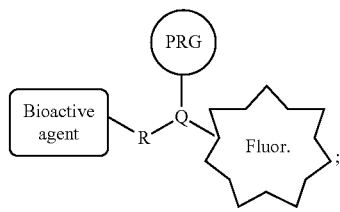

Q comprises CH or N; and R comprises —NH—, —C(O)NH—, —OC(O)NH—, —O—, —$(CH_2)_{0-2}NH(CH_2)_{0-2}$—, —(CH$_2$)$_{0-2}$C(O)NH(CH$_2$)$_{0-2}$—, —(CH$_2$)$_{0-2}$OC(O)NH (CH$_2$)$_{0-2}$—, or —(CH$_2$)$_{0-2}$(CH$_2$)$_{0-2}$—. In other embodiments, the general structure of a PRG/fluorophore probe is:

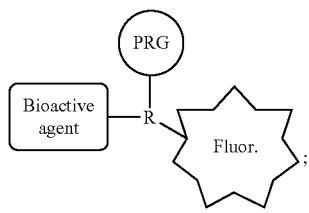

and R is N, C(O)N, OC(O)N, (CH$_2$)$_{0-2}$N(CH$_2$)$_{0-2}$—, —(CH$_2$)$_{0-2}$C(O)N(CH$_2$)$_{0-2}$—, or —(CH$_2$)$_{0-2}$OC(O)N(CH$_2$)$_{0-2}$—.

In some embodiments, the bioactive agent is a small molecule or peptide. In some embodiments, as with the PRG/HA probes above, a suitable bioactive agent for use in a PRG/fluorophore probe is any molecule that binds or potentially binds to a protein, cellular target, molecule of interest, etc. In some embodiments, a bioactive agent is a small molecule. In some embodiments, a bioactive agent is a peptide. In some embodiments, a bioactive agent is a drug or putative drug. In some embodiments, a suitable bioactive agent is derivatizable for attachment to the other components (e.g., PRG, fluorophore) of the probes herein. In some embodiments, a suitable bioactive agent comprises a functional group for attachment to the other components (e.g., PRG, fluorophore) of the probes herein. In some embodiments, the derivatized group or functional group on the bioactive agent that is used for attachment to the probe does not disturb that activity of the bioactive agent and/or binding of the bioactive agent to a protein, cellular target, molecule of interest, etc. In some embodiments, a bioactive agent comprises a reactive moiety or a reactive moiety is placed on the bioactive agent to produce a bioactive agent capable of being attached to a reactive probe reagent. In some embodiments, the bioactive agent comprises or is modified to comprise a reactive group selected from NH$_2$, NH, —C(O) OH, OC(O)O-phenyl, C(O)O-phenyl, OH, C=O, aldehyde, difluorosulfinate, sulfonyl fluoride, sulfonyl chloride, and halogen. In some embodiments, such reactive groups are suitable for reaction with one or more reactive groups displayed on the reactive probe reagent. In some embodiments, an active groups displayed on the reactive probe reagent is selected from —(CH$_2$)$_{0-2}$NH$_2$, —(CH$_2$)$_{0-2}$C(O) OH, (CH$_2$)$_{0-2}$OC(O)O-phenyl, (CH$_2$)$_{0-2}$C(O)O-phenyl, (CH$_2$)$_{0-2}$H, (CH$_2$)$_{0-2}$C=O, (CH$_2$)$_{0-2}$Cl, and (CH$_2$)$_{0-2}$Br.

In some embodiments, the PRG is selected from any of the PRGs described herein (e.g., suitable aryl azides, alkylaryl azides (e.g., methylaryl azide), substituted aryl azides, or substituted alkylaryl azides (e.g., substituted methylaryl azide)) and/or understood in the field. Exemplary PRGs are depicted in Table 1 (above). In some embodiments, other photoaffinity labels and photoreactive groups find use at the PRG portion of the probes herein (e.g., those described above and elsewhere herein). For example, suitable PRGs include phenylazides, phenyldiazirines, and benzophenones, where the reactive intermediates formed on irradiation with specific wavelengths of light are a nitrene, a carbene and a diradical, respectively. In some embodiments, the PRG or photoreactive group is stable (e.g. non-reactive) in visible light. In some embodiments, the activation energy of the PRG or photoreactive group is greater than the absorption wavelength of proteins. Proteins absorb UV light at 280 and 200 nm, where absorbance at 280 nm is due to the aromatic amino acids, tryptophan, tyrosine, and phenylalanine, while peptide bonds are responsible for absorbance at 200 nm. Excess absorption of UV light by proteins leads to the formation of an electronically excited state molecule, which is then capable of undergoing degradative chemical transformations. In some embodiments, a PRG or photoreactive group comprises a diazo group, diazocarbonyl, enone, sulfur radical, halogenated substrate, nitrobenzens, diazonium salt, alkyl derivatives of azides and diazirines, etc. Fleming has comprehensively reviewed the variety of different chemical reagents used in photoaffinity labeling (See, Fleming SA. Chemical reagents in photoaffinity labelling. Tetrahedron. 1995; 51:12479-12250; herein incorporated by reference in its entirety). Sakurai et al. recently reported a study comparing the main photoreactive groups and assessing their reactivity (See Sakurai et al. Comparison of the reactivity of carbohydrate photoaffinity probes with different photoreactive groups. Chem. Bio. Chem. 2014; 15:1399-1403; herein incorporated by reference in its entirety).

In some embodiments, the PRG is covalently connected to the rest of the compound by a PRG linker moiety. In some embodiments, the PRG linker moiety is (CH$_2$)$_{0-4}$.

In some embodiments, the fluorophore is selected from any suitable fluorophores (e.g., small molecule fluorescent dyes) understood in the field. Suitable fluorophores include, but are not limited to, xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA Fluors (Invitrogen), DYLIGHT Fluors (Thermo Scientific, Pierce), ATTO and TRACY dyes (Sigma Aldrich), FluoProbes (Interchim), DY and MEGASTOKES dyes (Dyomics), SULFO CY dyes (CYANDYE, LLC), SETAU AND SQUARE dyes (SETA BioMedicals), QUASAR and CAL FLUOR dyes (Biosearch Technologies), SURELIGHT dyes (APC, RPE, PerCP, Phycobilisomes)(Columbia Biosciences), APC, APCXL, RPE, and BPE dyes (Phyco-Biotech), etc. In some embodiments, a fluorophore herein is a rhodamine analog (e.g., carboxy rhodamine analog) such as those described in U.S. patent application Ser. No. 13/682, 589, herein incorporated by reference in its entirety. In some embodiments, a suitable fluorophore is selected based on its physical properties such as size, emission spectrum, excitation spectrum, solubility, cell permeability, etc.

In some embodiments, the fluorophore is covalently connected to the rest of the compound by a fluorophore linker moiety. In some embodiments, the fluorophore linker moiety is (CH$_2$)$_{0-4}$. In some embodiments, the fluorophore linker moiety comprises a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O) OCH$_2$CH=CHCH$_2$OC(O)—. In some embodiments, the cleavable linker comprises the cleavable moiety flanked on one or both sides by alkylene or heteroalkylene chains. In some embodiments, the alkylene or heteroalkylene chains comprise any suitable combination of $C_{1-6}$-alkylene, —O—, —(CH$_2$)$_2$O—, and —OC(O)NH— groups.

In some embodiments, linkers herein (e.g., the linkers of the probes herein (e.g., linking fluorophore to Q/R groups) comprise any suitable moieties to yield the desired structure/function (e.g., length, flexibility/rigidity, solubility, cell permeability, etc.). The probes herein are not limited to any particular linker moieties. Indeed, a variety of linker moieties are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), an oligonucleotide linker, phospholipid derivatives, alkenyl chains, alkynyl chains, disulfide, or a combination thereof. In some embodiments, a linker comprises any combination of alkyl, alkenyl, alkynyl, amide, phenyl, benzyl, carbamate, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention. In some embodiments, a linker comprises a cleavable moiety and one or more of the aforementioned functional groups/moieties.

II. Reagents

Figure 5A:
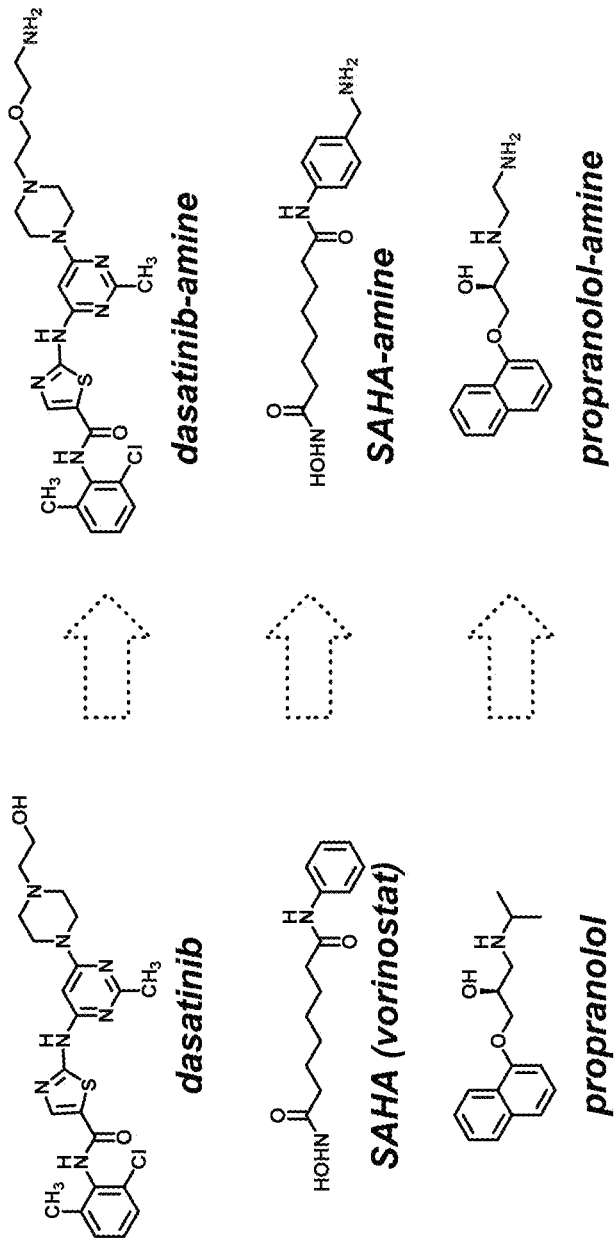
FIGS. 5A-B. Schematics depicting (A) the exemplary derivatizable bioactive agents from of parent bioactive agents, and (B) reaction of the derivatizable bioactive agents with PRG/fluorophore reagents to yield a PRG/fluorophore probes.
Figure 5B:
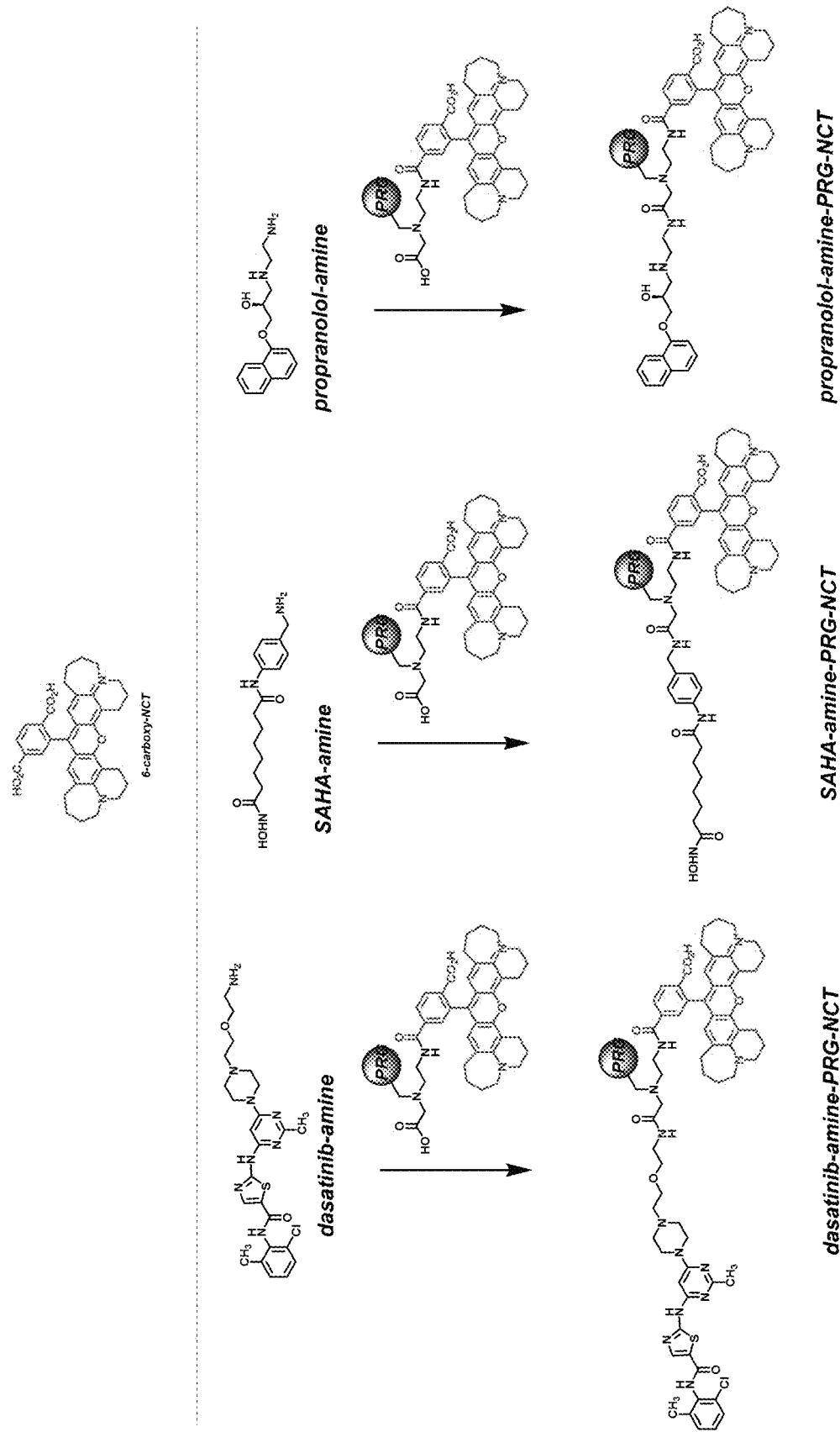

A key aspect of the platforms described herein is the preparation of bioactive agents capable of covalently interacting with the other reagent(s) to form the probe. In some embodiments, a bioactive agent comprises a reactive group suitable for reaction with the other reagent(s). However, in other embodiments, a reactive derivative of the bioactive agent is generated using the methods and regents described herein. The reactive derivative displays a first reactive group (e.g., R") capable of reacting with a second reactive group (R') displayed on the other reagent(s) (e.g., a linked PRG and capture moiety, a linked PRG and fluorophore, etc.) to form a covalent linkage (e.g., R). A variety of reactive group pairings have been contemplated and tested for attachment to bioactive agents and formation of multi-modal probes within the scope described herein. For example, FIG. 5A depicts the addition of reactive amine groups onto several known drugs to form reactive derivatives of the parent bioactive agents. FIG. 5B depicts the reaction of the reactive derivatives with PRG/fluorophore reagents displaying a complementary reactive group (e.g., COOH) to for PRG/fluorophore probes with the bioactive agents.

Figure 6A:
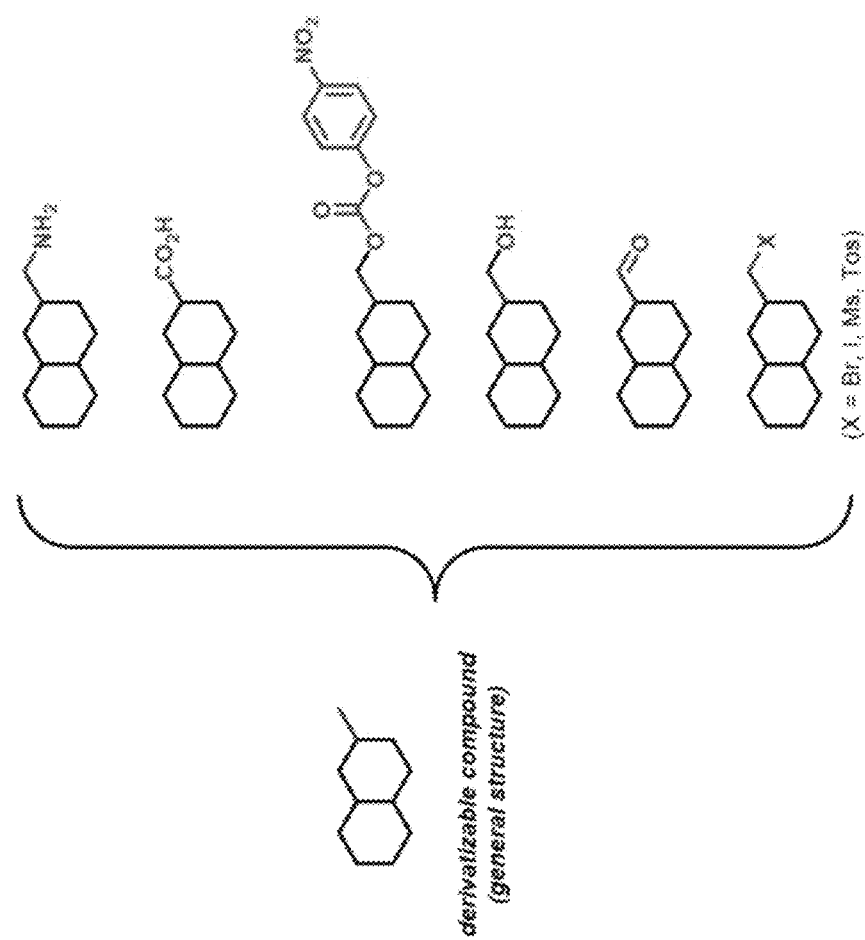
FIG. 6A-B. Schematic representations of (A) an exemplary derivatizable bioactive agent displaying various suitable reactive groups, and (B) an exemplary PRG/chloroalkane reagent displaying various complementary reactive groups.
Figure 7:
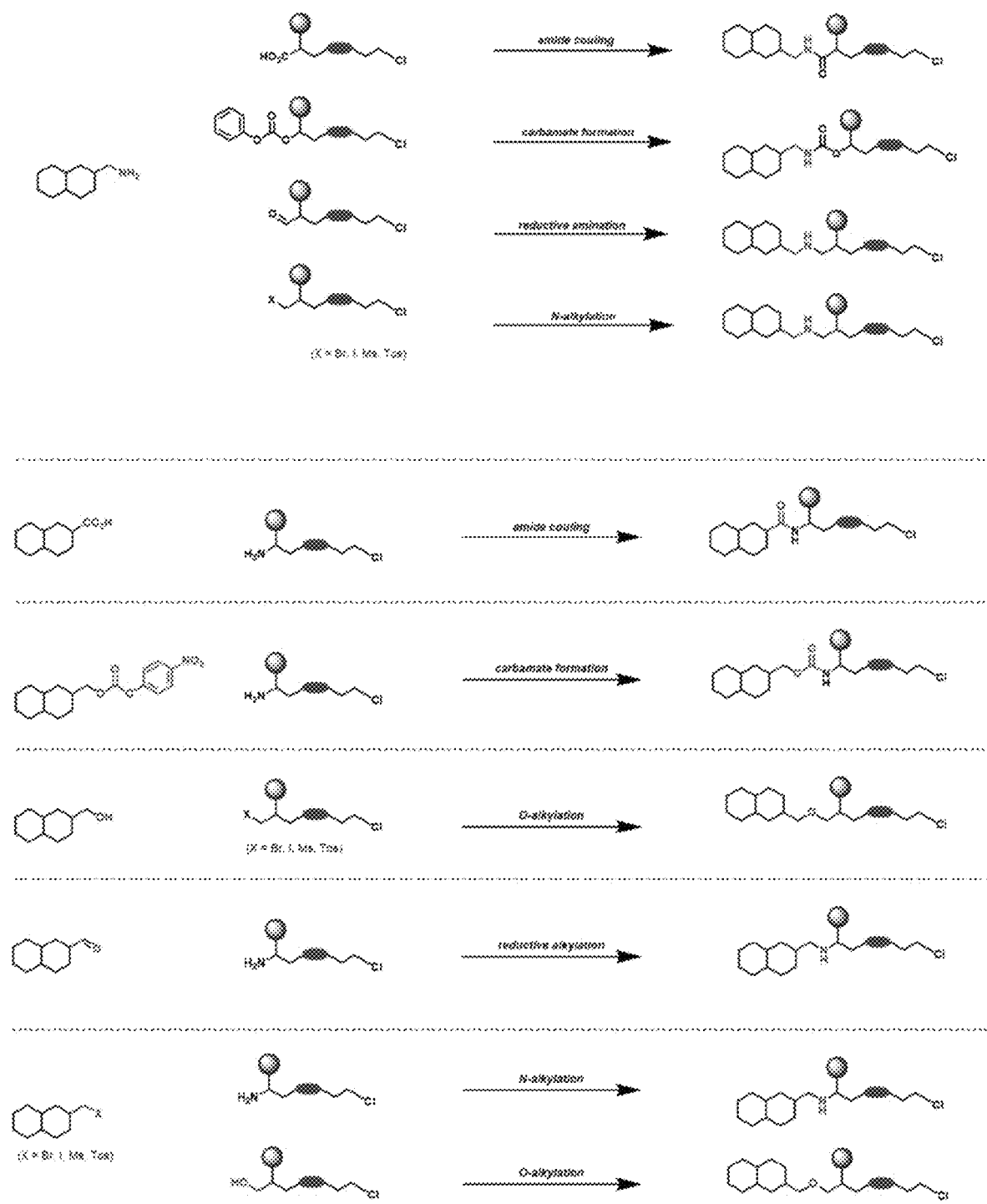
FIG. 7. Schematics depicting attachment of generic derivatizable bioactive agent to a PRG/CA reagent to form PRG/CA probes.
Figure 8:
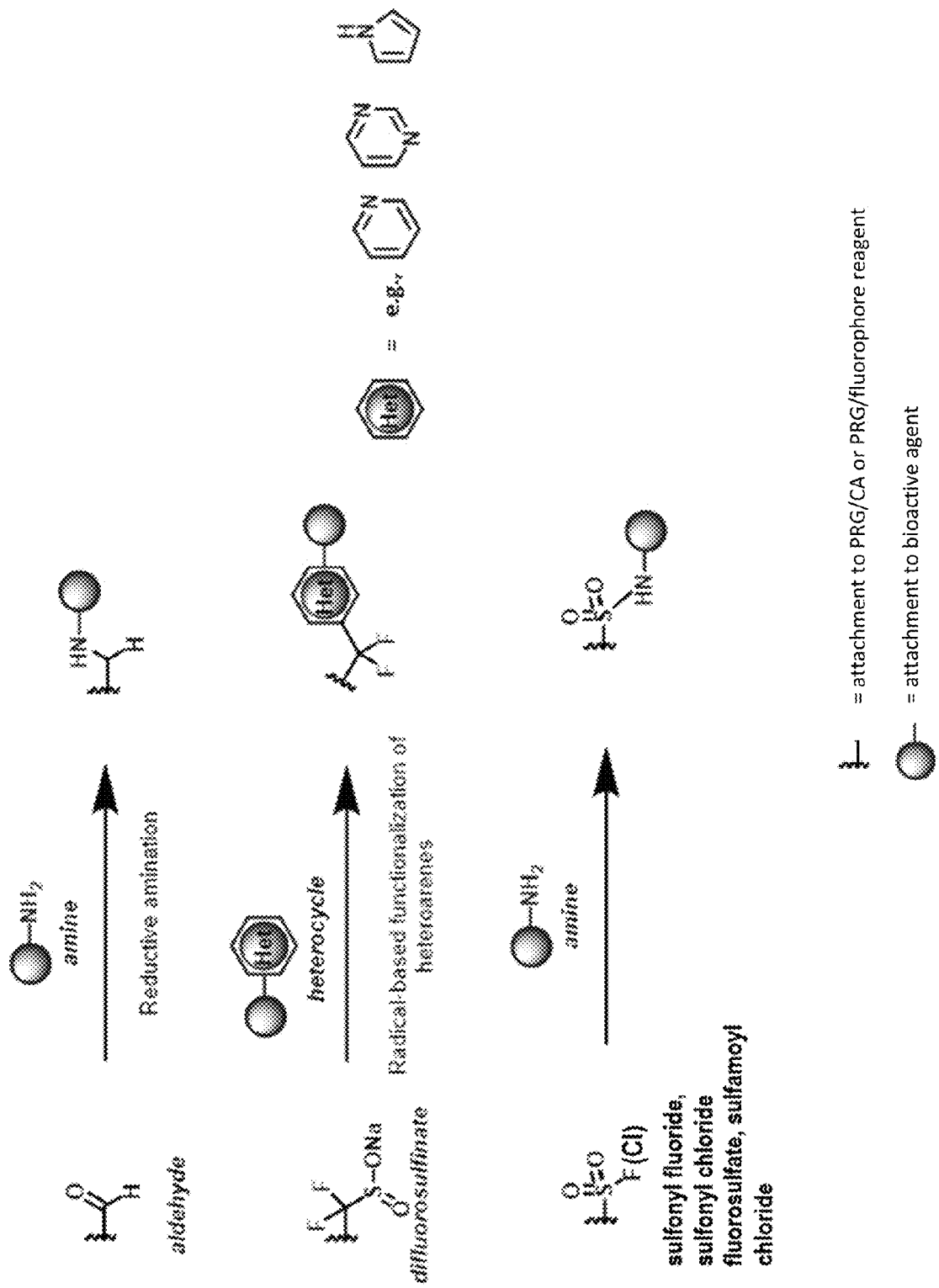
FIG. 8. Schematic depicting attachment of generic derivatizable bioactive agent to a PRG/HA or PRG/fluorophore reagent to form PRG/HA or PRG/fluorophore probes.

Suitable reactive groups for attachment to a parent bioactive agent to yield a derivatizable bioactive agent include NH$_2$, NH, —C(O)OH, OC(O)O-phenyl, C(O)O-phenyl, OH, C=O, aldehyde, difluorosulfinate, sulfonyl fluoride, sulfonyl chloride, and halogens. An example of a generic compound that has been modified to display a variety of potential reactive groups is depicted in FIG. 6A. For example, an NH$_2$ reactive group on a bioactive agent is reacted with a PRG/CA (or PRG/fluorophore reagent) displaying a carboxylate group to produce an amide coupling; a COOH reactive group on a bioactive agent is reacted with a PRG/CA (or PRG/fluorophore reagent) displaying an amine to produce an amide coupling; a OC(O)O-phenyl reactive group on a bioactive agent is reacted with a PRG/CA (or PRG/fluorophore reagent) displaying an amine to produce a carbamate coupling; an OH reactive group on a bioactive agent is reacted with a PRG/CA (or PRG/fluorophore reagent) displaying an alkylating agent via alkylation; an aldehyde reactive group on a bioactive agent is reacted with a PRG/CA (or PRG/fluorophore reagent) displaying an amine via reductive amination; a halogen reactive group on a bioactive agent is reacted with a PRG/CA (or PRG/fluorophore reagent) displaying an amine via alkylation; etc. Examples of the attachment of a generic drug-like bioactive agent to PRG/HA reagents via complementary reactive pairs is depicted in FIG. 7. Other examples of the attachment of a bioactive agent to PRG/HA or PRG/fluorophore reagents via complementary reactive pairs is depicted in FIG. 8. In some embodiments, any of the reactive groups depicted and/or described herein as being positioned on a bioactive agent may also find use as a reactive group on a PRG/HA or PRG/fluorophore reagent. Likewise, any of the reactive groups depicted and/or described herein as being positioned on a PRG/HA or PRG/fluorophore reagent may also find use as a reactive group on a bioactive agent.

Figure 6B:
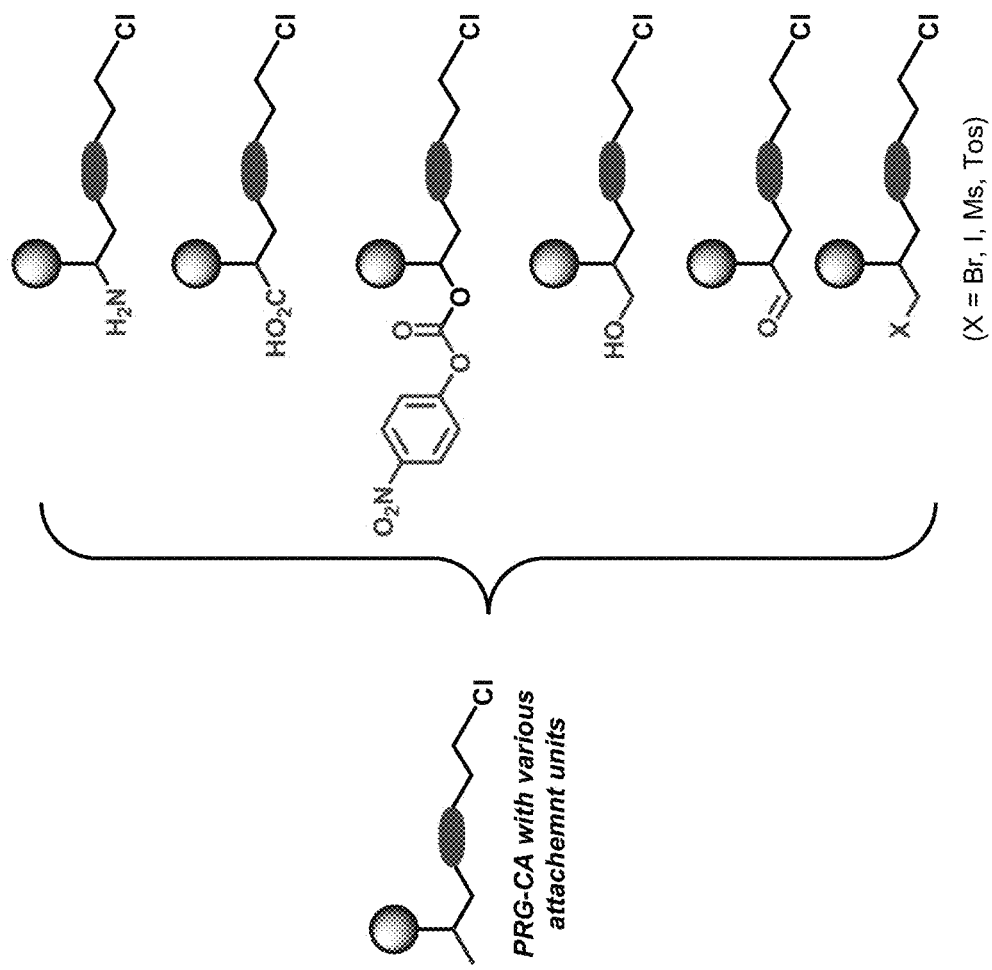

Any bioactive agent displaying one of the reactive groups described herein, capable of being modified to display one of the reactive groups described herein, displaying another suitable reactive group, and/or capable of being modified to display a suitable reactive group will find use in embodiments herein. Examples of PRG/chloroalkane reagents suitable for reaction with a complementary derivatizable bioactive agent are depicted in FIG. 6B. Each of the potential reactive groups on the PRG/CA reagent may be reacted with a commentary reactive group on a bioactive agent (See, e.g., FIG. 7).

A key aspect of the platforms described herein are reagents comprising a PRG linked to either a capture ligand (e.g., HA, CA, etc.) or fluorophore and displaying a reactive moiety capable of covalently interacting with a complementary reactive moiety on a bioactive agent to form the probe. In some embodiments, PRG/HA or PRG/fluorophore reagents displaying a suitable reactive moiety are reacted with bioactive agents displaying a complementary reactive moiety to produce a PRG/HA or PRG/fluorophore probe. In some embodiments, PRG/HA or PRG/fluorophore reagents reactive derivative displays a first reactive group (e.g., R') capable of reacting with a second reactive group (R") displayed on the bioactive agent to form a covalent linkage (e.g., R). A variety of reactive group pairings have been contemplated and tested for attachment to bioactive agents and formation of multi-modal probes within the scope described herein. Examples of suitable reactive moieties for PRG/HA or PRG/fluorophore reagents are selected from NH$_2$, NH, —C(O)OH, OC(O)O— phenyl, C(O)O-phenyl, OH, C=O, aldehyde, difluorosulfinate, sulfonyl fluoride, sulfonyl chloride, and halogen. In other embodiments, suitable reactive moieties for PRG/HA or PRG/fluorophore reagents are selected from —(CH$_2$)$_{0-2}$NH$_2$, —(CH$_2$)$_{0-2}$C(O) OH, (CH$_2$)$_{0-2}$OC(O)O-phenyl, (CH$_2$)$_{0-2}$C(O)O-phenyl, (CH$_2$)$_{0-2}$H, (CH$_2$)$_{0-2}$C=O, (CH$_2$)$_{0-2}$Cl, or (CH$_2$)$_{0-2}$Br. Complementary reactive moieties are selected for the PRG/

HA reagent or PRG/fluorophore reagent and the bioactive agent to allow reaction to form a probe.

In some embodiments, a bioactive agent is modified by a user to display a reactive moiety. In some embodiments, a PRG/HA or PRG/fluorophore reagent displaying a complementary reactive moiety is synthesized by the user or obtained commercially. In some embodiments, a user reacts the reactively-modified bioactive agent with the PRG/HA or PRG/fluorophore reagent to yield the PRG/HA or PRG/fluorophore probe. The assembled probe is then ready for use in a variety of assays and applications described herein.

A. PRG/HA Reagents

In some embodiments, provided herein are reagents comprising a photoreactive group (PRG) and a capture ligand (e.g., haloalkane) for reaction with a bioactive agent for assembling the PRG/HA probes described herein. In some embodiments, the PRG/HA reagents comprise a linker moiety.

In some embodiments, provided herein are compositions comprising a reactive PRG/HA reagent comprising: a photoreactive group (PRG), a linker, and a capture ligand (e.g., haloalkane) covalently connected in a single compound of the general structure:

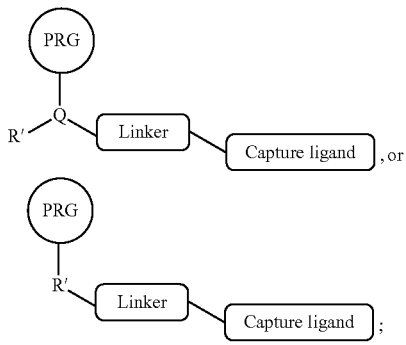

wherein R' is a first reactive moiety capable for forming a covalent bond upon reaction with a second reactive moiety (R"), wherein -A-X is a substrate for a dehalogenase, and wherein Q is CH or N.

In some embodiments, R' comprises —NH$_2$, NH, —C(O)OH, OC(O)O-phenyl, C(O)O— phenyl, OH, C=O, aldehyde, difluorosulfinate, sulfonyl fluoride, sulfonyl chloride, or halogen. In some embodiments, R' comprises —(CH$_2$)$_{0-2}$NH$_2$, —(CH$_2$)$_{0-2}$C(O)OH, (CH$_2$)$_{0-2}$OC(O)O-phenyl, (CH$_2$)$_{0-2}$C(O)O-phenyl, (CH$_2$)$_{0-2}$OH, (CH$_2$)$_{0-2}$C=O, (CH$_2$)$_{0-2}$Cl, or (CH$_2$)$_{0-2}$Br.

In some embodiments, the PRG/HA reagent has the general structure:

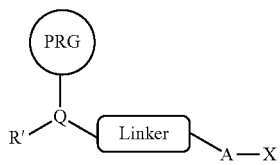

wherein R' comprises —NH$_2$, —C(O)OH, OC(O)O-phenyl, C(O)O-phenyl, OH, aldehyde, difluorosulfinate, sulfonyl fluoride, sulfonyl chloride, or a halogen. In other embodiments, the PRG/HA reagent has the general structure:

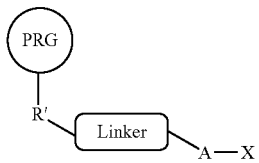

wherein R' comprises NH or C=O.

In some embodiments, the linker is a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O)OCH$_2$CH=CHCH$_2$OC(O)—. In some embodiments, the cleavable linker comprises the cleavable moiety flanked on one or both sides by alkylene or heteroalkylene chains. In some embodiments, the alkylene or heteroalkylene chains comprise any suitable combination of C$_1$-6-alkylene, —O—, —(CH$_2$)$_2$O—, and —OC(O)NH— groups.

In some embodiments, linkers herein (e.g., the linkers of the probes herein (e.g., linking capture ligand to Q/R' groups) comprise any suitable moieties to yield the desired structure/function (e.g., length, flexibility/rigidity, solubility, cell permeability, etc.). The probes herein are not limited to any particular linker moieties. Indeed, a variety of linker moieties are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), an oligonucleotide linker, phospholipid derivatives, alkenyl chains, alkynyl chains, disulfide, or a combination thereof. In some embodiments, a linker comprises any combination of alkyl, alkenyl, alkynyl, amide, phenyl, benzyl, carbamate, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention. In some embodiments, a linker comprises a cleavable moiety and one or more of the aforementioned functional groups/moieties.

In some embodiments, the PRG is selected from any of the PRGs described herein and/or understood in the field (e.g., aryl azides, alkylaryl azides (e.g., methylaryl azide), substituted aryl azides, or substituted alkylaryl azides (e.g., substituted methylaryl azide)). Exemplary PRGs are depicted in Table 1 (above). In some embodiments, other photoreactive groups find use at the PRG portion of the probes herein (e.g., those described above and elsewhere herein). For example, suitable photoreactive groups include phenylazides, phenyldiazirines, and benzophenones, where the reactive intermediates formed on irradiation with specific wavelengths of light are a nitrene, a carbene and a diradical, respectively. In some embodiments, the PRG or photoreactive group is stable (e.g. non-reactive) in visible light. In some embodiments, the activation energy of the PRG or photoreactive group is greater than the absorption wavelength of proteins. Proteins absorb UV light at 280 and 200 nm, where absorbance at 280 nm is due to the aromatic amino acids, tryptophan, tyrosine, and phenylalanine, while peptide bonds are responsible for absorbance at 200 nm. Excess absorption of UV light by proteins leads to the formation of an electronically excited state molecule, which is then capable of undergoing degradative chemical transformations. In some embodiments, a PRG or photoaffinity group comprises a diazo group, diazocarbonyl, enone, sulfur radical, halogenated substrate, nitrobenzene, diazonium salt, alkyl derivatives of azides and diazirines, etc. Fleming has comprehensively reviewed the variety of different chemical reagents used in photoaffinity labeling (See, Fleming SA. Chemical reagents in photoaffinity labelling. Tetrahedron. 1995; 51:12479-12250; herein incorporated by reference in its entirety). Sakurai et al. recently reported a study comparing the main photoreactive groups and assessing their reactivity (See Sakurai et al. Comparison of the reactivity of carbohydrate photoaffinity probes with different photoreactive groups. Chem. Bio. Chem. 2014; 15:1399-1403; herein incorporated by reference in its entirety).

In some embodiments, the PRG is covalently connected to the rest of the compound by a PRG linker moiety. In some embodiments, the PRG linker moiety is $(CH_2)_{0-4}$.

In some embodiments, the capture ligand is a haloalkane (e.g., chloroalkane). In some embodiments, the capture ligand is -A-X, wherein A is $(CH_2)_n$ and n=4-10, wherein X is a halogen. In some embodiments, X is Cl. In some embodiments, -A-X is $—(CH_2)_6Cl$.

In some embodiments, provided herein are systems, kits, and reaction mixtures comprising: (i) a PRG/HA reagent described herein, and (ii) a bioactive agent displaying the second reactive moiety R". In some embodiments, the bioactive agent is a small molecule or peptide. In some embodiments, the bioactive agent comprises a drug or natural compound modified to display the R". In some embodiments, R" comprises $—NH_2$, $—OC(O)O—$ nitrophenyl, $—OH$, $—C=O$, -aldehyde, -difluorosulfinate, -sulfonyl fluoride, sulfonyl chloride or -halogen. In some embodiments, R" comprises $—(CH_2)_{0-2}NH_2$, $—(CH_2)_{0-2}OC(O)O$-nitrophenyl, $—(CH_2)_{0-2}OH$, $—(CH_2)_{0-2}C=O$, $—(CH_2)_{0-2}Cl$, or $—(CH_2)_{0-2}Br$.

In some embodiments, provided herein are methods of generating a PRG/HA probe comprising contacting (i) a PRG/HA reagent described herein with (ii) a bioactive agent the second reactive moiety R". In some embodiments, provided herein are PRG/HA probes produced by the methods described herein.

B. PRG/Fluorophore Reagents

In some embodiments, provided herein are reagents comprising a photoreactive group (PRG) and a fluorophore for reaction with a bioactive agent for assembling the PRG/fluorophore probes described herein. In some embodiments, the PRG/fluorophore reagents comprise a linker moiety.

In some embodiments, provided herein are reactive PRG/fluorophore reagents comprising: a photoreactive group (PRG) and a fluorophore connected in a single compound of the general structure:

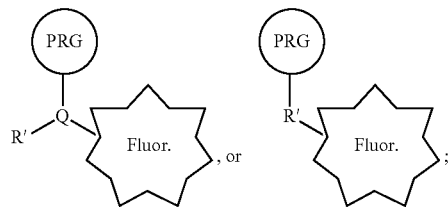

wherein R' is a first reactive moiety capable for forming a covalent bond upon reaction with a second reactive moiety (R"), and wherein Q is CH or N.

In some embodiments, R' comprises $—NH_2$, NH, $—C(O)OH$, $OC(O)O$-phenyl, $C(O)O—$ phenyl, OH, $C=O$, aldehyde, difluorosulfinate, sulfonyl fluoride, sulfonyl chloride or halogen. In some embodiments, R' comprises $—(CH_2)_{0-2}NH_2$, $—(CH_2)_{0-2}C(O)OH$, $(CH_2)_{0-2}OC(O)O$-phenyl, $(CH_2)_{0-2}C(O)O$-phenyl, $(CH_2)_{0-2}H$, $(CH_2)_{0-2}C=O$, $(CH_2)_{0-2}Cl$, or $(CH_2)_{0-2}Br$.

In some embodiments, the PRG/fluorophore reagent has the general structure:

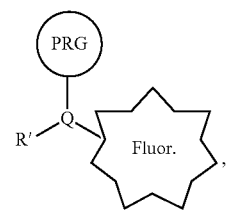

wherein R' comprises $—NH_2$, $—C(O)OH$, $OC(O)O$-phenyl, $C(O)O—$ phenyl, OH, aldehyde, difluorosulfinate, sulfonyl fluoride, sulfonyl chloride, or halogen. In other embodiments, the PRG/fluorophore reagent has the general structure:

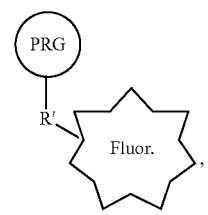

wherein R' comprises $—NH—$ or CO.

In some embodiments, the PRG is selected from any of the PRGs described herein and/or understood in the field (e.g., aryl azides, alkylaryl azides (e.g., methylaryl azide), substituted aryl azides, or substituted alkylaryl azides (e.g., substituted methylaryl azide)). Exemplary PRGs are depicted in Table 1 (above). In some embodiments, other photoreactive groups find use at the PRG portion of the probes herein (e.g., those described above and elsewhere herein). For example, suitable PRGs include phenylazides, phenyldiazirines, and benzophenones, where the reactive intermediates formed on irradiation with specific wavelengths of light are a nitrene, a carbene and a diradical, respectively. In some embodiments, the PRG or photoreactive group is stable (e.g. non-reactive) in visible light. In some embodiments, the activation energy of the PRG or photoreactive group is greater than the absorption wavelength of proteins. Proteins absorb UV light at 280 and 200 nm, where absorbance at 280 nm is due to the aromatic amino acids, tryptophan, tyrosine and phenylalanine, while peptide bonds are responsible for absorbance at 200 nm. Excess absorption of UV light by proteins leads to the formation of an electronically excited state molecule, which is then capable of undergoing degradative chemical transformations. In some embodiments, a PRG or photoaffinity group comprises a diazo group, diazocarbonyl, enone, sulfur radical, halogenated substrate, nitrobenzenes, diazonium salt, alkyl derivatives of azides, and diazirines, etc. Fleming has comprehensively reviewed the variety of different chemical reagents used in photoaffinity labeling (See, Fleming SA. Chemical reagents in photoaffinity labelling. Tetrahedron. 1995; 51:12479-12250; herein incorporated by reference in its entirety). Sakurai et al. recently reported a study comparing the main photoreactive groups and assessing their reactivity (See Sakurai et al. Comparison of the reactivity of carbohydrate photoaffinity probes with different photoreactive groups. Chem. Bio. Chem. 2014; 15:1399-1403; herein incorporated by reference in its entirety).

In some embodiments, the PRG is covalently connected to the rest of the compound by a PRG linker moiety. In some embodiments, the PRG linker moiety is $(CH_2)_{0-4}$.

In some embodiments, the fluorophore is selected from any suitable fluorophores (e.g., small molecule fluorescent dyes) understood in the field. Suitable fluorophores include, but are not limited to, xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA Fluor (Invitrogen), DYLIGHT Fluor (Thermo Scientific, Pierce), ATTO and TRACY dyes (Sigma Aldrich), FluoProbes (Interchim), DY and MEGASTOKES dyes (Dyomics), SULFO CY dyes (CYANDYE, LLC), SETAU AND SQUARE dyes (SETA BioMedicals), QUASAR and CAL FLUOR dyes (Biosearch Technologies), SURELIGHT dyes (APC, RPE, PerCP, Phycobilisomes)(Columbia Biosciences), APC, APCXL, RPE, and BPE dyes (Phyco-Biotech), etc. In some embodiments, a fluorophore herein is a rhodamine analog (e.g., carboxy rhodamine analog) such as those described in U.S. patent application Ser. No. 13/682, 589, herein incorporated by reference in its entirety. In some embodiments, a suitable fluorophore is selected based on its physical properties, such as size, emission spectrum, excitation spectrum, solubility, cell permeability, etc.

In some embodiments, the fluorophore is covalently connected to the rest of the compound by a fluorophore linker moiety. In some embodiments, the fluorophore linker moiety is $(CH_2)_{0-4}$. In some embodiments, the fluorophore linker moiety comprises a cleavable linker. In some embodiments, the cleavable linker is chemically cleavable, enzymatically cleavable, or photocleavable. In some embodiments, the cleavable linker comprises a cleavable moiety selected from the group consisting of a disulfide, tert-butyl carbamate, silyl ether, diazobenzene, 1,2-diol, and —C(O) $OCH_2CH=CHCH_2OC(O)$—. In some embodiments, the cleavable linker comprises the cleavable moiety flanked on one or both sides by alkylene or heteroalkylene chains. In some embodiments, the alkylene or heteroalkylene chains comprise any suitable combination of $C_{1-6}$-alkylene, —O—, —(CH_2)_2O—, and —OC(O)NH— groups.

In some embodiments, linkers herein (e.g., the linkers of the probes herein (e.g., linking capture ligand to Q/R' groups) comprise any suitable moieties to yield the desired structure/function (e.g., length, flexibility/rigidity, solubility, cell permeability, etc.). The probes herein are not limited to any particular linker moieties. Indeed, a variety of linker moieties are contemplated, and suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, a linker comprises any combination of alkyl, alkenyl, alkynyl, amide, phenyl, benzyl, carbamate, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention. In some embodiments, a linker comprises a cleavable moiety and one or more of the aforementioned functional groups/moieties.

In some embodiments, provided herein are systems, kits, and reaction mixtures comprising: (i) a reactive PRG/fluorophore reagent described herein and (ii) a bioactive agent displaying the second reactive moiety R". In some embodiments, the bioactive agent is a small molecule or peptide. In some embodiments, the bioactive agent comprises a drug or natural compound modified to display the R". In some embodiments, R" comprises —NH$_2$, —OC(O)O-nitrophenyl, —OH, —C=O, -aldehyde, -difluorosulfinate, -sulfonyl fluoride, sulfonyl chloride, or halogen. In some embodiments, R" comprises —(CH$_2$)$_{0-2}$NH$_2$, —(CH$_2$)$_{0-2}$OC(O) O— nitrophenyl, —(CH$_2$)$_{0-2}$OH, —(CH$_2$)$_{0-2}$C=O, —(CH$_2$)$_{0-2}$Cl, or —(CH$_2$)$_{0-2}$Br.

In some embodiments, provided herein are methods of generating a PRG/fluorophore probe comprising contacting (i) a reactive PRG/fluorophore reagent described herein with (ii) a bioactive agent displaying the second reactive moiety R". In some embodiments, provided herein is a PRG/fluorophore probe produced by the method described herein.

III. Capture Methods

In some embodiments, the PRG/HA probes described herein find use in the capture of target molecules that bind to the bioactive agent of the probe. PRG/HA probes are particularly useful for capture of cellular targets, because upon irradiation the probe becomes covalently bound to target and thus target association with the probe (e.g., capture) is no longer affected by cell lysis or other treatment.

In some embodiments, once captured (e.g., immobilized, enriched, isolated, purified, etc.) release through cleavage of a cleavable linker on the probe allows the target to by manipulated, analyzed, or used for a downstream application (e.g., assay).

In some embodiments, provided herein are methods of capturing a target molecule comprising: contacting a sample comprising the target molecule (e.g., target protein, cellular target, etc.) with a PRG/capture-ligand probe described herein (e.g., PRG/HA probe), wherein the bioactive agent is capable of associating with the target molecule; allowing the bioactive agent to associate with the target molecule; and irradiating the sample with a wavelength of light that converts the PRG into a reactive form of the PRG, wherein the reactive form of the PRG forms a covalent bond with the target molecule. In some embodiments, the sample contains cells and the target molecule is on the surface of or within the cells.

In some embodiments, methods further comprise lysing the cells of the sample to form a lysate comprising the target molecule covalently attached to the probe.

In some embodiments, methods further comprise contacting the sample with a capture protein (e.g., modified dehalogenase enzyme) that binds the capture ligand (e.g., forms a covalent bond with a haloalkane substrate upon association therewith); and allowing the capture protein (e.g., modified dehalogenase enzyme) to covalently bind the capture ligand (e.g., haloalkane) of the probe.

In some embodiments, the capture protein (e.g., modified dehalogenase enzyme) is immobilized on a solid surface, and upon binding of the capture protein (e.g., modified dehalogenase enzyme) to the capture ligand (e.g., haloalkane), the target molecule is immobilized on the solid surface. In some embodiments, methods further comprise: (i) removing the solid surface from the sample and/or (ii) washing non-immobilized components of the sample from the solid surface. In some embodiments, the solid surface is a bead, particle, chip, tube, plate, or membrane. In some embodiments, the solid surface is a paramagnetic particle. Suitable solid surfaces include, but are not limited to, glass and modified or functionalized glass, plastics (e.g., acrylics, polystyrene and copolymers of styrene and other materials, polypropylene, polyethylene, polybutylene, polyurethanes, Teflon, etc.), polyvinyl pyrrolidine (PVP), co-polymers of vinyl and acrylamide, polystyrene, polystyrene cross-linked with divinylbenzene or the like (see, Merrifield Biochemistry 1964, 3, 1385-1390; herein incorporated by reference in its entirety), polysaccharides, cellulose or derivatives thereof, nylon or nitrocellulose, resins, silica or silica-based materials including silicon and modified silicon, carbon, metals, inorganic glasses, plastics, optical fiber bundles, and a variety of other polymers. In some embodiments, paramagnetic beads comprise a paramagnetic resin such as those described in Example 9 of WO2014093671; herein incorporated by reference in its entirety.

In some embodiments, methods further comprise cleaving the linker of the probe to release the PRG- and bioactive agent-bound target molecule (e.g., from the capture protein, from the solid surface, etc.). In some embodiments, methods further comprise detecting and/or quantitating the target molecule. In some embodiments, the target molecule is detected and/or quantitated by mass spectrometry.

In some embodiments, the sample comprises a cell, and the target molecule is located within or on the surface of the cell. In some embodiments, contacting the sample comprising the target molecule with the probe further comprises allowing the probe to enter the cell. In some embodiments, methods further comprise lysing the cell after the PRG forms a covalent bond with the target molecule. In some embodiments, the bioactive agent is capable of non-covalently binding to the target molecule upon associating of the bioactive agent with the target molecule. In some embodiments, the target protein is a cell-surface protein, transmembrane protein, cytoplasmic protein, nuclear protein, or mitochondrial protein.

In some embodiments, provided herein are methods of capturing a cellular target protein comprising: contacting a cell containing the target protein with a probe (e.g., PRG/capture-ligand probe (e.g., PRG/HA probe)) described herein, wherein the bioactive agent is capable of binding the target protein; allowing the probe to enter the cell; allowing the bioactive agent to bind the target protein; irradiating the cell with a wavelength of UV light that converts the PRG into a reactive form of the PRG, wherein the reactive form of the PRG forms a covalent bond with the target protein; lysing the cell to form a lysate; contacting the lysate with a solid-surface-immobilized capture protein (e.g., modified dehalogenase enzyme) that forms a covalent bond with the capture ligand (e.g., haloalkane substrate) upon association therewith; allowing the capture protein (e.g., modified dehalogenase enzyme) to covalently bind the capture ligand (e.g., haloalkane) of the probe; and removing the solid surface from the lysate and/or washing non-immobilized components of the lysate from the solid surface. In some embodiments, methods further comprise cleaving the linker of the probe to release the PRG- and bioactive agent-bound target protein from the solid surface. In some embodiments, methods further comprise detection and/or quantitation of the target molecule. In some embodiments, the target protein is a cell-surface protein, transmembrane protein, cytoplasmic protein, nuclear protein, or mitochondrial protein.

In some embodiments, provided herein are methods of measuring photocrosslinking efficiency of a bioagent-linked PRG, comprising: contacting sample comprising a target molecule with a PRG/fluorophore probe described herein, wherein the target molecule is tethered to a bioluminescent reporter, and wherein the emission spectrum of the bioluminescent reporter overlaps with the excitation spectrum of the fluorophore; allowing the bioactive agent to bind the target molecule; irradiating the sample with a wavelength of light (e.g., UV light)) that converts the PRG into a reactive form of the PRG, wherein the reactive form of the PRG is capable of forming a covalent bond with the target molecule; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore, and wherein the amount of light emission from the fluorophore correlates with the amount of PRG/fluorophore probe bound to target molecules; further contacting the sample with untagged bioactive agent to competitively displace the PRG/fluorophore probe that is not covalently attached to the target; contacting the sample with a bioluminescent reporter substrate and detecting light emission within emission spectra of the bioluminescent reporter and fluorophore, wherein light emission from the fluorophore is the result of bioluminescence resonance energy transfer (BRET) from the bioluminescent reporter to the fluorophore, and wherein the amount of light emission from the fluorophore correlates with the amount of PRG/fluorophore probe covalently attached to the target molecule. In some embodiments, methods further comprise calculating the percent crosslinking by normalizing the amount of PRG/fluorophore probe covalently attached to the target molecule to the amount of PRG/fluorophore probe bound to target molecules before the addition of the untagged bioactive agent. In some embodiments, methods further comprise detecting light emission within emission spectra of the bioluminescent reporter. In some embodiments, the bioluminescent reporter is a bioluminescent protein or a peptide or polypeptide that is component of a bioluminescent complex. In some embodiments, the concentration of the untagged bioactive agent in the sample is greater than the concentration of PRG/fluorophore probe in the sample.

In some embodiments, provided herein are methods of measuring photocrosslinking efficiency of a bioagent-linked PRG, comprising: contacting sample comprising a target molecule with a PRG/HA probe described herein, wherein the target molecule is tethered to a bioluminescent reporter; allowing the bioactive agent to bind the target molecule; irradiating the sample with a wavelength of light that converts the PRG into a reactive form of the PRG, wherein the reactive form of the PRG is capable of forming a covalent bond with the target molecule; contacting the sample with excess BRET reagent comprising the bioactive agent covalently tethered to a fluorophore, wherein the emission spectrum of the bioluminescent reporter overlaps with the excitation spectrum of the fluorophore; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore and wherein the amount of light emission from the fluorophore correlates to the amount of BRET reagent bound to the target molecule. In some embodiments, methods further comprise: not contacting the sample comprising a target molecule with a PRG/HA probe described herein, wherein the target molecule is tethered to a bioluminescent reporter; irradiating the sample and then contacting the sample with an excess of BRET reagent comprising the bioactive agent covalently tethered to a fluorophore, wherein the emission spectrum of the bioluminescent reporter overlaps with the excitation spectrum of the fluorophore; contacting the sample with a bioluminescent reporter substrate and detecting light emission within emission spectra of the bioluminescent reporter and the fluorophore, wherein light emission from the fluorophore is the result of bioluminescence resonance energy transfer (BRET) from the bioluminescent reporter to the fluorophore. In some embodiments, methods further comprise comparing (i) the emission spectra collected after irradiating the sample with a wavelength of light that converts the PRG into a reactive form a sample treated with the PRG/HA probe and irradiated with a wavelength of light that converts the PRG into a reactive form of the PRG with (ii) the emission spectra collected from a sample not treated with the PRG/HA probe and irradiated with the same wavelength of light that converts the PRG into a reactive form of the PRG; wherein the decrease in BRET due to prior treatment with the PRG/HA probe inversely correlates with the photocrosslinking efficiency of the PRG (photocrosslinking of the PRG/HA probe to the target prevents displacement of the probe by the excess BRET reagent and thereby results in reduced BRET signal).

IV. PRG/Bioactive Agent Conjugates

In some embodiments, provide herein are PRGS for conjugation to bioactive agents and/or PRG/bioactive agent conjugates that provide distinct and/or favorable characteristics (e.g., covalent attachment efficiency, reactivity, solubility, size, cell permeability, etc.) compared to available PRGs. In some embodiments, provided herein are compositions comprising a photoreactive group (PRG) linked to a bioactive agent, wherein the PRG is selected from:

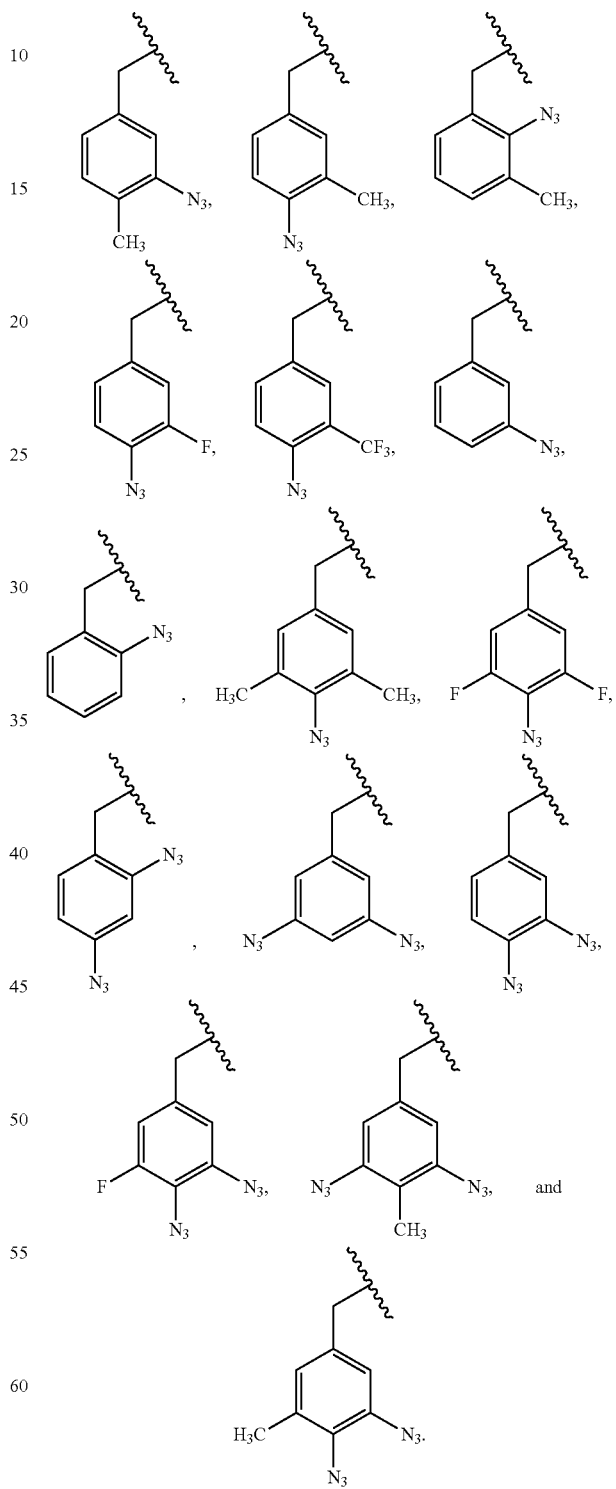

In some embodiments, provided herein are methods of covalently attaching a bioactive agent to a target protein comprising: contacting the target molecule with a bioactive agent linked to one of the above photoaffinity labels (PRG), wherein the bioactive agent is capable of associating with the target molecule; allowing the bioactive agent to associate with the target molecule; and irradiating with a wavelength of light that converts the PRG into a reactive form of the PRG, wherein the reactive form of the PRG forms a covalent bond with the target molecule.

V. Bioluminescent Reporters

The present disclosure includes materials and methods related to bioluminescent polypeptides, bioluminescent complexes and components thereof, and bioluminescence resonance energy transfer (BRET). For example, embodiments herein include BRET displacement assays where BRET is measured between a PRG/fluorophore probe and a fusion of a target of the bioactive agent and a bioluminescent reporter (e.g., bioluminescent protein, bioluminescent complex, etc.). Some embodiments herein include a BRET-based approach for systematic estimation of photocrosslinking efficiency of multiple PRGs.

Experiments conducted during development of embodiments herein demonstrate that estimation of photocrosslinking efficiencies by this approach is in good correlation with enrichment efficiencies of target proteins from live cells in several model systems. These methods demonstrate that aryl azides generally provide higher photocrosslinking efficiency than other commonly used PRGs. Furthermore, certain substituted aryl azides consistently provided higher crosslinking efficiency, superior to commonly employed diazirines and benzophenone.

Any embodiments utilizing bioluminescent proteins or complexes with the probes, assays, etc., described herein are within the scope herein. The following paragraphs describe bioluminescent proteins (e.g., NANOLUC, etc.), bioluminescent complexes (e.g., NANOBIT, NANOTRIP, etc.) and resonance energy transfer therewith (e.g., NANOBRET) that may find use in embodiments herein.

In some embodiments, provided herein are assays, methods, compositions, reagents, systems, etc., incorporating bioluminescent polypeptides and/or bioluminescent complexes (of peptide(s) and/or polypeptide components) based on (e.g., structurally, functionally, etc.) the luciferase of Oplophorus gracilirostris, NanoLuc® luciferase (Promega Corporation; U.S. Pat. No. 8,557,970; U.S. Pa. No. 8,669,103; herein incorporated by reference in their entireties), NanoBiT (U.S. Pat. No. 9,797,889; herein incorporated by reference in its entirety) or NanoTrip (U.S. Prov. Appln. Ser. No. 62/684,014) complementation systems, and/or Nano-BRET (U.S. Pat. Nos. 10,067,149; 10,024,862; herein incorporated by reference in their entireties) system. As described below, in some embodiments, the compositions, assays, reagents, methods, and systems herein incorporate commercially available NANOLUC-based technologies (e.g., NANOLUC luciferase, NANOBRET, NANOBIT, NANO-TRIP, NANOGLO, etc.), but in other embodiments, various combinations, variations, or derivations from the commercially available NANOLUC-based technologies are employed.

PCT Appln. No. PCT/US2010/033449, U.S. Pat. No. 8,557,970, PCT Appln. No. PCT/2011/059018, and U.S. Pat. No. 8,669,103 (each of which is herein incorporated by reference in their entirety and for all purposes) describe compositions and methods comprising bioluminescent polypeptides. Such polypeptides find use in embodiments herein and can be used in conjunction with the compositions, assays, reagents, systems, and methods described herein.

In some embodiments, compositions, assays, devices, systems, and methods provided herein comprise a bioluminescent polypeptide of SEQ ID NO: 5 or having at least 60% (e.g., 60%, 65%, 70%, 75%, 80%, 85%, 90%, 95%, 96%, 97%, 98%, 99%, 100%, or ranges therebetween) sequence identity with SEQ ID NO: 5. In some embodiments, provided herein is a fusion of (i) a bioluminescent polypeptide having at least 60% (e.g., 60%, 65%, 70%, 75%, 80%, 85%, 90%, 95%, 96%, 97%, 98%, 99%, 100%, or ranges therebetween) sequence identity with SEQ ID NO: 5 and (ii) a target protein (e.g., cellular target).

In some embodiments, a bioluminescent polypeptide is linked (e.g., fused, chemically linked, etc.) to a molecule of interest, a protein of interest, or another component of the assays and systems described herein. In some embodiments, any of the bioluminescent polypeptides, or fusions or conjugates thereof described herein, are immobilized to a solid surface or a device.

PCT Appln. No. PCT/US14/26354 and U.S. Pat. No. 9,797,889 (each of which is herein incorporated by reference in their entirety and for all purposes) describe compositions and methods for the assembly of bioluminescent complexes; such complexes, and the peptide and polypeptide components thereof, find use in embodiments herein and can be used in conjunction with the assays and methods described herein. Some embodiments herein employ a NANOBIT-based technology.

In some embodiments, provided herein are polypeptides components of a bioluminescent complex, the polypeptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 9, but less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, and SEQ ID NO: 6. In some embodiments, provided herein are peptide components of a bioluminescent complex, the peptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 10, but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8. In some embodiments, In some embodiments, provided herein are peptide components of a bioluminescent complex, the peptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 11, but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8. In some embodiments, a peptide or polypeptide component of a bioluminescent complex is linked (e.g., fused, chemically linked, etc.) to a target molecule, cellular target, or other component of the compositions, assays, reagents, methods, and systems described herein. In some embodiments, a peptide or polypeptide component of a bioluminescent complex, or fusions or conjugates thereof, are immobilized to a portion of a solid surface or device.

U.S. Prov. Appln. Ser. No. 62/684,014; U.S. application Ser. No. 16/439,565; and U.S. Prov. Appln. Ser. No. 62/941,255 (herein incorporated by reference in their entireties and for all purposes) describe compositions, systems, and methods for the assembly of bioluminescent complexes, for example, from three or more peptide/polypeptide components. Such complexes, and the peptides and polypeptide components thereof (e.g., NanoTrip-based peptides, polypeptides, and complexes), find use in embodiments herein and can be used in conjunction with the assays and methods described herein.

In some embodiments, provided herein are polypeptide components of a bioluminescent complex, the polypeptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 12, but less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, SEQ ID NO: 6, and SEQ ID NO: 9. In some embodiments, provided herein are peptide components of a bioluminescent complex, the peptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 11, but less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and SEQ ID NO: 8. In some embodiments, provided herein are peptide components of a bioluminescent complex, the peptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 13, but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 5, and SEQ ID NO: 7. In some embodiments, provided herein are peptide components of a bioluminescent complex, the peptides having at least 60% (e.g., 60%, 65%, 70%, 75%, 80%, 85%, 90%, 95%, 96%, 97%, 98%, 99%, 100%, or ranges therebetween) sequence identity with SEQ ID NO: 14, but less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 4, SEQ ID NO: 5, SEQ ID NO: 7, and SEQ ID NO: 8.

In some embodiments, one or more of the aforementioned NanoTrip-based peptides or polypeptides are linked (e.g., fused, chemically linked, etc.) to a target molecule or cellular target or other component of the compositions, methods, reagents, assays, and systems described herein. In some embodiments, one or more of the aforementioned NanoTrip-based peptides or polypeptides are immobilized to a solid surface or device.

PCT Appln. No. PCT/US13/74765, U.S. Pat. Nos. 10,067, 149, and 10,024,862 (herein incorporated by reference in their entireties and for all purposes) describe bioluminescence resonance energy transfer (BRET) compositions, systems, and methods (e.g., incorporating NANOLUC-based technologies); such compositions, systems, and methods, and the bioluminescent polypeptides and fluorophore-conjugated components thereof, find use in embodiments herein and can be used in conjunction with the compositions, systems, reagents, assays, and methods described herein. In some embodiments, these NANOBRET technologies find use with the compositions, systems, and methods described herein in detection and analysis of intracellular binding of a bioactive agent to a cellular target.

U.S. Pat. Nos. 10,168,323 and 9,551,705 (herein incorporated by reference in their entireties and for all purposes) describe compositions and methods for capture and identification of cellular targets of bioactive agents; in particular, these patents describe bioactive agents tethered to capture ligands, cellular targets (optionally tagged with a reporter), capture proteins (optionally present as capture dimers), surfaces (e.g., displaying, capture ligands, capture proteins, or capture dimers), and methods of capturing and identifying the cellular targets of a bioactive agent therewith. In some embodiments, these technologies find use with the compositions, systems, and methods described herein in detection and analysis of intracellular binding of a bioactive agent to a cellular target.

In some embodiments, any of the NANOLUC-based, NANOBIT-based, and/or NanoTrip-based peptides, polypeptides, complexes, fusions, and conjugates may find use in BRET-based applications with the compositions, assays, methods, reagents, and systems described herein. BRET applications of the technologies described herein utilize one or more energy acceptors. As used herein, the term "energy acceptor" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA Fluor (Invitrogen), DYLIGHT Fluor (Thermo Scientific, Pierce), ATTO and TRACY dyes (Sigma Aldrich), FluoProbes (Interchim), DY and MEGASTOKES dyes (Dyomics), SULFO CY dyes (CYANDYE, LLC), SETAU AND SQUARE dyes (SETA BioMedicals), QUASAR and CAL Fluor dyes (Biosearch Technologies), SURELIGHT dyes (APC, RPE, PerCP, Phycobilisomes)(Columbia Biosciences), APC, APCXL, RPE, and BPE dyes (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety. In some embodiments, a fluorophore is linked to a bioactive agent and PRG in a PRG-fluorophore probe described herein.

EXPERIMENTAL

Example 1

Figure 12:
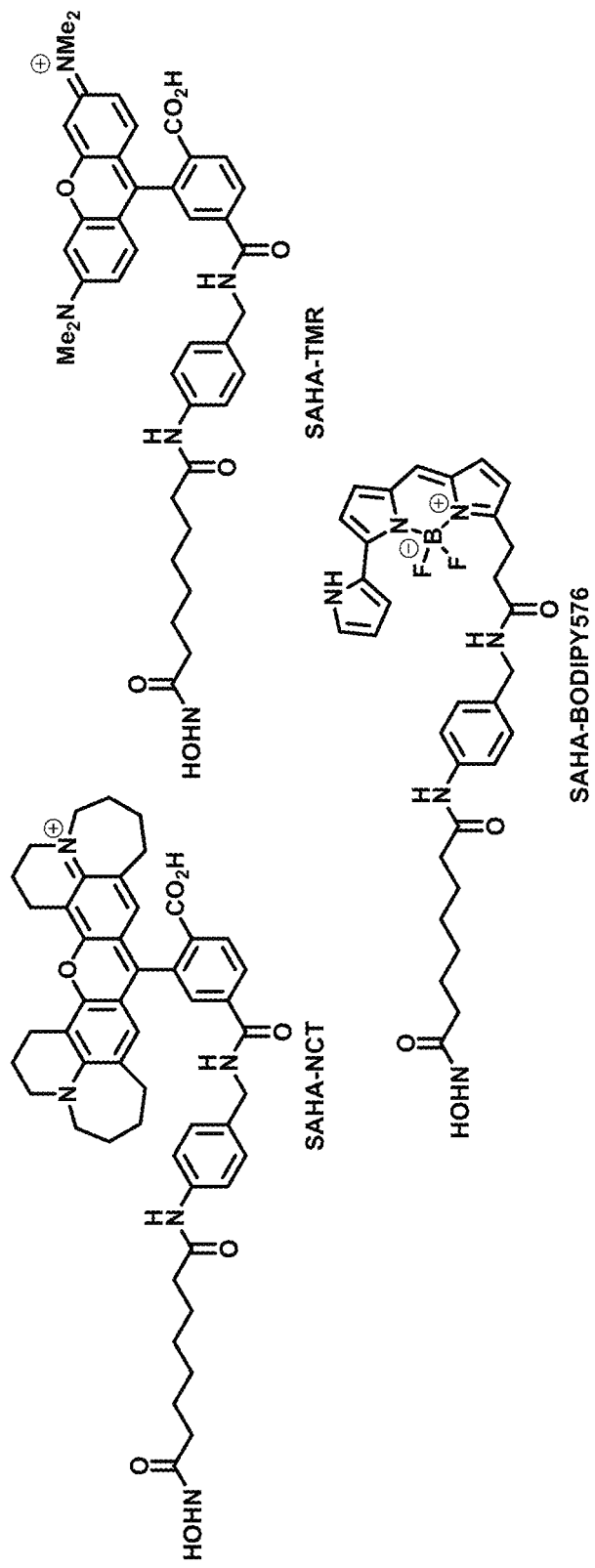
FIG. 12. Structures of SAHA-dye tracers.
Figure 13:
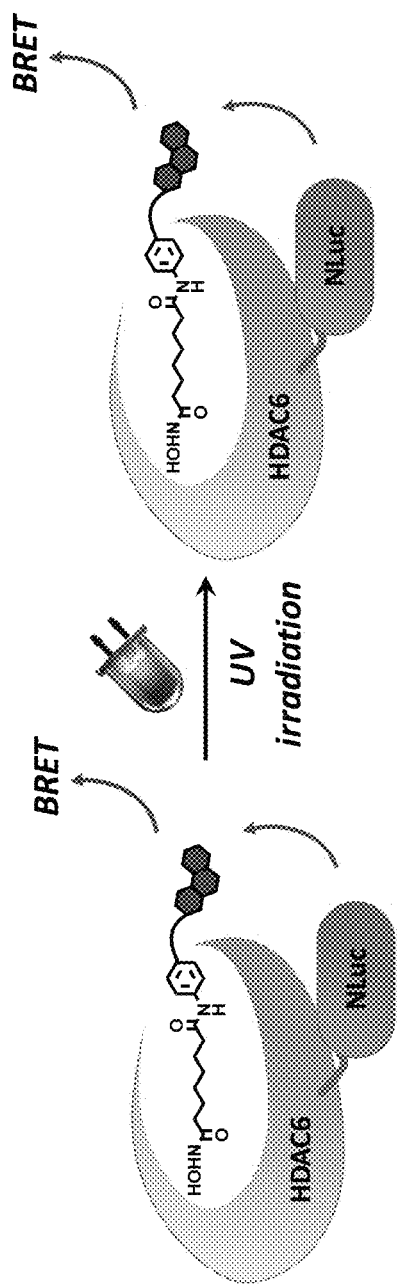
FIG. 13. Experiment set-up for testing the influence of UV irradiation on signal intensity of both NanoLuc and fluorescent dyes.
Figure 14:
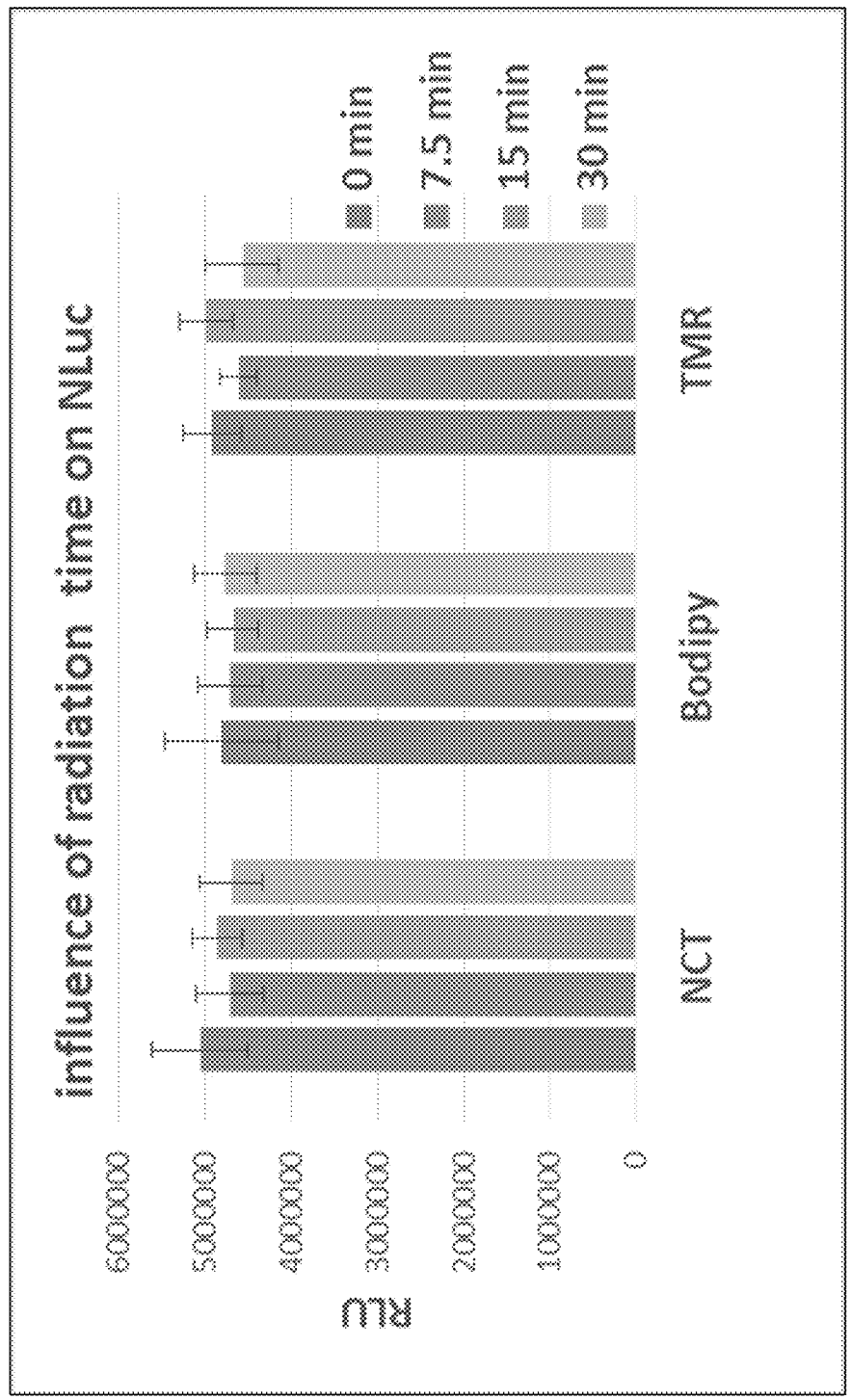
FIG. 14. Influence of UV irradiation on the bioluminescent signal intensity of NanoLuc.
Figure 15:
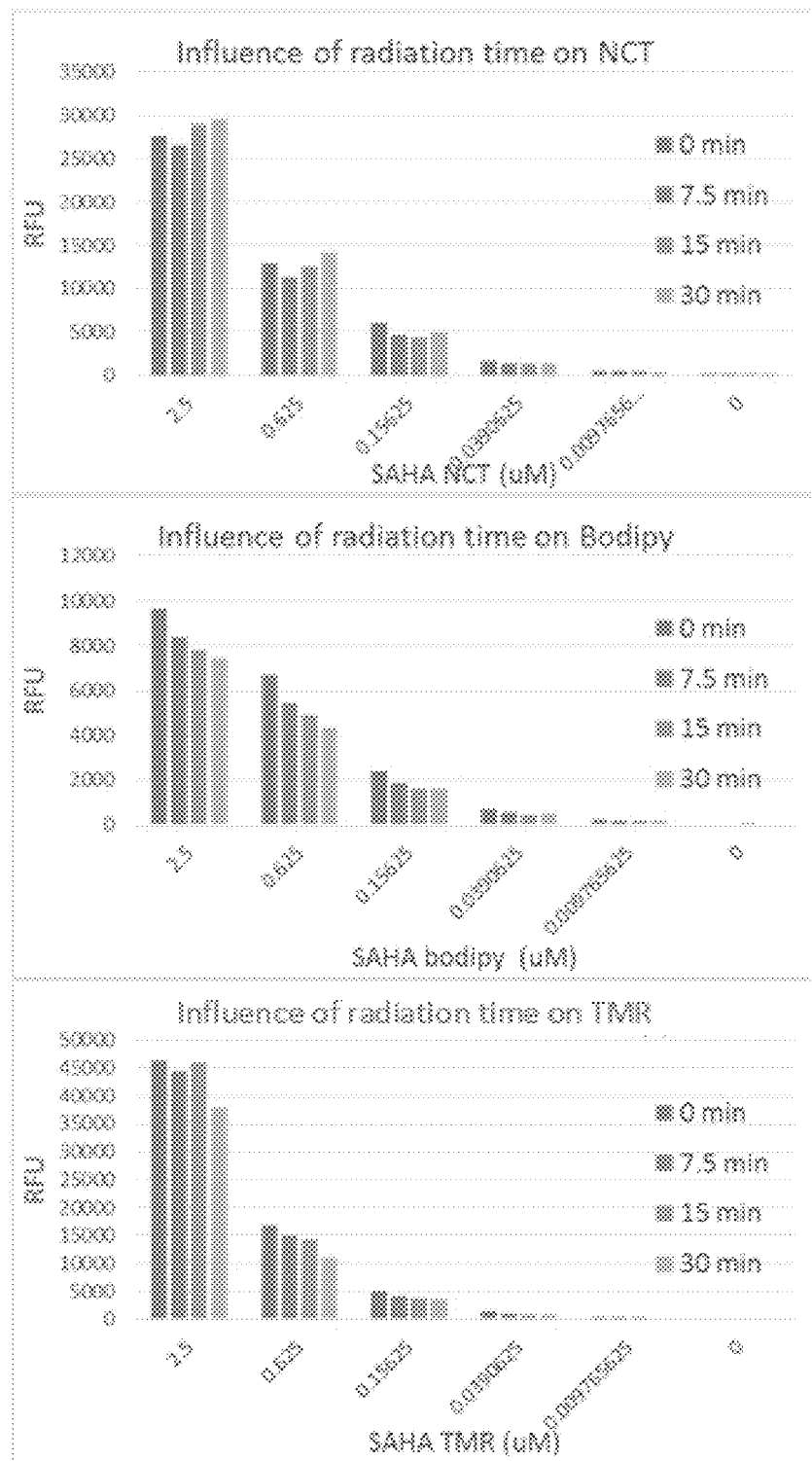
FIG. 15. Influence of UV irradiation on the fluorescence intensity of NCT, BODIPY, and TMR fluorophores conjugated to SAHA at multiple probe concentrations and different irradiation duration.

During development of the BRET approach described herein for estimating crosslinking efficiency, experiments were conducted to determine the influence of UV irradiation on the bioluminescent intensity of the energy donor NANOLUC, and the fluorescence intensity of three fluorophores that can be used as energy acceptors (FIGS. 12-15). The model system for these experiments (FIG. 13) was the interaction between HDAC6 fused to NANOLUC and SAHA (vorinostat), which binds to HDAC6 and was conjugated to one of three fluorophores NCT, TAMRA, and BODIPY576 (FIG. 12). In these experiments HEK293T cells transiently expressing HAD6-NANOLUC fusion were treated for 2 hours with serial dilution of SAHA-fluorophore conjugate, then UV irradiated for 0-30 minutes and subsequently treated with NANOGLO detection reagent. As shown in FIG. 14, the NANOLUC signal was not affected by up to 30 minutes UV irradiation, thus indicating that under UV irradiation conditions, NANOLUC can serve as a robust bioluminescence donor. On the other hand, measurements of fluorescence intensity indicated that UV irradiation decreased the fluorescence intensity of SAHA-BODIPY576 and SAHA-TMR in a manner that was dependent on UV irradiation time (FIG. 15). At the same time, the fluorescent intensity of SAHA-NCT was not significantly affected by up to 30 minutes of irradiation. Thus, NANOLUC and NCT were chosen as a BRET donor and acceptor pair for the assays estimating photocrosslinking efficiency. Notably, other luciferase and fluorophore combinations are within the contemplated and within the scope of embodiments herein.

Example 2

Figure 16:
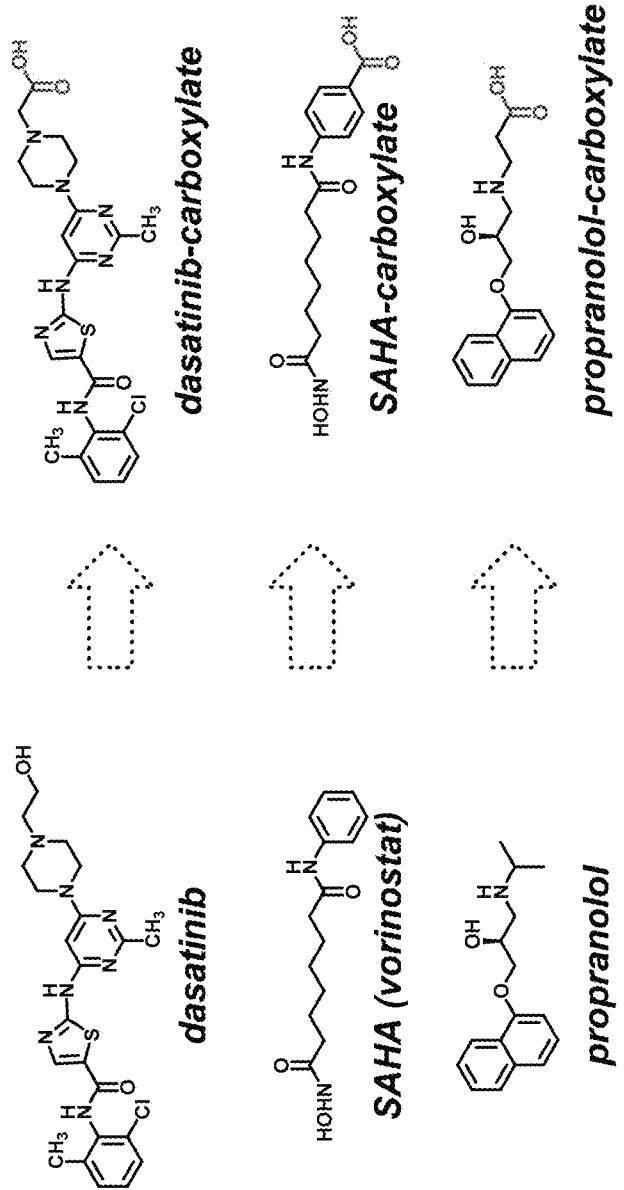
FIG. 16. Parent drugs and their modifiable cores for exemplary chemical probes synthesis. Building blocks for probe synthesis containing appropriate protecting groups for SAHA and propranolol.
Figure 17:
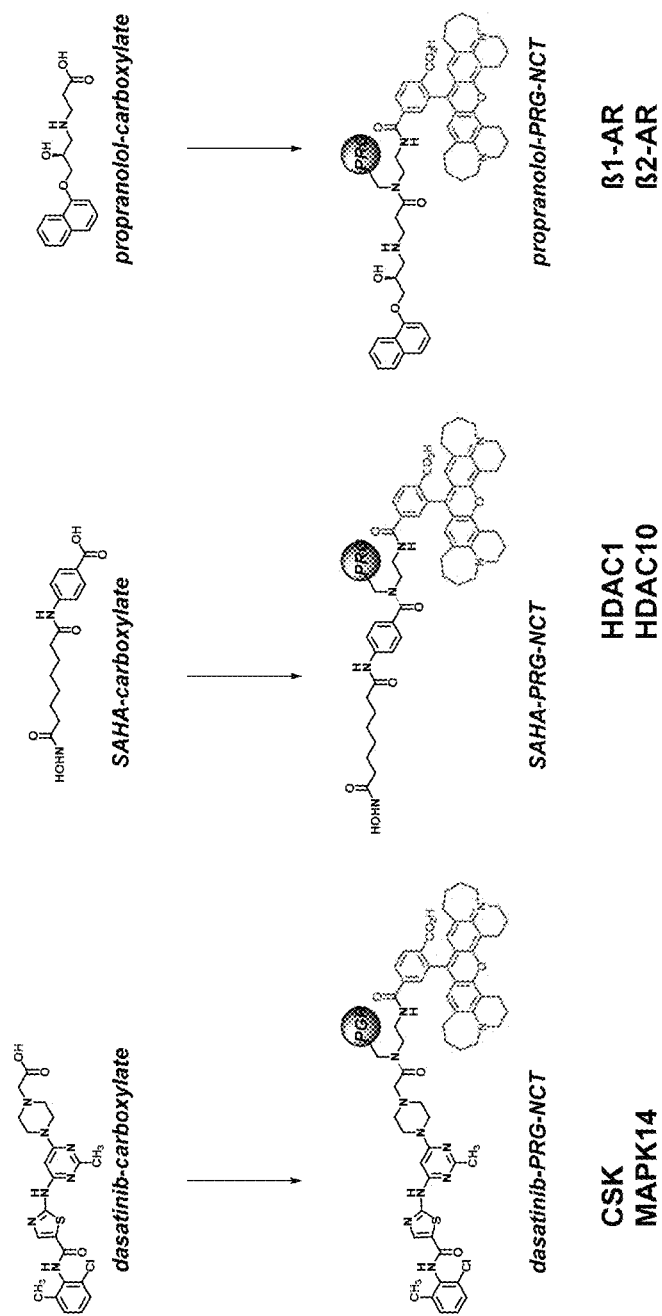
FIG. 17. Generic structures of fluorescent photoaffinity-labeling probes and their respective targets for photoaffinity labeling studies.

This example (FIG. 16-21) demonstrate the capacity of the BRET approach illustrated in FIG. 11 to estimate crosslinking efficiency for different photoreactive groups. For these experiments, three model compounds were selected: SAHA, dasatinib, and propranolol (FIGS. 16 and 17). Introduction of the carboxylic acid functionality at the highlighted positions (FIG. 16) allows attachment of functional elements (e.g., dye, chloroalkane, PRG etc.) via a probe reagent using an amide coupling reaction without a significant influence on the binding properties of the bioactive agent to its targets.

Figure 32:
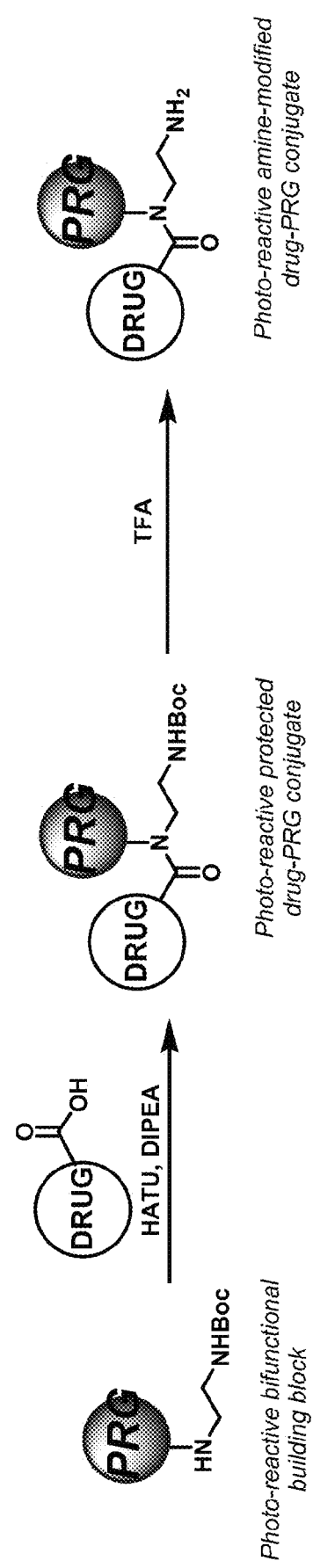
FIG. 32. Exemplary general scheme for synthesis of drug-PRG conjugates FIG. 33. Exemplary general scheme for synthesis of drug-PRG-NCT and drug-PRG-CA chemical probes.
Figure 33:
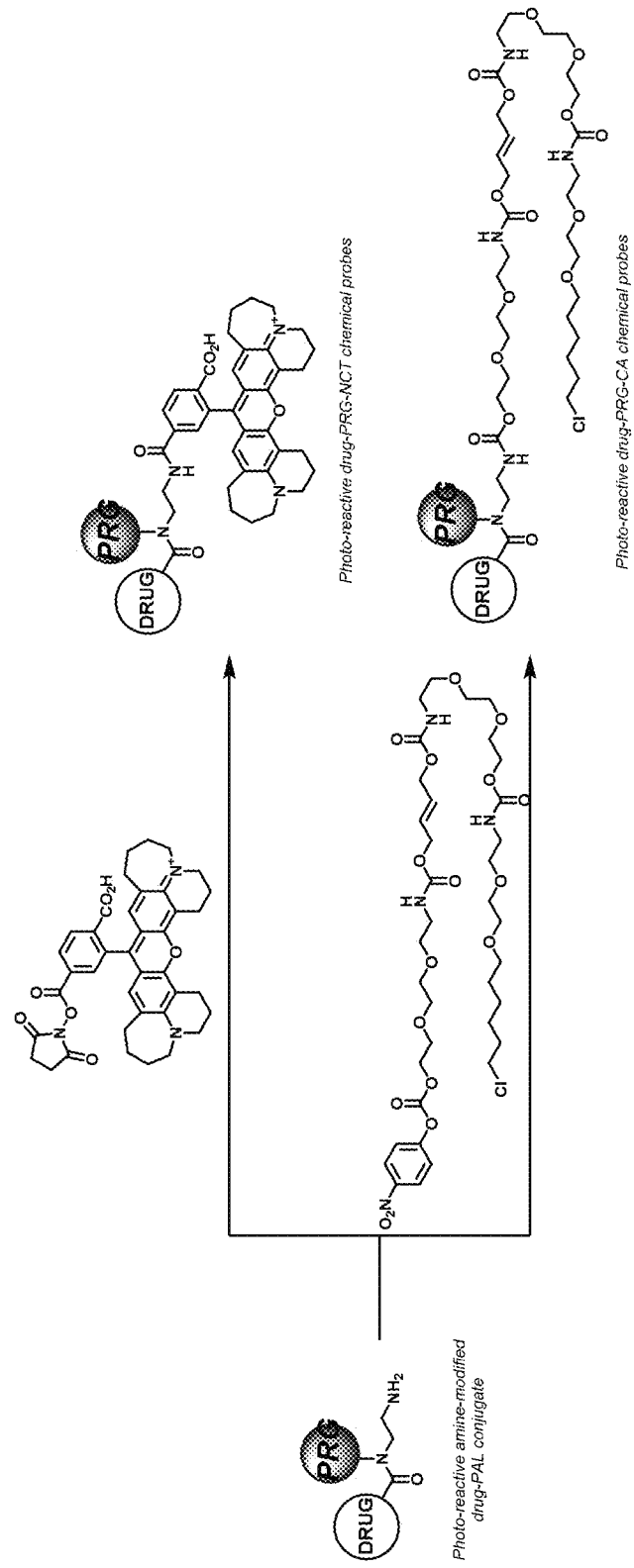

Syntheses of NCT/PRG chemical probes of dasatinib, SAHA, and propranolol were accomplished as depicted in FIGS. 32, 33, and Example 7. The structures of the NCT photoaffinity probes and their respective targets (fused to NANOLUC) used in the BRET assay are shown in FIG. 17.

Experiments conducted during the development of embodiments herein interrogated the crosslinking efficiencies of photoaffinity probes to their respective protein targets fused to NANOLUC. Briefly, as depicted in FIG. 11, three replicates of cells or lysates from cells expressing a protein target fused to NANOLUC were plated into wells of 96-well plates and treated with (a) 0.3 or 1 µM NCT/PRG probes (controls for maximal probe occupancy at a given concentration), (b) 0.3 or 1 µM NCT/PRG probes (experimental samples), and (c) 0.3 or 1 µM NCT/PRG probes and 40 µM of untagged bioactive compound (controls for minimal probe occupancy) for 90 minutes protected from light before being UV irradiated for 15 minutes. Following irradiation, experimental samples were treated with 40 µM untagged bioactive compound for 60 min to outcompete the non-covalently bound NCT/PRG probe while control samples remained untreated. Subsequently, BRET was measured upon treatment with NANOGLO detection reagent. Residual BRET values in the experimental samples, resulting from probes that were not outcompeted, were normalized to the maximal and minimal probe occupancy controls. These normalized residual BRET values, which reflect the fraction occupancies of covalently bound probes were used to derive crosslinking efficiencies. Identical 96-well plates that were treated in a similar way, but were not UV irradiated were used to derive background values, which were then subtracted from the calculated crosslinking efficiencies. The data in FIGS. 18-21 are presented as background corrected crosslinking efficiencies.

Figure 18:
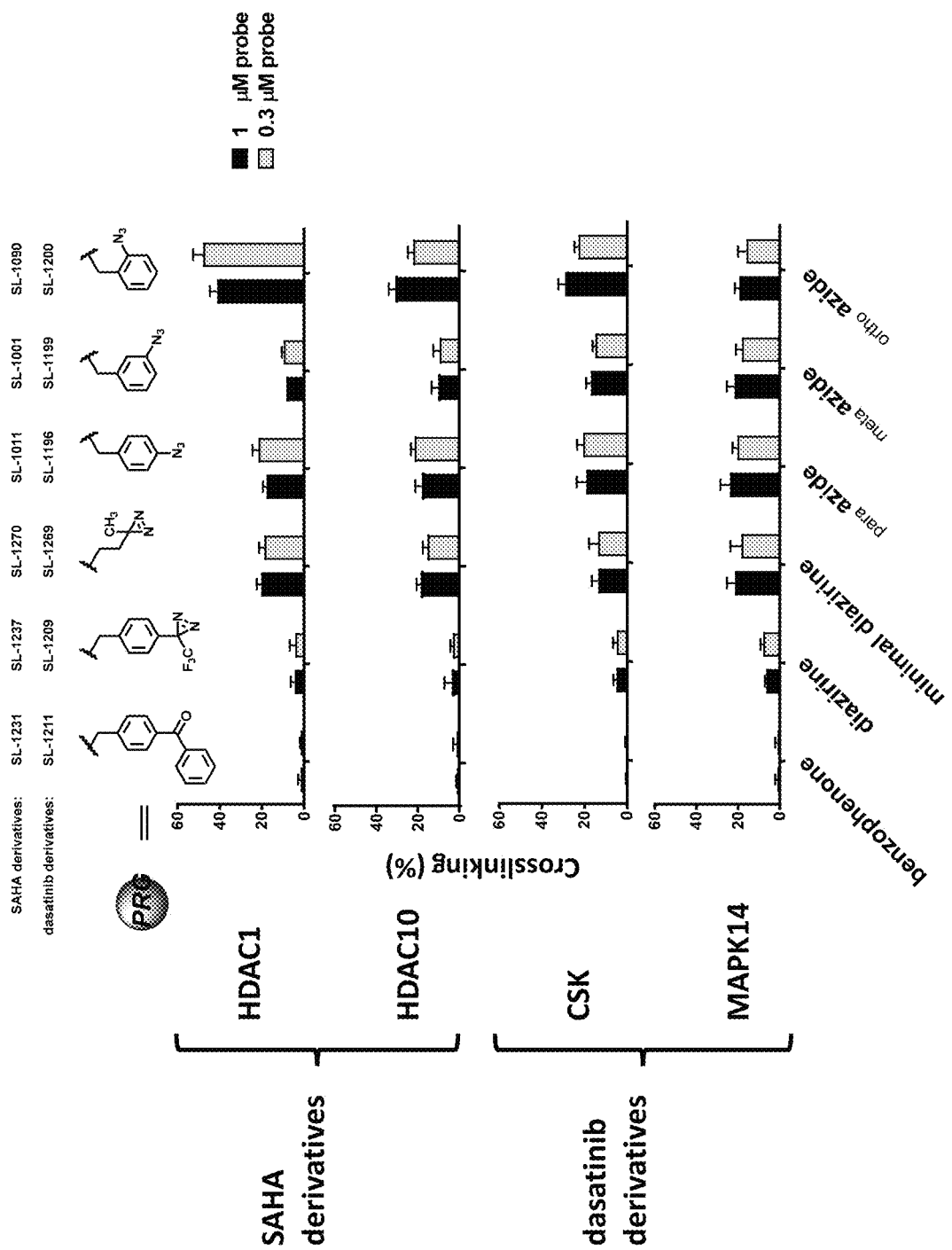
FIG. 18. Comparison of photocrosslinking efficiencies for SAHA and dasatinib PRG/fluorophore probes containing commonly used photoreactive groups and simple arylazides.
Figure 19:
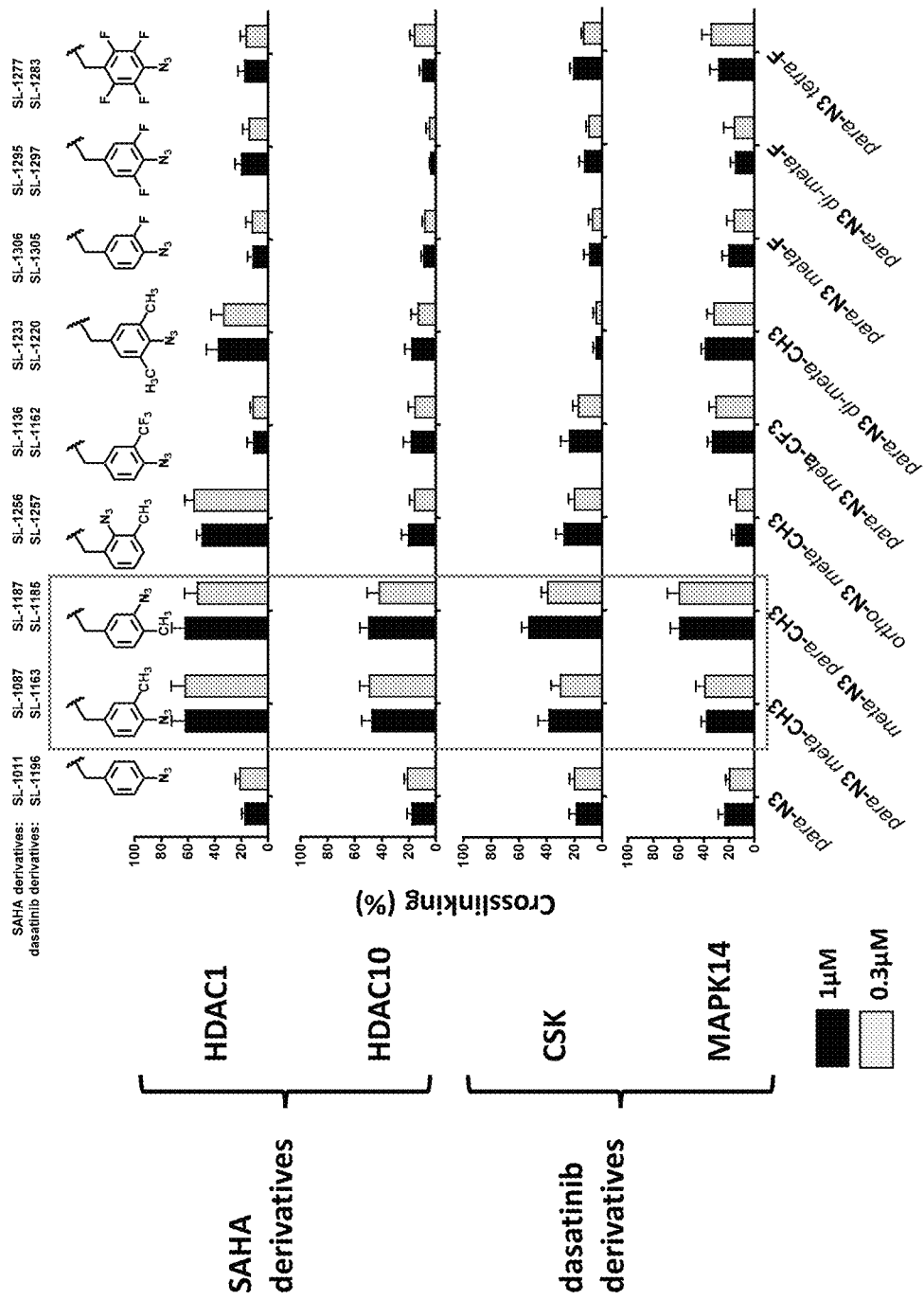
FIG. 19. Comparison of photocrosslinking efficiencies for SAHA and dasatinib PRG/fluorophore probes containing arylazides with different substituents.

Initially, SAHA and dasatinib probes containing commonly used PRGs (benzophenone and diazirines, both aryl and alkyl) and mono-substituted aryl azides were tested for crosslinking efficiency. FIG. 18 illustrates the photocrosslinking efficiencies of these probes to their targets (HDAC1 and HDAC10 for SAHA probes and CSK and MAPK14 for dasatinib probes), which were determined by the BRET assay described herein. In each case, both benzophenone and trifluoromethyl aryldiazirine showed the lowest levels of photocrosslinking to their targets. Alkyl diazirine and aryl azides showed significantly improved crosslinking efficiencies across the tested targets compared to both benzophenone and aryldiazirine. 4-Phenylazide provided consistent crosslinking efficiencies across all targets.

The position of the azido group on the phenyl ring relative to the attachment point influenced the photocrosslinking efficiency of the probe (FIG. 18). To interrogate further the influence of substitution of the aryl ring on photocrosslinking efficiency, eight additional arylazides were tested in the BRET assay. Results in FIG. 19 demonstrate that for both model compounds, the two ortho-methylsubstituted aryl azides consistently provided improved crosslinking efficiencies, overperforming simple 4-phenylazide. Other phenyl or benzyl azides, including known PRG—4-azido-2,3,5,6-tetrafluobezyl, provided inferior or inconsistent crosslinking efficiencies.

Figure 20:
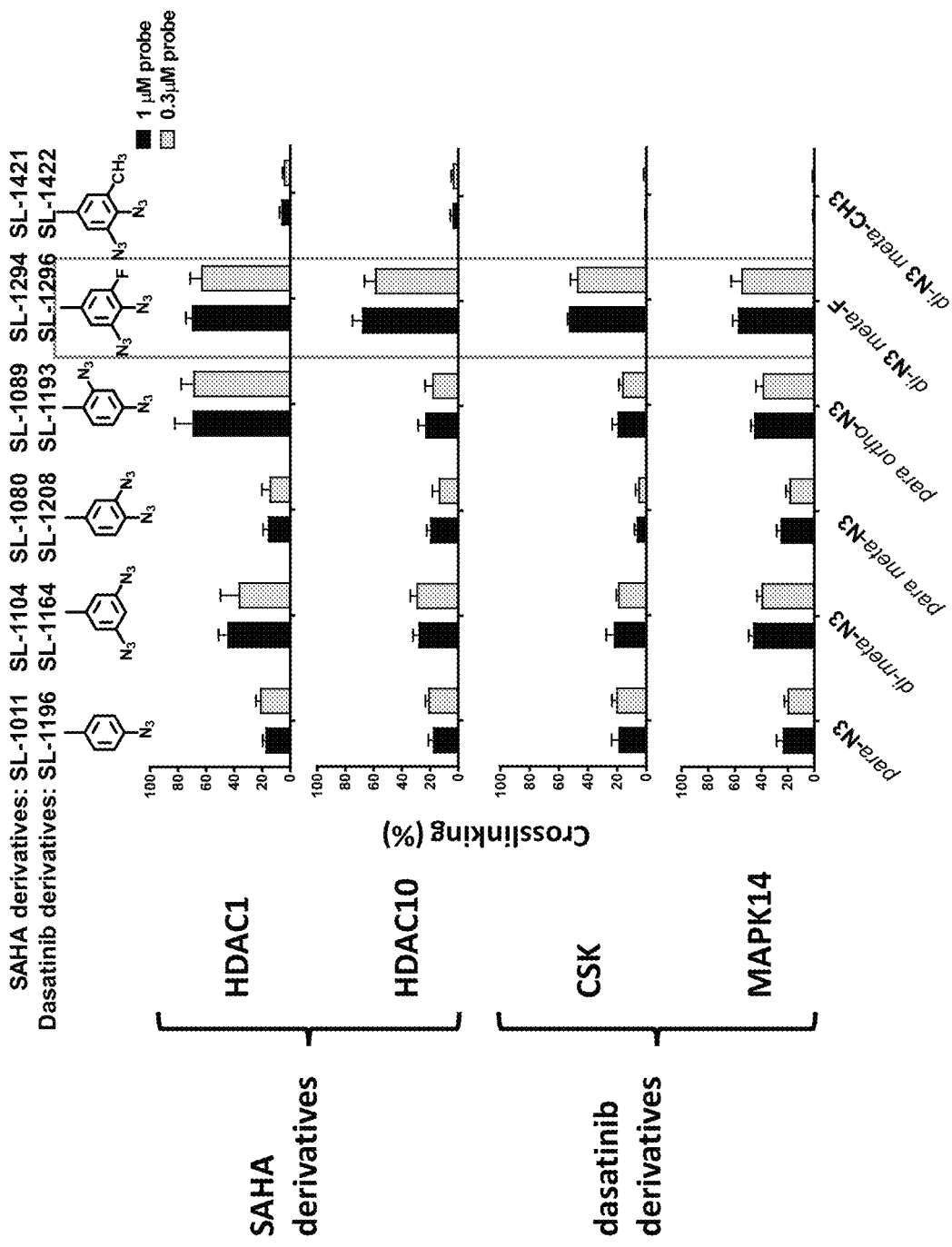
FIG. 20. Comparison of photocrosslinking efficiencies for SAHA and dasatinib PRG/fluorophore probe containing various aryldiazides.

Next, the influence of a second azido-group on the PRGs crosslinking efficiency was interrogated (FIG. 20). Among simple aryldiazides, the ortho relationship between azido groups resulted in a lower crosslinking efficiency than that of a simple 4-phenylazide. On the other hand, the meta-relationship between two azido functions showed improved crosslinking efficiency compared to 4-phenylazide. Surprisingly, introduction of the o-methylsubstituent to the o-aryldiazide moiety resulted in poor crosslinking efficiency. At the same time, introduction of an o-fluoro substituent next to and o-aryldiazide provided superior performance.

Figure 21:
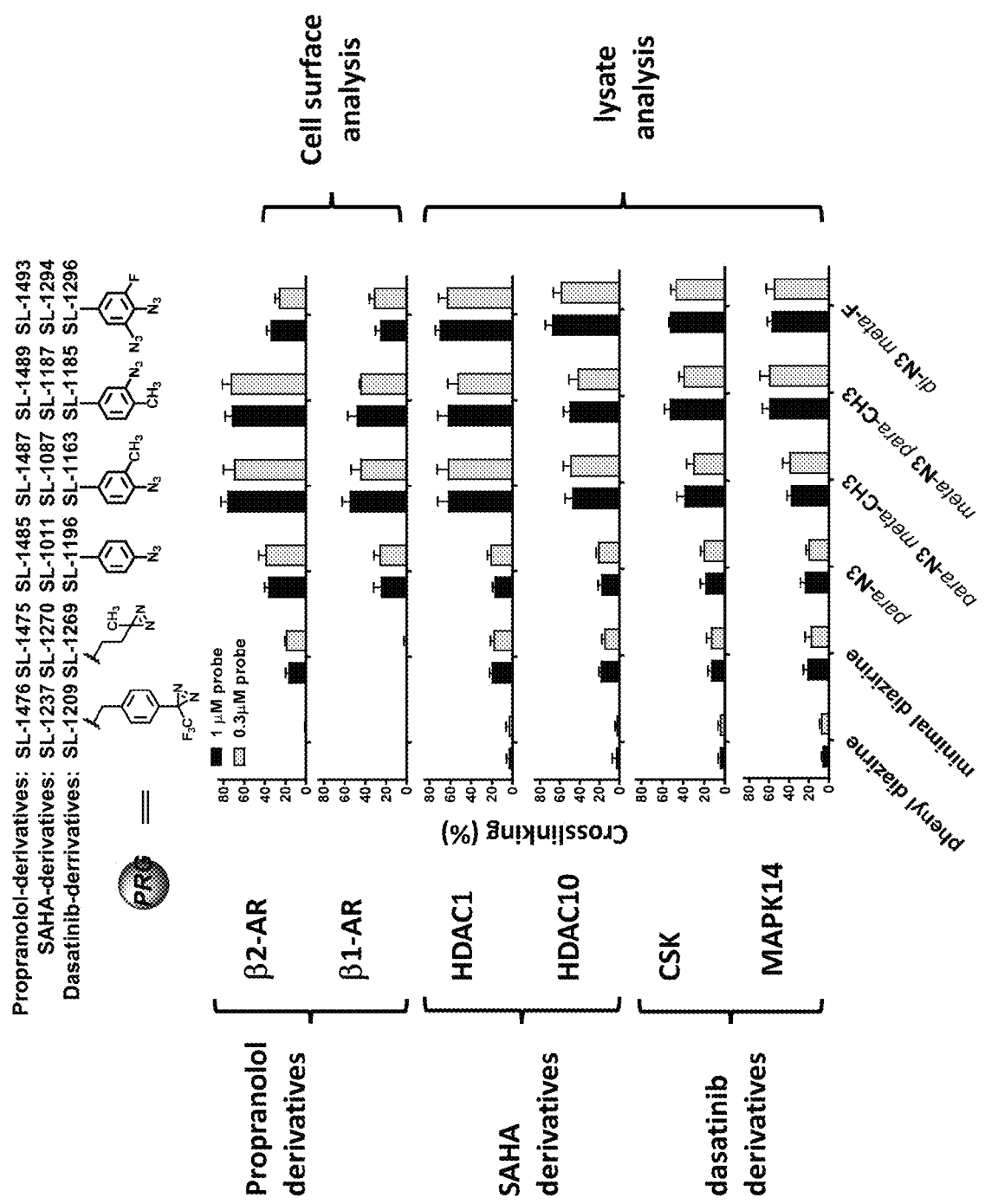
FIG. 21. Comparison of photocrosslinking efficiencies for selected PRG/fluorophore probes. In all 6 model systems, o-tolylazide probes overperformed diazirine probes.

FIG. 21 summarize the crosslinking efficiencies for probes containing common PRGs and superior arylazides in six model systems. The results clearly show that arylazides provide a significant boost to photocrosslinking efficiencies compared to diazirines. Furthermore, ortho-tolylazides overperformed other PRG groups in all six model systems. Furthermore, similar photocrosslinking efficiencies determined at two different concentrations of NCT/PRG probe suggest that these efficiencies are not driven by concentration and are rather intrinsic properties of the PRGs.

Example 3

Figure 22:
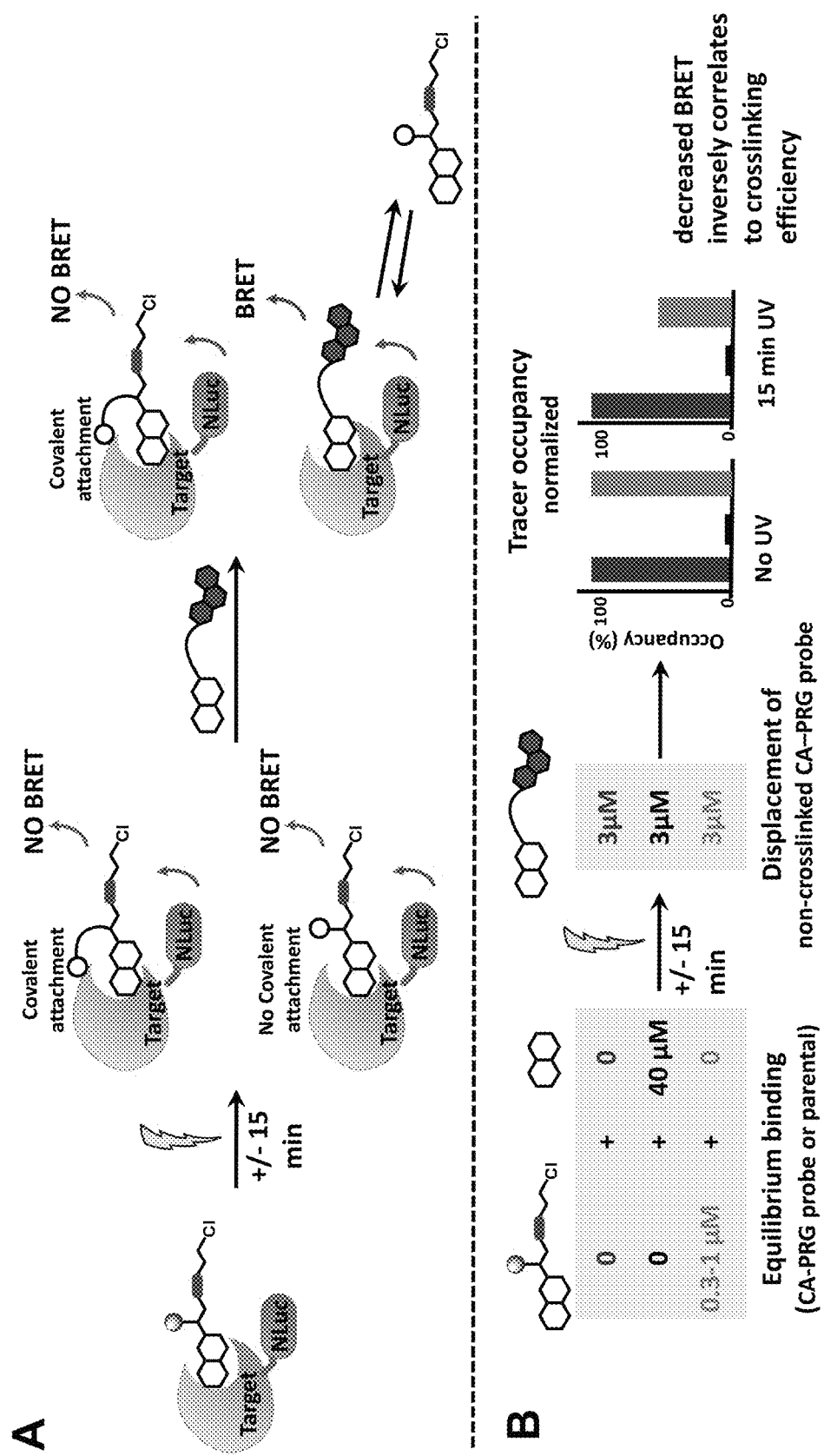
FIG. 22, panels A-B. Reverse-BRET approach to estimate photocrosslinking efficiency. (Panel A) A general scheme of Reverse-BRET assay for quantifying crosslinking efficiency. Binding of a PRG/HA probe to a target tethered to NanoLuc does not result in BRET. UV irradiation induces covalent crosslinking of the PRG/HA probe to its target. Treatment with an excess BRET reagent would displace the non-covalently bound PRG/HA probe resulting in BRET. (Panel B) Decreased BRET resulting from covalently bound PRG/HA probe, which could not compete with the BRET reagent, is normalized to maximal BRET from an equivalent sample that was not treated with the PRG/HA. The normalized decreased BRET inversely correlates to crosslinking efficiency. The chloroalkane portion of the probe is not required for this experiment.
Figure 23:
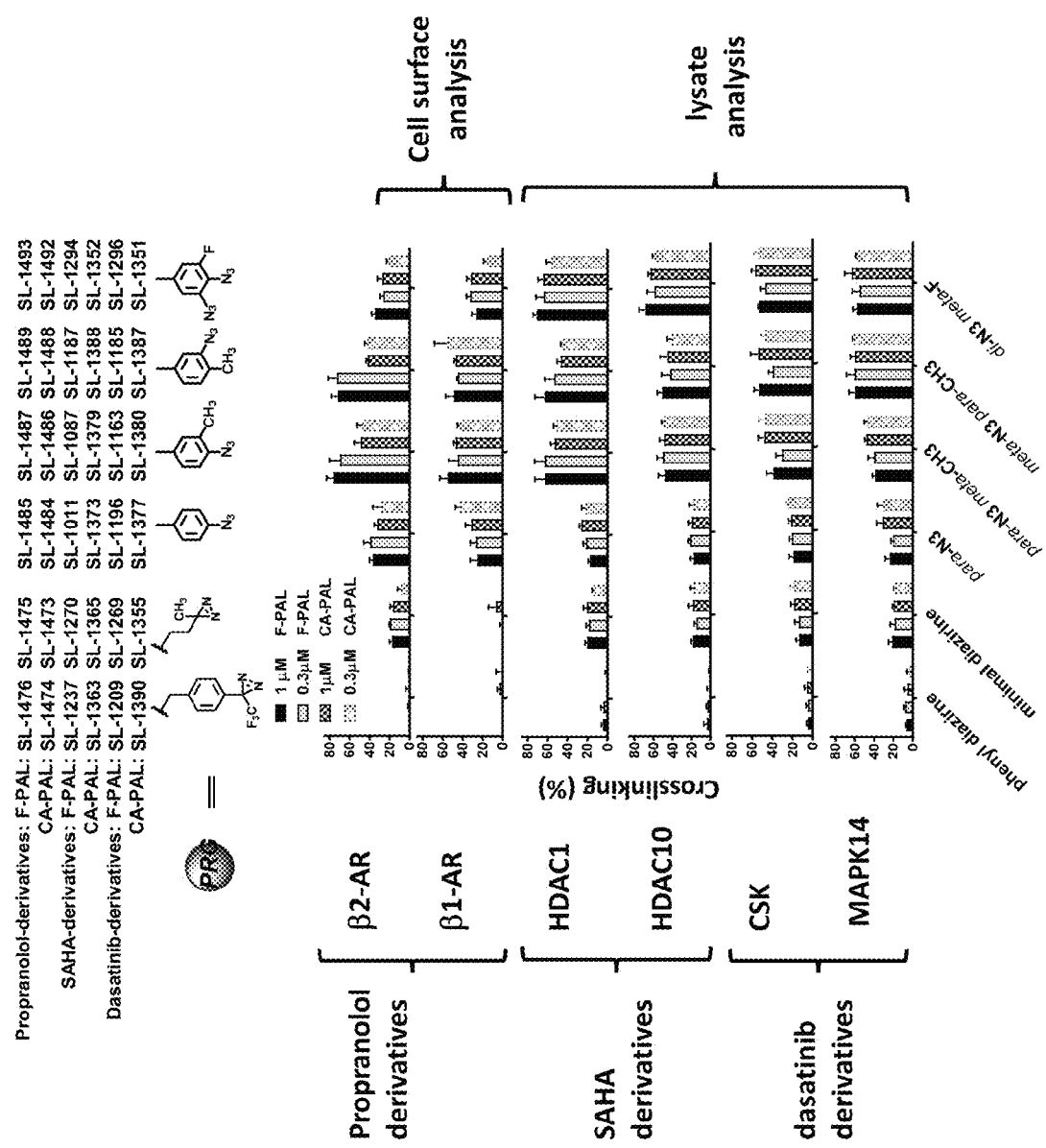
FIG. 23. Estimation of photocrosslinking efficiencies for selected photoaffinity probes by "direct" and "reverse" BRET methods.

This example further validates the crosslinking efficiencies estimated by the BRET approach. It is generally known that the fluorescent signal from a dye can be environmentally sensitive, thus fluorescent readout from a dye could provide misleading results for different fluorescent probes. To address this, a "reverse BRET" approach described in FIG. 22 was developed to complement the "direct BRET" method for estimating PRGs crosslinking efficiencies. Unlike direct BRET, reverse BRET relies on the fluorescent readout from a single fluorescent tracer (probe) that does not undergo any chemical changes during UV irradiation (e.g., a bioactive agent linked to a fluorophore, but without a PRG), thus eliminating any possible influence of UV irradiation on fluorescence. Briefly, as depicted in FIG. 22, three replicates of cells or lysates from cells transiently expressing a target fused to NANOLUC were plated in wells of 96-well plates and treated with (a) nothing (controls for maximal occupancy of fluorescent tracer), (b) 0.3 or 1 µM HA/PRG probes (experimental samples), and (c) 40 µM of untagged bioactive compound (controls for minimal occupancy of fluorescent tracer) for 90 minutes protected from light before being UV irradiated for 15 minutes. Following irradiation, all samples were treated with 3 μM of a fluorescent tracer for 60 min, which outcompete in the experimental samples the non-covalently bound HA/PRG probes. Subsequently, BRET was measured upon treatment with NANOGLO detection reagent. To calculate crosslinking efficiency, the normalized BRET values in the experimental samples relative to the controls were subtracted form theoretical 100% maximal crosslinking efficiencies. Identical 96-well plates that were treated in a similar way, but were not UV irradiated were used to derive background values, which were subtracted from the calculated crosslinking efficiencies. The data in FIG. 23 is presented as background corrected crosslinking efficiencies.

Figure 24:
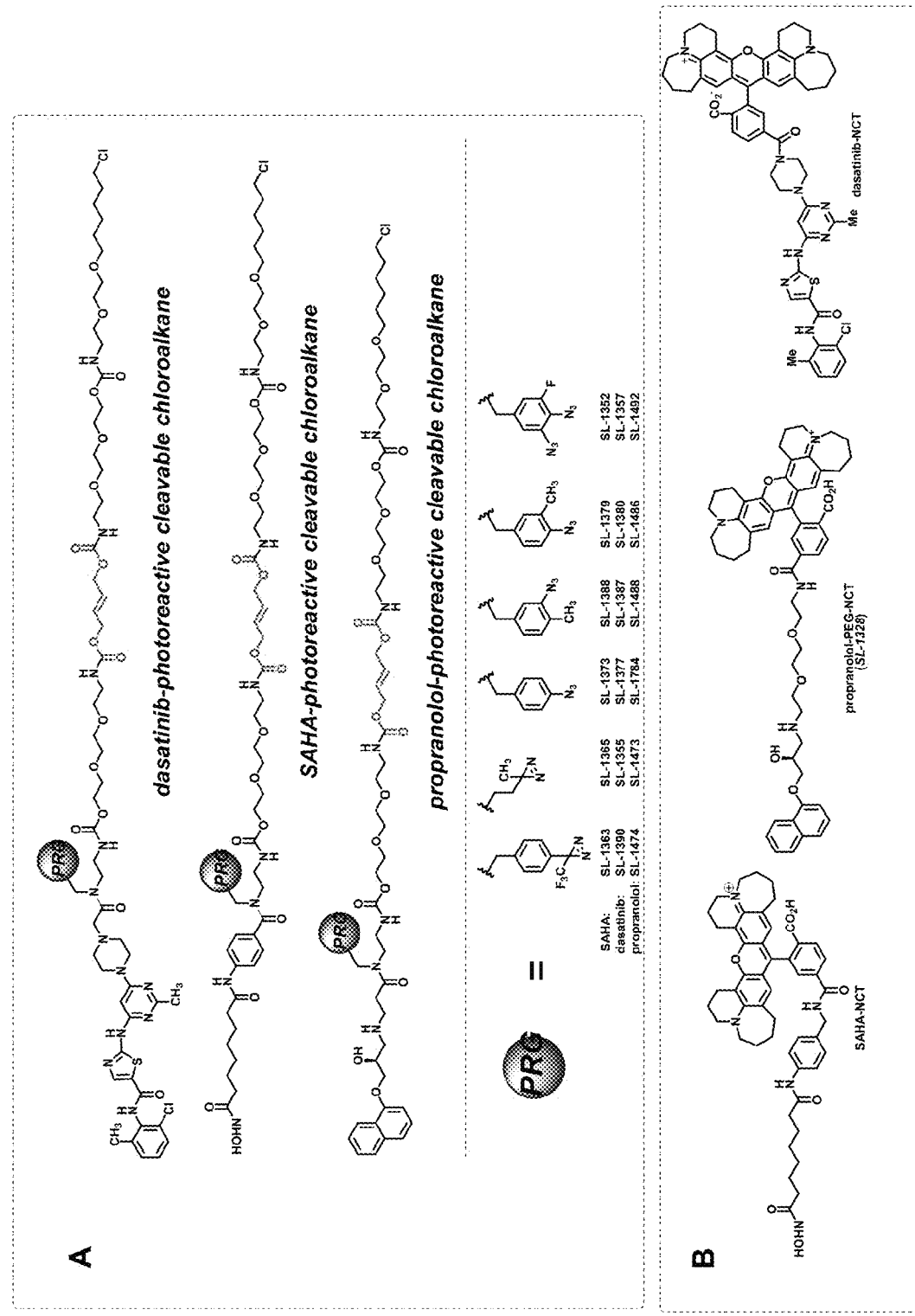
FIG. 24, panels A-B. (Panel A) Exemplary structures of photoaffinity cleavable chloroalkane probes tested. (Panel B) Structures of fluorescent probes used in reverse BRET experiments.

For the reverse BRET approach, the fluorophore in fluorophore/PRG probes was swapped with a cleavable chloroalkane (the presence of the chloroalkane would not be required for this experiment; a bioactive agent/PRG conjugate would suffice). Chemical structures of the probes are shown on FIG. 24. FIG. 23 illustrates comparison of photocrosslinking efficiencies estimated by both reverse BRET and direct BRET methods. The results indicate that both methods provide very similar results, thus validating the data provided by each BRET method. Furthermore, the similar photocrosslinking efficiencies determined for two different concentrations of NCT/PRG or HA/PRG probes suggest that these efficiencies are not driven by concentration and are rather intrinsic properties of the PRGs.

Example 4

Figure 25:
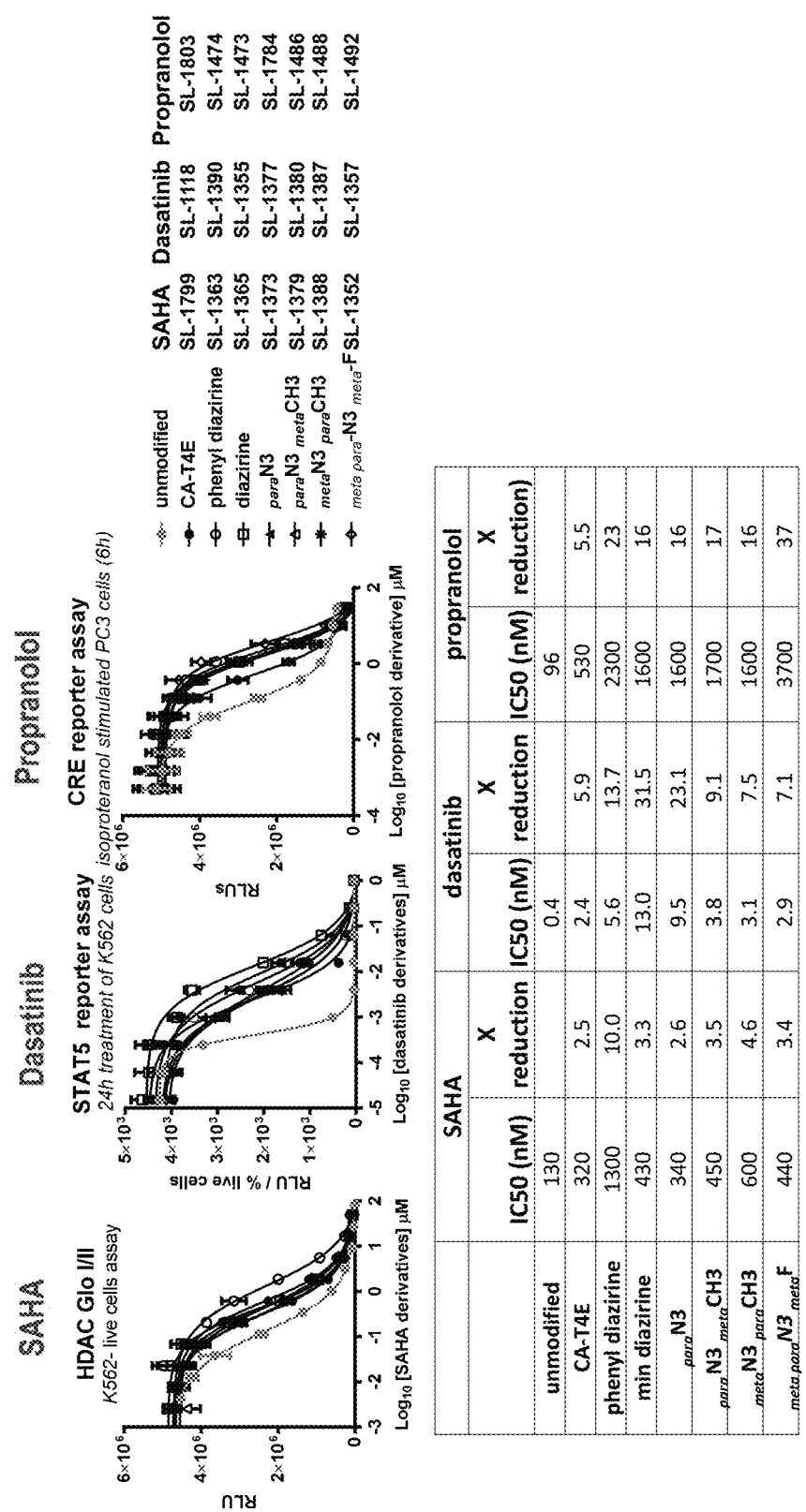
FIG. 25. Influence of chloroalkane tags on compounds' phenotypic potencies.

This example demonstrates the generally small influence of the PRG/cleavable chloroalkane on the phenotypic potency of three model compounds (FIG. 25). SAHA is a broad histone deacetylase (HDAC's) inhibitor. K562 cells ($2 \times 10^5$ cells/mL) were treated with serial dilution of SAHA or a derivative having cleavable chloroalkane tag (+/−a PRG) for 2 hours and then tested for intracellular HDAC activity using the non-lytic HDAC-Glorm I/II assay (Promega). Results revealed high cellular potency against HDAC class I/IIb with IC50 values of 0.1 μM and 0.3-1 μM for SAHA and chloroalkane derivatives (depending on the PRG group), respectively. Dasatinib is a broad kinase inhibitor targeting the BCR-ABL oncogenic pathway, thereby reducing the downstream activation of STAT5. K-562 cells transiently expressing a STAT5 reporter ($2 \times 10^5$ cells/mL) were treated with serial dilution of dasatinib or a derivative having cleavable chloroalkane tag (+/−a PRG) for 24 hours and then tested for expression of the STAT5 reporter. Results indicated inhibited expression of a STAT5 reporter with IC50 values of 0.4 nM and 2.4-13 nM for dasatinib and dasatinib derivatives (depending on the PRG group), respectively. Propranolol is a beta blocker targeting the P-adrenergic receptors. PC3 cells transiently expressing a CRE reporter ($2 \times 10^5$ cells/mL) and stimulated with 400 nM isoproterenol were treated with serial dilution of propranolol or a derivative having cleavable chloroalkane tag (+/−a PRG) for 6 hours and then tested for expression of the CRE reporter. Results indicated inhibited expression of the CRE reporter with IC50 values of 96 nM and 0.5-3.7 μM for propranolol and the chloroalkane derivative (depending on the PRG group), respectively. Together these results demonstrate the generally small influence of the photoreactive chloroalkane tag on a compound cellular potency and membrane permeability.

Example 5

Figure 26:
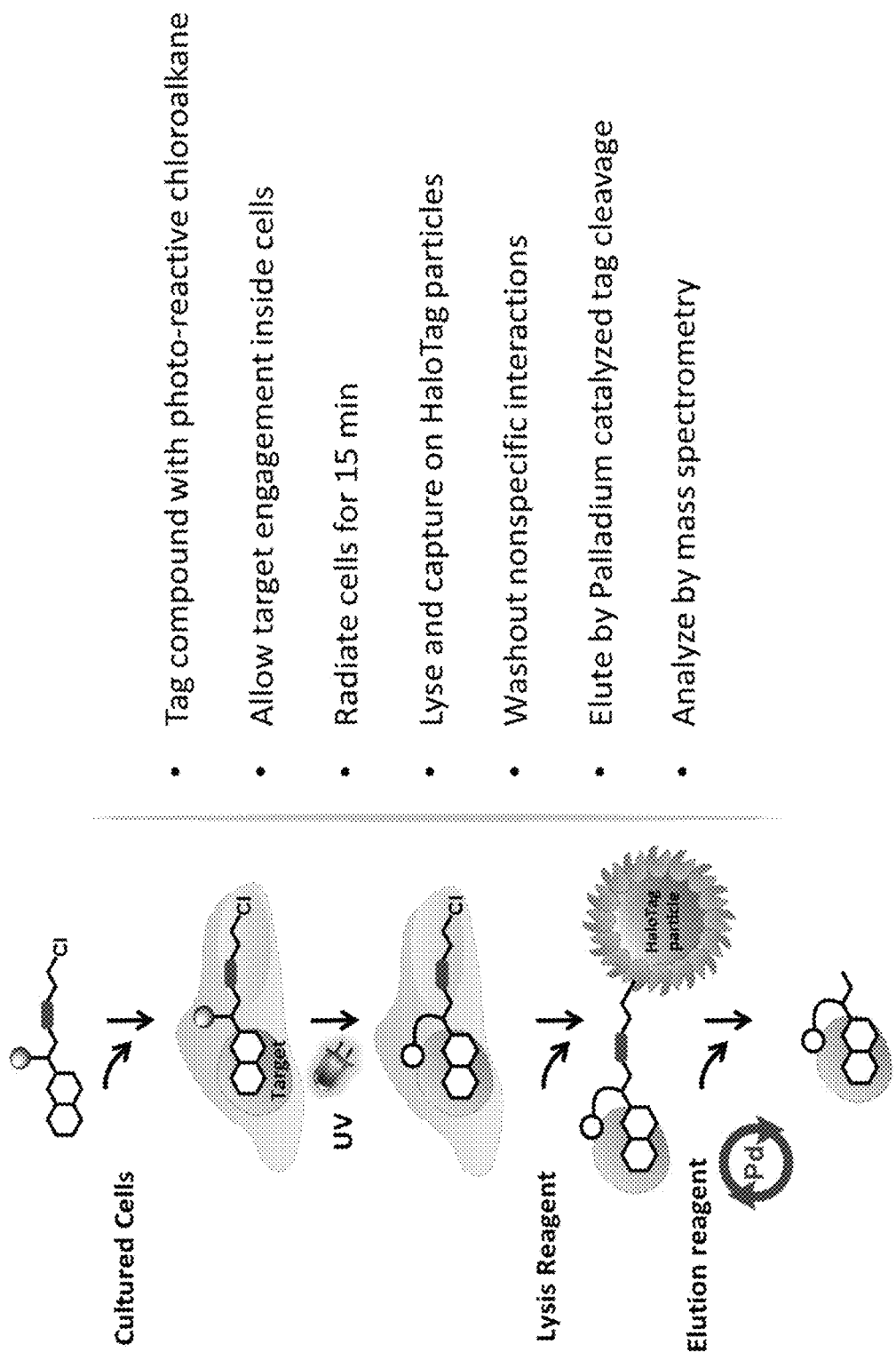
FIG. 26. Schematic representation of an exemplary workflow utilizing a photoaffinity chloroalkane probe to enrich the targets of a bioactive compound.
Figure 27:
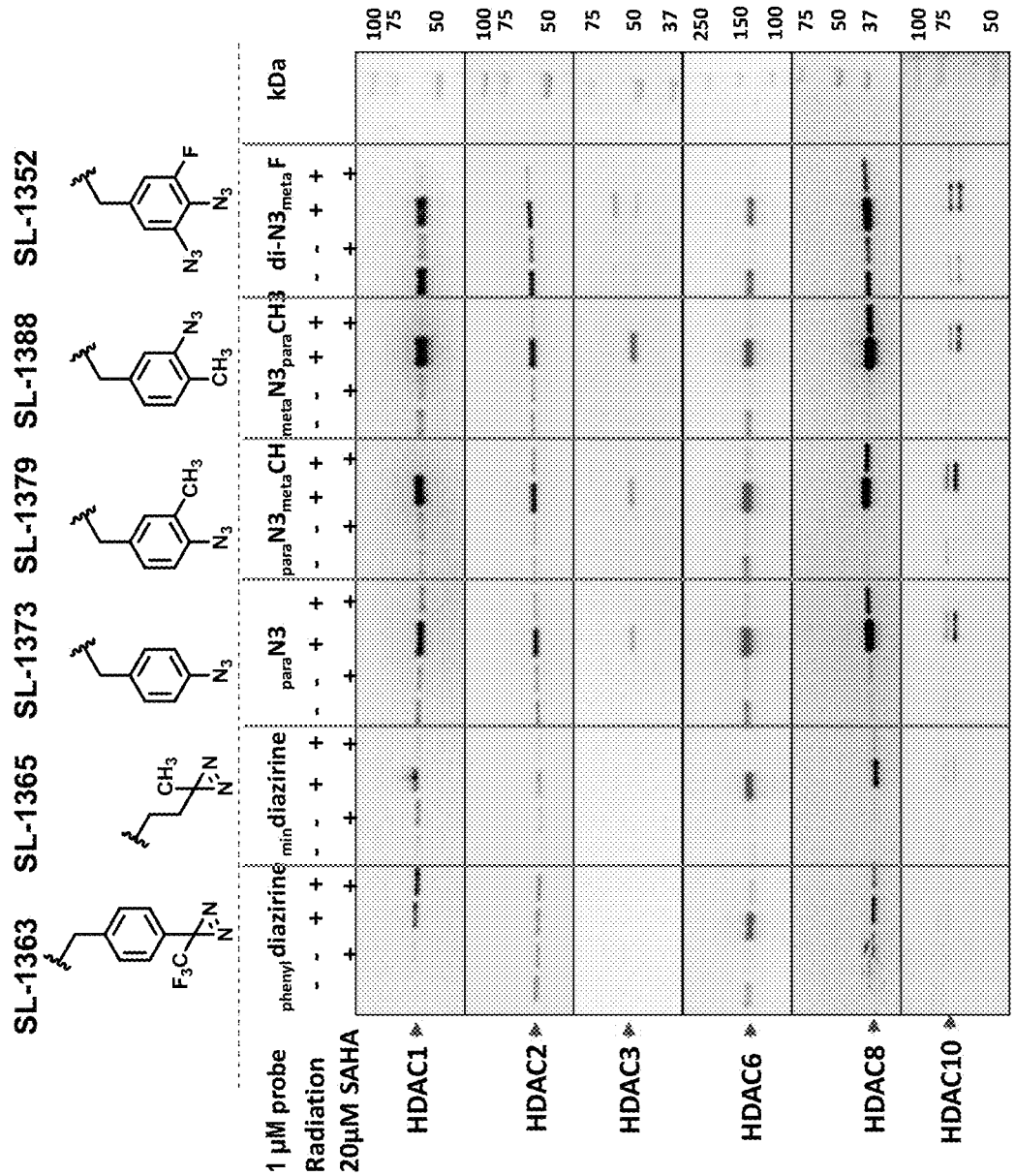
FIG. 27. Western analysis comparing the influence of PRG groups on enrichment efficiencies of SAHA targets from K562 cells in the presence and absence of UV irradiation.

This example demonstrates the capacity of the aryllazides-cleavable chloroalkane probes to enrich the endogenous targets for SAHA. FIG. 26 provides schematic illustration of the enrichment workflow. Briefly, K562 cells were plated in 100 mm dishes at $2 \times 10^6$ cell/mL and treated with a final concentration of 1 μM PRG-cleavable chloroalkane SAHA probes in the presence or absence of 20 μM SAHA. Following 2.5 hours equilibrium binding, cells were irradiated for 15 minutes while control cells were not irradiated. Media was then removed, and cells were washed with PBS, lysed, and centrifuged at 3000×g for 1 min. Clear lysates were added to 30 μL of settled paramagnetic HaloTag® beads and incubated overnight with constant mixing. Following binding, the unbound fractions were removed, the HaloTag® paramagnetic beads were washed 5×, and captured targets were released from the beads by palladium-catalyzed cleavage (ACS Chem. Biol., 2016, 11, 2608; herein incorporated by reference in its entirety). The released targets were subjected to western blot analysis (FIG. 27) with anti-HDAC1 antibody (ABCAM); anti-HDAC2 antibody (ABCAM); anti-HDAC6 antibody (Cell signaling); anti-HDAC3 antibody (Cell signaling); anti-HDAC8 antibody (ABCAM); and anti-HDAC10 antibody (ABCAM). Results in FIG. 27 demonstrate the requirement for UV irradiation for efficient enrichment, and the capacity of arylazides probes to provide enhanced enrichment of all the known SAHA targets including low affinity targets (HDAC8) and low abundance targets (HDAC3, HDAC6 and HDAC10). 3-fluoro-4,5-phenyldiazide displayed relatively high enrichment for most targets even without irradiation suggesting an additional mechanism to stabilize probe-target interaction.

Example 6

Figure 28:
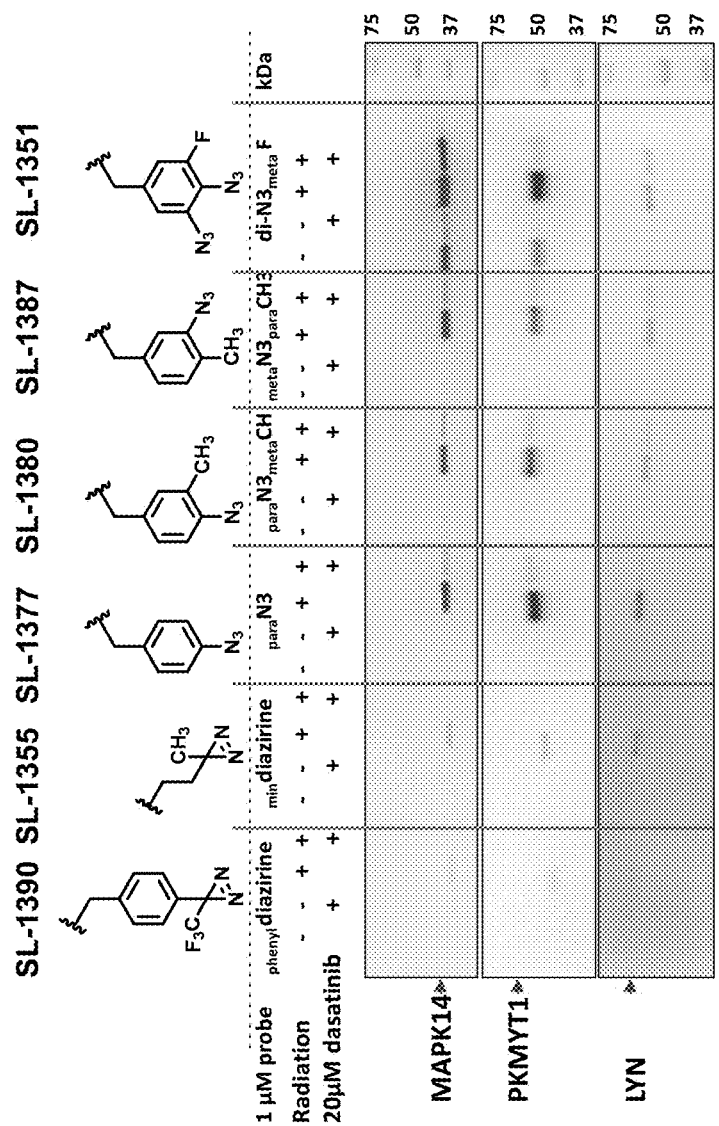
FIG. 28. Western analysis comparing the influence of PRG groups on enrichment efficiencies of dasatinib targets from K562 cells in the presence and absence of UV irradiation.
Figure 29A:
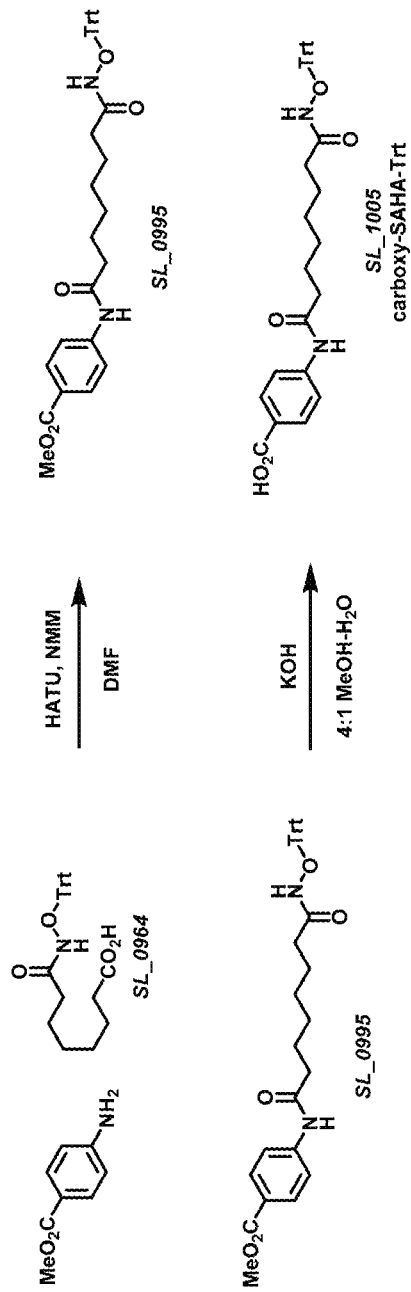
FIG. 29 Synthesis of carboxylate modified bioactive agents (A) SAHA-carboxylate; (B) dasatinib carboxylate; and (C) propranolol carboxylate.
Figure 29B:
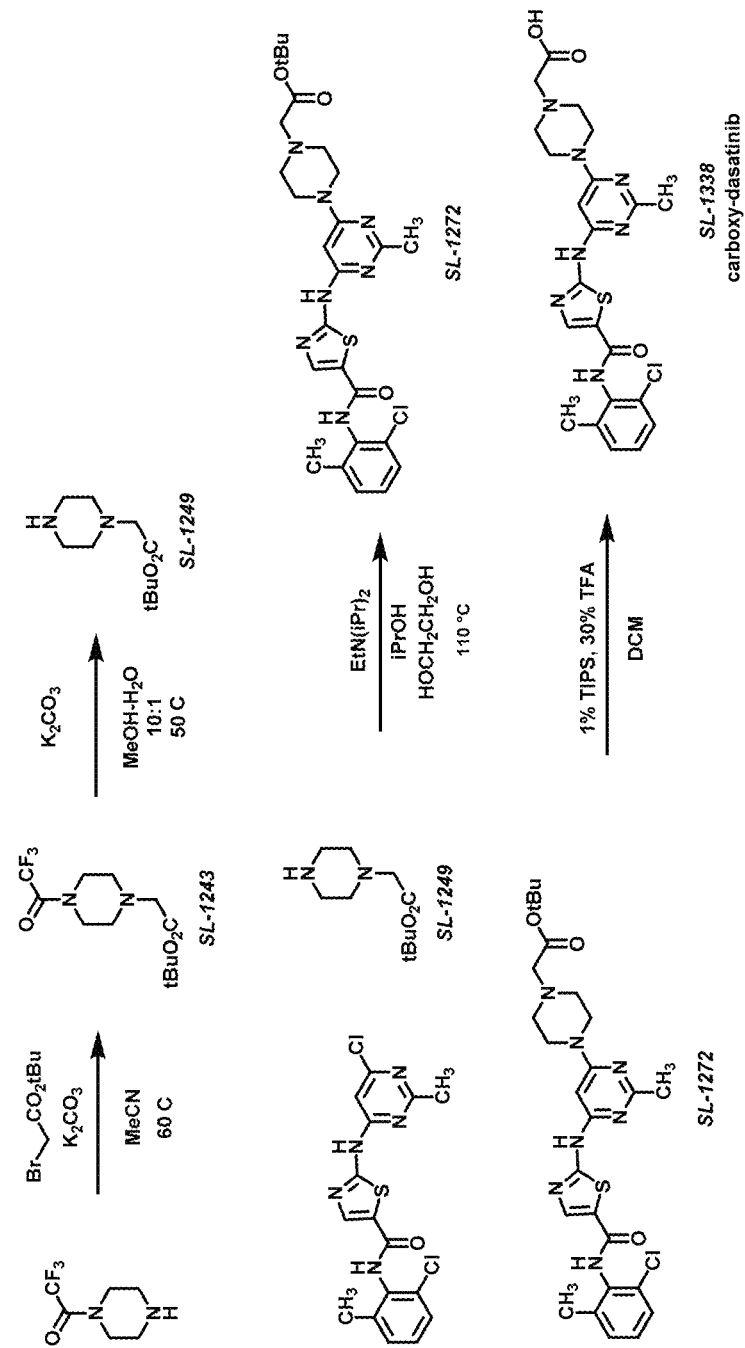
Figure 29C:
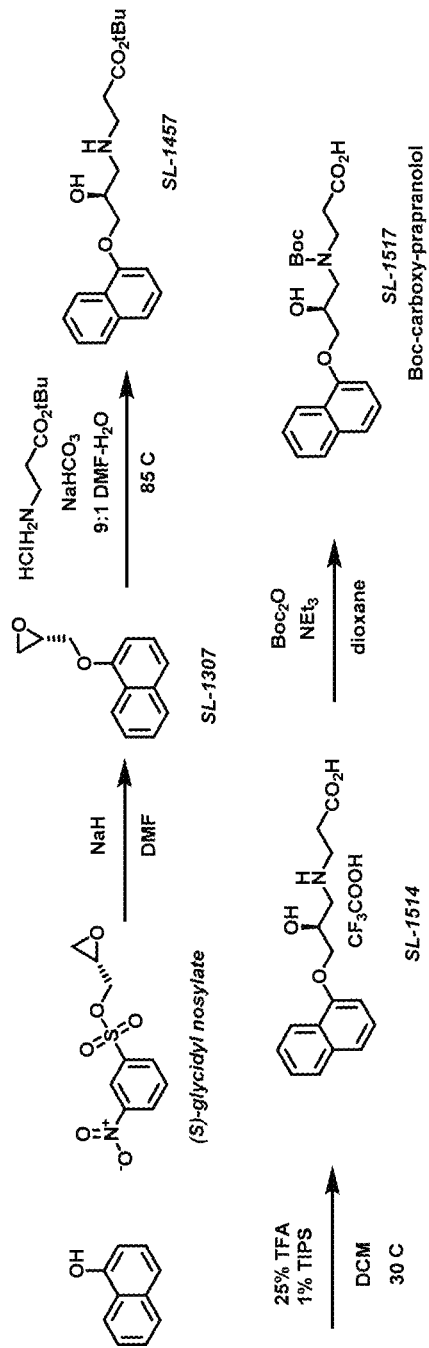
Figure 30:
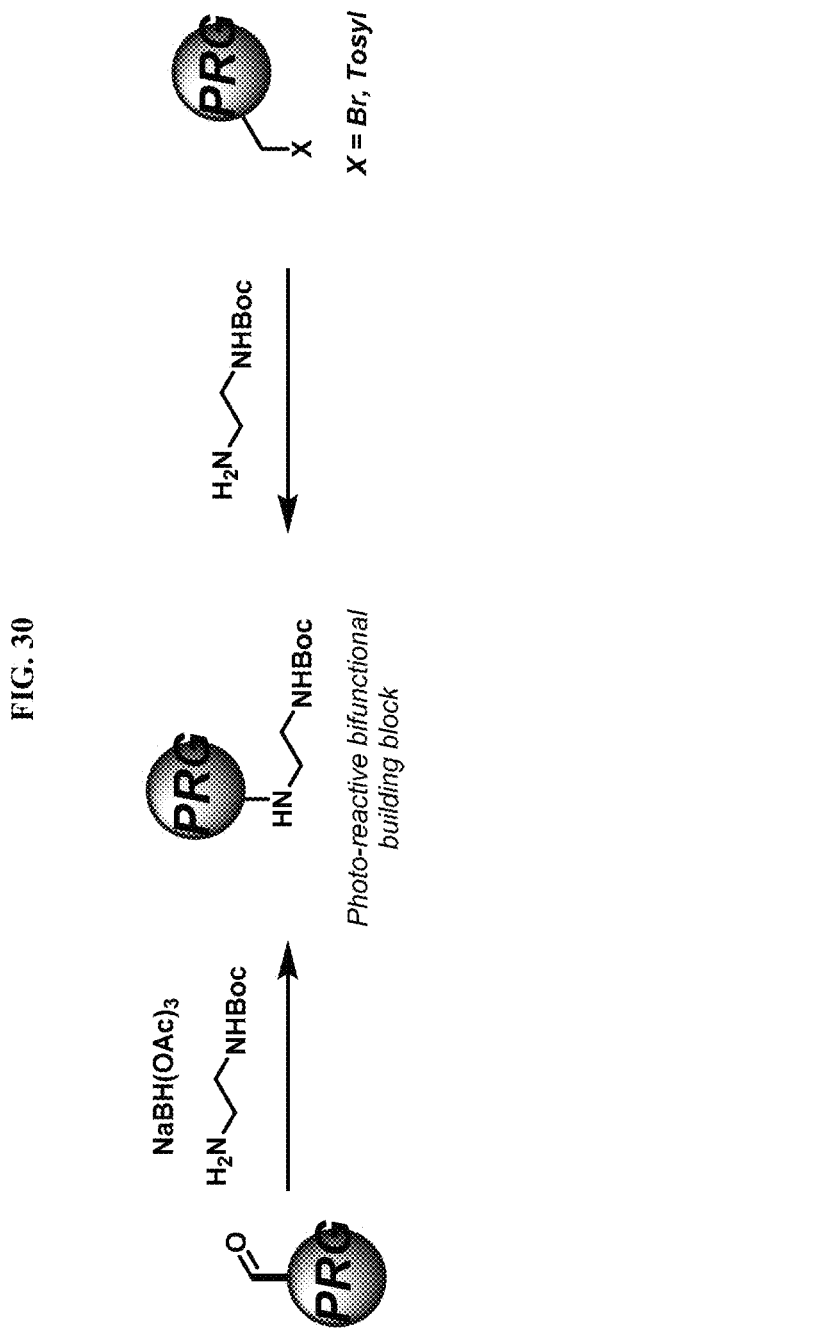
FIG. 30. Exemplary general scheme for synthesis of the bifunctional PRG building blocks.
Figure 31:
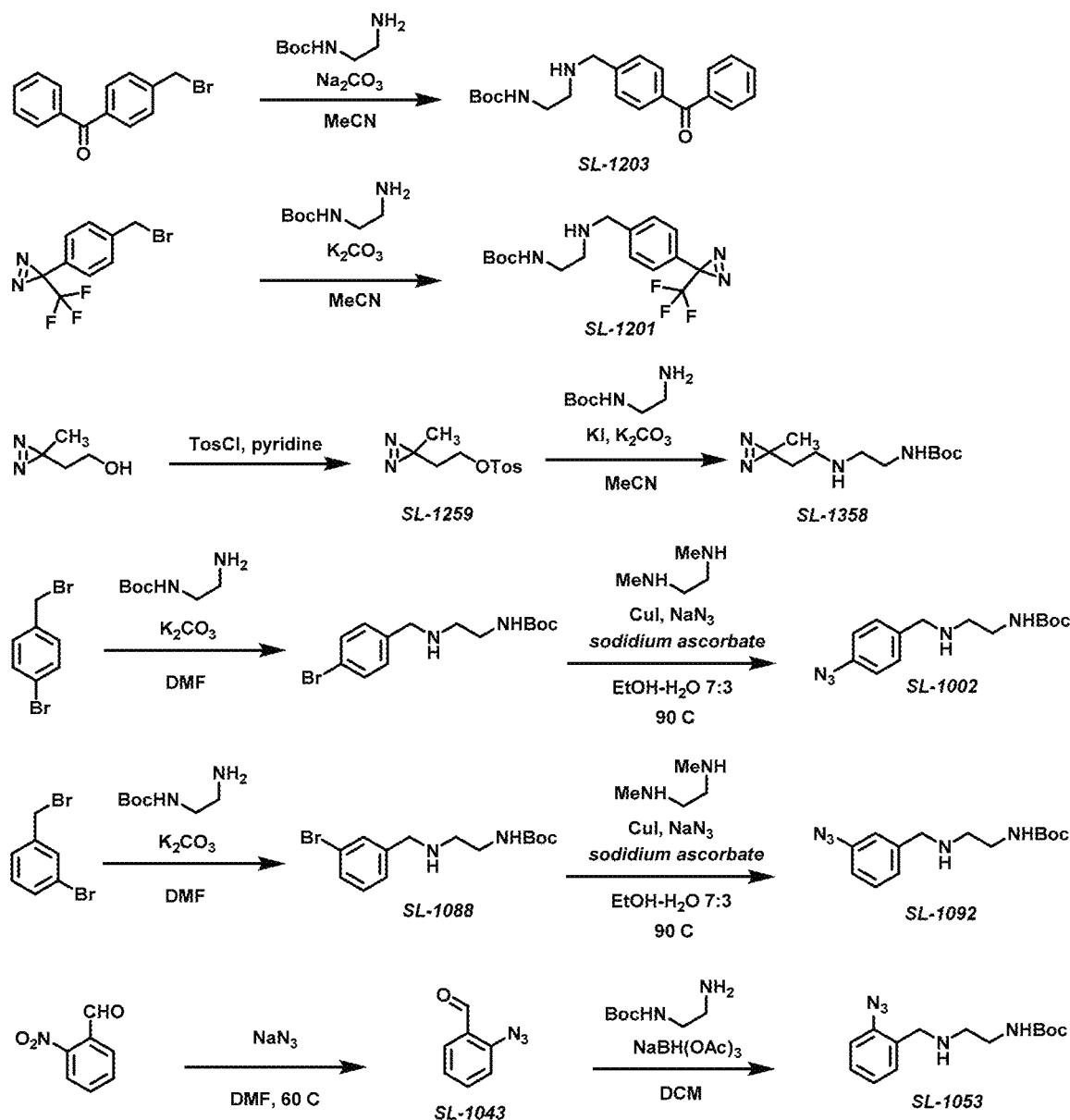
FIG. 31. Exemplary synthesis of bifunctional PRG building blocks.
Figure 31:
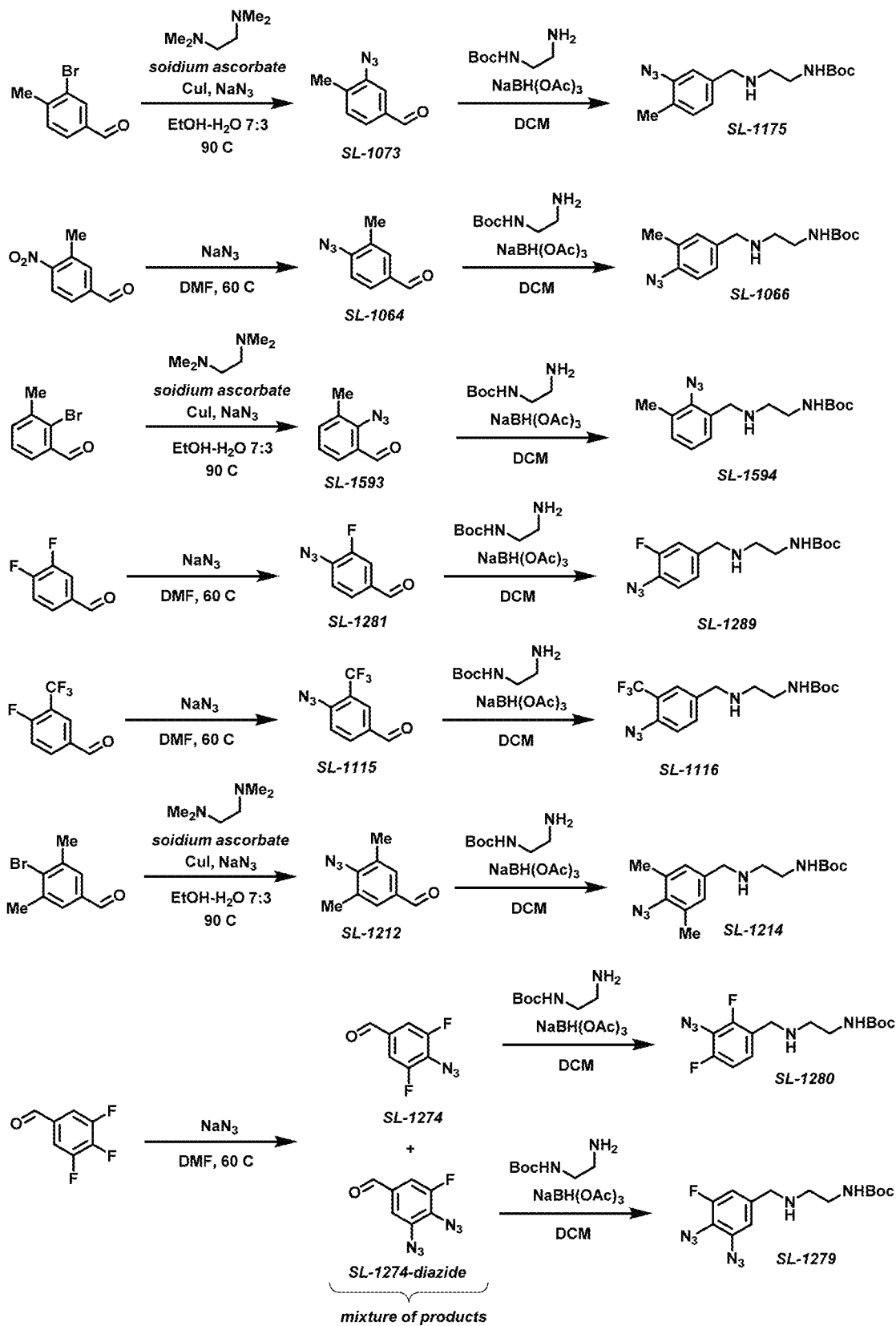
Figure 31:
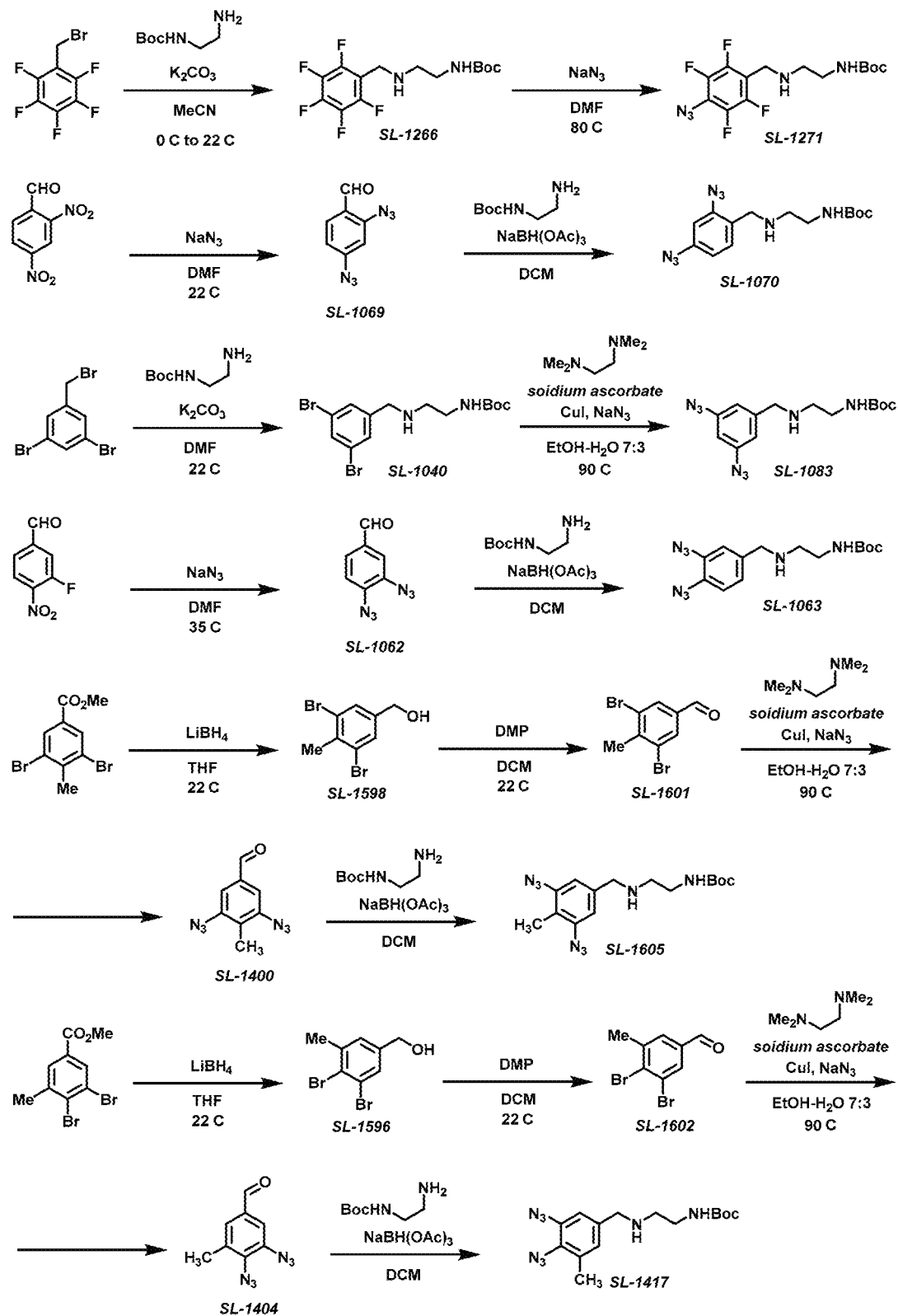

This example demonstrates the capacity of the arylazides-cleavable chloroalkane probes to enrich the endogenous targets for dasatinib. FIG. 26 provides schematic illustration of the enrichment workflow. Briefly, K562 cells were plated in 100 mm dishes at $2 \times 10^6$ cell/mL and treated with a final concentration of 1 μM PRG-cleavable chloroalkane dasatinib probes in the presence or absence of 20 μM dasatinib. Following 2.5 hours equilibrium binding, cells were irradiated for 15 minutes while control cells were not irradiated. Media was then removed, and the cells then washed with PBS, lysed, and centrifuged at 3000×g for 1 min. Clear lysates were added to 30 μL of settled paramagnetic HaloTag® beads and incubated overnight with constant mixing. Following binding, the unbound fractions were removed, the HaloTag® paramagnetic beads were washed 5×, and captured targets were released from the beads by palladium catalyzed cleavage. The released targets were subjected to western blot analysis (FIG. 28) with anti-MAPK14 antibody (ABCAM), anti-PKMYT1 antibody (Cell signaling), and anti-LYN antibody (cell signaling). Results in FIG. 28 demonstrate the requirement for UV irradiation for efficient enrichment, and the capacity of arylazides probes to provide enhanced enrichment of known dasatinib targets. 3-Fluoro-4,5-phenyldiazide displayed relatively high enrichment even without irradiation, suggesting an additional mechanism to stabilize probe-target interaction.

Example 7

Synthesis and Characterization of Probes and Reagents

Synthesis of Carboxy-SAHA:

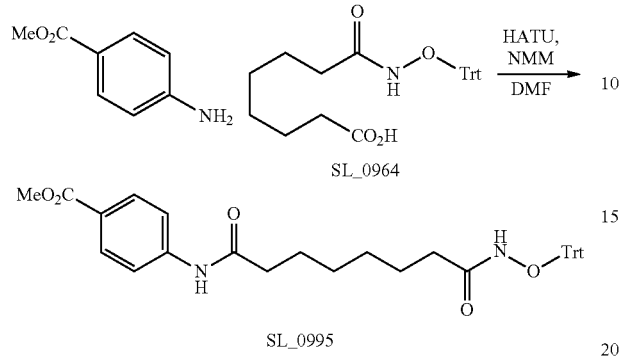

To a solution of methyl 4-aminobenzoate (190 mg, 1.26 mmol) in DMF (75 mL), HATU (597 mg, 1.57 mmol) and N-methylmorpholine (0.97 mL, 8.8 mmol) followed by SL_0964 (524 mg, 1.26 mmol) was added. The resulting solution was stirred at 22° C. for 24 hours at which point LCMS analysis indicated full consumption of starting material. Solvent was removed under reduced pressure, and the crude residue was purified by silica gel chromatography (0→10% MeOH/DCM, silica was neutralized with 0.5% trimethylamine in DCM during equilibration) to provide 350 mg (49% yield) of anilide SL_0995 as a white solid. $^{1}$H-NMR (400 MHz, DMSO-d6) δ 10.20 (s, 1H), 10.17 (s, 1H), 7.90 (app. d, J=8.7 Hz, 2H), 7.73 (app. d, J=8.7 Hz, 2H), 7.47-7.08 (m, 15H), 3.81 (s, 3H), 2.29 (t, J=7.4 Hz, 2H), 1.77 (t, J=7.3 Hz, 2H), 1.49 (p, J=7.4 Hz, 2H), 1.28-1.07 (m, 4H), 1.03-0.93 (m, 2H); MS (SI) Calc'd for $C_{35}H_{35}N_2O_5$ [M–H]– 563.26, found 563.40.

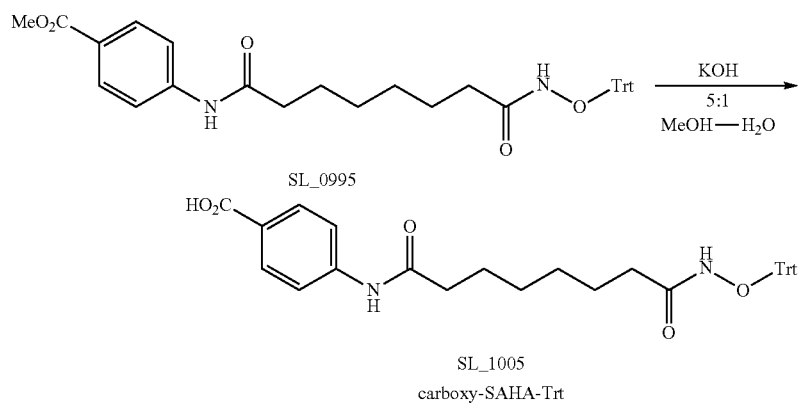

To a suspension of SL_0995 (350 mg, 620 μmol) in MeOH (25 mL) and H$_2$O (5 mL), KOH (70 mg, 1.2 mmol) was added. The resulting suspension was gently heated until a clear solution formed and left stirred at 40° C. for 24 hours at which point LCMS analysis indicated full consumption of starting material. The reaction mixture was passed through the pad of DOVEX 50WX4 resin. Resin was washed with extra 50 mL MeOH. Solutions were combined and concentrated to provide 330 mg (97% yield) of acid SL_1005 as a white solid. $^{1}$H-NMR (400 MHz, DMSO-d6) δ 12.68 (s, 1H), 10.16 (s, 2H), 7.87 (d, J=8.6 Hz, 2H), 7.70 (d, J=8.7 Hz, 2H), 7.32 (d, J=4.2 Hz, 15H), 2.28 (t, J=7.5 Hz, 1H), 1.77 (m, 2H), 1.49 (m, J=7.6 Hz, 2H), 1.15 (m, 4H), 0.99 (m, 2H); MS (SI) Calc'd for $C_{34}H_{33}N_2O_5$ [M–H]– 549.24, found 549.07.

Synthesis of Carboxy-Dasatinib:

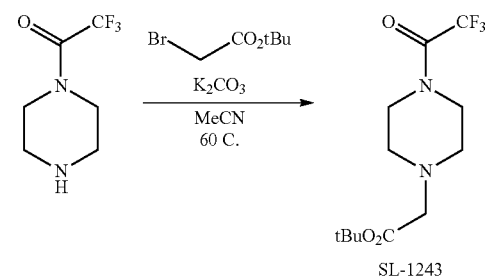

To a solution of trifluoroacetylpiperazine (2.00 g, 11.0 mmol) in dry MeCN (60 mL), K$_2$CO$_3$ (3.04 g, 22.0 mmol) followed by tert-butyl 2-bromoacetate (1.62 mL, 11.0 mmol) was added. The resulting solution was heated to 60° C. under Ar for 22 hours at which point LCMS analysis indicated full consumption of starting material. The reaction mixture was filtered through the pad of celite, and the pad washed with extra MeCN (100 mL) and combined with the filtrate. Solvent was removed under reduced pressure, and the crude residue was purified by silica gel chromatography (0→100% EtOAc/Heptane) to provide 2.34 g (72% yield) of ester SL-1243 as a white solid. H-NMR (400 MHz, DMSO-d6) δ 3.59-3.52 (m, 4H), 3.19 (s, 2H), 2.70-2.56 (m, 4H), 1.41 (s, 9H); MS (SI) Calc'd for $C_{12}H_{20}F_3N_2O_3$ [M+H]+ 297.14, found 297.07.

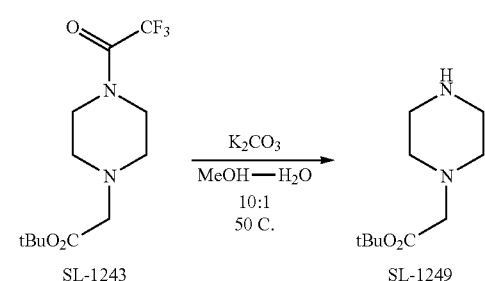

To a solution of SL-1243 (2.34 g, 7.90 mmol) in MeOH (40 mL) and water (4 mL), K$_2$CO$_3$ (2.18 g, 15.8 mmol) was added. The resulting suspension was stirred at 50° C. for 2 hours at which point HPLC analysis indicated full consumption of starting material. MeOH was removed under reduced pressure, and the residue was partitioned between water (50 mL) and EtOAc (100 mL). Aqueous layer was additionally washed with EtOAc (100 mL), organics were combined and dried MgSO4, and solvent was removed under reduced pressure to provide 605 mg (38% yield) of yellow oil. $^1$H NMR (400 MHz, DMSO-d6) δ 3.05 (s, 2H), 2.76-2.68 (m, 4H), 2.45-2.41 (m, 4H), 1.40 (s, 9H).

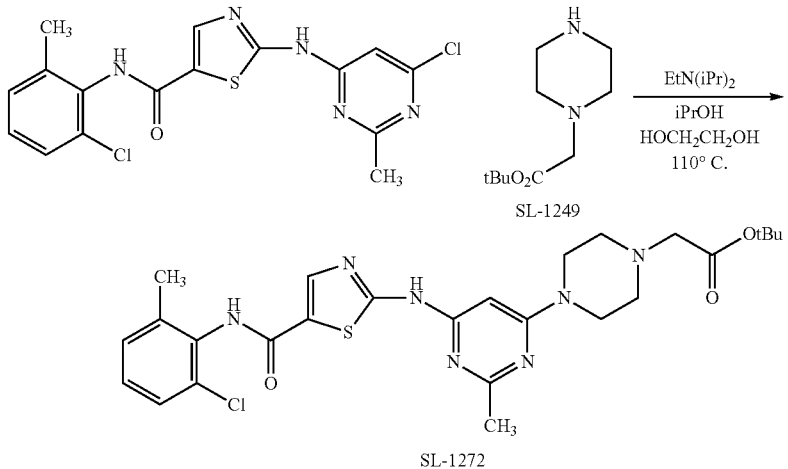

A 50 mL round-bottom flask equipped with stir bar and a condenser was charged with 2-((6-chloro-2-methylpyrimidin-4-yl)amino)-N-(2-chloro-6-methylphenyl)thiazole-5-carboxamide (380 mg, 1.90 mmol), SL-1249 (471 mg, 7.59 mmol), isopropyl alcohol (3 mL), ethylene glycol (3 mL), and EtN(iPr)$_2$ (1 mL). The resulting suspension was heated to 110° C. for 20 hours at which point HPLC analysis indicated full consumption of starting material. Precipitate filtered out, and both filtrate and precipitate were purified by preparative RP HPLC (5→95% MeCN/H$_2$O buffered with 0.5% TFA) to provide 375 mg (35% yield) of ester SL-1272 as a white solid. $^1$H NMR (400 MHz, DMSO-d6) δ 11.62 (s, 1H), 9.89 (s, 1H), 8.23 (s, 1H), 7.40 (dd, J=7.4, 2.0 Hz, 1H), 7.35-7.09 (m, 2H), 6.12 (s, 1H), 4.42-3.49 (m, 4H), 3.27-2.98 (m, 4H), 2.44 (s, 3H), 2.24 (s, 3H), 1.48 (s, 9H).

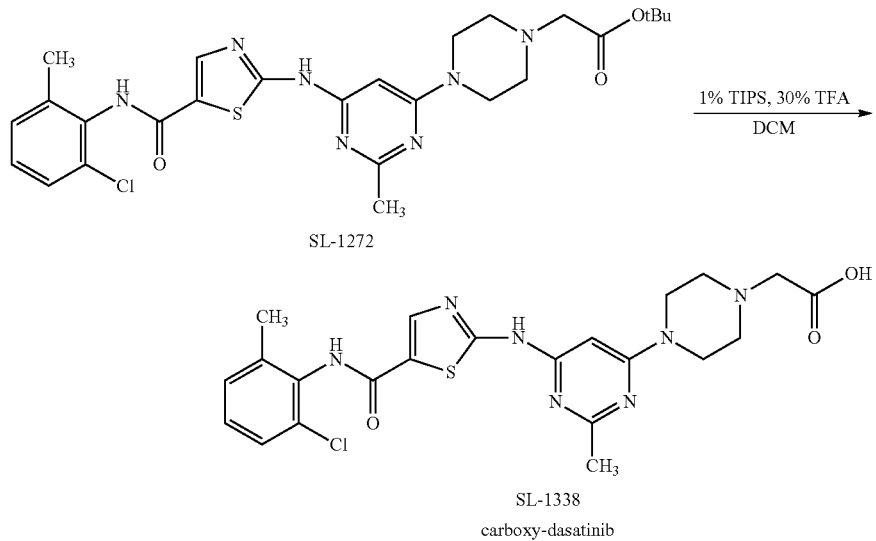

To a suspension of SL-1272 in DCM (10 mL), TiPS (0.15 mL) followed by TFA (5 mL) was added, the resulting solution stirred for 15 minutes, and another 5 mL TFA was added. The resulting solution was stirred at 22° C. for 3 hours at which point HPLC analysis indicated full consumption of starting material. Volatiles were removed under vacuum, and the residue was filtered and dried under vacuum to provide 180 mg (96% yield) of SL-1338 as a white solid. $^1$H NMR (400 MHz, DMSO-d6) δ 11.63 (s, 1H), 9.90 (s, 1H), 8.24 (s, 1H), 7.64-7.36 (m, 1H), 7.36-7.13 (m, 2H), 6.13 (s, 1H), 4.11 (s, 4H), 2.44 (br. s, 4H), 2.44 (s, 3H). 2.24 (s, 3H); MS (SI) Calc'd for $C_{22}H_{24}ClN_7O_3S$ [M+H]+ 501.14, found 502.12.

Synthesis of Carboxy-(S)-Propranolol:

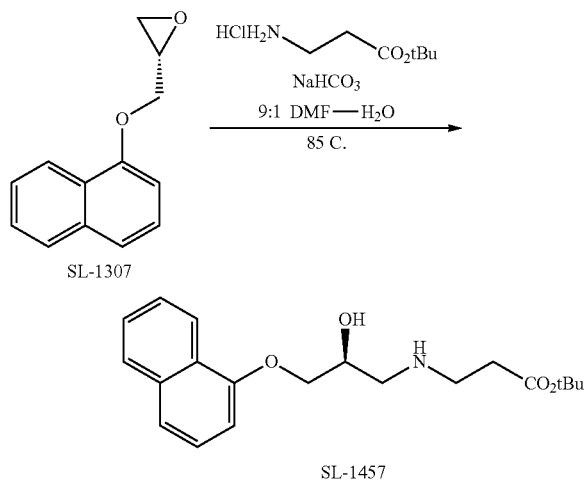

SL-1307

SL-1457

To a solution of (S)-2-((naphthalen-1-yloxy)methyl)oxirane (308 mg, 1.54 mmol, prepared according to *J. Org. Chem.* 1989, 54, 1295-1304) and β-alanine t-butyl ester hydrochloride (699 mg, 3.85 mmol) in 9:1 DMF-water (10 mL), NaHCO$_3$(323 mg, 3.85 mmol) was added. The stirred suspension was heated to 85° C. for 21 hours at which point HPLC analysis indicated full consumption of starting material. The reaction mixture was filtered, and volatiles were removed under reduced pressure. The crude residue was purified by silica gel chromatography (0→20% MeOH/DCM) to provide 181 mg (34% yield) of ester SL-1457 as a yellow oil. $^1$H NMR (400 MHz, DMSO-d6) δ 8.23 (ddd, J=7.4, 2.3, 0.9 Hz, 1H), 7.89-7.77 (m, 1H), 7.50 (dtd, J=8.1, 6.8, 5.2 Hz, 2H), 7.45 (dt, J=8.5, 0.9 Hz, 1H), 7.40 (dd, J=8.3, 7.4 Hz, 1H), 6.93 (dd, J=7.5, 1.2 Hz, 1H), 5.08 (d, J=4.8 Hz, 1H), 4.12 (dd, J=9.2, 4.4 Hz, 1H), 4.06-3.97 (m, 1H), 2.80-2.72 (m, 3H), 2.72-2.58 (m, 1H), 2.34 (t, J=6.7 Hz, 2H), 1.83 (s, 1H), 1.37 (s, 9H); HRMS (SI) Calc'd for $C_{20}H_{28}NO_4$ [M+H]+ 346.2013, found 346.2013.

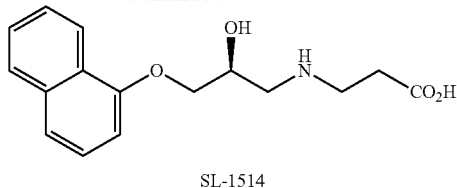

SL-1514

To a solution of SL-1457 (430 mg, 1.24 mmol) in DCM (20 mL), TiPS (0.26 mL) followed by TFA (6 mL) was added. The resulting solution was heated at 30° C. for 4 hours at which point HPLC analysis indicated full consumption of starting material. Volatiles were removed under reduced pressure, and crude residue dissolved in 10 mL MeOH, and volatiles removed under vacuum. The crude residue was dried under high vacuum and used in the next step without further purification.

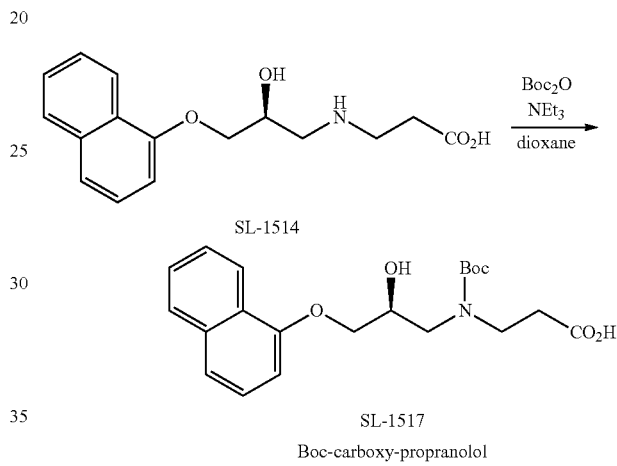

SL-1514

SL-1517
Boc-carboxy-propranolol

To a solution of SL-1514 (540 mg, 1.34 mmol) in dioxane (25 mL), trimethylamine (1.31 mL, 9.37 mmol) followed by Boc$_2$O (877 mg, 4.02 mmol) was added. The resulting solution was stirred at 22° C. for 21 hours at which point HPLC analysis indicated full consumption of starting material. Volatiles were removed under reduced pressure, crude residue dissolved in 10 mL MeOH, and volatiles removed under vacuum. The crude residue was purified by silica gel chromatography (0→20% MeOH/DCM) to provide 397 mg (76% yield) of acid SL-1517 as a clear glassy residue. $^1$H NMR (400 MHz, DMSO-d6, reported for mixture of rotamers) δ $^1$H NMR (400 MHz, DMSO-d6) δ 12.18 (s, 1H), 8.26 (d, J=8.0 Hz, 1H), 7.98-7.74 (m, 1H), 7.59-7.49 (m, 2H), 7.47 (d, J=8.2 Hz, 1H), 7.41 (t, J=7.9 Hz, 1H), 6.94 (m, 1H), 5.31 (m, 1H), 4.14 (m, 1H), 4.05 (m, 2H), 3.65-3.58 (m, 1H), 3.48 (m, 2H), 3.30-3.20 (m, 1H), 1.39 (s, 4.5H), 1.35 (s, 4.5H); MS (SI) Calc'd for $C_{21}H_{26}NO_6$ [M-H]- 388.18, found 388.09.

Synthesis of Photoreactive Bifunctional Building Blocks:

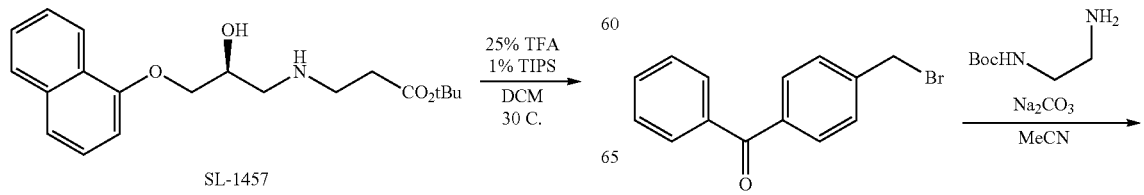

SL-1457

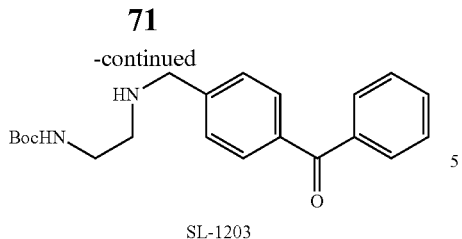

SL-1203

To a solution of N-Boc-ethylenediamine (571 mg, 3.57 mmol) in MeCN (25 mL), Na₂CO₃ (378 mg, 3.57 mmol) followed by 4-(bromomethyl)benzophenone (327 mg, 1.19 mmol) was added. The resulting solution was stirred at 22° C. for 22 hours at which point HPLC analysis indicated full consumption of starting material. The reaction mixture was filtered, and volatiles removed under reduced pressure. The crude residue was purified by silica gel chromatography (0→10% MeOH/DCM) to provide 350 mg (83% yield) of amine SL-1203. ¹H NMR (400 MHz, DMSO-d6) δ 7.82-7.60 (m, 5H), 7.60-7.53 (m, 2H), 7.53-7.37 (m, 2H), 6.91-6.64 (m, 1H), 3.79 (s, 2H), 3.04 (q, J=6.2 Hz, 2H), 2.55 (t, J=6.5 Hz, 2H), 1.37 (s, 9H); MS (SI) Calc'd for C₂₁H₂₇N₂O₃ [M+H]+ 355.20, found 354.62.

SL-1358

To a solution of N-Boc-ethylenediamine (101 mg, 629 μmol) in MeCN (10 mL), K₂CO₃ (130 mg, 944 μmol), and KI (10.4 mg, 629 μmol) followed by SL-1259 (80.0 mg, 315 μmol, prepared according to J Am. Chem. Soc. 2014, 136, 10777-10782) was added. The resulting solution was stirred at 80° C. for 19 hours at which point HPLC analysis indicated full consumption of starting material. The reaction mixture was filtered, and volatiles removed under reduced pressure. The crude residue was purified by silica gel chromatography (0→100% MeOH/DCM) to provide 66 mg (87% yield) of amine SL-1358. ¹H NMR (400 MHz, Methanol-d4) δ 3.20 (t, J=6.2 Hz, 2H), 2.74 (t, J=5.9 Hz, 2H), 2.61 (t, J=7.4 Hz, 2H), 1.57 (dd, J=8.3, 7.2 Hz, 2H), 1.44 (s, 9H), 1.03 (s, 3H). MS (SI) Calc'd for C₁₁H₂₃N₄O₂ [M+H]+ 243.18, found 243.05.

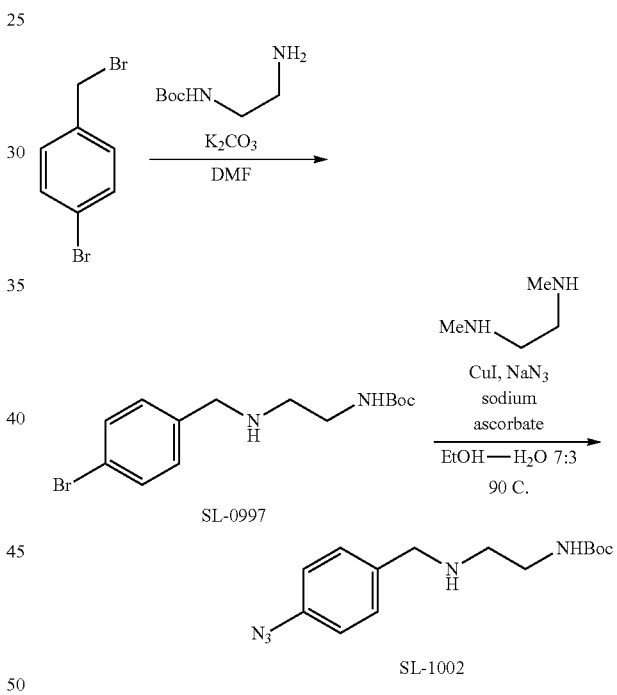

SL-1201

To a solution of N-Boc-ethylenediamine (250 mg, 1.56 mmol) in MeCN (30 mL), K₂CO₃ (215 mg, 1.56 mmol) followed by 4-[3-(trifluoromethyl)-3H-diazirin-3-yl]benzyl bromide (145 mg, 520 μmol) was added. The resulting solution was stirred at 22° C. for 24 hours at which point HPLC analysis indicated full consumption of starting material. The reaction mixture was filtered, and volatiles removed under reduced pressure. The crude residue was purified by silica gel chromatography (0→20% MeOH/DCM) to provide 115 mg (62% yield) of amine SL-1201. MS (SI) Calc'd for C₁₆H₂₂F₃N₄O₂ [M+H]+ 359.17, found 359.47.

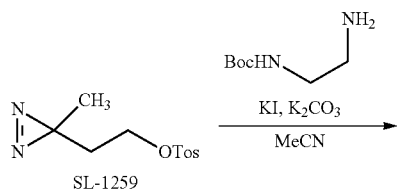

SL-1259

To a solution of N-Boc-ethylenediamine (962 mg, 6.00 mmol) in MeCN (150 mL), K₂CO₃ (1.11 g, 8.00 mmol) followed by 4-bromobenzyl bromide (1.00 g, 4.00 mmol) was added. The resulting solution was stirred at 22° C. for 23 hours at which point HPLC analysis indicated full consumption of starting material. The reaction mixture was filtered, and volatiles removed under reduced pressure. The crude residue was purified by silica gel chromatography (0→20% MeOH/DCM, and the column equilibrated with 0.5% TEA/DCM) to provide 1.03 g (78% yield) of amine SL-0997 as a clear oil. ¹H NMR (400 MHz, DMSO-d6) δ 7.65-7.41 (m, 2H), 7.41-7.11 (m, 2H), 6.74 (t, J=5.8 Hz, 1H), 3.63 (s, 2H), 3.00 (q, J=6.3 Hz, 2H), 2.48 (m, 2H, overlap with DMSO-d5), 2.16 (s, 1H), 1.36 (s, 9H); MS (SI) Calc'd for C₂₁H₂₇N₂O₃ [M+H]+ 329.09, found 329.13.

A 50 mL round-bottom flask equipped with stir bar and a condenser with a rubber septum was charged with SL-0997 (510 mg, 1.55 mmol), sodium ascorbate (15.3 mg, 77.5 µmol), NaN₃ (201 mg, 3.10 mmol), and CuI (59 mg, 310 µmol). The flask was evacuated and backfilled with Ar (3 times) and left under Ar atmosphere. Degassed EtOH (14 mL) and degassed water (6 mL) were added through septa followed by 1,2-dimethylethylenediamine (21 mg, 233 µmol). The resulting suspension was heated to 90° C. for 45 minutes at which point HPLC analysis indicated full consumption of starting material. The reaction mixture was absorbed onto celite and dried under high vacuum. Purification by silica gel chromatography (0→100% MeOH/DCM) afforded 353 mg (78% yield) of amine SL-1002 as a yellow oil. ¹H NMR (400 MHz, DMSO-d6) δ 7.44-7.28 (m, 2H), 7.13-6.98 (m, 2H), 6.77 (t, J=5.8 Hz, 1H), 3.66 (s, 2H), 3.01 (q, J=6.3 Hz, 2H), 2.48 (m, 2H, overlap with DMSO-d5), 1.37 (s, 9H); MS (SI) Calc'd for C₂₁H₂₇N₂O₃ [M+H]+ 292.18, found 292.19.

followed by a degassed solution of 1,2-dimethylethylenediamine (24 mg, 273 µmol) in EtOH (4 mL). The resulting suspension was heated to 90° C. for 70 minutes at which point HPLC analysis indicated full consumption of starting material. The reaction mixture was poured into 10% aq. Na₂CO₃ solution (50 mL) and extracted 3× with 75 mL DCM. Organics were combined, dried over MgSO₄, filtered, and solvent removed under vacuum. Purification by silica gel chromatography (0→10% MeOH/DCM) afforded 388 mg (73% yield) of amine SL-1092 as a yellow oil. ¹H NMR (400 MHz, DMSO-d6) δ 7.34 (t, J=7.8 Hz, 1H), 7.13 (d, J=7.6 Hz, 1H), 7.09 (t, J=2.0 Hz, 1H), 6.96 (dd, J=8.1, 2.3 Hz, 1H), 6.73 (t, J=5.8 Hz, 1H), 3.67 (s, 2H), 3.01 (q, J=6.3 Hz, 2H), 1.36 (s, 9H); MS (SI) Calc'd for C₂₁H₂₇N₂O₃ [M+H]+ 292.18, found 292.24.

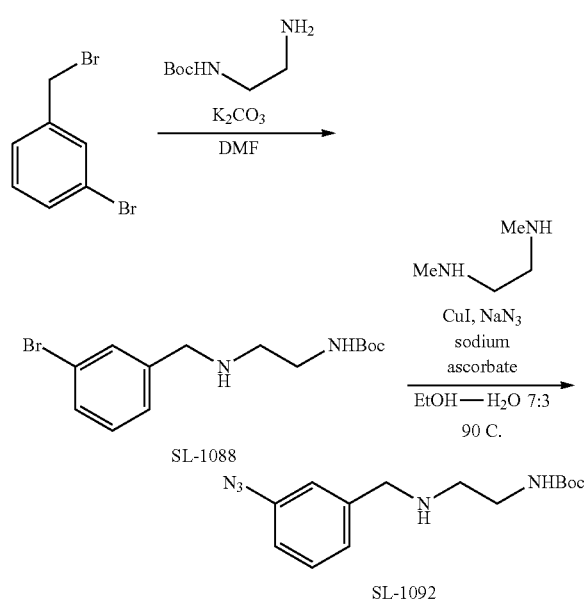

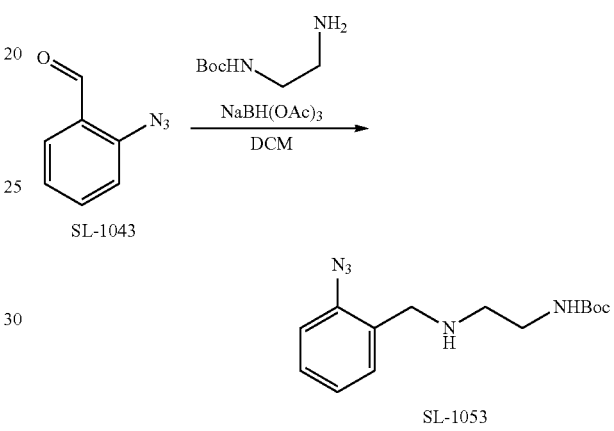

To a solution of N-Boc-ethylenediamine (606 mg, 3.78 mmol) in DMF (60 mL), K₂CO₃ (697 mg, 5.04 mmol) followed by 3-bromobenzyl bromide (630 g, 2.52 mmol) was added. The resulting solution was stirred at 22° C. for 25 hours at which point HPLC analysis indicated full consumption of starting material. The reaction mixture was filtered, and volatiles removed under reduced pressure. The crude residue was purified by silica gel chromatography (0→20% MeOH/DCM) to provide 670 mg (71% yield) of amine SL-1088 as a clear oil. ¹H NMR (400 MHz, DMSO-d6) δ 7.53 (t, J=1.9 Hz, 1H), 7.41 (dt, J=7.6, 1.7 Hz, 1H), 7.36-7.18 (m, 2H), 6.73 (t, J=5.7 Hz, 1H), 3.66 (s, 2H), 3.01 (q, J=6.3 Hz, 2H), 2.49 (m, 2H, overlap with DMSO-d5), 2.27 (s, 1H), 1.37 (s, 9H); MS (SI) Calc'd for C₂₁H₂₇N₂O₃ [M+H]+ 329.09, found 329.18.

A 50 mL round-bottom flask equipped with stir bar and a condenser with a rubber septum was charged with SL-1088 (600 mg, 1.82 mmol), sodium ascorbate (18.1 mg, 91.1 µmol), NaN₃ (237 mg, 3.64 mmol), and CuI (69 mg, 360 µmol). The flask was evacuated and backfilled with Ar (3× times) and left under Ar atmosphere. Degassed EtOH (10 mL) and degassed water (6 mL) were added through septa To a solution of N-Boc-ethylenediamine (491 mg, 3.07 mmol) in DCM (100 mL) and 2-azidobenzaldehyde (410 mg, 2.79 mmol, prepared according to Journal of the American Chemical Society, 2014,136, 15138), NaBH(OAc)₃ (1.48 g, 6.97 mmol) was added. The resulting solution was stirred at 22° C. for 5 hours at which point HPLC analysis indicated full consumption of starting material. The reaction mixture was quenched with aqueous 1M Na₂CO₃ (100 mL), and the resulting biphasic mixture was stirred for 1 hour. Organic layer was separated, and aqueous layer was extracted with additional DCM (100 mL). Organics were combined, dried over MgSO₄, filtered, and volatiles removed under reduced pressure. The crude residue was purified by silica gel chromatography (0→100% MeOH/DCM) to provide 553 mg (68% yield) of amine SL-1053. ¹H NMR (400 MHz, DMSO-d6) δ 7.39 (dd, J=7.5, 1.6 Hz, 1H), 7.34 (td, J=7.6, 1.7 Hz, 1H), 7.25 (dd, J=7.9, 1.2 Hz, 1H), 7.15 (td, J=7.4, 1.3 Hz, 1H), 6.81-6.60 (m, 1H), 3.60 (s, 2H), 3.01 (q, J=6.3 Hz, 2H), 1.36 (s, 9H); MS (SI) Calc'd for C₁₄H₂₂N₅O₂ [M+H]+ 292.18, found 291.80.

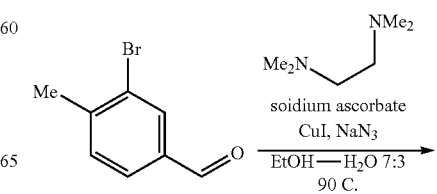

-continued

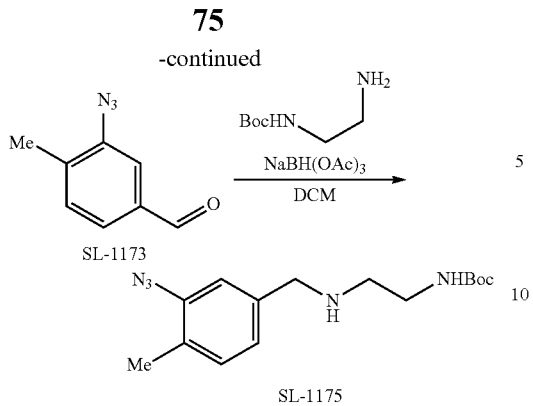

A 25 mL round-bottom flask equipped with stir bar and a condenser with a rubber septum was charged with 3-bromo-4-methylbenzaldehyde (795 mg, 3.99 mmol), sodium ascorbate (39.6 mg, 0.20 mmol), NaN₃ (519 mg, 7.99 mmol), and CuI (152 mg, 799 μmol). The flask was evacuated and backfilled with Ar (3× times) and left under Ar atmosphere. Degassed EtOH (7 mL) and degassed water (3 mL) were added through septa followed by 1,2-dimethylethylenediamine (23.0 mg, 600 μmol). The resulting suspension was heated to 90° C. for 3 hours at which point HPLC monitoring indicated that reaction stalled. The reaction mixture was poured into 10% aq. Na₂CO₃ solution (100 mL) and extracted 3× with 75 mL DCM. Organics were combined, dried over MgSO₄, filtered, and solvent removed under vacuum. Purification by silica gel chromatography (0→10% EtOAc/Heptane), afforded 57 mg (7% yield) of aldehyde SL-1173. $^1$H NMR (400 MHz, DMSO-d6) δ 9.99 (s, 1H), 7.74 (d, J=1.4 Hz, 1H), 7.64 (dd, J=7.7, 1.5 Hz, 1H), 7.48 (d, J=7.7 Hz, 1H), 2.25 (s, 3H); $^{13}$C NMR (100 MHz, DMSO-d6) δ 192.2, 139.0, 136.0, 135.6, 131.8, 126.0, 118.6, 17.4; MS (SI) Calc'd for $C_{21}H_{27}N_2O_3$ [M+H]+ 292.18, found 292.24.

To a solution of N-Boc-ethylenediamine (47 mg, 290 μmol) and SL-1173 (57 mg, 270 μmol) in DCM (5 mL), NaBH(OAc)₃ (140 mg, 660 μmol) was added. The resulting solution was stirred at 22° C. for 20 hours at which point HPLC analysis indicated full consumption of starting material. The reaction mixture was quenched with aqueous 1M Na₂CO₃ (15 mL), and the resulting biphasic mixture was stirred for 1 hour. Organic layer was separated, and aqueous layer was extracted with additional DCM (2×100 mL). Organics were combined, dried over MgSO₄, filtered, and volatiles removed under reduced pressure. The crude residue was purified by silica gel chromatography (0→10% MeOH/DCM) to provide 68 mg (84% yield) of amine SL-1175. $^1$H NMR (400 MHz, DMSO-d6) δ 7.20 (d, J=1.6 Hz, 1H), 7.16 (d, J=7.7 Hz, 1H), 7.02 (dd, J=7.7, 1.6 Hz, 1H), 6.72 (t, J=5.8 Hz, 1H), 3.66 (s, 2H), 3.01 (q, J=6.3 Hz, 2H), 2.13 (s, 3H), 1.37 (s, 9H); $^{13}$C NMR (100 MHz, MeOD) δ 155.6, 140.6, 137.3, 130.7, 126.8, 124.5, 117.5, 77.4, 52.0, 48.3, 28.2, 16.6; HRMS (SI) Calc'd for $C_{15}H_{24}N_5O_6$ [M+H]+ 306.1925, found 306.1922.

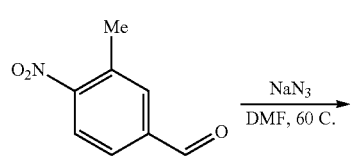

-continued

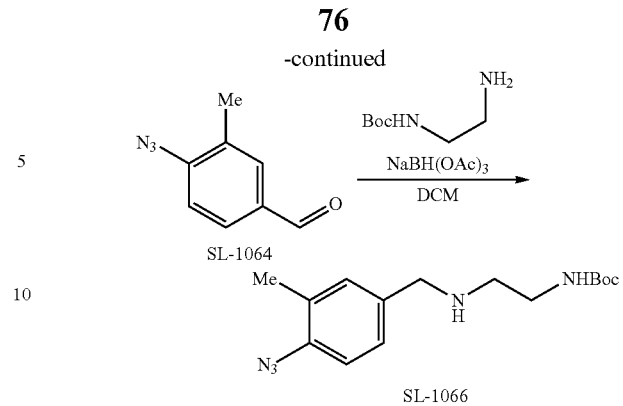

To a solution of 3-methyl-4-nitrobenzaldehyde (1.00 g, 6.06 mmol) in DMF (25 mL), NaN₃ (1.18 g, 18.2 mmol) was added. The resulting suspension was heated at 60° C. for 19 hours. The reaction mixture was cooled to room temperature, filtered, and volatiles removed under reduced pressure. The crude residue was purified by silica gel chromatography (0→20% EtOAc/Heptane) to provide 223 mg (23% yield) of azide SL-1064. $^1$H NMR (400 MHz, DMSO-d6) δ 9.92 (s, 1H), 7.75 (dd, J=8.2, 2.0 Hz, 1H), 7.69 (dd, J=1.8, 0.9 Hz, 1H), 7.24 (s, 1H), 2.27 (s, 3H).

To a solution of N-Boc-ethylenediamine (244 mg, 1.52 mmol) and SL-1064 (223 mg, 1.38 mmol) in DCM (50 mL), NaBH(OAc)₃ (733 mg, 3.46 mmol) was added. The resulting solution was stirred at 22° C. for 2 hours at which point HPLC analysis indicated full consumption of starting material. The reaction mixture was quenched with aqueous solution of K₂CO₃ (10%, 50 mL), and the resulting biphasic mixture stirred for 1 hour. Organic layer was separated, and aqueous layer extracted with additional DCM (2×75 mL). Organics were combined, dried over MgSO₄, filtered, and volatiles removed under reduced pressure. The crude residue was purified by silica gel chromatography (0→100% MeOH/DCM) to provide 263 mg (62% yield) of amine SL-1066. $^1$H NMR (400 MHz, DMSO-d6) δ 7.22 (dd, J=8.1, 2.0 Hz, 1H), 7.18 (d, J=1.9 Hz, 1H), 7.15 (d, J=8.1 Hz, 1H), 6.86-6.56 (m, 1H), 3.61 (s, 2H), 3.00 (q, J=6.3 Hz, 2H), 2.47 (s, 1H), 2.14 (s, 3H), 1.36 (s, 9H); MS (SI) Calc'd for $C_{15}H_{24}N_5O_6$ [M+H]+ 306.19, found 306.18.

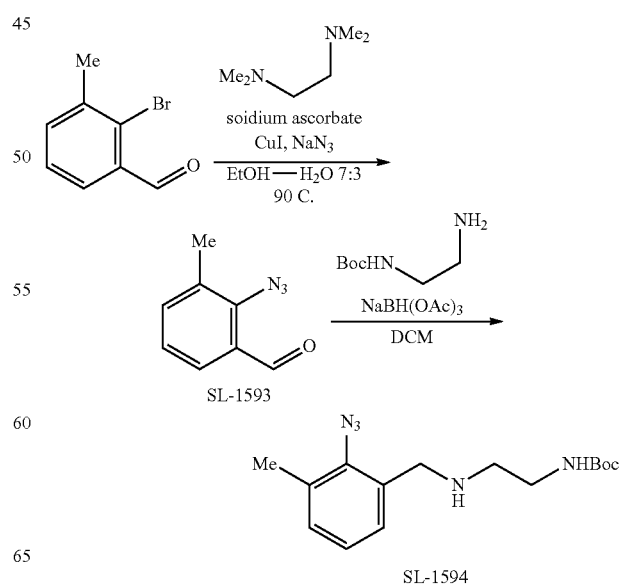

A 25 mL round-bottom flask equipped with stir bar and a condenser with a rubber septum was charged with 2-bromo-3-methylbenzaldehyde (672 mg, 3.38 mmol), sodium ascorbate (33.4 mg, 169 μmol), NaN$_3$ (439 mg, 6.75 mmol), and CuI (129 mg, 675 μmol). The flask was evacuated and backfilled with Ar (3 times) and left under Ar atmosphere. Degassed EtOH (10 mL) and degassed water (4 mL) were added through septa followed by 1,2-dimethylethylenediamine (45 mg, 500 μmol). The resulting suspension was heated to 90° C. for 60 minutes at which point HPLC analysis indicated full consumption of starting material. The reaction mixture was poured into 10% aq. Na$_2$CO$_3$ solution (100 mL) and extracted 3× with 75 mL DCM. Organics were combined, dried over MgSO$_4$, filtered, and solvent removed under vacuum. Purification by silica gel chromatography (0→30% EtOAc/Heptane), afforded 256 mg (49% yield) of aldehyde SL-1593. $^1$H NMR (400 MHz, DMSO-d6) δ 10.38 (d, J=0.5 Hz, 1H), 7.76 (dd, J=7.8, 1.7 Hz, 1H), 7.47 (ddq, J=7.5, 1.5, 0.7 Hz, 1H), 7.29 (d, J=7.9 Hz, 1H), 2.50 (s, 3H); $^{13}$C NMR (100 MHz, CDCl3) δ 190.0, 140.1, 137.1, 133.5, 129.2, 129.0, 125.8, 17.8.

To a solution of N-Boc-ethylenediamine (120 mg, 751 μmol) and SL-1593 (110 mg, 680 μmol) in DCM (5 mL), NaBH(OAc)$_3$ (362 mg, 1.71 mmol) was added. The resulting solution was stirred at 22° C. for 18 hours at which point HPLC analysis indicated full consumption of starting material. The reaction mixture was quenched with aqueous solution of K$_2$CO$_3$ (10%, 15 mL), and the resulting biphasic mixture was stirred for 1 hour. Organic layer was separated, and aqueous layer extracted with additional DCM (2×100 mL). Organics were combined, dried over MgSO$_4$, filtered, and volatiles removed under reduced pressure. The crude residue was purified by silica gel chromatography (0→30% MeOH/DCM) to provide 188 mg (90% yield) of amine SL-1594. $^1$H NMR (400 MHz, DMSO-d6) δ 7.23 (dd, J=7.4, 1.9 Hz, 1H), 7.18-7.00 (m, 2H), 6.72 (t, J=5.6 Hz, 1H), 3.72 (s, 2H), 3.02 (q, J=6.2 Hz, 2H), 2.54 (m, 2H, overlap with DMSO-d5), 2.33 (s, 3H), 1.99 (broad s, 1H), 1.36 (s, 9H); HRMS (SI) Calc'd for C$_{15}$H$_{24}$N$_5$O$_6$ [M+H]+ 306.1925, found 306.1932.

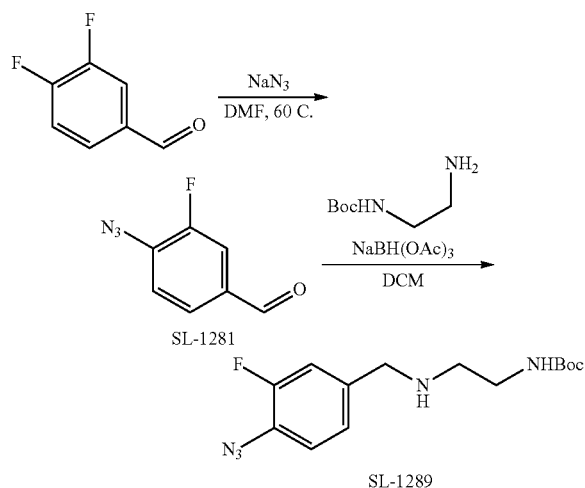

SL-1281

SL-1289

To a solution of 3,4-difluorobenzaldehyde (1.47 g, 10.4 mmol) in DMF (10 mL), NaN$_3$ (2.02 g, 31.0 mmol) was added. The resulting suspension was heated at 60° C. for 19 hours. The reaction mixture was cooled to room temperature, filtered through celite, and volatiles removed under reduced pressure. The crude residue was purified by silica gel chromatography (0→20% EtOAc/Heptane) to provide 1.16 mg (61% yield) of azide SL-1281 as a yellow solid. $^1$H NMR (400 MHz, DMSO-d6) δ 9.93 (d, J=1.9 Hz, 1H), 7.92-7.67 (m, 2H), 7.55 (t, J=8.2 Hz, 1H); $^{13}$C NMR (100 MHz, DMSO-d6) δ 190.97 (d, J=2.0 Hz), 153.67 (d, J=250.0 Hz), 133.90 (d, J=5.5 Hz), 133.68 (d, J=11.0 Hz), 127.12 (d, J=3.4 Hz), 122.12 (d, J=1 Hz), 116.51 (d, J=19.1 Hz).

To a solution of N-Boc-ethylenediamine (380 mg, 2.37 mmol) and SL-1281 (347 mg, 2.15 mmol) in DCM (5 mL), NaBH(OAc)$_3$ (1.14 g, 5.38 mmol) was added. The resulting suspension was stirred at 22° C. for 4 hours at which point HPLC analysis indicated full consumption of starting material. The reaction mixture was quenched with aqueous solution of K$_2$CO$_3$ (10%, 50 mL), and the resulting biphasic mixture was stirred for 1 hour. Organic layer was separated, and aqueous layer extracted with additional DCM (3×50 mL). Organics were combined, dried over MgSO$_4$, filtered, and volatiles removed under reduced pressure. The crude residue was purified by silica gel chromatography (0→20% MeOH/DCM) to provide 481 mg (72% yield) of amine SL-1289. $^1$H NMR (400 MHz, DMSO-d6) δ 7.27 (dd, J=12.4, 1.7 Hz, 1H), 7.22 (t, J=8.2 Hz, 1H), 7.17 (dd, J=8.2, 1.7 Hz, 1H), 6.73 (t, J=6.0 Hz, 1H), 3.65 (s, 2H), 3.00 (q, J=6.3 Hz, 2H), 2.47 (m, 2H, overlap with DMSO-d5), 2.25 (br. s, 1H), 1.36 (s, 9H); MS (SI) Calc'd for C$_{14}$H$_2$FN$_5$O$_2$ [M+H]+ 310.18, found 310.18.

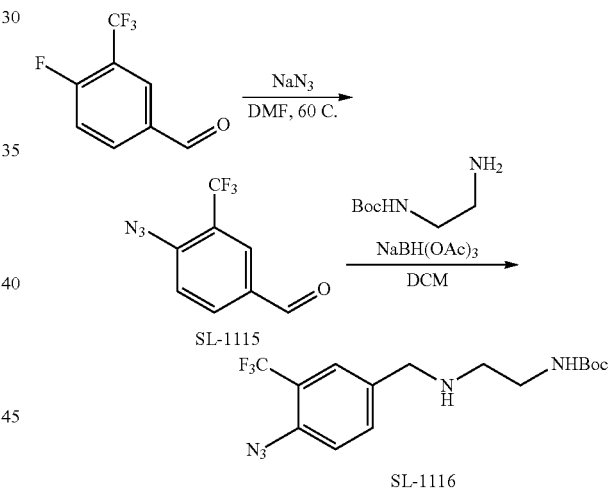

SL-1115

SL-1116

To a solution of 4-fluoro-3-(trifluoromethyl)benzaldehyde (1.73 g, 9.01 mmol) in DMF (40 mL), NaN$_3$ (1.76 g, 27.0 mmol) was added. The resulting suspension was heated at 60° C. for 19 hours. The reaction mixture was cooled to room temperature, filtered through celite, and volatiles removed under reduced pressure. The crude residue was purified by silica gel chromatography (0→30% EtOAc/Heptane) to provide 1.56 g (81% yield) of azide SL-1115 as a yellow oil. $^1$H NMR (400 MHz, DMSO-d6) δ 9.99 (d, J=0.5 Hz, 1H), 8.16 (dt, J=2.0, 0.6 Hz, 1H), 8.10 (ddd, J=8.3, 1.9, 0.6 Hz, 1H), 7.45 (dq, J=8.3, 0.6 Hz, 1H).

To a solution of N-Boc-ethylenediamine (803 mg, 5.01 mmol) and SL-1115 (980 mg, 4.56 mmol) in DCM (200 mL), NaBH(OAc)$_3$ (2.41 g, 11.4 mmol) was added. The resulting suspension was stirred at 22° C. for 4 hours at which point HPLC analysis indicated full consumption of starting material. The reaction mixture was quenched with aqueous solution of K$_2$CO$_3$ (10%, 200 mL), and the resulting biphasic mixture was stirred for 1 hour. Organic layer was separated, and aqueous layer extracted with additional DCM (2×100 mL). Organics were combined, dried over MgSO₄, filtered, and volatiles removed under reduced pressure. The crude residue was purified by silica gel chromatography (0→100% [3:1 EtOAc:EtOH]/DCM) to provide 1.31 g (80% yield) of amine SL-1116. $^1$H NMR (400 MHz, DMSO-d6) δ 7.69-7.65 (m, 2H), 7.51 (d, J=8.2 Hz, 1H), 6.74 (t, J=5.7 Hz, 1H), 3.72 (s, 2H), 3.02 (q, J=6.3 Hz, 2H), 2.49 (m, 1H, overlap with DMSO-d5), 1.37 (s, 9H); MS (SI) Calc'd for $C_{15}H_2F_3N_5O_2$ [M+H]+ 360.16, found 360.10.

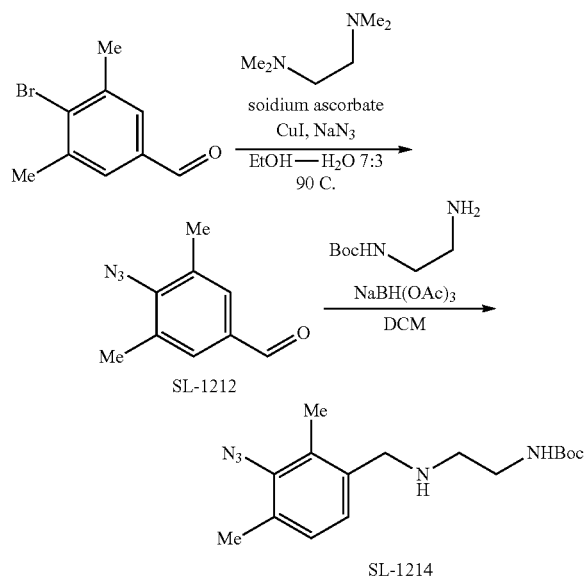

SL-1212

SL-1214

A 25 mL round-bottom flask equipped with stir bar and a condenser with a rubber septum was charged with 4-bromo-3,5-dimethylbenzaldehyde (650 mg, 3.05 mmol), sodium ascorbate (30.0 mg, 153 μmol), NaN₃ (397 mg, 6.10 mmol), and CuI (116 mg, 610 μmol). The flask was evacuated and backfilled with Ar (3 times) and left under Ar atmosphere. Degassed EtOH (10 mL) and degassed water (4 mL) were added through septa followed by 1,2-dimethylethylenediamine (40 mg, 458 μmol). The resulting suspension was heated to 90° C. for 3 hours (reaction was stopped before starting material was fully consumed). The reaction mixture was filtered over celite, and solvent removed under vacuum. Purification by silica gel chromatography (0→10% EtOAc/Heptane) afforded 157 mg (29% yield or 45% yield based on recovered starting material) of aldehyde SL-1212 as a white solid. $^1$H NMR (400 MHz, DMSO-d6) δ 9.89 (s, 1H), 7.67-7.39 (m, 2H), 2.44 (d, J=0.7 Hz, 6H); $^{13}$C NMR (100 MHz, CDCl₃) δ 191.3, 142.6, 133.4, 132.7, 130.4, 18.3.

To a solution of N-Boc-ethylenediamine (158 mg, 986 μmol) and SL-1212 (157 mg, 896 μmol) in DCM (15 mL), NaBH(OAc)₃ (475 mg, 2.24 mmol) was added. The resulting suspension was stirred at 22° C. for 17 hours at which point HPLC analysis indicated full consumption of starting material. The reaction mixture was quenched with aqueous solution of K₂CO₃ (10%, 15 mL), and the resulting biphasic mixture was stirred for 1 hour. Organic layer was separated, and aqueous layer extracted with additional DCM (3×50 mL). Organics were combined, dried over MgSO₄, filtered, and volatiles removed under reduced pressure. The crude residue was purified by silica gel chromatography (0→30% MeOH/DCM) to provide 212 mg (74% yield) of amine SL-1214. $^1$H NMR (400 MHz, DMSO-d6) δ 7.02 (s, 2H), 6.72 (t, J=5.8 Hz, 1H), 3.57 (s, 2H), 3.00 (q, J=6.3 Hz, 2H), 2.47 (m, 2H, overlap with DMSO-d5), 2.29 (s, 6H), 2.11 (br. s, 1H); MS (SI) Calc'd for $C_{16}H_{26}N_5O_2$ [M+H]+ 320.17, found 320.17.

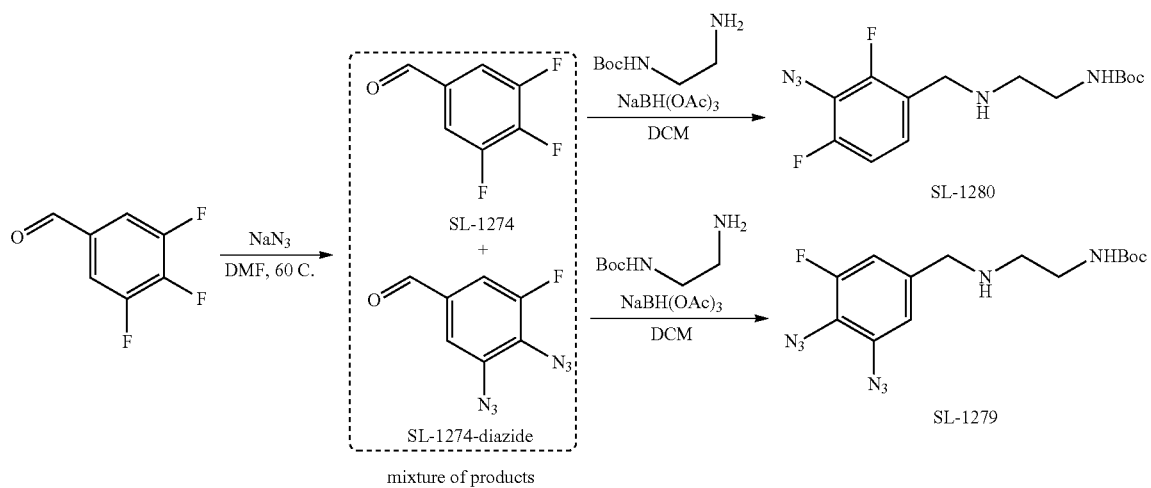

mixture of products

To a solution of 3,4,5-trifluorobenzaldehyde (1.00 g, 6.25 mmol) in DMF (10 mL), NaN₃ (1.22 g, 18.7 mmol) was added. The resulting suspension was heated at 60° C. for 20 hours. The reaction mixture was cooled to room temperature, filtered through celite, and volatiles removed under reduced pressure. The crude residue was purified by silica gel chromatography (0→15% EtOAc/Heptane) to provide 364 mg (32% yield) of azide SL-1274 as a white solid and 170 mg (13% yield) of SL-1274-diazide and 350 mg of mixed fractions of SL-1274 and SL-1274-diazide.

Azide SL-1274:

¹H NMR (400 MHz, DMSO-d6) δ 9.93 (d, J=2.0 Hz, 1H), 7.72 (t, J=1.4 Hz, 1H), 7.64 (dd, J=10.7, 1.7 Hz, 1H); ¹³C NMR (100 MHz, DMSO-d6) δ 190.60 (d, J=2.2 Hz), 155.90 (J=247.0 Hz), 134.03 (d, J=4.0 Hz), 133.16 (d, J=7.0 Hz), 124.30 (d, J=14.0 Hz), 117.58 (d, J=2.8 Hz), 112.29 (d, J=20.7 Hz); ¹⁹F NMR (376 MHz, DMSO-d6) δ−122.2 (ddd, J=10.8, 1.8, 1.3 Hz).

Diazide SL-1274:

¹H NMR (400 MHz, DMSO-d6) δ 9.89 (t, J=1.9 Hz, 1H), 7.79-7.71 (m, 2H); ¹³C NMR (100 MHz, DMSO-d6) δ 190.14 (s), 155.07 (dd, J=250.6, 4.5 Hz), 132.60 (t, J=7.5 Hz), 123.03 (s), 115.14-105.17 (m); ¹⁹F NMR (376 MHz, DMSO-d6) δ−121.15−−121.23 (m).

SL-1280:

To a solution of N-Boc-ethylenediamine (191 mg, 1.19 mmol) and azide SL-1274 (175 mg, 1.09 mmol) in DCM (25 mL), NaBH(OAc)₃ (575 mg, 2.71 mmol) was added. The resulting suspension was stirred at 22° C. for 2 hours at which point HPLC analysis indicated full consumption of starting material. The reaction mixture was quenched with aqueous solution of K₂CO₃ (10%, 25 mL), and the resulting biphasic mixture stirred for 1 hour. Organic layer was separated, and aqueous layer extracted with additional DCM (3×25 mL). Organics were combined, dried over MgSO₄, filtered, and volatiles removed under reduced pressure. The crude residue was purified by silica gel chromatography (0→20% MeOH/DCM) to provide 41 mg (12% yield) of amine SL-1280. ¹H NMR (400 MHz, DMSO-d6) δ 7.27-6.95 (m, 2H), 6.74 (t, J=5.7 Hz, 1H), 3.65 (s, 2H), 2.99 (q, J=6.3 Hz, 2H), 2.47 (m, 2H, overlap with DMSO-d5), 1.36 (s, 9H); MS (SI) Calc'd for C₁₄H₂₀F₂N₅O₂ [M+H]+ 328.16, found 328.17.

SL-1279:

To a solution of N-Boc-ethylenediamine (191 mg, 1.19 mmol) and diazide SL-1274 (175 mg, 1.09 mmol) in DCM (25 mL), NaBH(OAc)₃ (575 mg, 2.71 mmol) was added. The resulting suspension was stirred at 22° C. for 2 hours at which point HPLC analysis indicated full consumption of starting material. The reaction mixture was quenched with aqueous solution of K₂CO₃ (10%, 25 mL), and the resulting biphasic mixture stirred for 1 hour. Organic layer was separated, and aqueous layer extracted with additional DCM (3×25 mL). Organics were combined, dried over MgSO₄, filtered, and volatiles removed under reduced pressure. The crude residue was purified by silica gel chromatography (0→20% MeOH/DCM) to provide 41 mg (12% yield) of amine SL-1279. ¹H NMR (400 MHz, DMSO-d6) δ 7.30-6.92 (m, 2H), 6.73 (t, J=5.5 Hz, 1H), 3.66 (s, 2H), 3.00 (q, J=6.3 Hz, 2H), 2.47 (m, 2H, overlap with DMSO-d5), 1.36 (s, 9H); MS (SI) Calc'd for C₁₄H₂₀FN₈O₂ [M+H]+ 351.17, found 351.18.

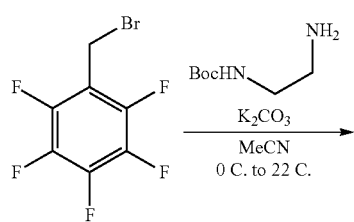

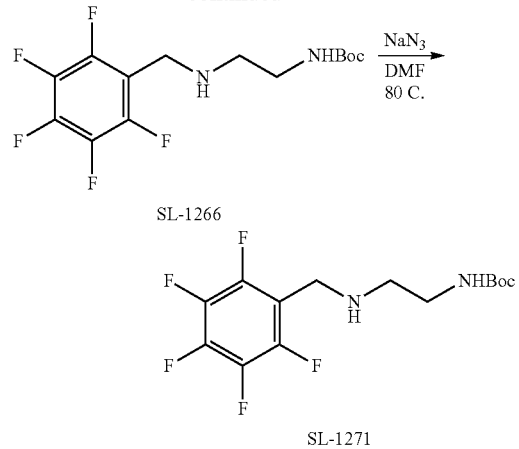

To an ice-cold solution of N-Boc-ethylenediamine (828 mg, 5.17 mmol) in MeCN (200 mL), K₂CO₃ (953 mg, 6.90 mmol) was added followed by 1-(bromomethyl)-2,3,4,5,6-pentafluorobenzene (900 mg, 3.45 mmol). The resulting solution was allowed to warm up to 22° C. and stirred for 25 hours at which point HPLC analysis indicated full consumption of starting material. The reaction mixture was filtered, and volatiles removed under reduced pressure. The crude residue was purified by silica gel chromatography (0→10% MeOH/DCM) to provide 1.22 g (quantitative) of amine SL-1266 as a yellow oil. ¹H NMR (400 MHz, DMSO-d6) δ 6.69 (t, J=5.7 Hz, 1H), 3.79 (s, 2H), 2.98 (q, J=6.2 Hz, 2H), 2.47 (m, 2H, overlap with DMSO-d5), 2.17 (s, 1H), 1.36 (s, 9H); ¹⁹F NMR (376 MHz, DMSO-d6) δ−143.92 (dd, J=24.3, 8.3 Hz), −156.98 (t, J=22.1 Hz), −161.43−−164.35 (m).

To a solution of SL-1266 (660 mg, 1.94 mmol) in DMF (8 mL), NaN₃ (378 mg, 5.82 mmol) was added. The resulting suspension was heated at 80° C. for 71 hours. The reaction mixture was cooled to room temperature, filtered through celite, and volatiles removed under reduced pressure. The crude residue was purified by silica gel chromatography (0→10% MeOH/DCM) to provide 298 mg (42% yield) of azide SL-1271 as a yellow oil. ¹H NMR (400 MHz, DMSO-d6) δ 6.72 (s, 1H), 3.79 (s, 2H), 2.99 (q, J=6.2 Hz, 2H), 1.37 (s, 9H); ¹⁹F NMR (376 MHz, DMSO-d6) δ−144.70 (s), −152.86 (dd, J=22.9, 9.8 Hz); HRMS (SI) Calc'd for C₁₄H₁₈F₄N₅O₂ [M+H]+ 364.1391, found 364.1386.

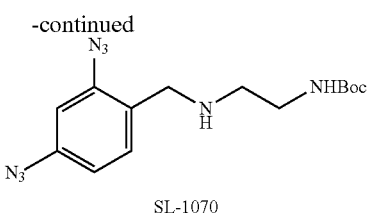

SL-1070

To a solution of 2,4-dinitrobenzaldehyde (240 mg, 1.22 mmol) in DMF (25 mL), NaN$_3$ (398 mg, 6.12 mmol) was added. The resulting suspension was stirred at 22° C. for 17 hours. The reaction mixture was poured into brine (25 mL) and extracted with DCM (3×50 mL). Organics were combined, dried over MgSO$_4$, filtered, and volatiles removed under reduced pressure. The crude residue was purified by silica gel chromatography (0→10% EtOAc/Heptane) to provide 164 mg (71% yield) of azide SL-1069 as a white solid. $^1$H NMR (400 MHz, DMSO-d6) δ 10.24 (d, J=0.8 Hz, 1H), 7.90 (d, J=8.4 Hz, 1H), 6.91 (ddd, J=8.4, 2.0, 0.8 Hz, 1H), 6.82 (d, J=2.0 Hz, 1H).

To a solution of N-Boc-ethylenediamine (154 mg, 959 µmol) and SL-1069 (164 mg, 872 µmol) in DCM (50 mL), NaBH(OAc)$_3$ (462 mg, 2.18 mmol) was added. The resulting suspension was stirred at 22° C. for 2 hours at which point HPLC analysis indicated full consumption of starting material. The reaction mixture was quenched with aqueous solution of K$_2$CO$_3$ (10%, 50 mL), and the resulting biphasic mixture stirred for 1 hour. Organic layer was separated, and aqueous layer extracted with additional DCM (2×75 mL). Organics were combined, dried over MgSO$_4$, filtered, and volatiles removed under reduced pressure. The crude residue was purified by silica gel chromatography (0→10% MeOH/DCM) to provide 206 mg (71% yield) of amine SL-1070. $^1$H NMR (400 MHz, DMSO-d6) δ 7.42 (d, J=8.0 Hz, 1H), 7.05-6.87 (m, 2H), 6.73 (t, J=5.8 Hz, 1H), 3.57 (s, 2H), 3.00 (q, J=6.3 Hz, 2H), 2.48 (m, 2H, overlap with DMSO-d5), 1.37 (s, 9H); MS (SI) Calc'd for C$_{14}$H$_{21}$N$_8$O$_6$ [M+H]+ 333.18, found 333.18.

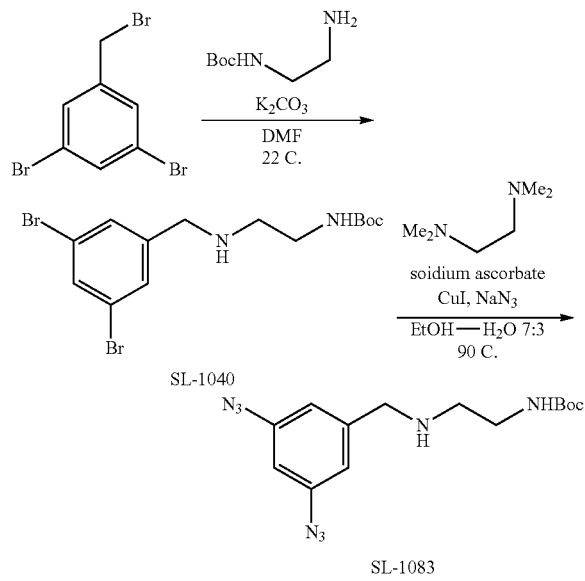

To a solution of N-Boc-ethylenediamine (390 mg, 2.44 mmol) in DMF (45 mL), K$_2$CO$_3$ (449 mg, 3.25 mmol) was added followed by 1,3-dibromo-5-(bromomethyl)benzene (534 mg, 1.62 mmol). The resulting solution was stirred at 22° C. for 20 hours at which point HPLC analysis indicated full consumption of starting material. The reaction mixture was filtered, and volatiles removed under reduced pressure. The crude residue was purified by silica gel chromatography (0→10% MeOH/DCM) to provide 568 mg (86% yield) of amine SL-1040 a clear oil. $^1$H NMR (400 MHz, DMSO-d6) δ 7.67 (t, J=1.8 Hz, 1H), 7.55 (d, J=1.8 Hz, 2H), 6.74 (t, J=5.5 Hz, 1H), 3.67 (s, 2H), 3.01 (q, J=6.3 Hz, 2H), 2.47 (m, 2H, overlap with DMSO-d5), 2.30 (s, 1H), 1.37 (s, 9H); MS (SI) Calc'd for C$_{14}$H$_2$Br$_2$N$_2$O$_2$ [M+H]+ 407.00, found 406.92.

A 25 mL round-bottom flask equipped with stir bar and a condenser with a rubber septum was charged with SL-1040 (260 mg, 637 µmol), sodium ascorbate (12.6 mg, 63.7 µmol), NaN$_3$ (166 mg, 2.55 mmol), and CuI (49 mg, 255 µmol). The flask was evacuated and backfilled with Ar (3 times) and left under Ar atmosphere. Degassed EtOH (6 mL) and degassed water (3 mL) were added through septa followed by a degassed solution of 1,2-dimethylethylenediamine (16.9 mg, 191 µmol) in EtOH (1.5 mL). The resulting suspension was heated to 90° C. for 2 hours at which point HPLC analysis indicated full consumption of starting material. The reaction mixture was poured into 10% aq. Na$_2$CO$_3$ solution (20 mL) and extracted 3× with 50 mL DCM. Organics were combined, dried over MgSO$_4$, filtered, and solvent removed under vacuum. Purification by silica gel chromatography (0→40% MeOH/DCM) afforded 134 mg (63% yield) of diazide SL-1083 as a clear oil. $^1$H NMR (400 MHz, DMSO-d6) δ 6.93 (d, J=2.1 Hz, 2H), 6.80-6.69 (m, 1H), 6.66 (t, J=2.1 Hz, 1H), 3.67 (s, 2H), 3.00 (q, J=6.3 Hz, 2H), 2.47 (m, 2H, overlap with DMSO-d5), 1.36 (s, 9H); MS (SI) Calc'd for C$_{14}$H$_{21}$N$_8$O$_2$ [M+H]+ 333.18, found 333.18.

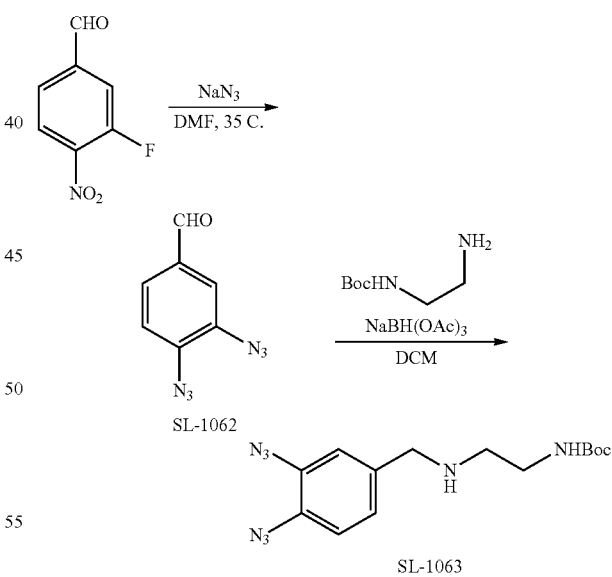

To a solution of 3-fluoro-4-nitrobenzaldehyde (400 mg, 2.37 mmol) in DMF (5 mL), NaN$_3$ (461 mg, 7.10 mmol) was added. The resulting suspension was stirred at 35° C. for 22 hours. The reaction mixture was poured into brine (5 mL) and extracted with DCM (3×10 mL). Organics were combined, dried over MgSO$_4$, filtered, and volatiles removed under reduced pressure. The crude residue was purified by silica gel chromatography (0→20% EtOAc/Heptane) to provide 115 mg (29% yield) of diazide SL-1062 as a white solid. $^1$H NMR (400 MHz, CDCl$_3$) δ 9.93 (s, 1H), 7.66 (dd, J=8.1, 1.7 Hz, 1H), 7.64 (d, J=1.6 Hz, 1H), 7.25 (d, J=8.0 Hz, 1H, overlap with CDCl$_3$); $^{19}$F NMR (376 MHz, CDCl$_3$) δ—NO SIGNALS.

To a solution of N-Boc-ethylenediamine (108 mg, 672 μmol) and SL-1062 (115 mg, 611 μmol) in DCM (50 mL), NaBH(OAc)$_3$ (324 mg, 1.53 mmol) was added. The resulting suspension was stirred at 2° C. for 3 hours at which point HPLC analysis indicated full consumption of starting material. The reaction mixture was quenched with aqueous solution of K$_2$CO$_3$ (10%, 50 mL), and the resulting biphasic mixture stirred for 1 hour. Organic layer was separated, and aqueous layer extracted with additional DCM (2×50 mL). Organics were combined, dried over MgSO$_4$, filtered, and volatiles removed under reduced pressure. The crude residue was purified by silica gel chromatography (0→10% MeOH/DCM) to provide 134 mg (66% yield) of amine SL-1063. $^1$H NMR (400 MHz, DMSO-d6) δ 7.24 (d, J=1.7 Hz, 1H), 7.21 (d, J=8.1 Hz, 1H), 7.17 (dd, J=8.2, 1.7 Hz, 1H), 6.72 (t, J=5.7 Hz, 1H), 3.66 (s, 2H), 3.00 (q, J=6.3 Hz, 2H), 2.47 (m, 2H, overlap with DMSO-d6), 2.25 (s, 1H), 1.36 (s, 9H); MS (SI) Calc'd for C$_{14}$H$_{21}$N$_8$O$_6$ [M+H]+ 333.18, found 333.18.

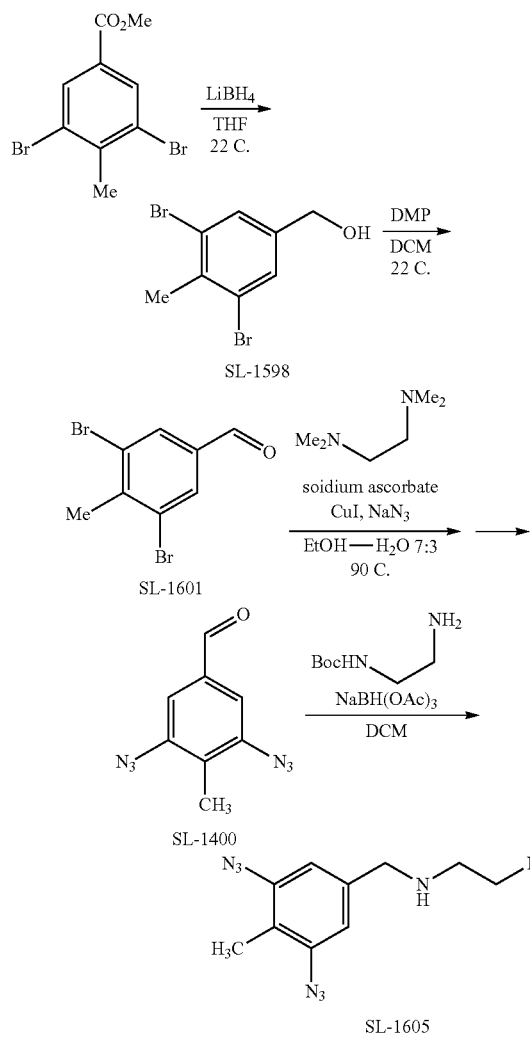

SL-1605

To a stirred solution of methyl 3,5-dibromo-4-methylbenzoate (643 mg, 2.09 mmol) in THF (15 mL) under argon, LiBH$_4$ solution (4M in THF, 6.26 mmol) was added. The resulting solution was left to react at 22° C. for 18 hours at which point HPLC analysis indicated full consumption of the starting material. The reaction mixture was quenched with water (10 mL), and the resulting biphasic mixture stirred for 3 hour and extracted with EtOAc (3×75 mL). Organics were combined, dried over MgSO$_4$, filtered, and volatiles removed under reduced pressure. The crude residue was purified by silica gel chromatography (0→30% EtOAc/Heptane) to provide 539 mg (92% yield) of alcohol SL-1598 as a white solid. $^1$H NMR (400 MHz, CDCl$_3$) δ 7.52 (s, 2H), 4.63 (d, J=0.9 Hz, 2H), 2.56 (s, 3H); MS (SI) Calc'd for C$_8$H$_8$Br$_2$OLi [M+Li]+ 284.91, found 284.36.

To a stirred solution of SL-1598 (447 mg, 1.60 mmol) in DCM (25 mL), DMP (Dess-Martin Periodinane) (711 mg, 1.68 mmol) was added. The resulting solution was stirred at 22° C. for 3 hours at which point HPLC analysis indicated full consumption of the starting material. The reaction mixture was loaded onto silica gel column and was purified by silica gel chromatography (0→10% EtOAc/Heptane) to provide 391 mg (88% yield) of aldehyde SL-1601 as a white solid. $^1$H NMR (400 MHz, CDCl$_3$) δ 9.87 (s, 1H), 8.00 (s, 2H), 2.65 (s, 3H); $^{13}$C NMR (100 MHz, CDCl$_3$) δ 189.0, 144.4, 136.1, 132.6, 126.1, 24.3.

A 25 mL round-bottom flask equipped with stir bar and a condenser with a rubber septum was charged with SL-1601 (179 mg, 644 μmol), sodium ascorbate (12.8 mg, 64.4 μmol), NaN$_3$ (168 mg, 2.58 mmol), and CuI (24.5 mg, 129 μmol). The flask was evacuated and backfilled with Ar (3× times) and left under Ar atmosphere. Degassed water (1.2 mL) was added through septa followed by 1,2-dimethylethylenediamine solution (40 mg, 458 μmol) in degassed EtOH (3 mL). The resulting suspension was heated to 90° C. for 7 hours. The reaction mixture was absorbed onto celite and purified by silica gel chromatography (0→20% EtOAc/Heptane) to afford 37 mg (28% yield) of diazide SL-1400 as a white solid. $^1$H NMR (400 MHz, CDCl$_3$) δ 9.95 (s, 1H), 7.42 (s, 2H), 2.15 (s, 3H); $^{13}$C NMR (100 MHz, CDCl$^3$) δ 190.1, 141.4, 135.6, 128.1, 114.6, 12.1; HRMS (SI) Calc'd for CH$_7$N$_6$O [M+H]+ 203.0676, found 203.0673.

To a solution of N-Boc-ethylenediamine (55.8 mg, 348 μmol) and SL-1400 (64 mg, 317 μmol) in DCM (10 mL), NaBH(OAc)$_3$ (168 mg, 791 μmol) was added. The resulting suspension was stirred at 22° C. for 20 hours at which point HPLC analysis indicated full consumption of starting material. The reaction mixture was quenched with aqueous solution of K$_2$CO$_3$ (10%, 10 mL), and the resulting biphasic mixture stirred for 1 hour. Organic layer was separated, and aqueous layer extracted with additional DCM (2×25 mL). Organics were combined, dried over MgSO$_4$, filtered, and volatiles removed under reduced pressure. The crude residue was purified by silica gel chromatography (0→10% MeOH/DCM) to provide 96 mg (88% yield) of amine SL-1605. $^1$H NMR (400 MHz, DMSO-d6) δ 7.05 (s, 2H), 6.82-6.58 (m, 1H), 3.69 (s, 2H), 3.01 (q, J=6.3 Hz, 2H), 2.5 (2H overlap with DMSO-d5), 1.99 (s, 3H), 1.36 (s, 9H); MS (SI) Calc'd for C$_{15}$H$_{23}$N$_8$O$_2$ [M+H]+ 347.19, found 347.21.

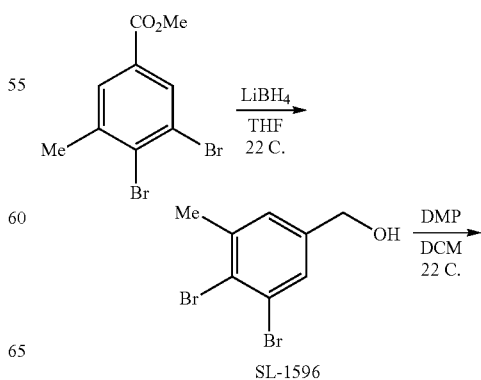

SL-1596

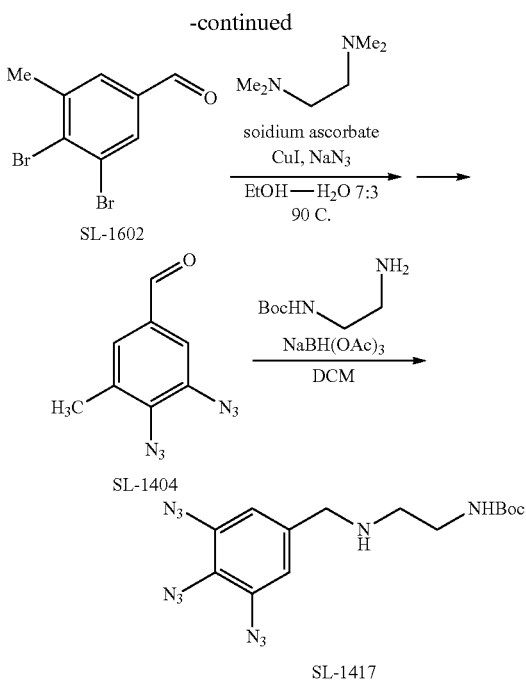

To a stirred solution of methyl 3,4-dibromo-5-methylbenzoate (264 mg, 857 μmol) in THF (8 mL) under argon, LiBH$_4$ solution (643 μL, 4M in THF, 2.57 mmol) was added. The resulting solution was left to react at 22° C. for 17 hours. The reaction mixture was quenched with water (2 mL), and the resulting biphasic mixture stirred for 1 hour and extracted with EtOAc (3×15 mL). Organics were combined, dried over MgSO$_4$, filtered, and volatiles removed under reduced pressure. The crude residue was purified by silica gel chromatography (0→30% EtOAc/Heptane) to provide 192 mg (80% yield) of alcohol SL-1596 as a white solid. $^1$H NMR (400 MHz, CDCl$_3$) δ 7.49 (d, J=2.0 Hz, 1H), 7.19-7.16 (m, 1H), 4.62 (s, 2H), 2.48 (s, 3H); $^{13}$C NMR (100 MHz, CDCl$_3$) δ 141.0, 140.8, 129.4, 127.7, 125.9, 125.6, 63.9, 25.0; MS (SI) Calc'd for CH$_7$Br$_2$ [M−OH]+ 260.8909, found 260.8913.

To a stirred solution of SL-1596 (122 mg, 436 μmol) in DCM (7 mL), DMP (Dess-Martin Periodinane)(194 mg, 456 μmol) was added. The resulting solution was stirred at 22° C. for 1.5 hours at which point HPLC analysis indicated full consumption of the starting material. The reaction mixture was loaded onto silica gel column and was purified by silica gel chromatography (0→10% EtOAc/Heptane) to provide 99 mg (82% yield) of aldehyde SL-1601 as a white solid. $^1$H NMR (400 MHz, CDCl$_3$) δ 9.91 (s, 1H), 7.95 (dd, J=1.9, 0.7 Hz, 1H), 7.66 (dd, J=1.9, 0.8 Hz, 1H), 2.57 (t, J=0.7 Hz, 3H); $^{13}$C NMR (100 MHz, CDCl$_3$) δ 190.1, 141.9, 135.7, 134.3, 132.0, 129.4, 126.7, 25.1.

A 25 mL round-bottom flask equipped with stir bar and a condenser with a rubber septum was charged with SL-1602 (141 mg, 507 μmol), sodium ascorbate (10.5 mg, 50.7 μmol), NaN$_3$ (132 mg, 2.03 mmol), and CuI (19.3 mg, 102 μmol). Flask was evacuated and backfilled with Ar (3× times) and left under Ar atmosphere. Degassed water (1.2 mL) was added through septa followed by 1,2-dimethylethylenediamine solution (13.4 mg, 152 μmol) in degassed EtOH (3 mL). The resulting suspension was heated to 90° C. for 3 hours. The reaction mixture was absorbed onto celite and purified by silica gel chromatography (0→10% EtOAc/Heptane) to afford 10 mg (10% yield) of diazide SL-1404 as a white solid. $^1$H NMR (400 MHz, CDCl$_3$) δ 9.88 (s, 1H), 7.52 (d, J=1.8 Hz, 1H), 7.43 (d, J=1.8 Hz, 1H), 2.30 (s, 3H); $^{13}$C NMR (100 MHz, CDCl$^3$) δ 190.1, 134.7, 134.2, 133.2, 133.1, 129.1, 116.8, 18.1.

To a solution of N-Boc-ethylenediamine (5.1 mg, 32 μmol) and SL-1404 (64 mg, 29 μmol) in DCM (5 mL), NaBH(OAc)$_3$ (16 mg, 73 μmol) was added. The resulting suspension was stirred at 22° C. for 7 hours at which point HPLC analysis indicated full consumption of starting material. The reaction mixture was quenched with aqueous solution of K$_2$CO$_3$ (10%, 10 mL), and the resulting biphasic mixture stirred for 1 hour. Organic layer was separated, and aqueous layer extracted with additional DCM (2×10 mL). Organics were combined, dried over MgSO$_4$, filtered, and volatiles removed under reduced pressure. The crude residue was purified by silica gel chromatography (0→10% MeOH/DCM) to provide 3.5 mg (35% yield) of amine SL-1417. $^1$H NMR (400 MHz, MeOD) δ 7.12 (d, J=1.8 Hz, 1H), 6.98 (d, J=1.8 Hz, 1H), 3.71 (s, 2H), 3.19 (t, J=6.3 Hz, 2H), 2.66 (t, J=6.3 Hz, 2H), 2.22 (s, 3H), 1.43 (s, 9H); 13C NMR (100 MHz, MeOD) δ 158.6, 138.9, 135.0, 133.9, 128.7, 128.5, 118.1, 80.1, 53.2, 40.7, 30.8, 28.7, 18.0. HRMS (SI) Calc'd for C$_5$H$_{23}$N$_8$O$_2$ [M+H]+ 347.1938, found 347.1942.

Synthesis of Fluorescent SAHA-PRG-NCT Conjugates:

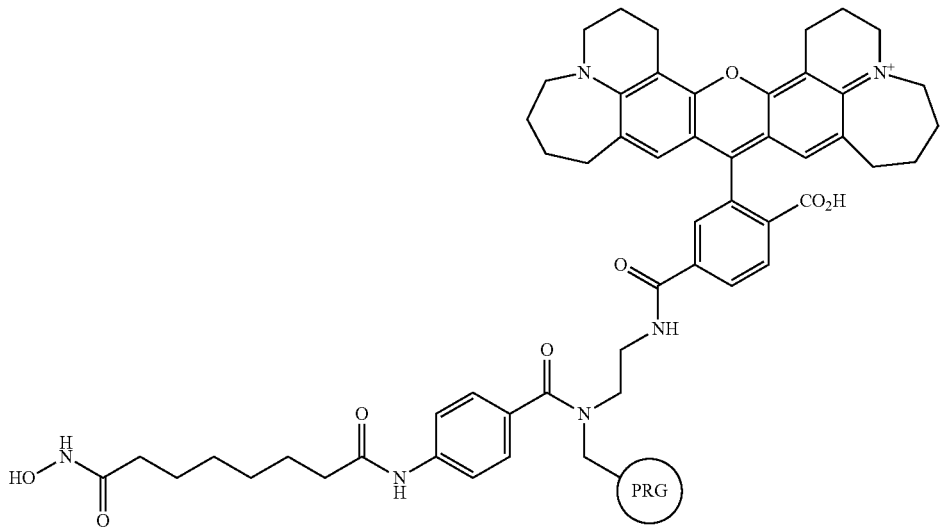 [SMILES: CCN(CCNC(=O)c1ccc(C(=O)O)c(C2=c3cc4c5c(c3Oc3c2cc2c6c3CCCN6CCCC2)CCC[N+]=5CCCC4)c1)C(=O)c1ccc(NC(=O)CCCCCCC(=O)NO)cc1]

General Structure of SAHA-PRG-NCT Probes
SAHA-PRG-NCT Probes
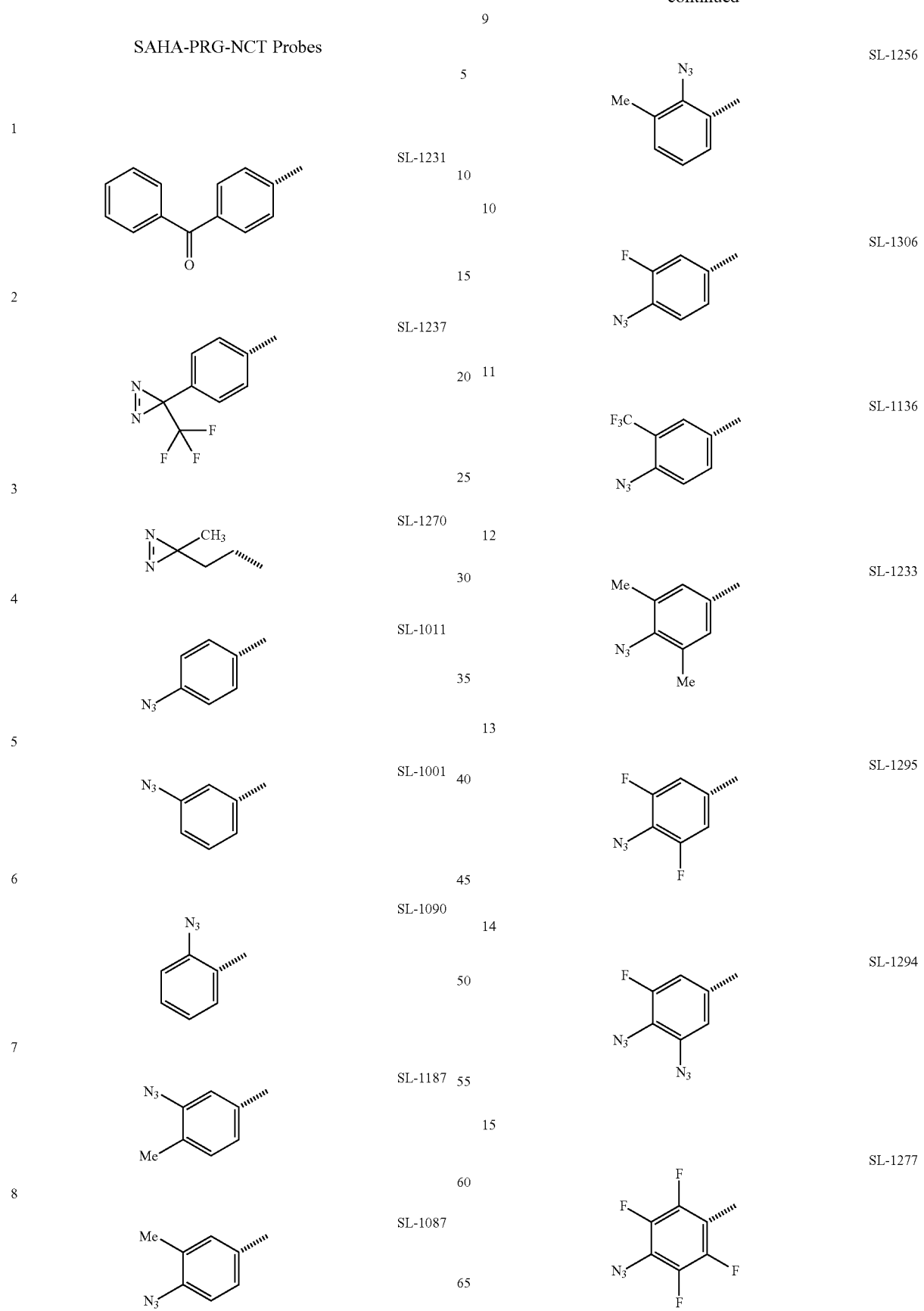

91
-continued
16
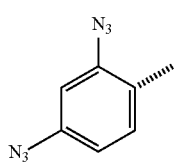
SL-1089
17
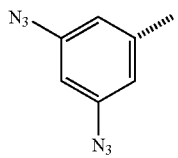
18
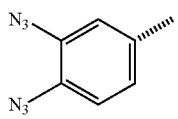
SL-1080
92
-continued
19
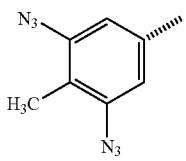
SL-1414
20
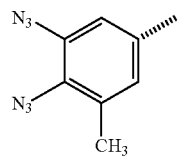
SL-1421
Synthetic Schemes for Synthesis of SAHA-PRG-NCT Probes
PROBES: SL-1231, SL-1011, SL-1001, SL-1090, SL-1187, SL-1087, SL-1136, SL-1233, SL-1089, SL-1080 (SAHA-PRG-NCT probes #: 1, 4, 5, 6, 7, 8, 11, 12, 16, 18) were synthesized according to general scheme SAHA-I
PROBES: SL-1237, SL-1270, SL-1056, SL-1306, SL-1295, SL-1294, SL-1277, SL-1104, SL-1414, SL-1421 (SAHA-PRG-NCT probes #: 2, 3, 9, 10, 13, 14, 15, 17, 19, 20) were synthesized according to general scheme SAHA-II
General Scheme SAHA-I:
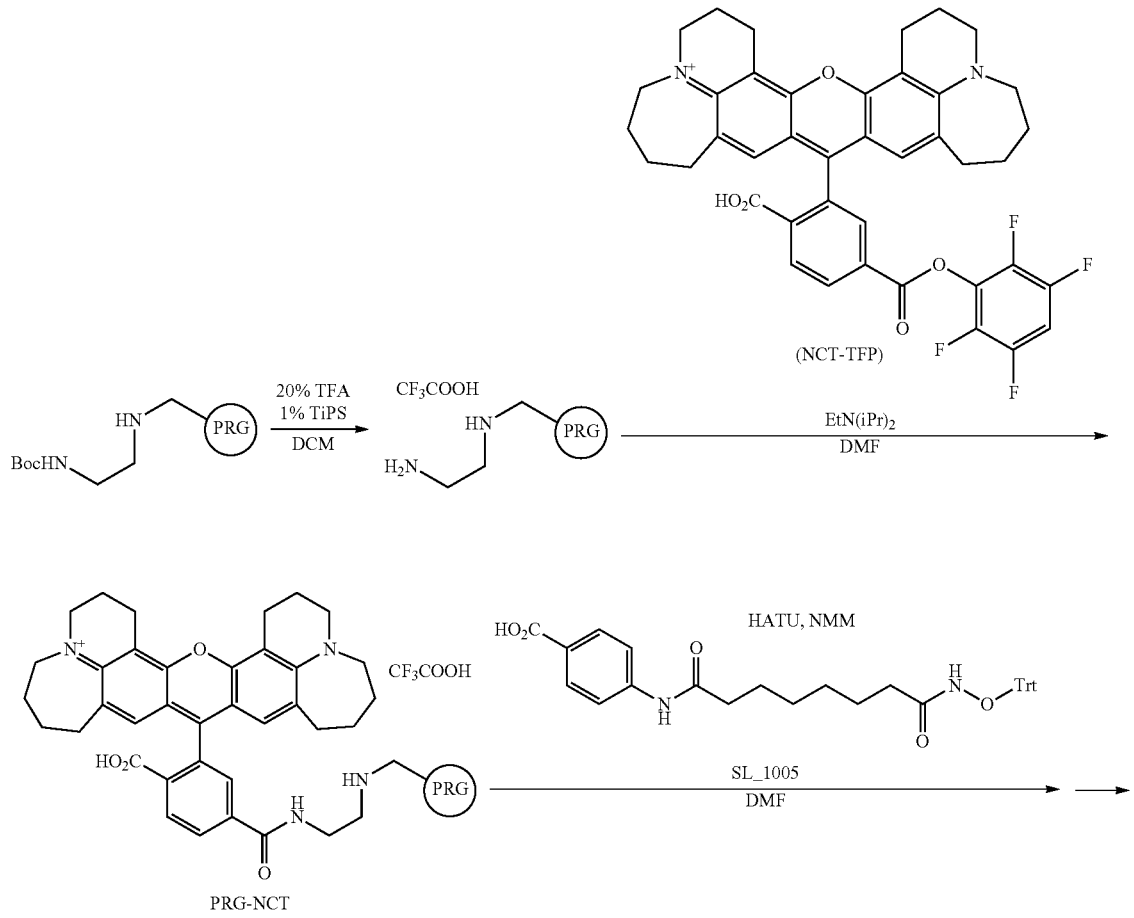

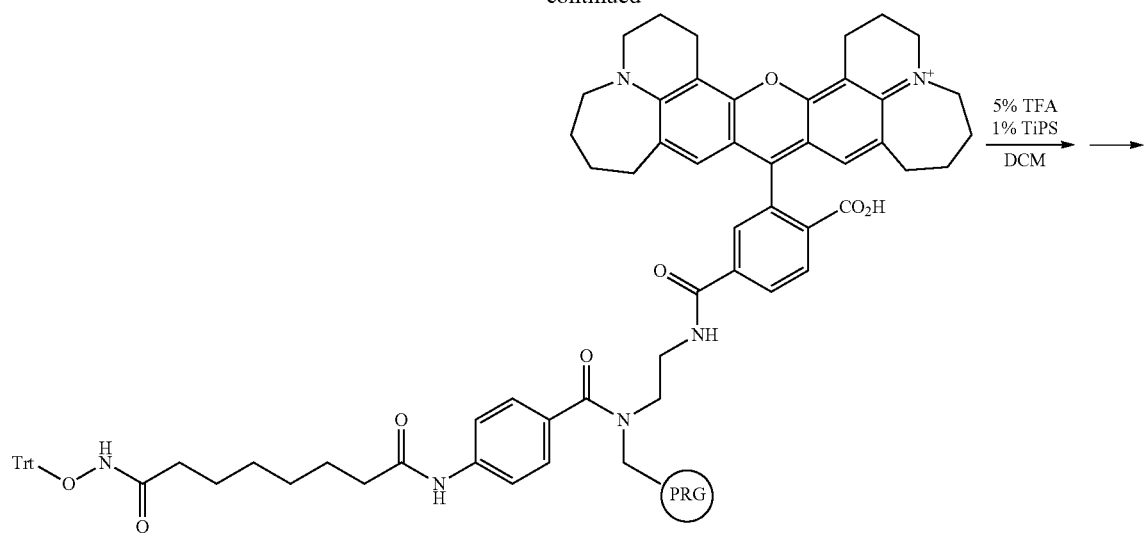
Trt-protected SAHA-PRG-NCT conjugate
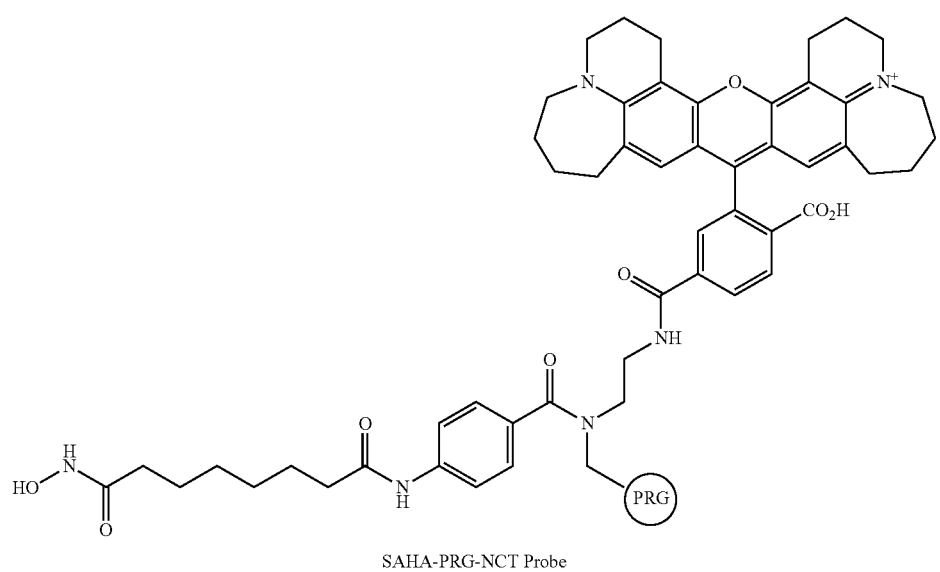 [SMILES: CCN(CCNC(=O)c1ccc(C(=O)O)c(C2=c3cc4c5c(c3Oc3c2cc2c6c3CCCN6CCCC2)CCC[N+]=5CCCC4)c1)C(=O)c1ccc(NC(=O)CCCCCCC(=O)NO)cc1]
SAHA-PRG-NCT Probe
General Scheme SAHA-II
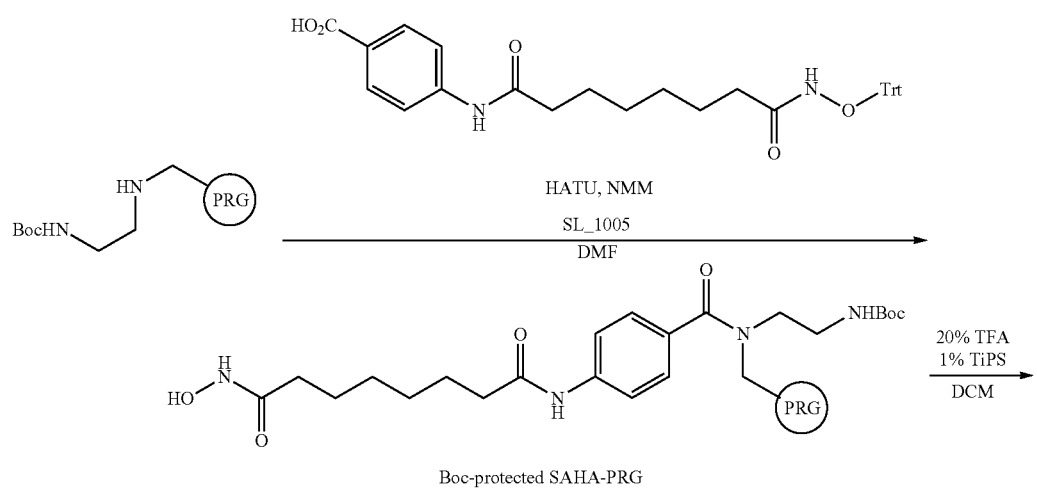
Boc-protected SAHA-PRG

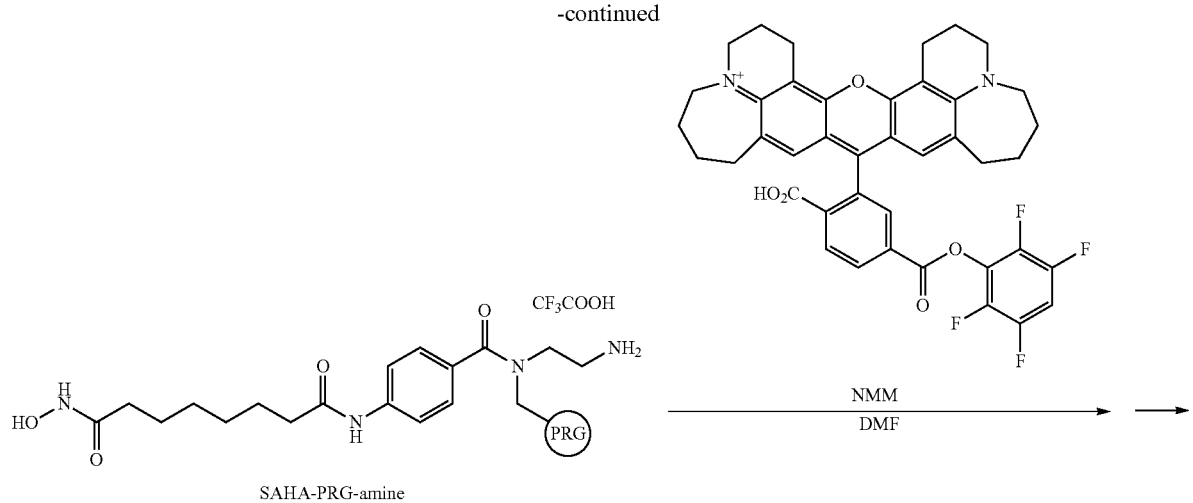

Exemplary Synthetic Procedures for General Scheme SAHA-I

Synthesis of Probe SL-1231 (SAHA-PRG-NCT Probe #1):

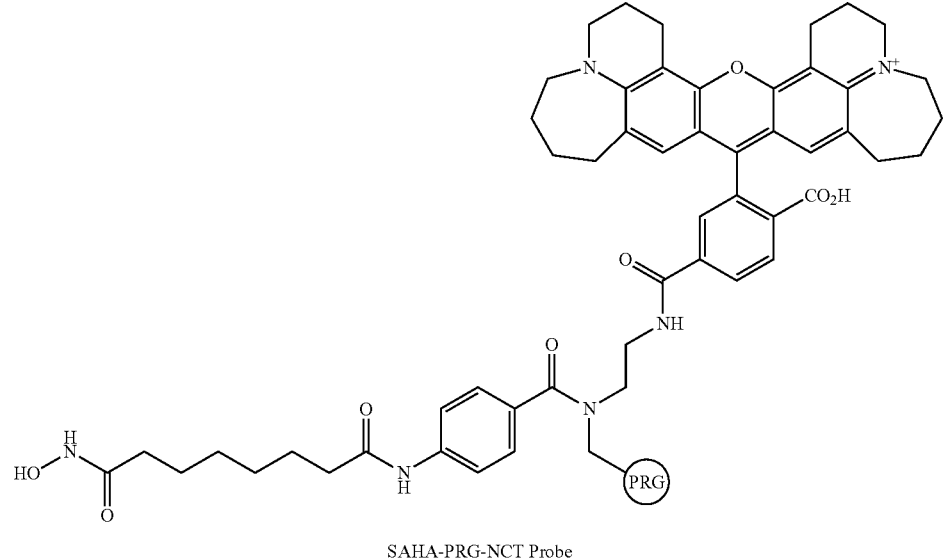

To a solution of SL-1203 (8.0 mg, 22 μmol) in DCM (4 mL), TiPS (50 μL) followed by TFA (1 mL) was added. The resulting solution was stirred at 22° C. for 1 hour at which point HPLC analysis indicated full consumption of starting material. Volatiles were removed under reduced pressure, crude residue dissolved in 5 mL MeOH, and volatiles removed under vacuum. The crude residue was dried under high vacuum and used in the next step without further purification. MS (SI) Calc'd for $C_{16}H_{18}N_2ONa$ [M+H]+ 277.13, found 277.03.

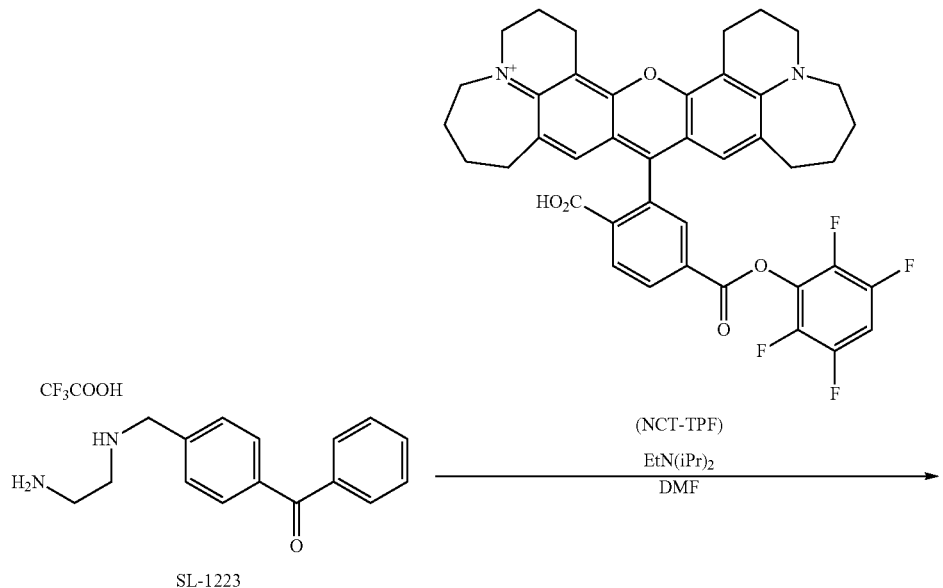

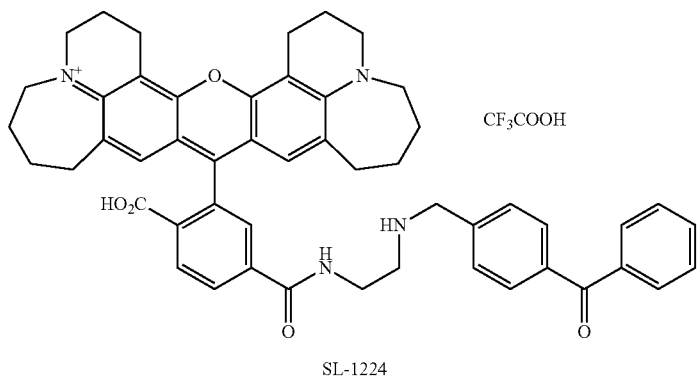

To a solution of SL-1223 (7.8 mg, 21 µmol) and DIPEA (13 µL, 70 µmol) in DMF (6 mL) was added NCT-TFP (5 mg, 7 µmol, prepared according to ACS Chem. Biol., 2016, 11, 2608-2617). The resulting solution was stirred at 22° C. for 1 hour, at which point HPLC analysis indicated full consumption of the starting material. The reaction mixture was purified by preparative RP HPLC (5→95% MeCN/H$_2$O buffered with 0.5% TFA) to provide 4.5 mg (70% yield) of amine SL-1224 as a deep blue film. HPLC: 97% purity at 254 nm; MS (SI) Calc'd for C$_{51}$H$_{51}$N$_4$O$_5$[M+]+ 799.38, found 799.45.

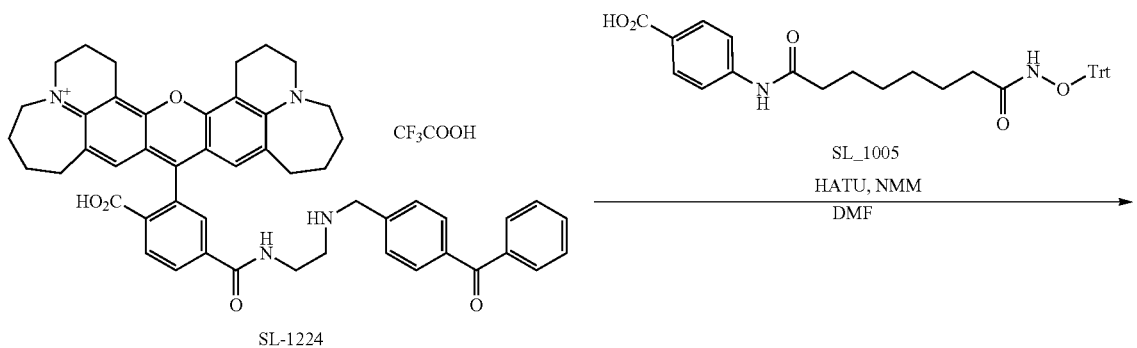

-continued

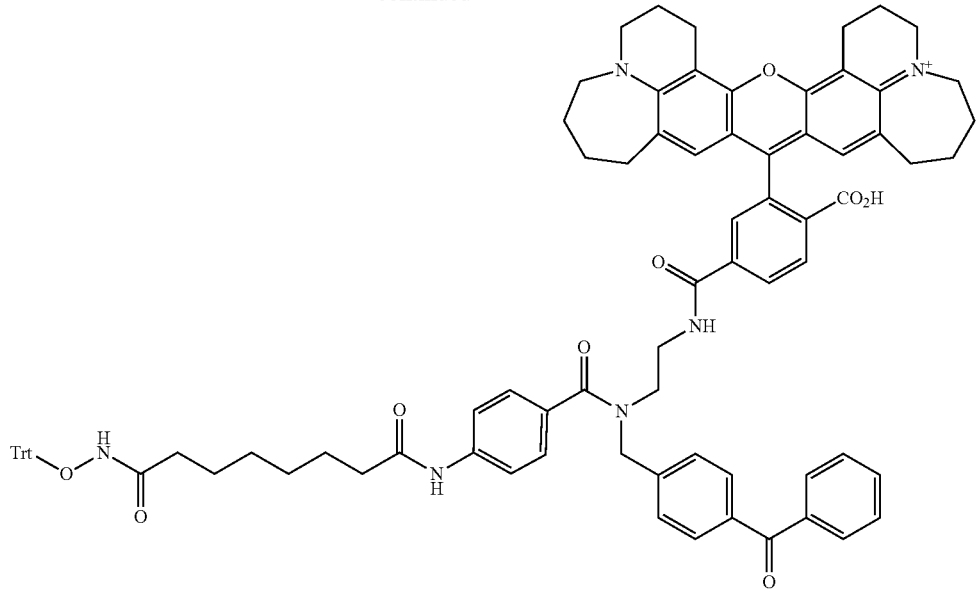

SL-1228

To a solution of SL_1005 (3 mg, 5 μmol), HATU (2.3 mg, 6.2 μmol), and N-methylmorpholine (6 μL, 50 μmol) in DMF (5 mL), SL-1224 (4.5 mg, 4.9 μmol) was added. The resulting solution was stirred at 22° C. for 18 hours at which point LCMS analysis indicated full consumption of starting material. The reaction mixture was purified by preparative RP HPLC (5→95% MeCN/H$_2$O buffered with 0.5% TFA) to provide 4.0 mg (61% yield) of conjugate SL-1228 as a deep blue film. HPLC: 99% purity at 254 nm; MS (SI) Calc'd for C$_{85}$H$_{83}$N$_6$O$_9$ [M+]+ 1331.62, found 1331.51.

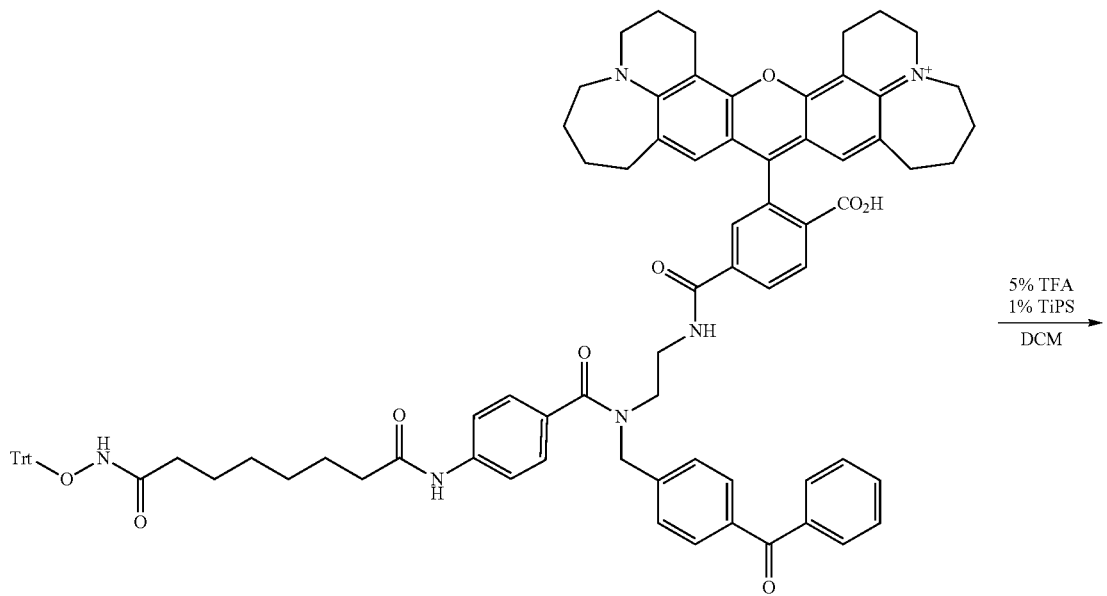

SL-1228

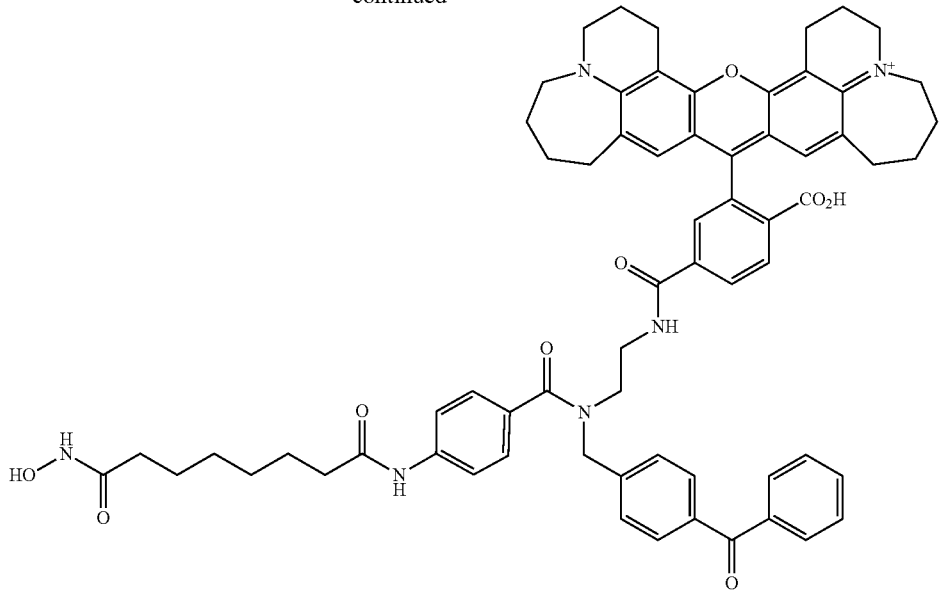

SL-1231

SAHA-benzophenone-NCT

SL-1228 (4.0 mg, 3 μmol) was treated with 4 mL of cleavage cocktail DCM:TFA:TiPS (95:5:0.1). The resulting solution was stirred at 22° C. for 30 minutes at which point HPLC analysis indicated full consumption of starting material. Volatiles were removed under reduced pressure, and crude residue dissolved in 5 mL MeOH and purified by preparative RP HPLC (5→95% MeCN/H$_2$O buffered with 0.5% TFA) to provide 2.2 mg (67% yield) of conjugate SL-1231 as a deep blue film. HPLC: 99% purity at 254 nm; HRMS (SI) Calc'd for C$_{66}$H$_{69}$N$_6$O$_9$ [M+]+ 1089.5121, found 1089.5119.

Exemplary Synthetic Procedures for General Scheme SAHA-IT

Synthesis of Probe SL-1237 (SAHA-PRG-NCT Probe #2):

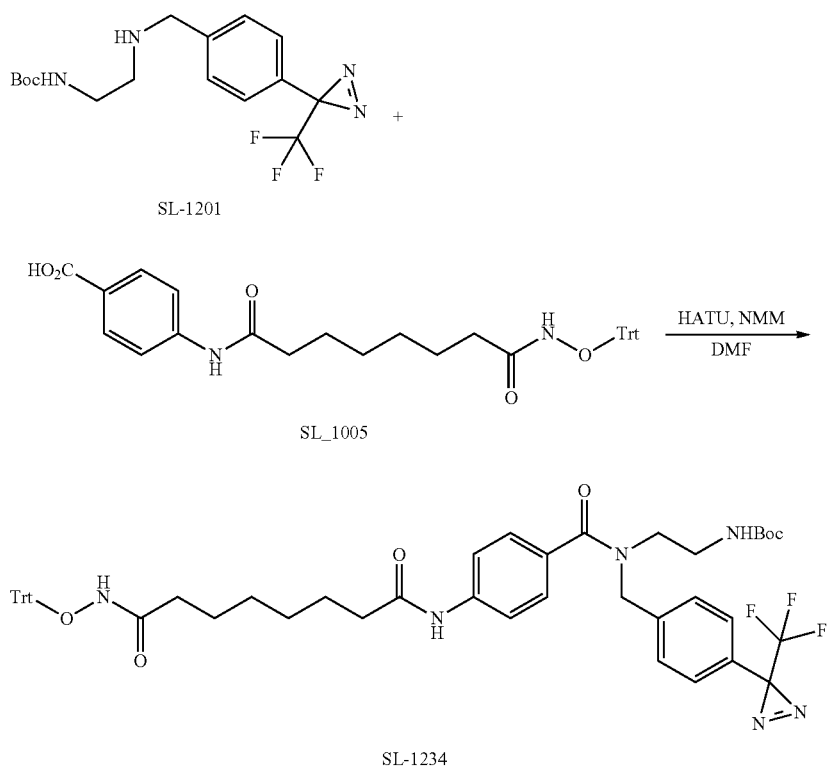

To a solution of SL_1005 (20 mg, 37 μmol), HATU (16 mg, 42 μmol), and N-methylmorpholine (26 μL, 0.24 mmol) in DMF (6 mL), SL-1201 (12 mg, 34 μmol) was added. The resulting solution was stirred at 22° C. for 2 hours at which point LCMS analysis indicated full consumption of starting material. The reaction mixture was purified by preparative RP HPLC (5→95% MeCN/H₂O buffered with 0.5% TFA) to provide 14 mg (47% yield) of conjugate SL-1234 as a clear film. HPLC: 99% purity at 254 nm; MS (SI) Calc'd for $C_{50}H_{54}F_3N_6O_6$ [M+]+ 891.41, found 891.46.

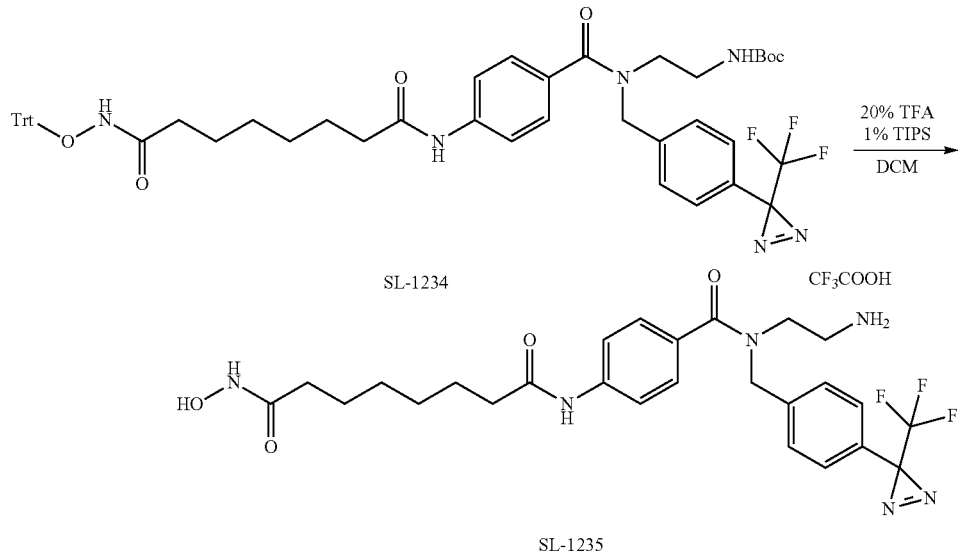

To a solution of SL-1234 (14 mg, 16 μmol) in DCM (9 mL), TiPS (100 μL) followed by TFA (1 mL) was added. The resulting solution was stirred at 22° C. for 2 hours at which point HPLC analysis indicated full consumption of starting material. Volatiles were removed under reduced pressure, crude residue was dissolved in 5 mL MeOH, and volatiles removed under vacuum. The crude residue was dried under high vacuum and used in the next step without further purification. MS (SI) Calc'd for $C_{26}H_{32}F_3N_6O_4$ [M+H]+ 549.24, found 549.17.

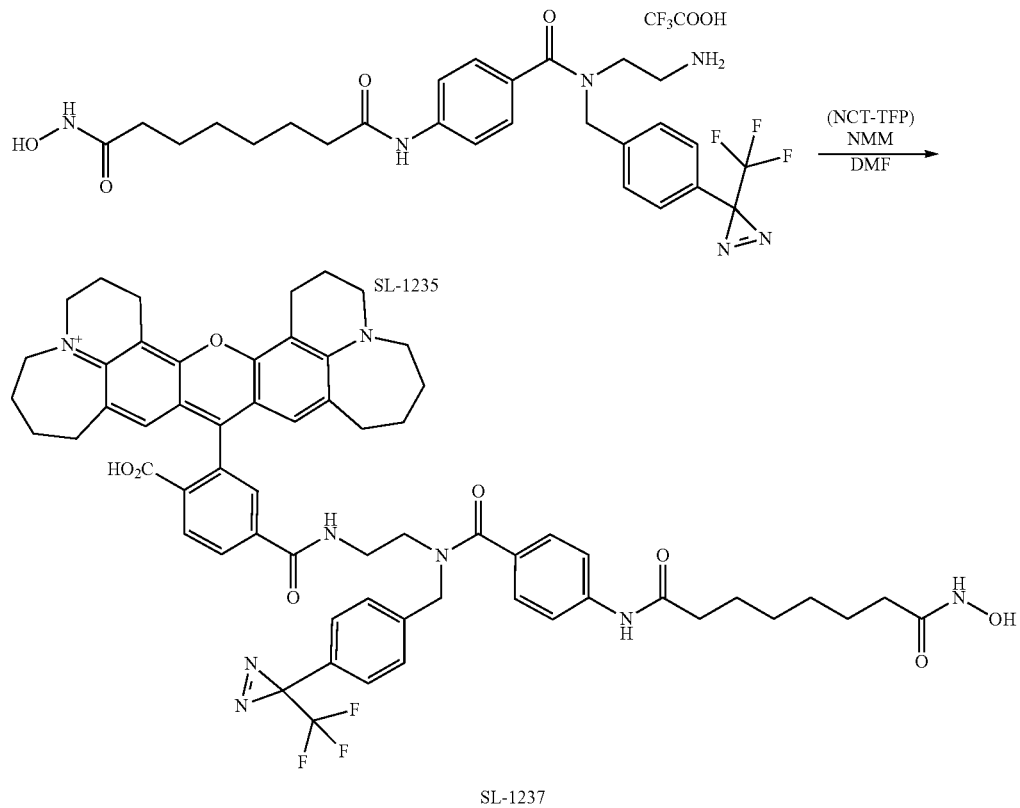

To a solution of SL-1235 (9 mg, 14 μmol) and NMM (8 μL, 70 μmol) in DMF (7 mL), NCT-TFP (5 mg, 7 μmol, prepared according to ACS Chem. Biol., 2016, 11, 2608-2617) was added. The resulting solution was stirred at 22° C. for 1 hour at which point HPLC analysis indicated full consumption of the starting material. The reaction mixture was purified by preparative RP HPLC (5→95% MeCN/H$_2$O buffered with 0.5% TFA) to provide 4.8 mg (62% yield) of conjugate SL-1237 as a deep blue film. HPLC: 99% purity at 254 nm; HRMS (SI) Calc'd for $C_{61}H_{64}F_3N_8O_8$ [M+]+ 1093.4794, found 1093.4778.

Characterization Data for SAHA-PRG-NCT Probes:

SL-1270

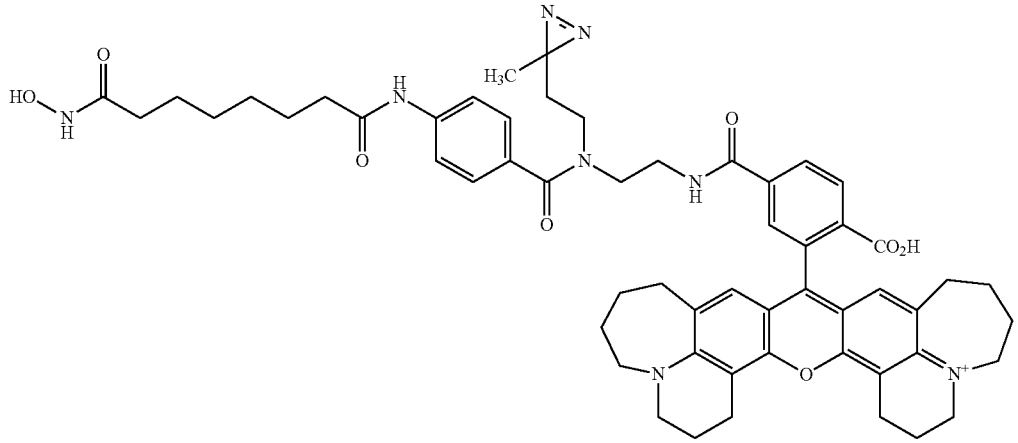

HPLC: 99% purity at 254 nm; $^1$H NMR (400 MHz, Methanol-d4, reported for mixture of rotamers) δ 8.37 (d, J=8.2 Hz, 1H), 8.20-8.13 (m, 1H), 8.12-8.10 (m, 1H), 7.74-7.64 (m, 1H), 7.56 (m, 1H), 7.39 (m, 1H), 7.21 (m, 2H), 6.67 (m, 2H), 3.79-3.50 (m, 12H), 3.07 (s, 3H), 2.79 (m, 4H), 2.35 (m, 2H), 2.08 (m, 5H), 1.99-1.76 (m, 7H), 1.75-1.57 (m, 5H), 1.49-1.25 (m, 7H), 1.09 (s, 1H), 1.01 (t, J=7.3 Hz, 1H), 0.76 (s, 1H); HRMS (SI) Calc'd for $C_{56}H_{65}N_8O_8$ [M+]+ 977.4920, found 977.4910.

SL-1011

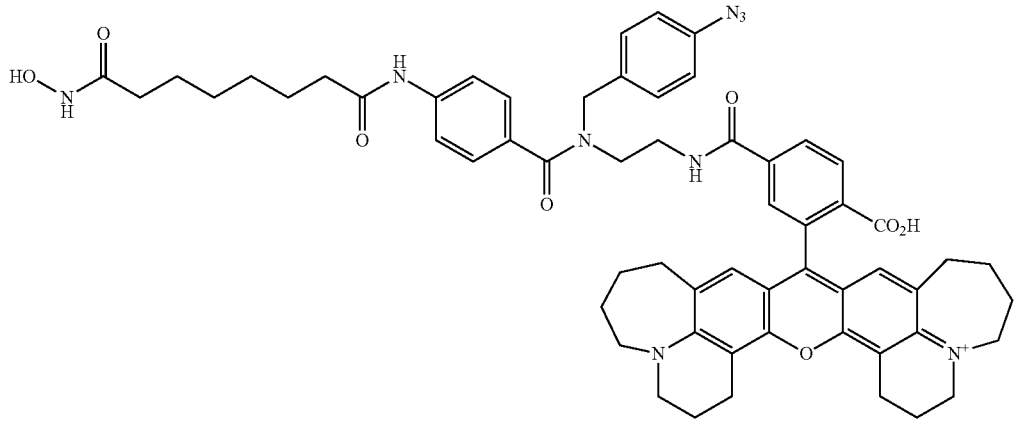

HPLC: 99% purity at 254 nm; $^1$H NMR (400 MHz, Methanol-d4, reported for mixture of rotamers) δ 8.37-6.60 (multiplets 13H), 4.80 (m, 1H), 4.59 (m, 1H), 3.79-3.51 (multiplets, 12H), 3.11-3.00 (m, 4H), 2.88-2.68 (m, 4H), 2.44-2.21 (m, 3H), 2.17-2.02 (m, 5H), 2.00-1.88 (m, 4H), 1.84-1.73 (m, 4H), 1.72-1.58 (m, 4H), 1.47-1.33 (m, 4H); HRMS (SI) Calc'd for $C_{59}H_{64}N_9O_8$ [M+]+ 1026.4872, found 1026.4898.

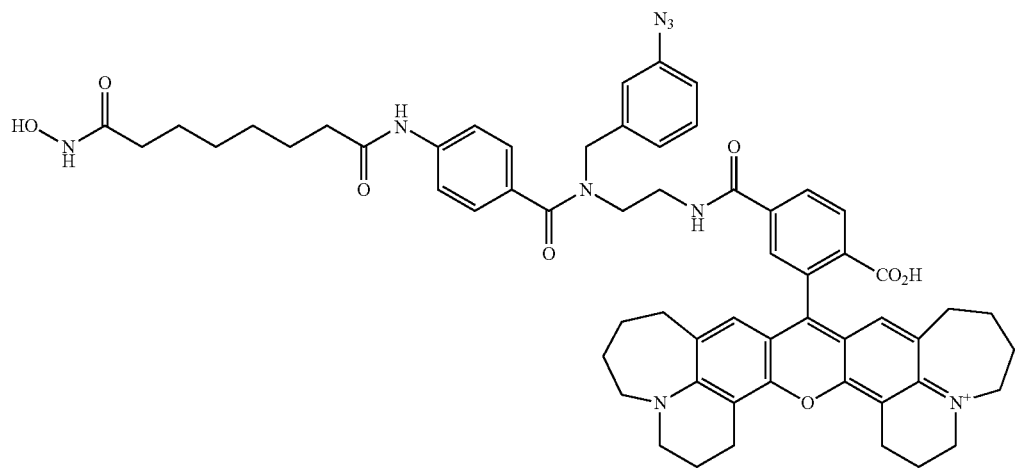
SL-1101
HPLC: 99% purity at 254 nm; HRMS (SI) Calc'd for $C_{59}H_{64}N_9O_8$ [M+]+ 1026.4872, found 1026.4879.
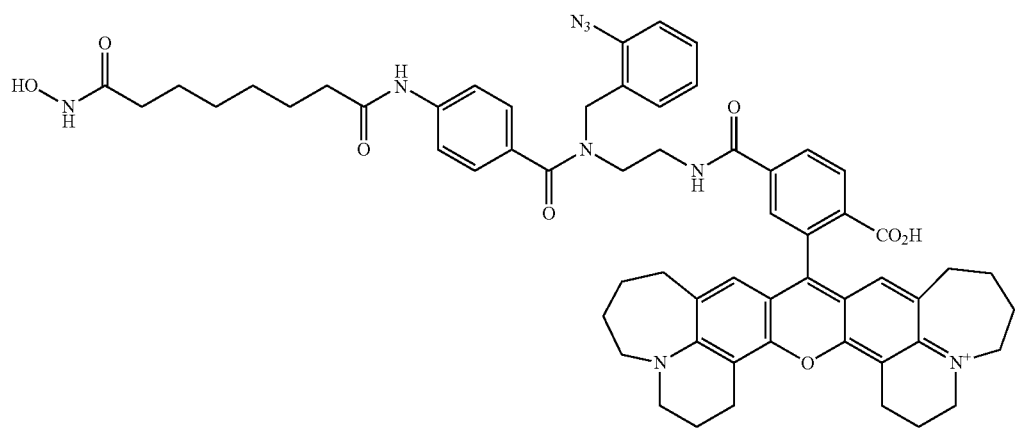
SL-1090
HPLC: 99% purity at 254 nm; HRMS (SI) Calc'd for $C_{59}H_{64}N_9O_8$ [M+]+ 1026.4872, found 1026.4874.
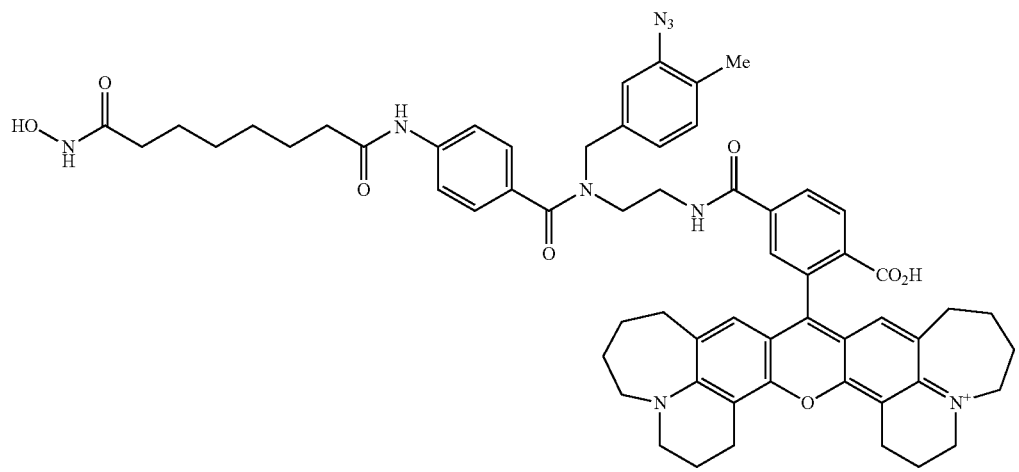
SL-1187

HPLC: 96% purity at 254 nm; MS (SI) Calc'd for C₆₀H₆₆N₉O [M+]+ 1040.50, found 1040.36.
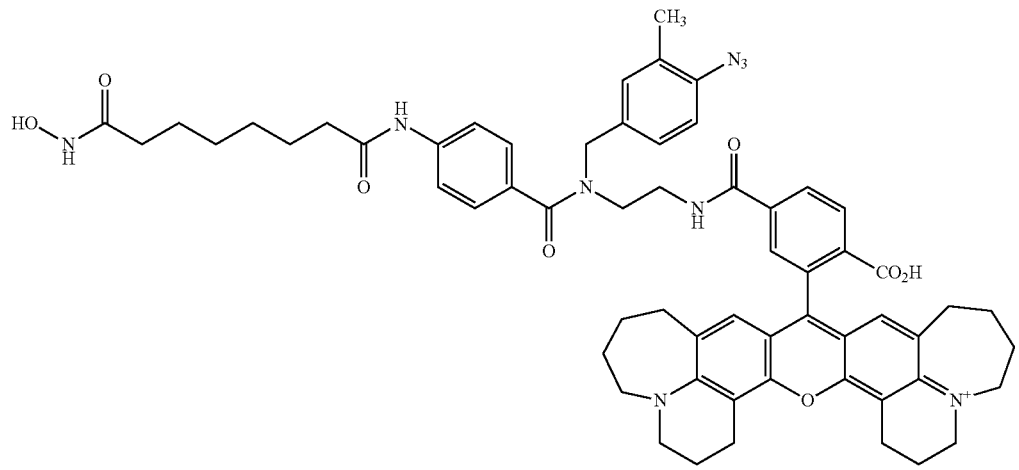
SL-1087
HPLC: 99% purity at 254 nm; HRMS (SI) Calc'd for C₆₀H₆₆N₉O₈ [M+]+ 1040.5029, found 1040.5048.
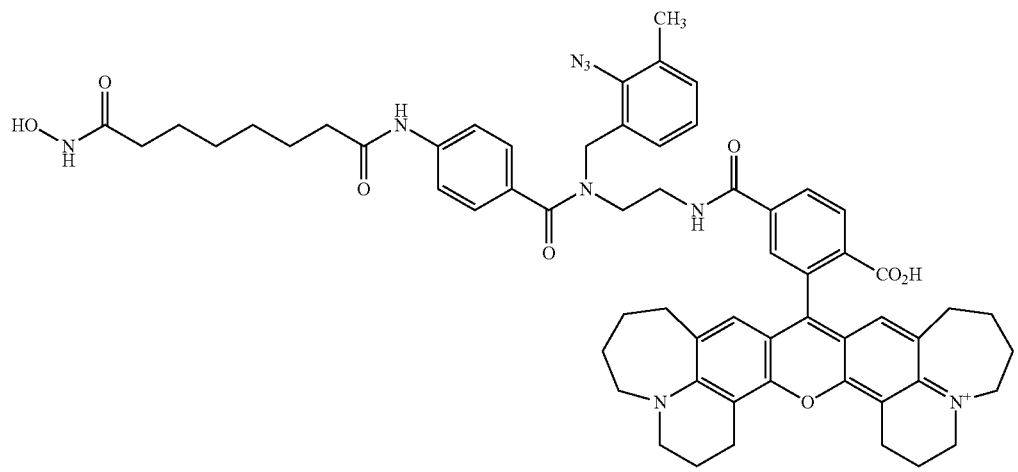
SL-1256
HPLC: 99% purity at 254 nm; HRMS (SI) Calc'd for C₆₀H₆₆N₉O₈ [M+]+ 1040.5029, found 1040.5027.
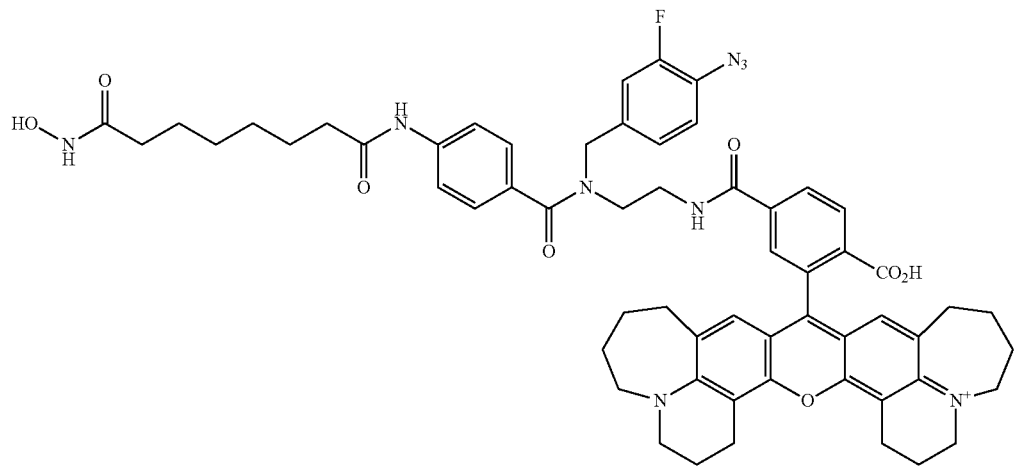
SL-1306

HPLC: 99% purity at 254 nm; $^1$H NMR (400 MHz, Methanol-d4, reported for mixture of rotamers) δ 8.43-6.61 (multiplets 12H), 4.77 (m, 1H), 4.58 (m, 1H), 3.79-3.49 (multiplets, 12H), 3.11-3.00 (m, 4H), 2.87-2.68 (m, 4H), 2.40-2.21 (m, 3H), 2.17-2.02 (m, 5H), 2.00-1.88 (m, 4H), 1.84-1.73 (m, 4H), 1.72-1.58 (m, 4H), 1.47-1.33 (m, 4H); MS (SI) Calc'd for $C_{59}H_{63}FN_9O_8$ [M+]+ 1044.48, found 1044.89.
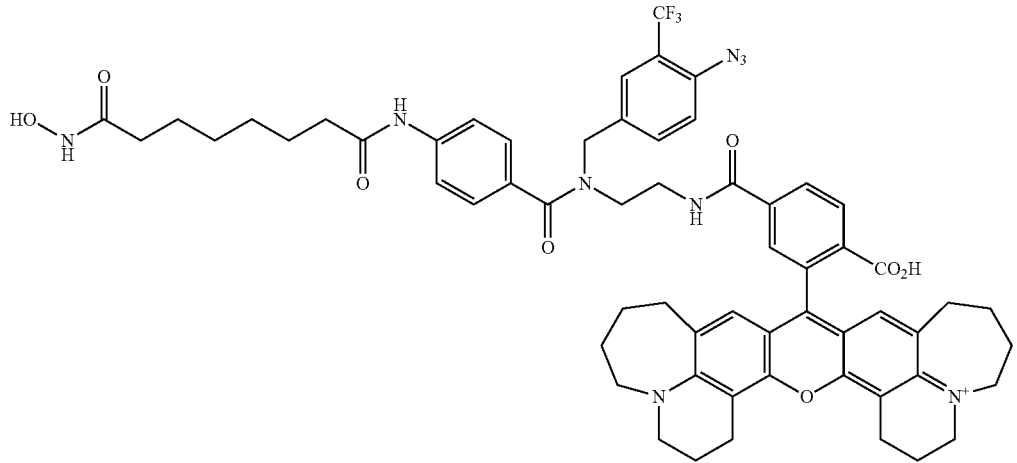
SL-1136
HPLC: 99% purity at 254 nm; HRMS (SI) Calc'd for $C_{60}H_{63}F_3N_9O_8$ [M+]+ 1094.4746, found 1094.4740.
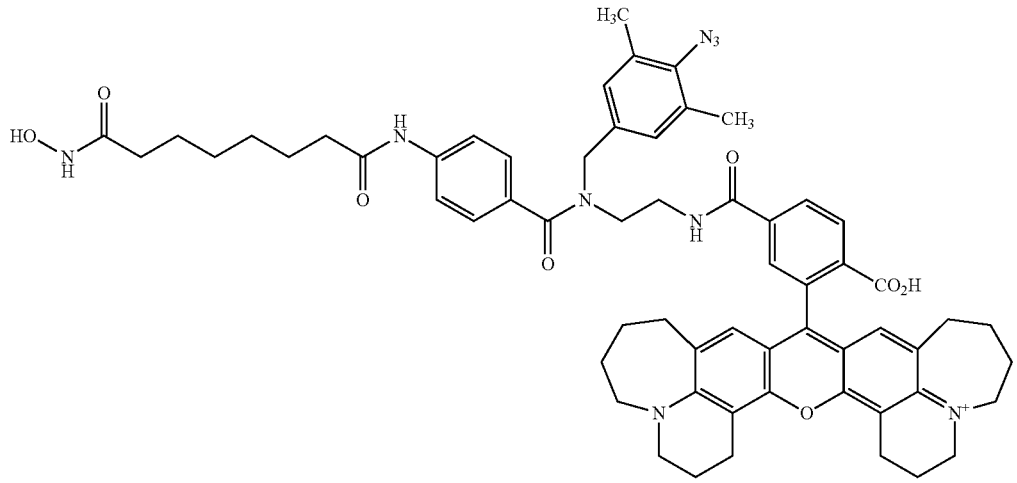
SL-1233
HPLC: 99% purity at 254 nm; HRMS (SI) Calc'd for $C_{61}H_{68}N_9O_8$ [M+]+ 1054.5185, found 1054.5186.
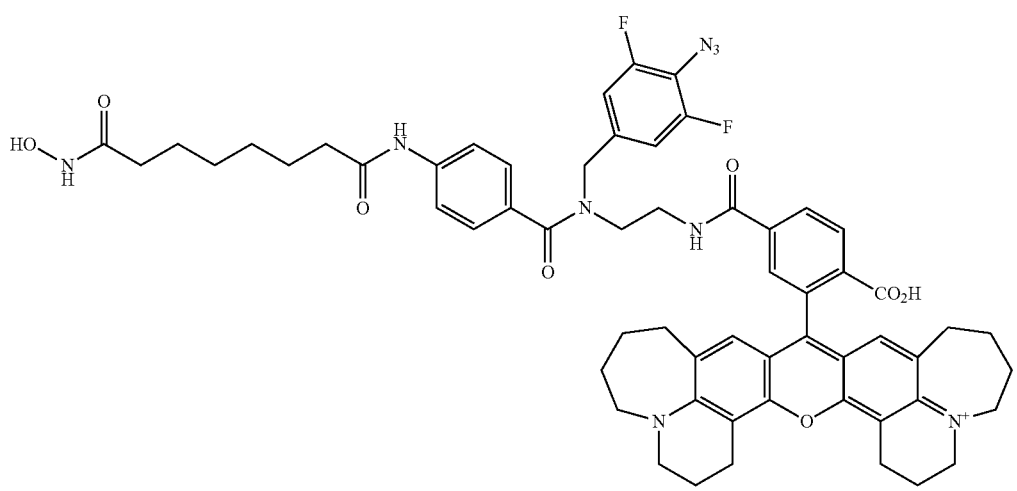
SL-1295

HPLC: 96% purity at 254 nm; ¹H NMR (400 MHz, Methanol-d4, reported for mixture of rotamers) δ 8.44-6.62 (multiplets 11H), 4.75 (m, 1H), 4.59 (m, 1H), 3.82-3.52 (multiplets, 12H), 3.12-2.99 (m, 4H), 2.91-2.65 (m, 4H), 2.44-2.23 (m, 3H), 2.17-2.02 (m, 5H), 2.00-1.88 (m, 4H), 1.84-1.73 (m, 4H), 1.72-1.54 (m, 4H), 1.47-1.30 (m, 4H); HRMS (SI) Calc'd for $C_{59}H_{62}F_2N_9O_8$ [M+]+ 1062.4684, found 1062.4715.

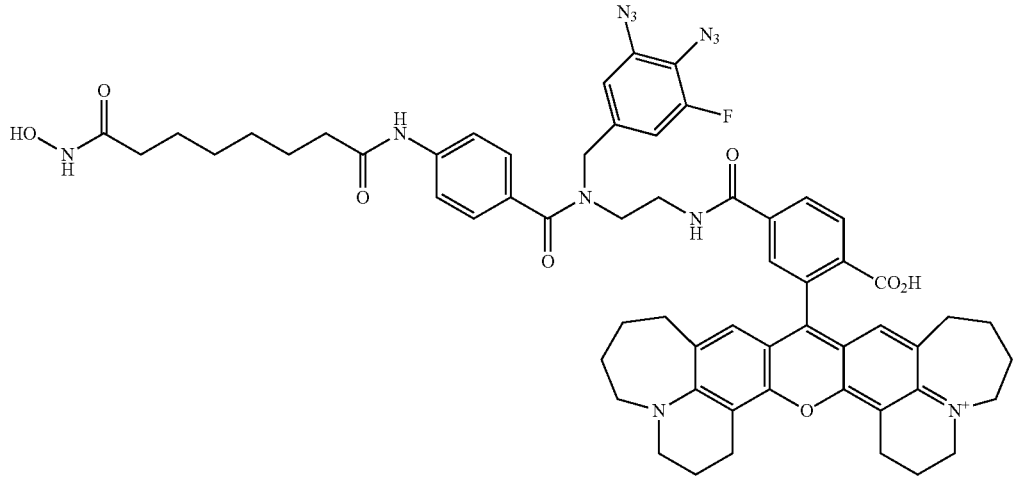

SL-1294

HPLC: 99% purity at 254 nm; ¹H NMR (400 MHz, Methanol-d4, reported for mixture of rotamers) δ 8.42-6.61 (multiplets 11H), 4.77 (m, 1H), 4.57 (m, 1H), 3.82-3.52 (multiplets, 12H), 3.10-2.99 (m, 4H), 2.88-2.65 (m, 4H), 2.42-2.23 (m, 3H), 2.14-2.02 (m, 5H), 2.00-1.88 (m, 4H), 1.84-1.73 (m, 4H), 1.72-1.54 (m, 4H), 1.47-1.30 (m, 4H); HRMS (SI) Calc'd for $C_{59}H_{62}FN_{12}O_8$ [M+]+ 1085.4792, found 1085.4817.

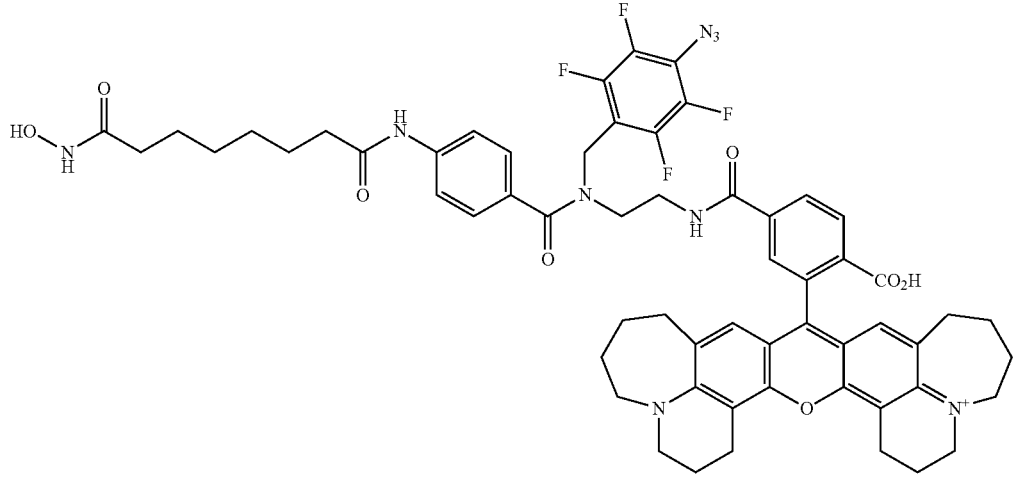

SL-1277

HPLC: 96% purity at 254 nm; ¹H NMR (400 MHz, Methanol-d4, reported for mixture of rotamers) δ 8.40-6.57 (multiplets 9H), benzylic CH₂ are under HOD peak, 3.82-3.51 (multiplets, 12H), 3.12-2.97 (m, 4H), 2.91-2.65 (m, 4H), 2.44-2.23 (m, 3H), 2.17-2.02 (m, 5H), 2.00-1.88 (m, 4H), 1.84-1.73 (m, 4H), 1.72-1.54 (m, 4H), 1.47-1.30 (m, 4H); HRMS (SI) Calc'd for $C_{59}H_{60}F_4N_9O_8$ [M+]+ 1098.4495, found 1098.4505.

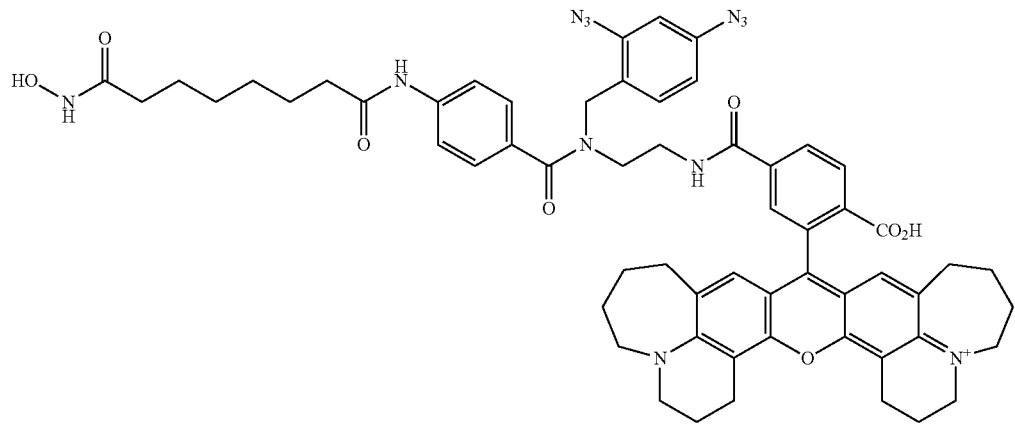
SL-1089
HPLC: 99% purity at 254 nm; HRMS (SI) Calc'd for $C_{59}H_{63}N_{12}O_8$ [M+]+ 1067.4886, found 1067.4889.
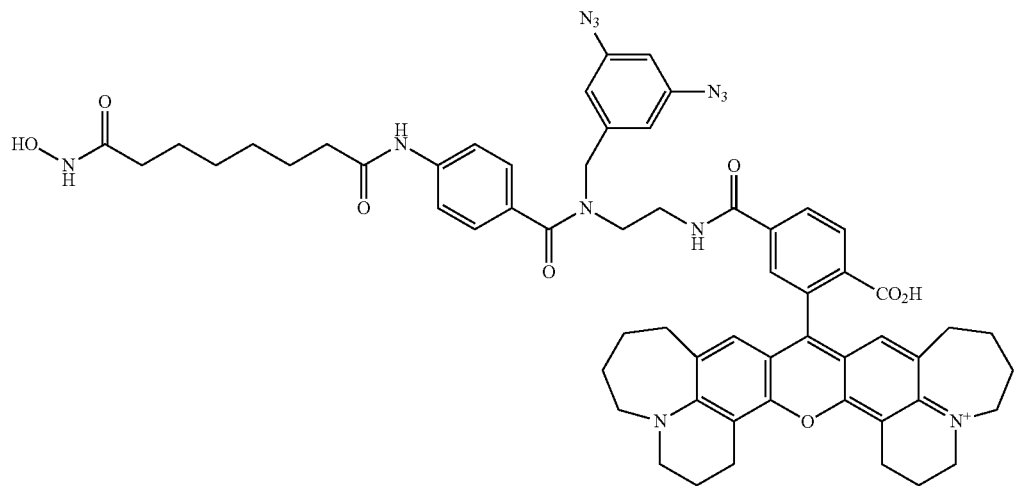
SL-1104
HPLC: 99% purity at 254 nm; HRMS (SI) Calc'd for $C_{59}H_{63}N_{12}O_8$ [M+]+ 1067.4886, found 1067.4878.
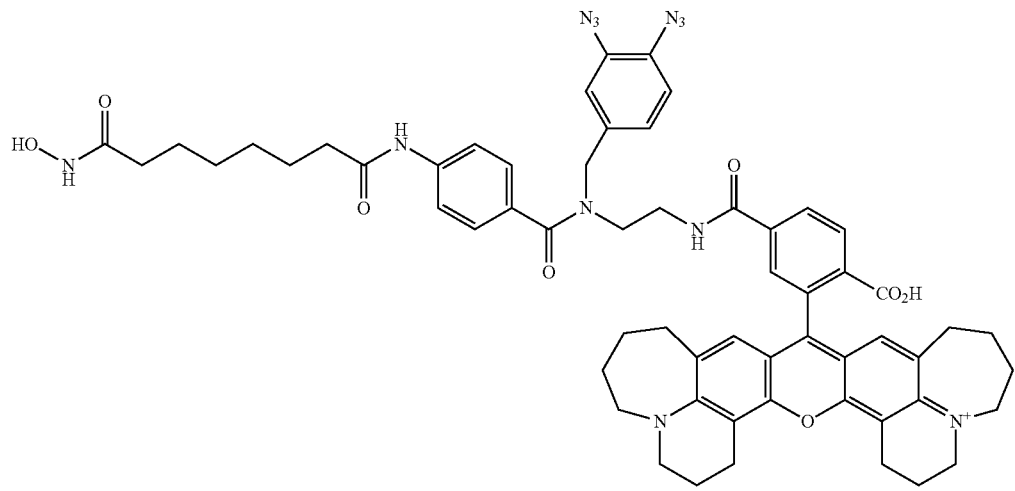
SL-1080

HPLC: 97% purity at 254 nm; HRMS (SI) Calc'd for C₅₉H₆₃N₁₂O₈ [M+]+ 1067.4886, found 1067.4899.

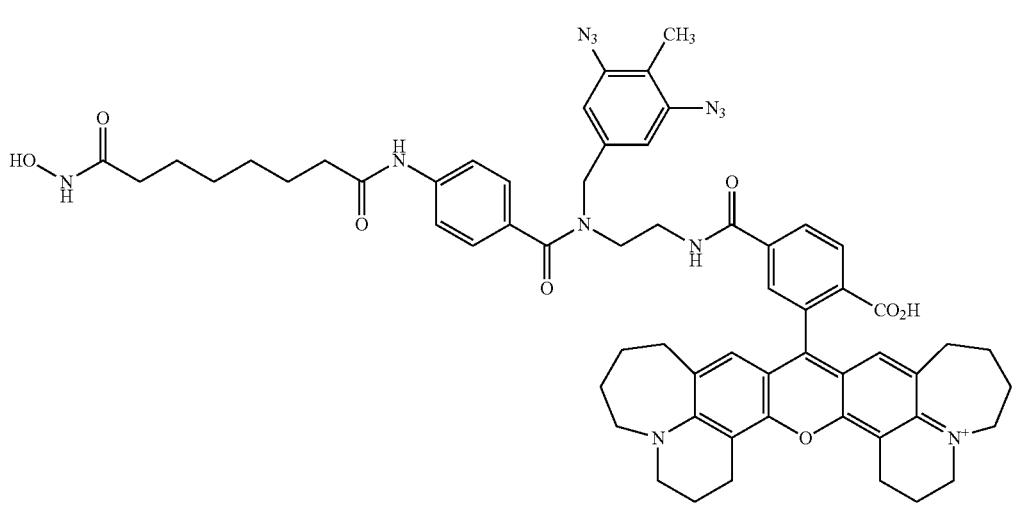

SL-1414

HPLC: 99% purity at 254 nm; 1H NMR (400 MHz, Methanol-d4, reported for mixture of rotamers) δ 8.37 (d, J=8.2 Hz, 1H), 8.11 (m, 1H), 7.74 (m, 1H), 7.49 (m, 2H), 7.23 (d, J=8.3 Hz, 2H), 7.02 (s, 1H), 6.67 (m, 3H), 4.62 (s, 1H), 3.83-3.62 (m, 6H), 3.56 (m, 6H), 3.03 (m, 4H), 2.82 (m, 4H), 2.42-2.24 (m, 3H), 2.14-2.05 (m, 5H), 2.03-1.96 (m, 3H), 1.96-1.88 (m, 4H), 1.85-1.74 (m, 4H), 1.75-1.57 (m, 4H), 1.46-1.33 (m, 4H); HRMS (SI) Calc'd for C₆₀H₆₅N₁₂O₈ [M+]+ 1081.5043, found 1081.5041.

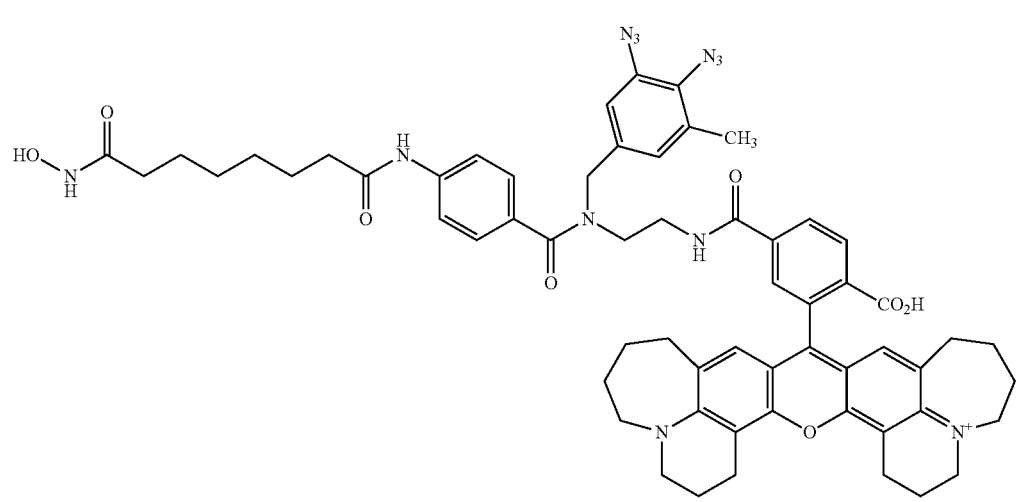

SL-1421

HPLC: 99% purity at 254 nm; ¹H NMR (400 MHz, Methanol-d4, reported for mixture of rotamers) δ 8.36-6.64 (multiplets 11H), 4.79 (m, 1H), 4.56 (m, 1H), 3.82-3.50 (multiplets, 12H), 3.10-2.97 (m, 4H), 2.88-2.65 (m, 4H), 2.42-2.26 (m, 2H), 2.26-2.14 (m, 3H), 2.14-2.02 (m, 6H), 2.00-1.88 (m, 4H), 1.84-1.73 (m, 4H), 1.72-1.54 (m, 4H), 1.47-1.30 (m, 4H); HRMS (SI) Calc'd for C₆₀H₆₅N₂O₈ [M+]+ 1081.5043, found 1081.5030.

Synthesis of Fluorescent Dasatinib-PRG-NCT Conjugates:
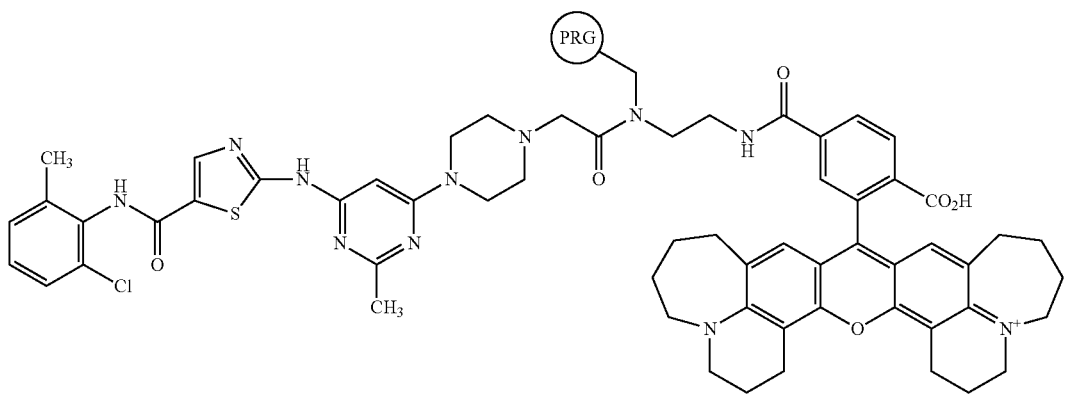 [SMILES: CCN(CCNC(=O)c1ccc(C(=O)O)c(C2=c3cc4c5c(c3Oc3c2cc2c6c3CCCN6CCCC2)CCC[N+]=5CCCC4)c1)C(=O)CN1CCN(c2cc(Nc3ncc(C(=O)Nc4c(C)cccc4Cl)s3)nc(C)n2)CC1]
General Structure of Dasatinib-PRG-NCT Probes
SL-1211
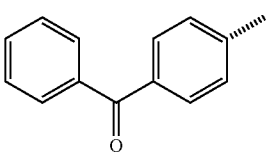
SL-1200
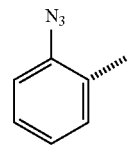
SL-1162
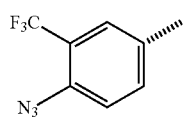
SL-1193
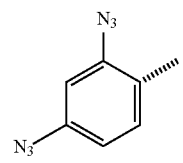
SL-1209
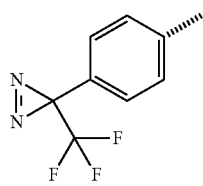
SL-1185
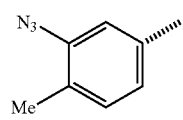
SL-1220
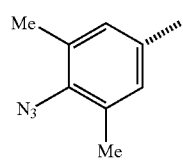
-continued
SL-1164
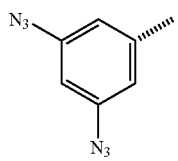
SL-1269
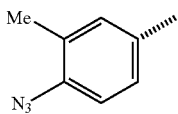
SL-1163
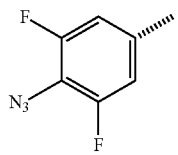
SL-1297
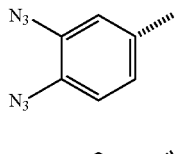
SL-1208
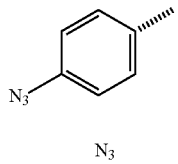
SL-1196
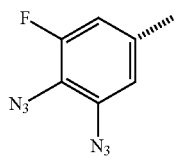
SL-1257
SL-1296

121
-continued
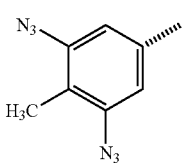
SL-1413
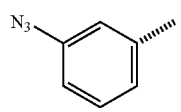
SL-1199
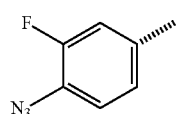
SL-1305
122
-continued
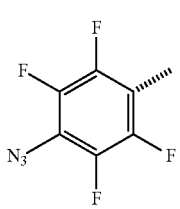
SL-1283
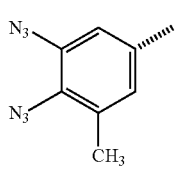
SL-1422
General Scheme for Dasatinib-PRG-NCT Probes Synthesis
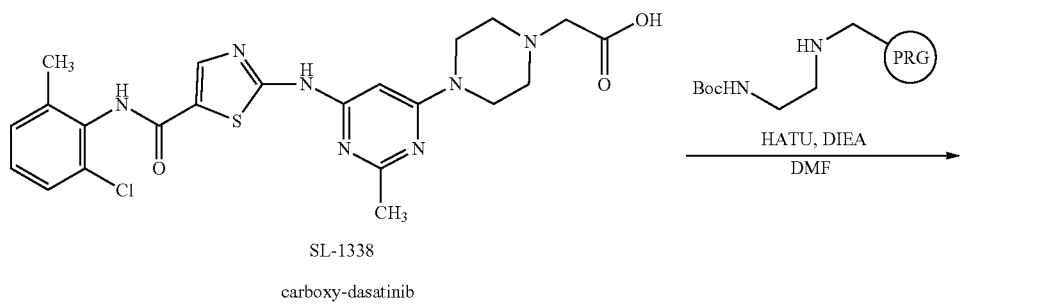
SL-1338
carboxy-dasatinib
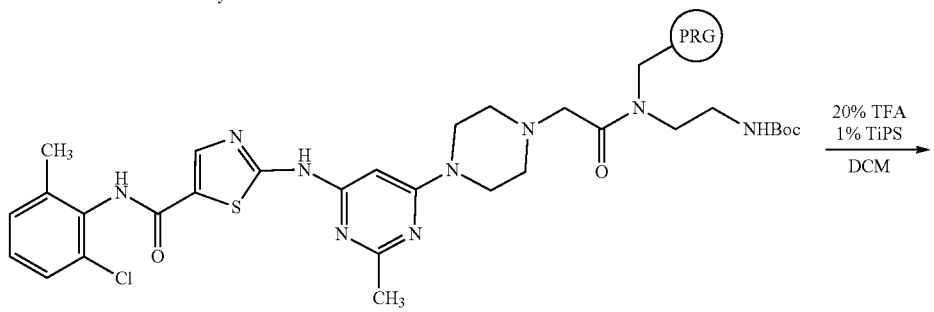
Boc-protected dasatinib-PRG
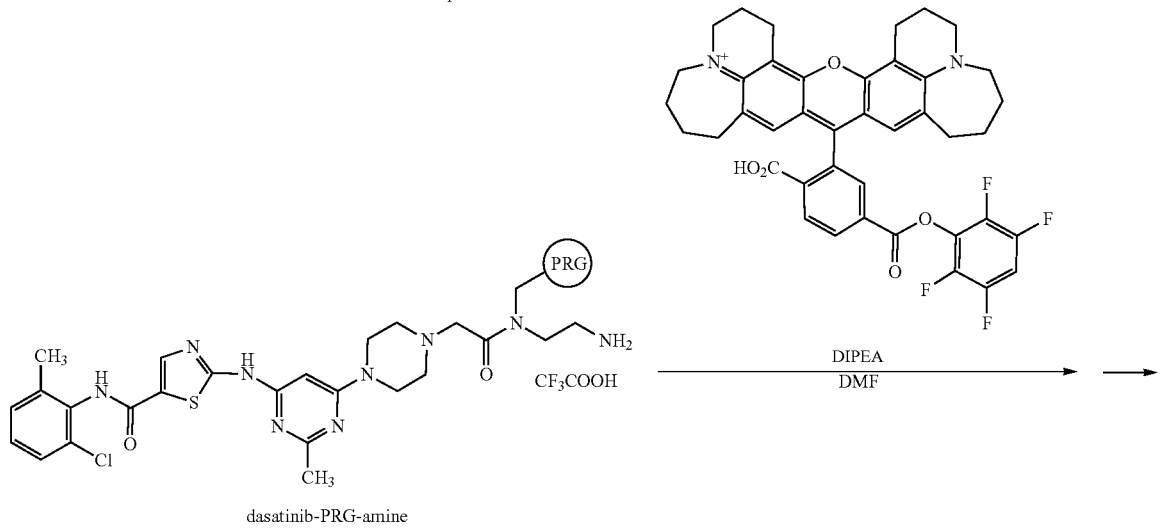
dasatinib-PRG-amine

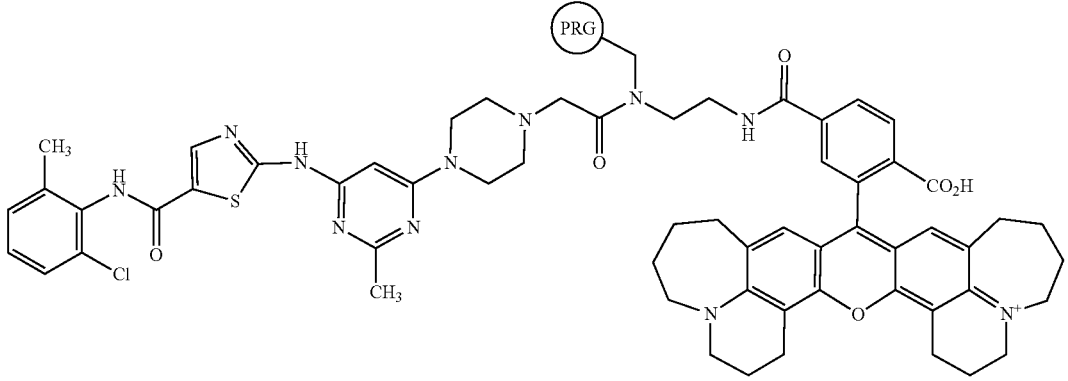

dasatinib-PRG-NCT probe

Exemplary Synthetic Procedures for Dasatinib-PRG-NCT Probes

Synthesis of Probe SL-1269 (Dasatinib-PRG-NCT Probe #3):

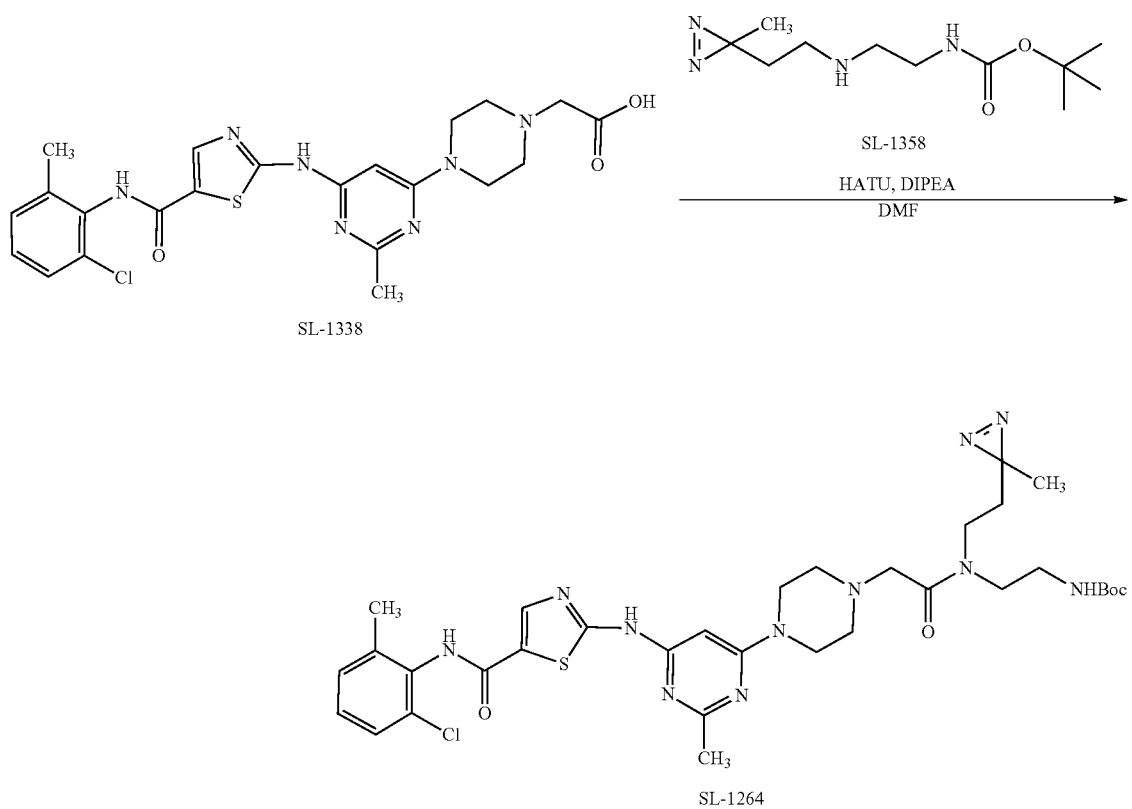

To a solution of SL-1338 (9.0 mg, 18 μmol), HATU (8.5 mg, 22 μmol), and DIPEA (16 μL, 0.09 mmol) in DMF (7 mL), SL-1358 (4.3 mg, 18 μmol) was added. The resulting solution was stirred at 22° C. for 19 hours at which point LCMS analysis indicated full consumption of starting material. The reaction mixture was purified by preparative RP HPLC (5→95% MeCN/H$_2$O buffered with 0.5% TFA) to provide 11 mg (85% yield) of conjugate SL-1264 as a clear film. HPLC: 99% purity at 254 nm; $^1$H NMR (400 MHz, Methanol-d4, reported for mixture of rotamers) δ 8.18 (s, 1H), 7.36 (dd, J=7.3, 2.2 Hz, 1H), 7.31-7.14 (m, 2H), 6.17 (s, 1H), 4.35 (s, 1.4H), 4.27 (s, 0.6H), 4.21-3.63 (m, 3H), 3.60-3.40 (m, 5H), 3.29-3.20 (m, 3H), 2.52 (s, 3H), 2.33 (s, 3H), 1.73-1.65 (m, 0.6H), 1.60 (t, J=7.4 Hz, 1.4H), 1.47-1.40

(m, 9H), 1.07 (m, 3H); HRMS (SI) Calc'd for C$_{33}$H$_{45}$ClN$_{11}$O$_4$S [M+H]+ 726.3060, found 726.3082.

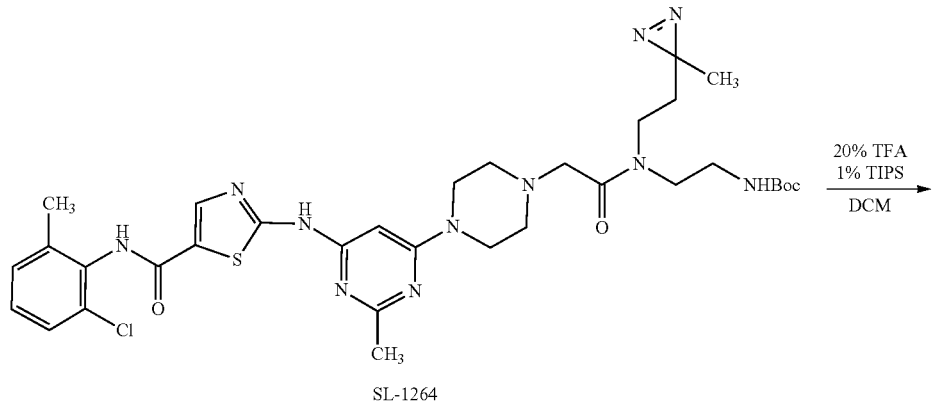

SL-1264

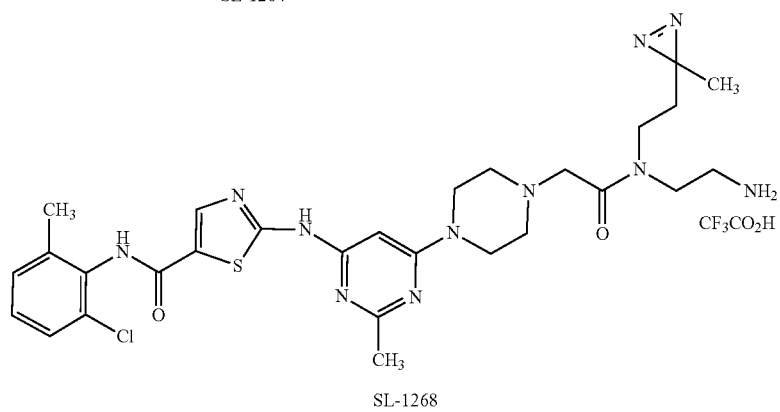

SL-1268

To a solution of SL-1264 (11 mg, 15 µmol) in DCM (8 mL), TiPS (100 µL) followed by TFA (2 mL) was added. The resulting solution was stirred at 22° C. for 1.5 hours at which point HPLC analysis indicated full consumption of starting material. Volatiles were removed under reduced pressure, crude residue dissolved in 5 mL MeOH, and volatiles removed under vacuum. The crude residue was dried under high vacuum and used in the next step without further purification. HRMS (SI) Calc'd for C$_{28}$H$_{37}$ClN$_{11}$O$_2$S [M+H]+ 626.2535, found 626.2531.

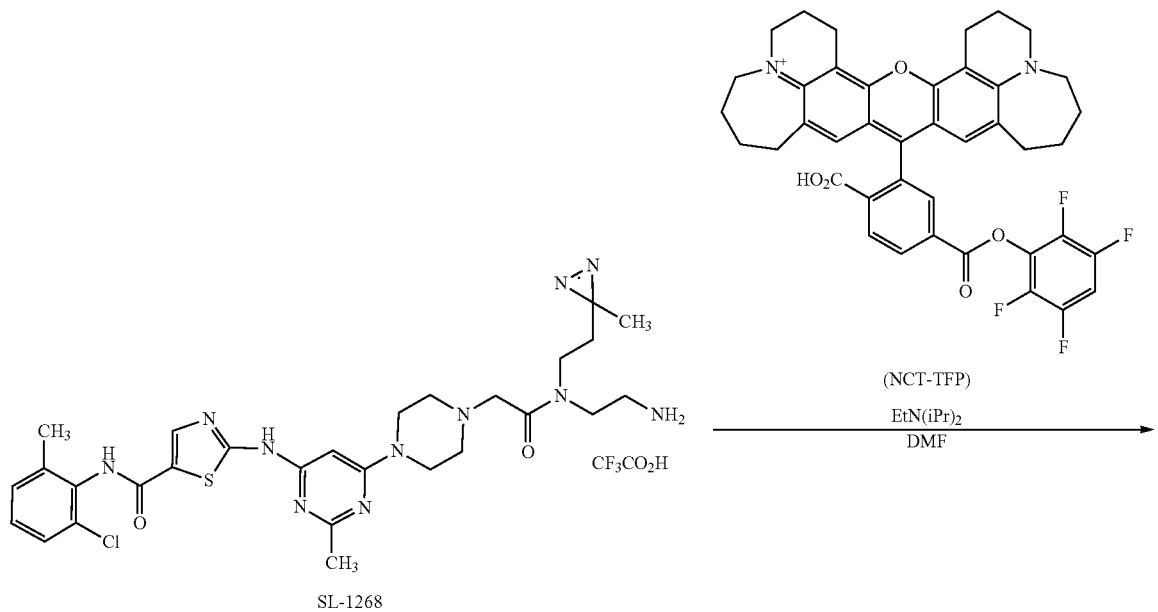

SL-1268

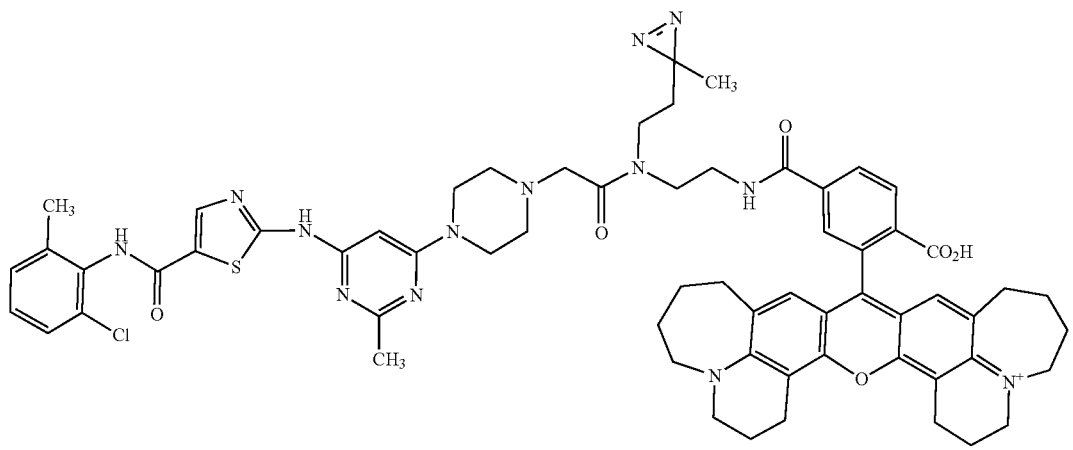

SL-1269

To a solution of SL-1268 (11 mg, 15 μmol) and DIPEA (6.0 μL, 34 μmol) in DMF (6 mL), NCT-TFP (3.5 mg, 5 μmol, prepared according to ACS Chem. Biol., 2016, 11, 2608-2617) was added. The resulting solution was stirred at 22° C. for 1 hour at which point HPLC analysis indicated full consumption of the starting material. The reaction mixture was purified by preparative RP HPLC (5→95% MeCN/H$_2$O buffered with 0.5% TFA) to provide 1.3 mg (23% yield) of conjugate SL-1269 as a deep blue film. HPLC: 97% purity at 254 nm; 1H NMR (400 MHz, Methanol-d4, reported for mixture of rotamers) δ 8.42-8.36 (m, 1H), 8.25-8.07 (m, 2H), 7.90-7.72 (m, 1H), 7.44-7.31 (m, 1H), 7.29-7.16 (m, 2H), 6.66 (s, 1H), 6.64 (s, 1H), 6.10 (s, 0.6H), 6.00 (s, 0.4H), 4.48 (s, 1H), 4.26 (s, 1H), 4.16-3.80 (br. s. 2H) 3.80-3.62 (m, 5H), 3.62-3.51 (m, 5H), 3.51-3.42 (m, 4H), 3.33 (m, 2H, overlap with CD$_2$HOD), 3.27 (m, 2H, overlap with CD$_2$HOD), 3.10-2.98 (m, 4H), 2.86-2.62 (m, 4H), 2.51-2.43 (m, 3H), 2.33 (s, 3H), 2.05 (m, 4H), 1.93 (m, 4H), 1.88-1.75 (m, 4H), 1.75-1.65 (m, 1H), 1.61 (m, 1H), 1.06-1.03 (m, 3H); HRMS (SI) Calc'd for C$_{63}$H$_{69}$ClN$_{13}$O$_6$S [M+]+ 1170.4898, found 1170.4881.

Characterization Data for Dasatinib-PRG-NCT Probes:

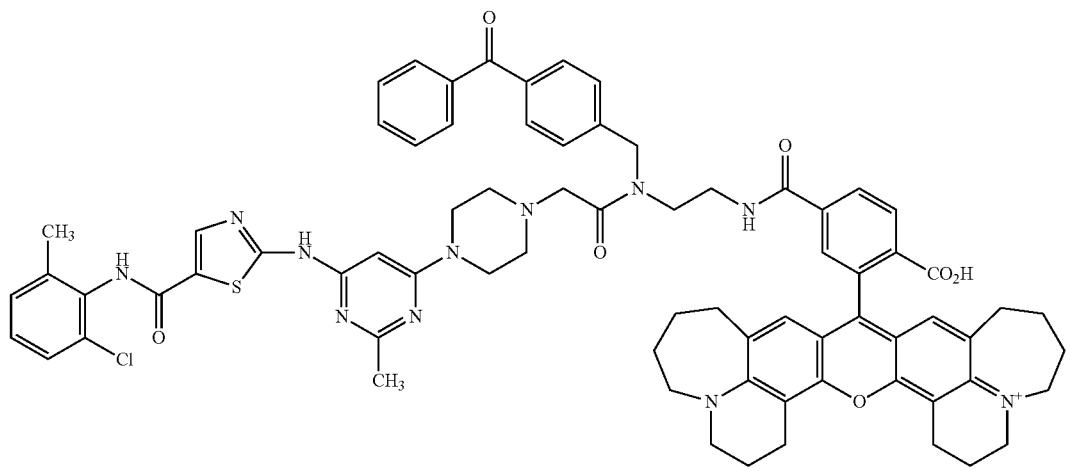

SL-1211

HPLC: 97% o purity at 254 nm; HRMS (SI) Calc'd for C$_{73}$H$_{73}$ClN$_{11}$O$_7$S [M+]+ 1282.5098, found 1282.5079.
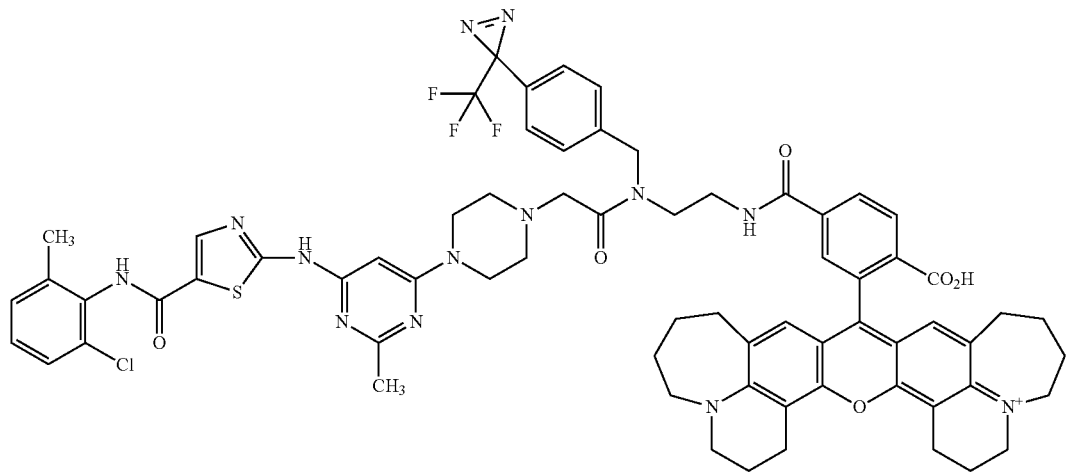
SL-1209
HPLC: 95% purity at 254 nm; HRMS (SI) Calc'd for C$_{68}$H$_{68}$ClF$_3$N$_{13}$O$_6$S [M+]+1286.4771, found 1286.4779.
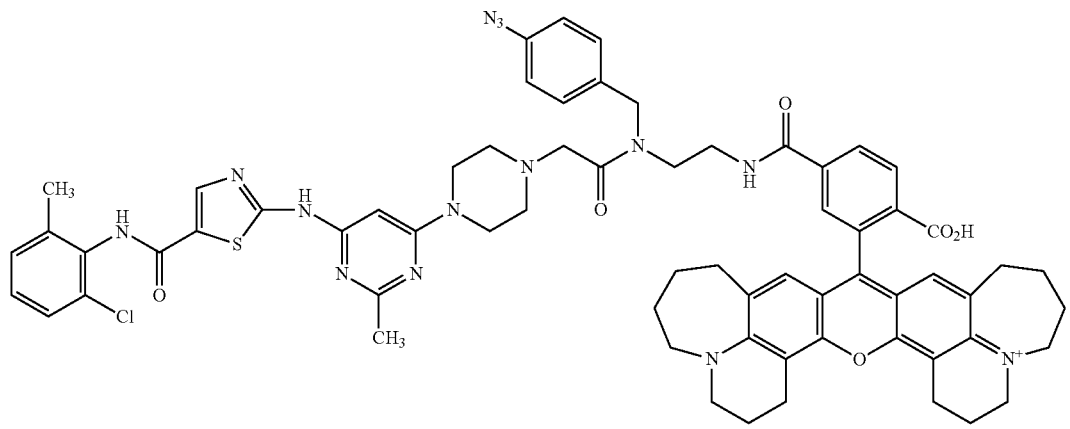
SL-1196
HPLC: 99% purity at 254 nm; HRMS (SI) Calc'd for C$_{68}$H$_{68}$ClN$_{14}$O$_6$S [M+]+ 1219.4850, found 1219.4853.
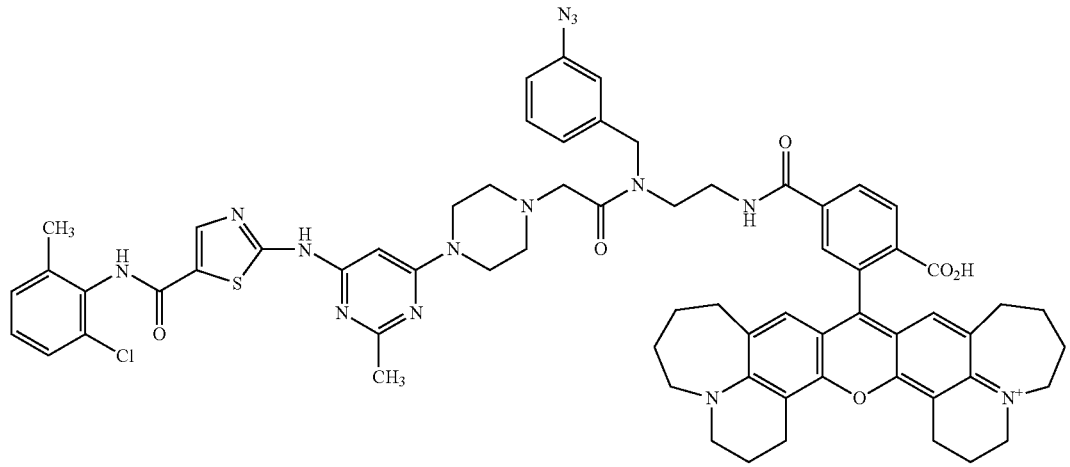
SL-1199

HPLC: 98% purity at 254 nm; HRMS (SI) Calc'd for $C_{68}H_{68}ClN_{14}O_6S[M+]+$ 1219.4850, found 1219.4848.
SL-1200
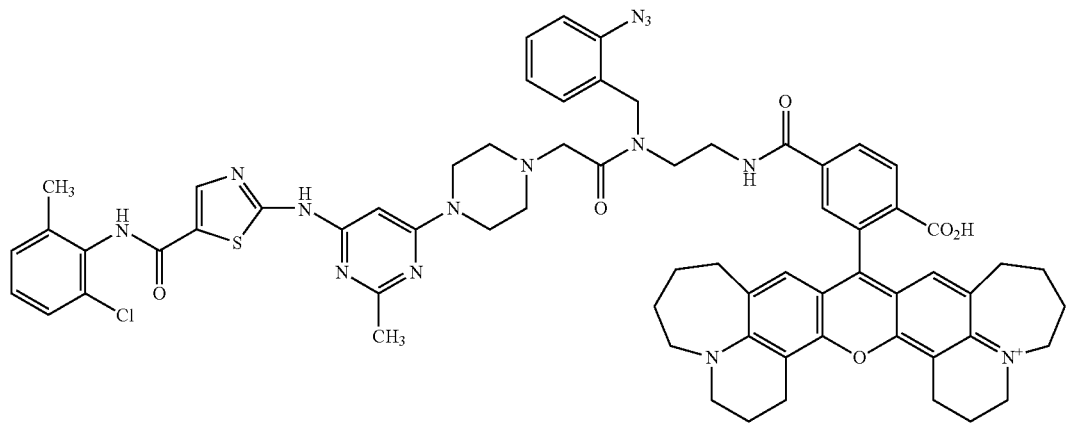
HPLC: 97% purity at 254 nm; HRMS (SI) Calc'd for $C_{68}H_{68}ClN_{14}O_6S$ [M+]+ 1219.4850, found 1219.4862.
SL-1185
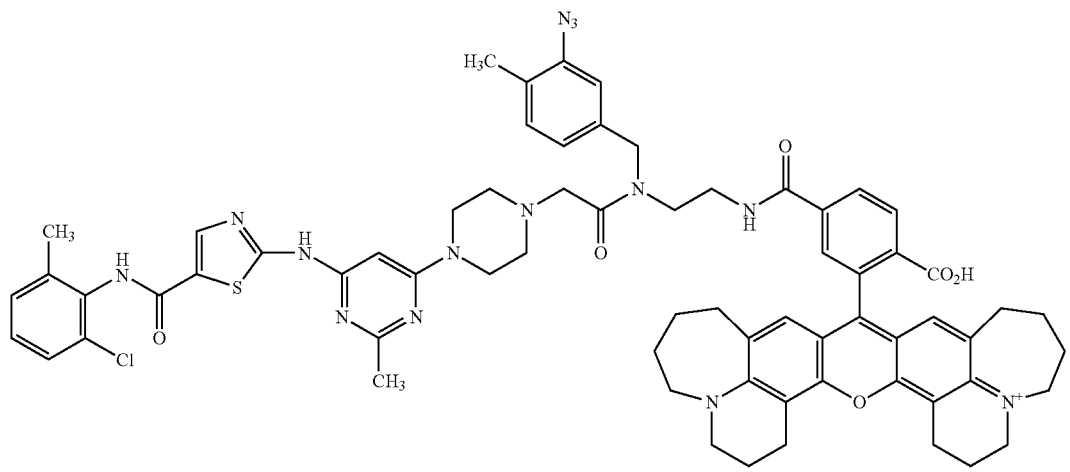
HPLC: 98% purity at 254 nm; HRMS (SI) Calc'd for $C_{67}H_{70}ClN_{14}O_6S$ [M+]+ 1233.5007, found 1233.4992.
SL-1163
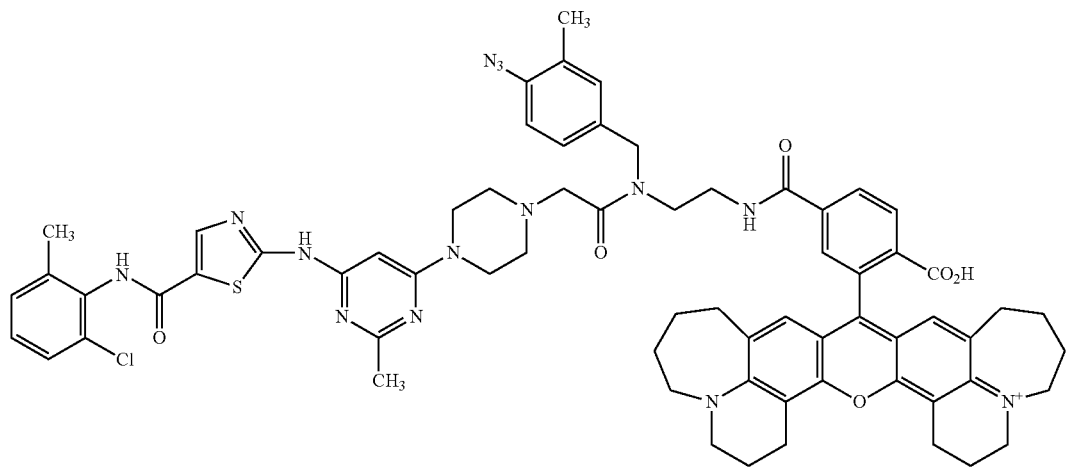

HPLC: 95% purity at 254 nm; MS (SI) Calc'd for $C_{67}H_{70}ClN_{14}O_6S$ [M+]+ 1233.50, found 1234.2.
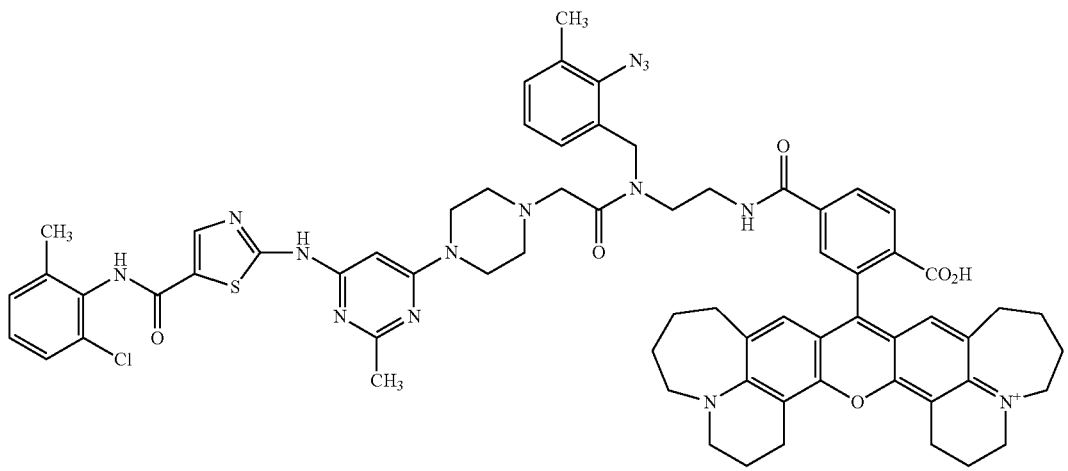
SL-1257
HPLC: 99% purity at 254 nm; HRMS (SI) Calc'd for $C_{67}H_{70}ClN_{14}O_6S$ [M+]+ 1233.5007, found 1233.4998.
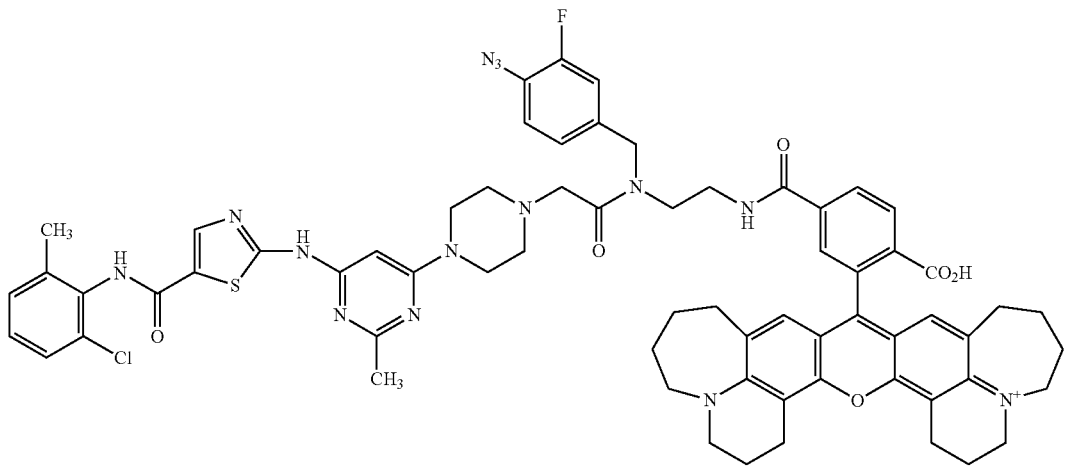
SL-1305
HPLC: 99% purity at 254 nm; $^1$H NMR (400 MHz, Methanol-d4, reported for mixture of rotamers) δ 8.38 (m, 1H), 8.18 (s, 1H), 8.11 (m, 1H), 7.82 (d, J=1.8 Hz, 0.4H), 7.76 (d, J=1.8 Hz, 0.5H), 7.37 (m, 1H), 7.33-7.21 (m, 2H), 7.21-7.07 (m, 3H), 6.69 (s, 1H), 6.64 (s, 1H), 6.11 (s, 0.4H), 5.99 (s, 0.3H), 4.68 (s, 1H), 4.60 (s, 1H), 4.57 (s, 1H), 4.27 (s, 1H), 4.19-3.77 (m, 3H), 3.78-3.62 (m, 5H), 3.62-3.42 (m, 8H), 3.08-2.98 (m, 4H), 2.84-2.71 (m, 4H), 2.47 (m 3H), 2.33 (s, 3H), 2.11-2.03 (m, 4H), 1.97-1.90 (m, 4H), 1.86-1.76 (m, 4H); MS (SI) Calc'd for $C_{66}H_{67}CFN_{14}O_6S$ [M+]+ 1237.48, found 1238.07.
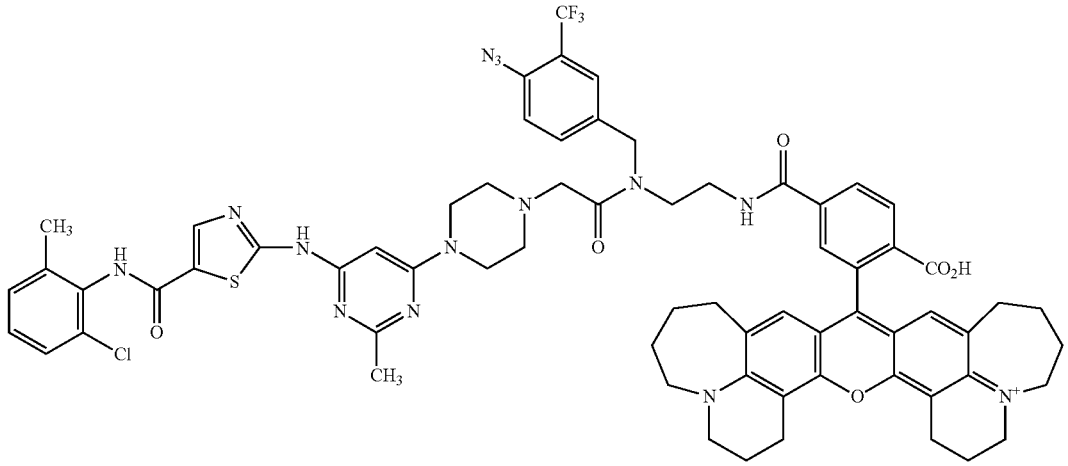
SL-1162

HPLC: 98% purity at 254 nm; HRMS (SI) Calc'd for C₆₇H₆₇ClF₃N₁₄O₆S [M+]+ 1287.4724, found 1287.4706.
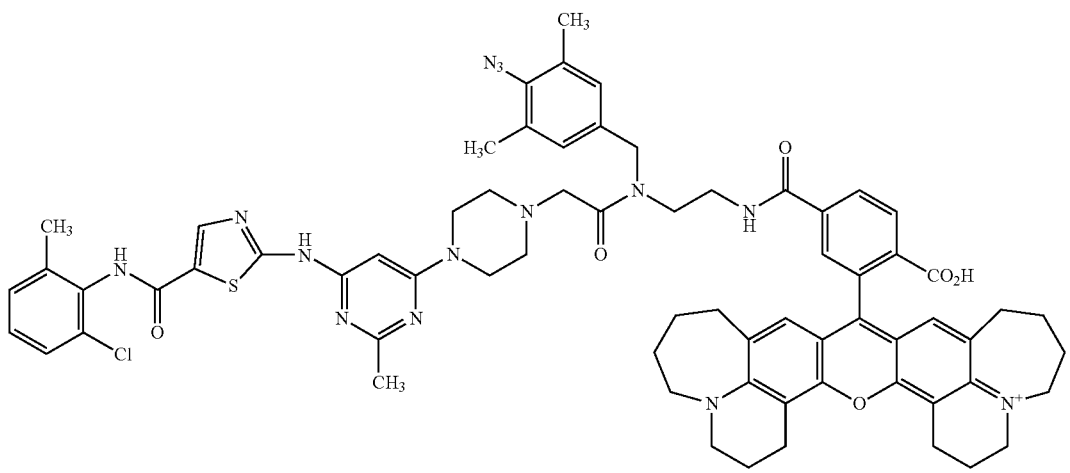
SL-1220
HPLC: 98% purity at 254 nm; HRMS (SI) Calc'd for C₆₈H₇₂ClN₁₄O₆S [M+]+ 1247.5163, found 1247.5101.
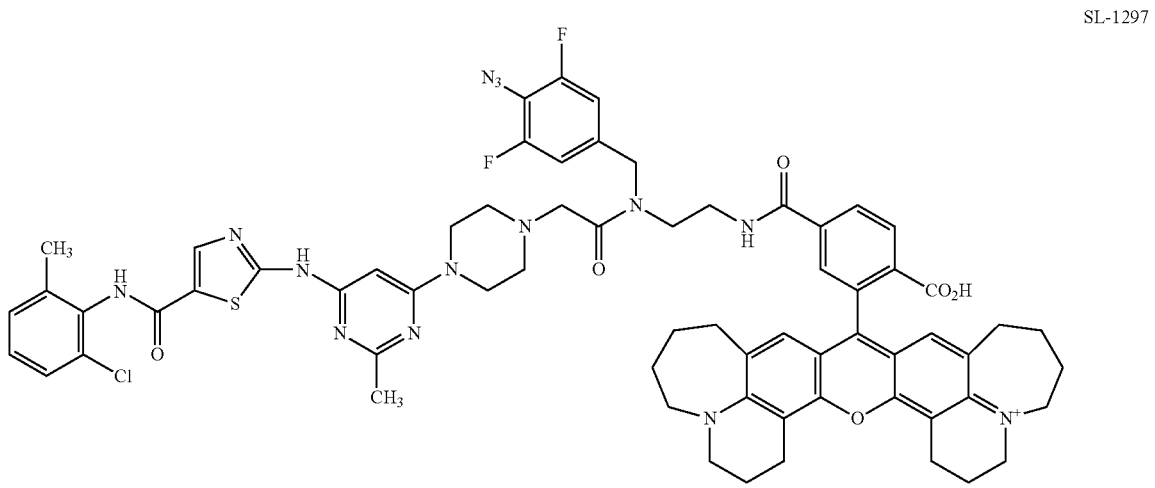 [SMILES: Cc1nc(Nc2ncc(C(=O)Nc3c(C)cccc3Cl)s2)cc(N2CCN(CC(=O)N(CCNC(=O)c3ccc(C(=O)O)c(C4=c5cc6c7c(c5Oc5c4cc4c8c5CCCN8CCCC4)CCC[N+]=7CCCC6)c3)Cc3cc(F)c(N=[N+]=[N-])c(F)c3)CC2)n1]
SL-1297
HPLC: 99% purity at 254 nm; ¹H NMR (400 MHz, Methanol-d4, reported for mixture of rotamers) δ 8.38 (m, 1H), 8.18 (s, 1H), 8.11 (m, 1H), 7.80 (m, 1H), 7.37 (m, 1H), 7.31-7.18 (m, 2H), 7.03 (m, 2H), 6.66 (m, 2H), 6.05 (m, 1H), 4.67 (s, 1H), 4.58 (s, 2H), 4.26 (s, 1H), 4.16-3.80 (m, 3H), 3.69 (m, 6H), 3.64-3.41 (m, 10H), 3.11-2.98 (m, 4H), 2.79 (m, 4H), 2.47 (m, 3H), 2.33 (s, 3H), 2.06 (m, 4H), 1.93 (m, 4H), 1.81 (m, 4H); HRMS (SI) Calc'd for C₆₆H₆₆CF₂N₁₄O₆S [M+]+1255.4662, found 1255.4682.
SL-1296
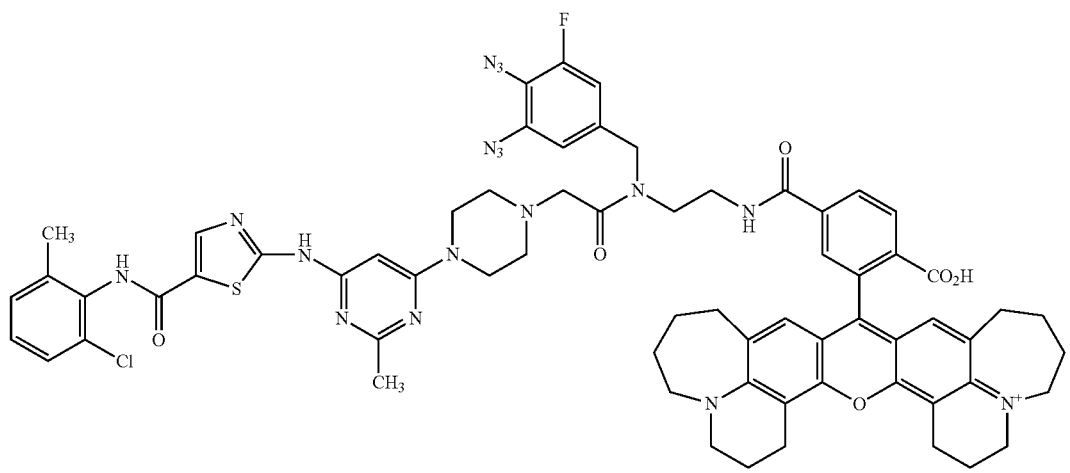

HPLC: 99% purity at 254 nm; $^1$H NMR (400 MHz, Methanol-d4, reported for mixture of rotamers) δ 8.27 (m, 1H), 8.08 (s, 1H), 7.98 (m, 1H), 7.73-7.65 (m, 1H), 7.26 (m, 1H), 7.22-7.03 (m, 2H), 7.03-6.75 (m, 2H), 6.58 (m, 2H), 6.05-5.93 (m, 1H), 4.57 (s, 1H), 4.47 (m, 2H), 4.21 (s, 1H), 3.88 (s, 3H), 3.70-3.53 (m, 5H), 3.53-3.28 (m, 9H), 3.02-2.91 (m, 4H), 2.75-2.57 (m, 4H), 2.37 (m, 3H), 2.23 (s, 3H), 2.05-1.89 (m, 4H), 1.84 (m, 4H), 1.72 (m, 4H); HRMS (SI) Calc'd for $C_{66}H_{66}ClFN_{17}O_6S$ [M+]+ 1278.4770, found 1278.4789.
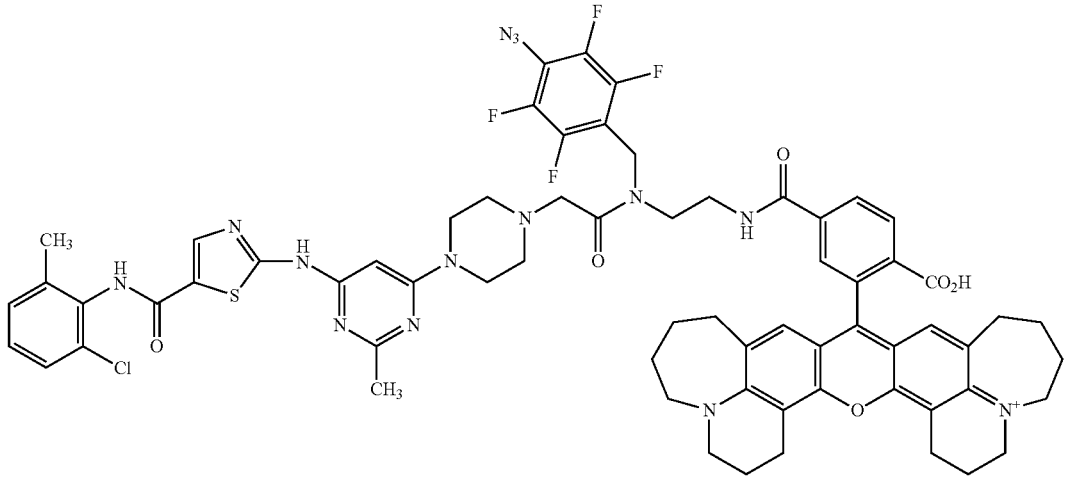
SL-1283
HPLC: 99% purity at 254 nm; $^1$H NMR (400 MHz, Methanol-d4, reported for mixture of rotamers) δ 8.41-8.38 (m, 1H), 8.17 (s, 1H), 8.17-8.00 (m, 1H), 7.86 (d, J=1.9 Hz, 0.5H), 7.80 (d, J=1.9 Hz, 0.5H), 7.37 (m, 1H), 7.33-7.15 (m, 2H), 6.71 (s, 1H), 6.65 (s, 1H), 6.05 (s, 0.5H), 5.93 (s, 0.5H), 4.73 (s, 1H), 4.45 (s, 1H), 4.32 (s, 1H), 3.89 (s, 3H), 3.80-3.47 (m, 14H), 3.02 (m, 4H), 2.89-2.70 (m, 4H), 2.46 (m, 3H), 2.33 (m, 3H), 2.14-2.00 (m, 4H), 1.94 (m, 4H), 1.82 (m, 4H); HRMS (SI) Calc'd for $C_{66}H_{64}CF_4N_{14}O_6S$ [M+]+ 1291.4473, found 1291.4469.
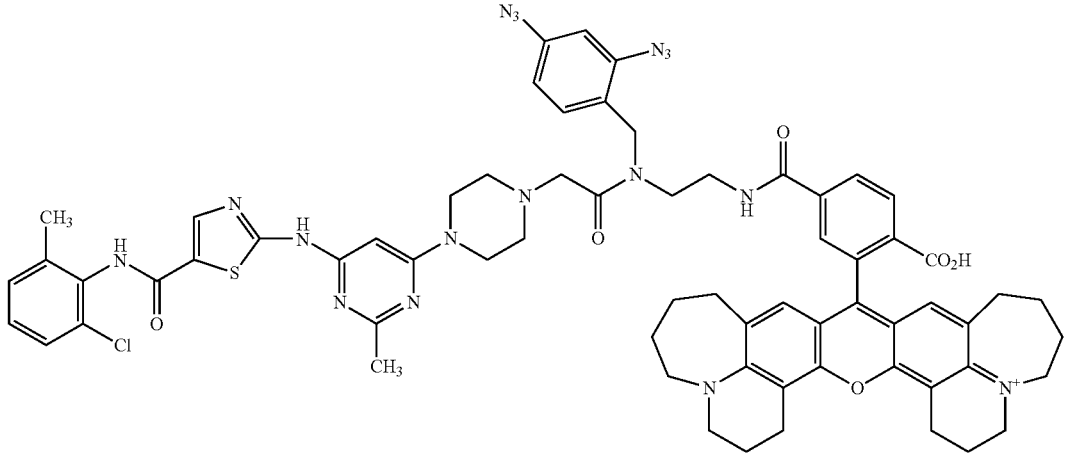
SL-1193

HPLC: 95% purity at 254 nm; HRMS (SI) Calc'd for $C_{66}H_{67}ClN_{15}O_6S$ [M+]+ 1260.4864, found 1260.4837.
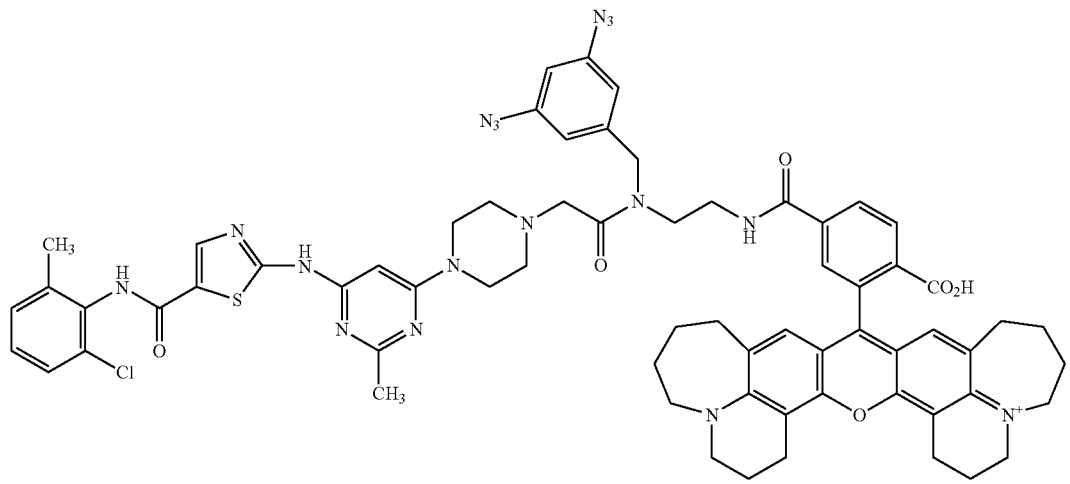
SL-1164
HPLC: 97% purity at 254 nm; MS (SI) Calc'd for $C_{66}H_{67}ClN_{15}O_6S$ [M+]+ 1260.49 found 1260.66.
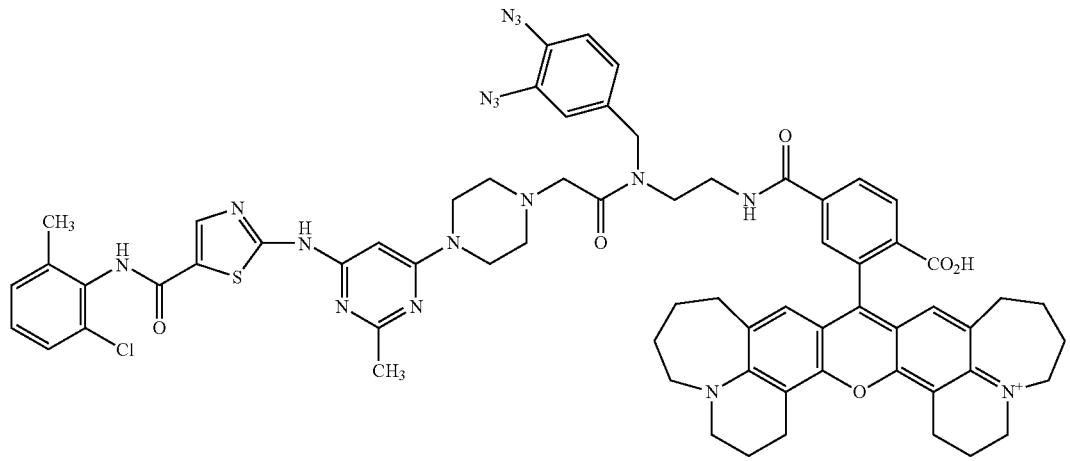
SL-1208
HPLC: 96% purity at 254 nm; HRMS (SI) Calc'd for $C_{66}H_{67}ClN_{15}O_6S$ [M+]+ 1260.4864, found 1260.4861.
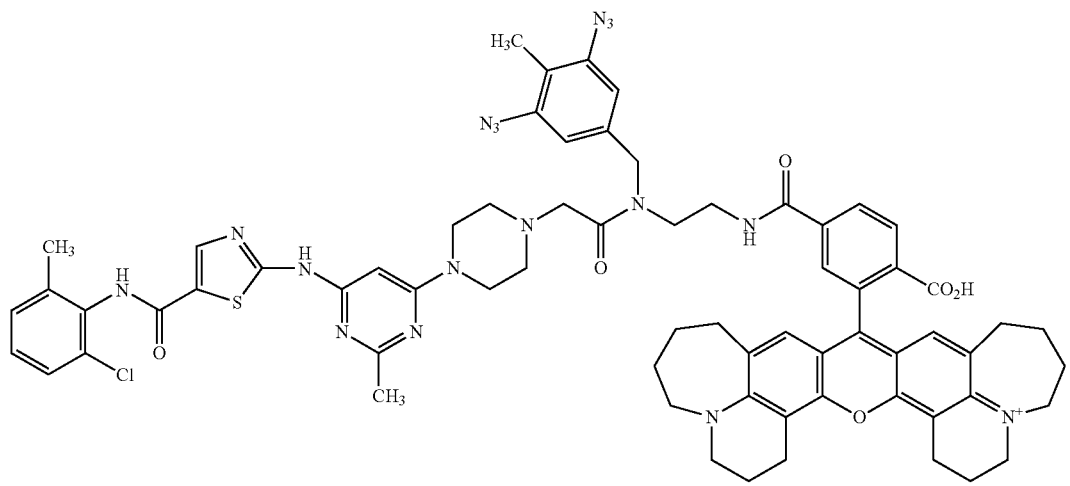
SL-1413

HPLC: 97% purity at 254 nm; ¹H NMR (400 MHz, Methanol-d4, reported for mixture of rotamers) δ 8.36 (m, 1H), 8.17 (m, 1H), 8.06 (m, 1H), 7.81 (m, 1H), 7.37 (m, 1H), 7.33-7.12 (m, 2H), 6.97 (s, 1H), 6.86 (s, 1H), 6.70 (s, 1H), 6.65 (s, 1H), 6.11 (s, 0.6H), 6.00 (s, 0.4H), 4.72 (s, 1H), 4.64 (s, 1H), 4.58 (s, 1H), 4.31 (s, 1H), 4.27-3.80 (m, 3H), 3.80-3.64 (m, 6H), 3.56 (m, 9H), 3.02 (m, 4H), 2.87-2.69 (m, 4H), 2.46 (m, 3H), 2.33 (s, 3H), 2.19-2.03 (m, 4H), 2.00 (m, 3H), 1.94 (m, 4H), 1.81 (m, 4H); HRMS (SI) Calc'd for $C_{67}H_{69}ClN_{17}O_6S$ [M+]+ 1274.5020, found 1274.4988.

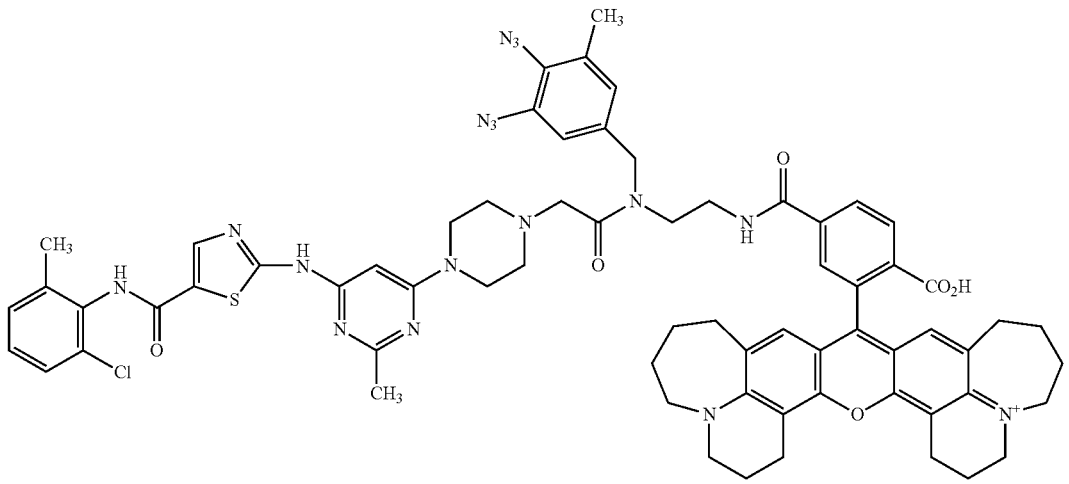

SL-1422

HPLC: 97% purity at 254 nm; ¹H NMR (400 MHz, Methanol-d4, reported for mixture of rotamers) δ 8.37 (m, 1H), 8.17 (m, 1H), 8.07 (m, 1H), 7.83 (d, J=1.7 Hz, 0.5H), 7.75 (d, J=1.7 Hz, 0.5H), 7.37 (m, 1H), 7.25 (m, 2H), 7.11-6.84 (m, 2H), 6.70 (s, 1H), 6.65 (s, 1H), 6.08 (s, 0.5H), 5.90 (s, 0.5H), 4.66 (s, 1H), 4.61 (s, 1H), 4.47 (s, 1H), 4.12 (s, 1H), 3.71 (m, 6H), 3.55 (m, 6H), 3.10-2.86 (m, 4H), 2.78 (m, 4H), 2.48 (s, 1.5H), 2.44 (s, 1.5H), 2.33 (s, 3H), 2.22 (s, 1.5H), 2.20 (s, 1.5H), 2.06 (m, 4H), 1.93 (m, 4H), 1.81 (m, 4H); HRMS (SI) Calc'd for $C_{67}H_{69}ClN_{17}O_6S$ [M+]+ 1274.5020, found 1274.45008.

Synthesis of Fluorescent Propranolol-PRG-NCT Conjugates:

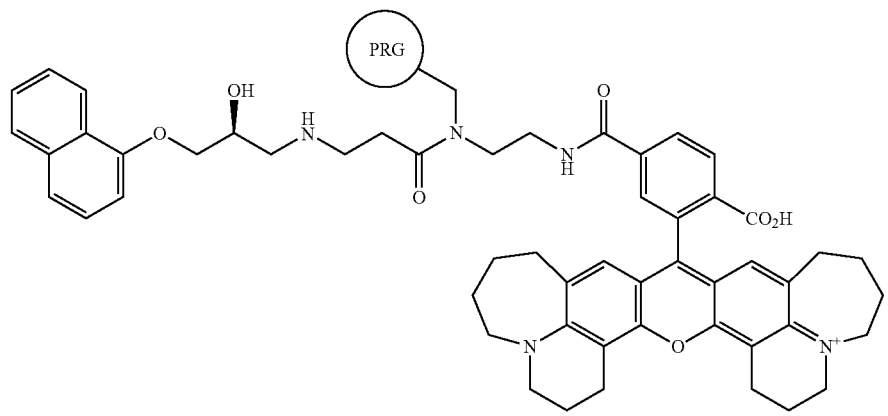 [SMILES: CCN(CCNC(=O)c1ccc(C(=O)O)c(C2=c3cc4c5c(c3Oc3c2cc2c6c3CCCN6CCCC2)CCC[N+]=5CCCC4)c1)C(=O)CCNC[C@H](O)COc1cccc2ccccc12]

General Structure of Propranolol-PRG-NCT Probes
Propranolol-PRG-NCT Probes
1
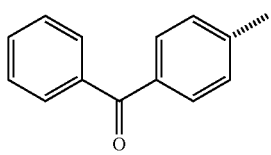
2
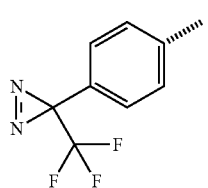
3
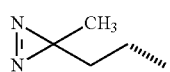
4
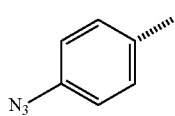
5
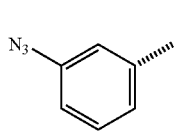
6
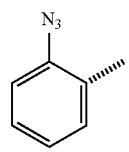
7
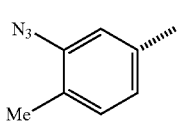
8
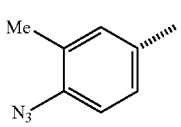
9
SL-1570
10
SL-1476
11
SL-1475
12
SL-1485
13
SL-1502
14
SL-1501
15
SL-1489
16
SL-1487
-continued
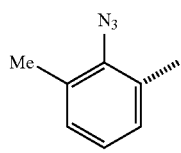 SL-1600
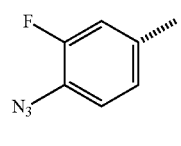 SL-1522
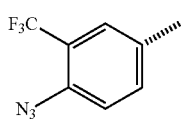 SL-1527
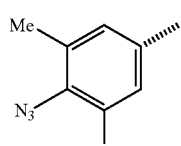 SL-1578
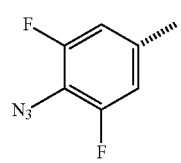 SL-1553
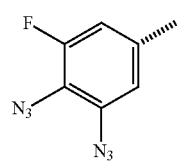 SL-1493
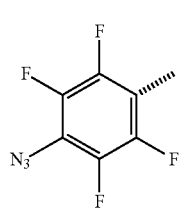 SL-1556
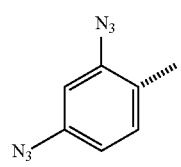 SL-1526

17 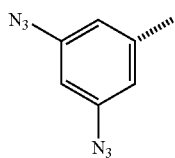
SL-1518
18 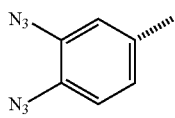
SL-1566
19 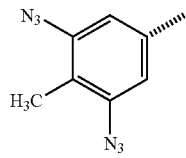
SL-1610
20 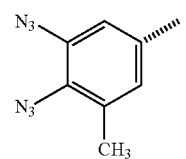
SL-1619
General Scheme for Propranolol-PRG-NCT Probes Synthesis
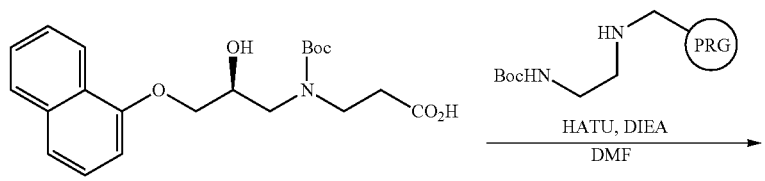
SL-1517
Boc-carboxy-prapranolol
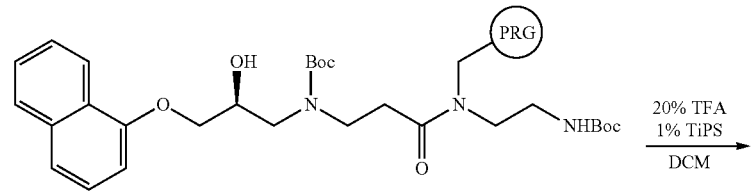
diBoc-protected propranolol-PRG
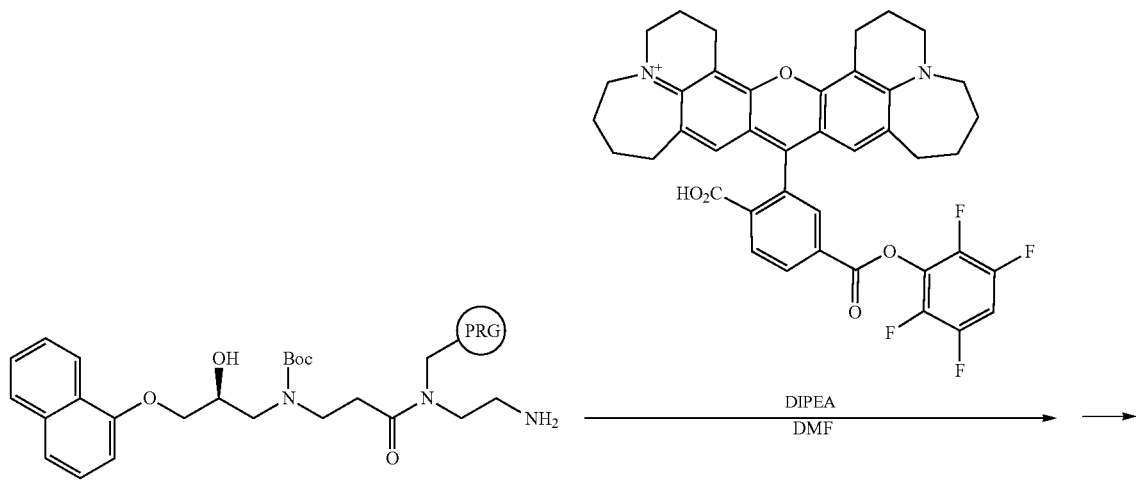
propranolol-PRG-amine

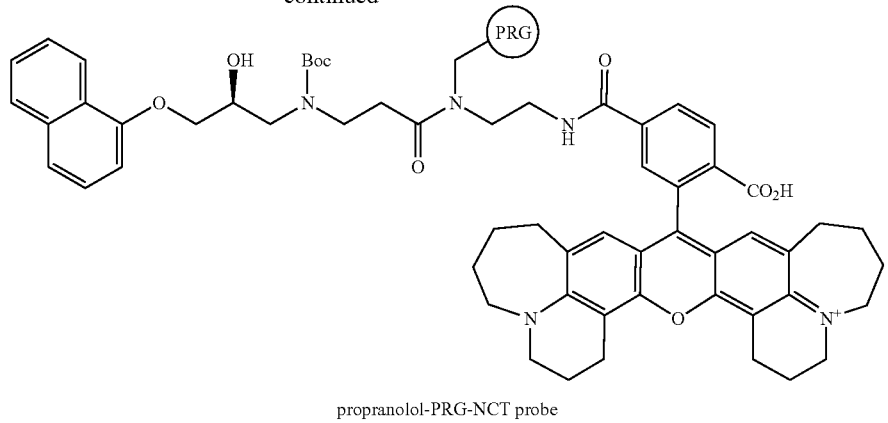

propranolol-PRG-NCT probe

Exemplary Synthetic Procedures for Propranolol-PRG-NCT Probes

Synthesis of Probe SL-1475 (Propranolol-PRG-NCT Probe #3):

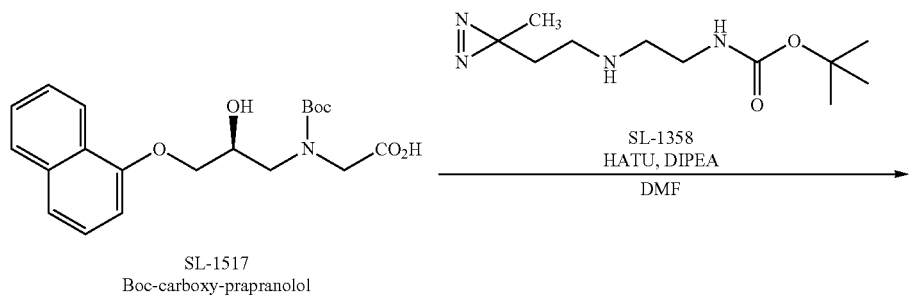

SL-1517
Boc-carboxy-prapranolol

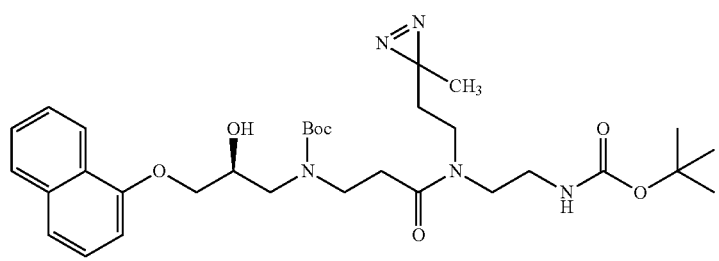

SL-1469

To a solution of SL-1517 (14 mg, 35 µmol), HATU (17 mg, 44 µmol), and DIPEA (31 µL, 170 µmol) in DMF (5 mL), SL-1358 (8.5 mg, 35 µmol) was added. The resulting solution was stirred at 22° C. for 19 hours at which point LCMS analysis indicated full consumption of starting material. The reaction mixture was purified by preparative RP HPLC (5→95% MeCN/H$_2$O buffered with 0.5% TFA) to provide 20 mg (93% yield) of conjugate SL-1469 as a clear film. HPLC: 99% purity at 254 nm; $^1$H NMR (400 MHz, Methanol-d4, reported for mixture of rotamers) δ 8.33 (s, 1H), 7.85-7.72 (m, 1H), 7.55-7.41 (m, 3H), 7.40-7.30 (m, 1H), 6.90 (m, 1H), 4.31 (s, 1H), 4.23-4.04 (m, 2H), 3.71 (m, 1H), 3.68-3.58 (m, 2H), 3.51-3.33 (m, 4H), 3.17 (m, 2H), 2.71 (m, 2H), 1.59 (m, 1H), 1.53-1.20 (m, 20H), 1.03 (s, 1H), 0.97 (s, 2H); HRMS (SI) Calc'd for C$_{32}$H$_{48}$N$_5$O$_7$ [M+H]+ 614.3548, found 614.3546.

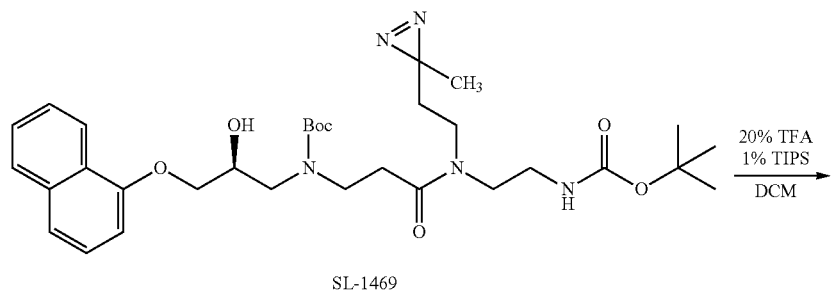

SL-1469

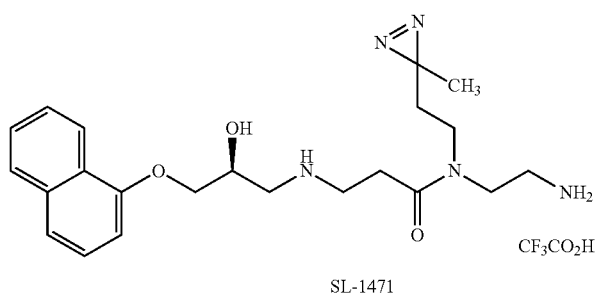

SL-1471

To a solution of SL-1469 (22 mg, 36 μmol) in DCM (8 mL), TiPS (100 μL) was added followed by TFA (2 mL). The resulting solution was stirred at 22° C. for 1 hour at which point HPLC analysis indicated full consumption of starting material. Volatiles were removed under reduced pressure, crude residue dissolved in 5 mL MeOH, and volatiles removed under vacuum. The crude residue was dried under high vacuum and used in the next step without further purification. MS (SI) Calc'd for $C_{22}H_{32}N_5O_3$ [M+H]+ 414.25, found 414.27.

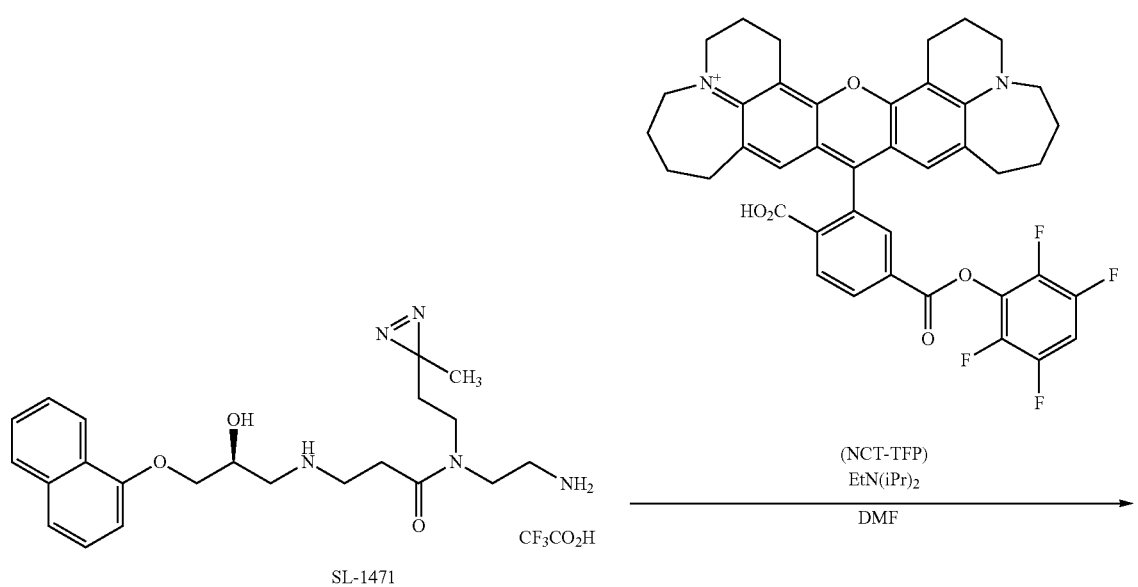

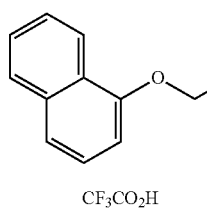 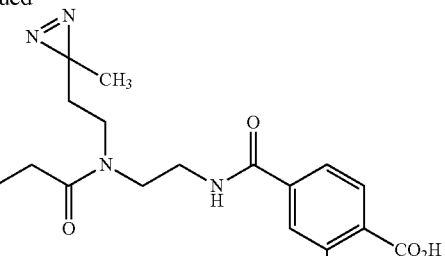

SL-1475

To a solution of SL-1471 (6.0 mg, 14 μmol) and DIPEA (9.0 μL, 51 μmol) in DMF (6 mL), NCT-TFP (5.2 mg, 7.3 μmol, prepared according to ACS Chem. Biol., 2016, 11, 2608-2617) was added. The resulting solution was stirred at 22° C. for 2 hours at which point HPLC analysis indicated full consumption of the starting material. The reaction mixture was purified by preparative RP HPLC (5→95% MeCN/H$_2$O buffered with 0.5% TFA) to provide 3.9 mg (56% yield) of conjugate SL-1475 as a deep blue film. HPLC: 97% purity at 254 nm; $^1$H NMR (400 MHz, Methanol-d4, reported for mixture of rotamers) δ 8.35 (m, 1H), 8.20 (m, 1H), 8.13 (m, 1H), 7.92-7.67 (m, 2H), 7.55-7.18 (m, 4H), 6.87 (dd, J=7.7, 1.0 Hz, 0.5H), 6.78 (dd, J=7.7, 1.0 Hz, 0.5H), 6.63 (d, J=2.1 Hz, 1H), 6.59 (s, 1H), 6.54 (s, 1H), 4.38 (m, 1H), 4.26-3.98 (m, 2H), 3.71 (m, 4H), 3.68-3.58 (m, 3H), 3.55 (m, 4H), 3.52-3.33 (m, 7H), 3.11-3.03 (m, 1H), 2.97 (m, 4H), 2.93-2.85 (m, 1H), 2.79 (m, 4H), 2.07 (m, 4H), 1.94 (m, 4H), 1.83 (m, 4H), 1.74-1.61 (m, 1H), 1.55 (m, 1H), 1.04 (s, 1H), 1.00 (s, 2H); HRMS (SI) Calc'd for C$_{57}$H$_{64}$N$_7$O$_7$ [M+]+ 958.4862, found 958.4869.

Characterization Data for Propranolol-PRG-NCT Probes:

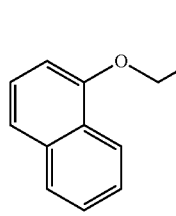 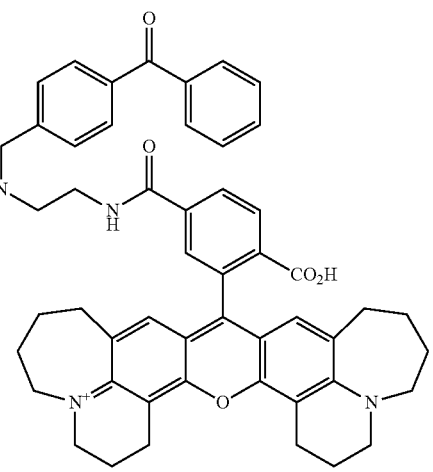

SL-1570

HPLC: 98% purity at 254 nm; HRMS (SI) Calc'd for C$_{67}$H$_{68}$N$_5$O$_8$ [M+]+ 1070.5062, found 1070.5071.

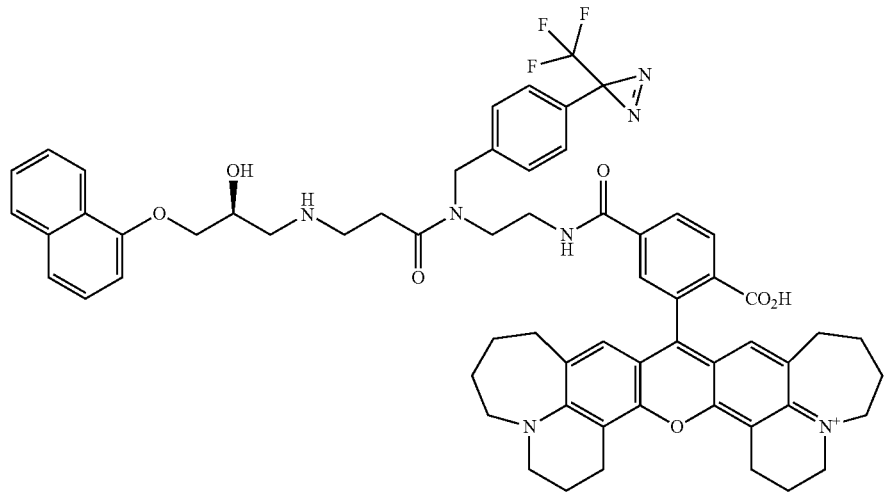

SL-1476

HPLC: 99% purity at 254 nm; $^1$H NMR (400 MHz, Methanol-d4, reported for mixture of rotamers) δ 8.34 (m, 1H), 8.21 (m, 1H), 8.09 (m, 1H), 7.87-7.66 (m, 2H), 7.54-7.12 (m, 8H), 6.98-6.73 (m, 1H), 6.68-6.47 (m, 2H), 4.75 (s, 1H), 4.69 (s, 1H), 4.43-4.29 (m, 1H), 4.29-3.99 (m, 2H), 3.70 (m, 4H), 3.67-3.57 (m, 3H), 3.54 (m, 4H), 3.51-3.34 (m, 4H), 3.27-3.07 (m, 2H), 3.07-2.90 (m, 4H), 2.86 (m, 1H), 2.82-2.64 (m, 3H), 2.06 (m, 4H), 1.94 (m, 4H), 1.82 (m, 4H); HRMS (SI) Calc'd for C$_{57}$H$_{64}$N$_7$O$_7$ [M+]+ 1074.4736 found 1074.4744.

HPLC: 99% purity at 254 nm; $^1$H NMR (400 MHz, Methanol-d4, reported for mixture of rotamers) δ 8.35 (m, 1H), 8.23 (m, 1H), 8.10 (m, 1H), 7.88-7.66 (m, 2H), 7.51-7.44 (m, 1H), 7.44-7.36 (m, 2H), 7.36-7.23 (m, 3H), 7.12-6.94 (m, 2H), 6.94-6.77 (m, 1H), 6.67 (d, J=1.5 Hz, 1H), 6.62 (s, 0.5H), 6.54 (s, 0.5H), 4.68 (s, 1H), 4.66 (s, 1H), 4.40 (m, 1H), 4.19 (m, 1H), 4.11 (m, 1H), 3.72 (m, 4H), 3.69-3.59 (m, 4H), 3.56 (m, 4H), 3.53-3.38 (m, 4H),

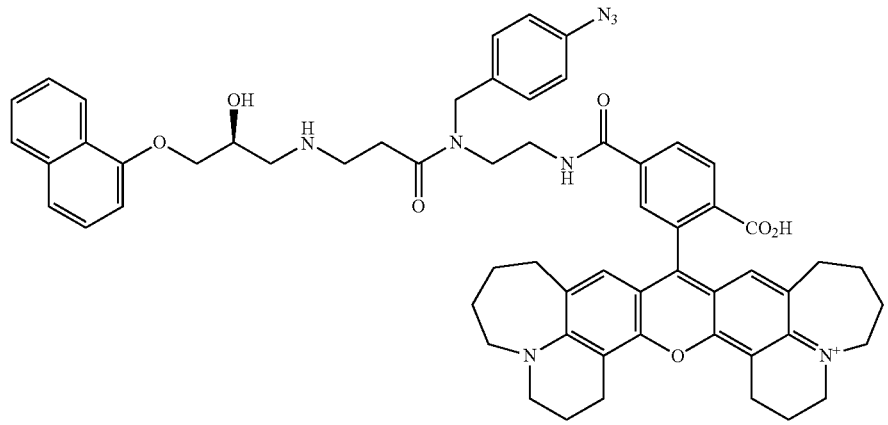

SL-1485

3.30-3.11 (m, 2H), 3.01 (m, 4H), 2.94 (m, 1H), 2.80 (m, 4H), 2.08 (m, 4H), 1.96 (m, 4H), 1.85 (m, 4H); HRMS (SI) Calc'd for $C_{57}H_{64}N_7O_7$ [M+]+ 1007.4814 found 1007.4823.

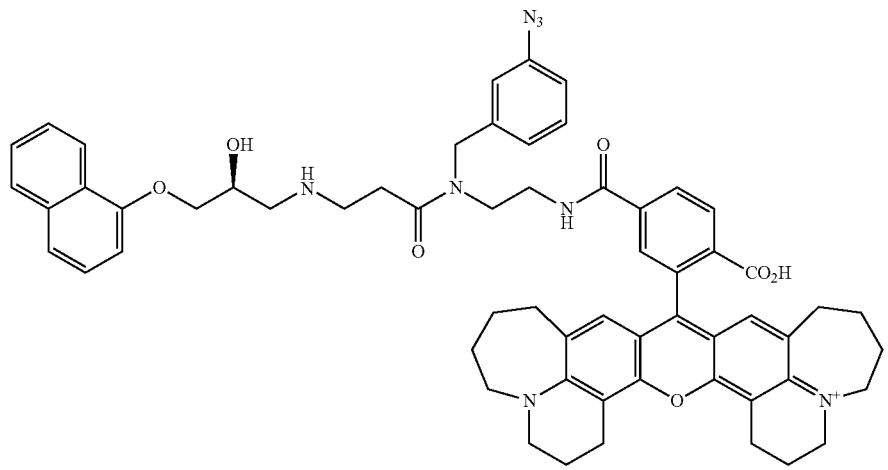

SL-1502

HPLC: 99% purity at 254 nm; $^1$H NMR (400 MHz, Methanol-d4, reported for mixture of rotamers) δ 8.34 (m, 1H), 8.26-8.15 (m, 1H), 8.09 (m, 1H), 7.84-7.66 (m, 2H), 7.52-7.22 (m, 5H), 7.17-7.02 (m, 1H), 7.02-6.90 (m, 2H), 6.89-6.71 (m, 1H), 6.64 (m, 1H), 6.60 (s, 0.5H), 6.52 (s, 0.5H), 4.70 (s, 1H), 4.66 (d, J=2.2 Hz, 1H), 4.39 (m, 1H), 4.25-4.12 (m, 1H), 4.09 (m, 1H), 3.71 (m, 4H), 3.66-3.57 (m, 3H), 3.57-3.45 (m, 6H), 3.45-3.35 (m, 2H), 3.23 (m, 2H), 2.97 (m, 4H), 2.92-2.84 (m, 1H), 2.84-2.68 (m, 4H), 2.05 (m, 4H), 1.94 (s, 4H), 1.80 (m, 4H); HRMS (SI) Calc'd for $C_{57}H_{64}N_7O_7$ [M+]+ 1007.4814 found 1007.4811.

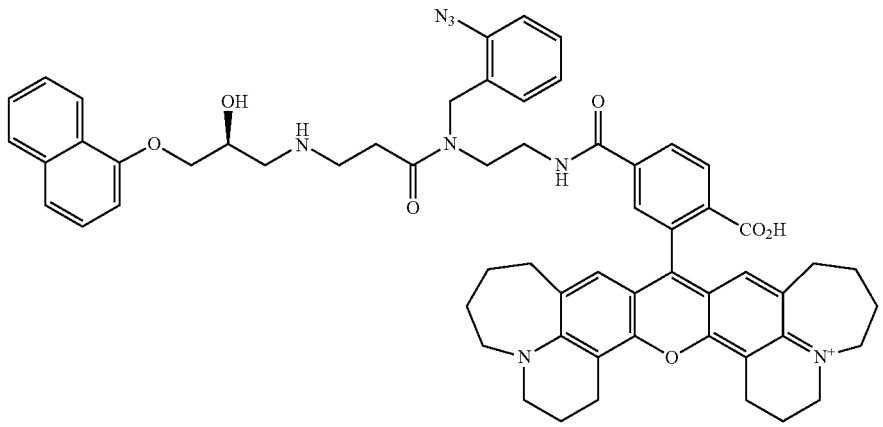

SL-1501

HPLC: 99% purity at 254 nm; $^1$H NMR (400 MHz, Methanol-d4, reported for mixture of rotamers) δ 8.35 (m, 1H), 8.29-8.15 (m, 1H), 8.12 (m, 1H), 7.90-7.66 (m, 2H), 7.49-7.05 (m, 8H), 6.83 (m, 1H), 6.65 (m, 1H), 6.60 (s, 0.5H), 6.55 (s, 0.5H), 4.70-4.50 (m, 2H), 4.40 (m, 1H), 4.19 (m, 1H), 4.10 (m, 1H), 3.76-3.62 (m, 5H), 3.62-3.36 (m, 11H), 3.19 (m, 1H), 2.98 (m, 5H), 2.87-2.56 (m, 4H), 2.21-1.98 (m, 4H), 1.98-1.86 (m, 4H), 1.80 (m, 4H); HRMS (SI) Calc'd for $C_{57}H_{64}N_7O_7$ [M+]+ 1007.4814 found 1007.4789.

HPLC: 99% purity at 254 nm; ¹H NMR (400 MHz, Methanol-d4, reported for mixture of rotamers) δ 8.33 (m, 1H), 8.21 (m, 1H), 8.06 (m, 1H), 7.92-7.65 (m, 2H), 7.52-7.23 (m, 4H), 7.16 (m, 1H), 7.11-7.00 (m, 1H), 7.00-6.93 (m, 1H), 6.83 (m, 1H), 6.65 (m, 1H), 6.60 (s, 0.5H), 6.53 (s, 0.5H), 4.72-4.56 (m, 2H), 4.40 (m, 1H), 4.18 (m, 1H), 4.10 (m, 1H), 3.81-3.37 (m, 17H), 3.24-3.16 (m, 1H), 3.08-2.88 (m, 5H), 2.77 (m, 4H), 2.13 (s, 3H), 2.07 (m, 4H), 1.93 (m, 4H), 1.82 (m, 4H); HRMS (SI) Calc'd for $C_{57}H_{64}N_7O_7$ [M+]+ 1021.4971 found 1021.4993.
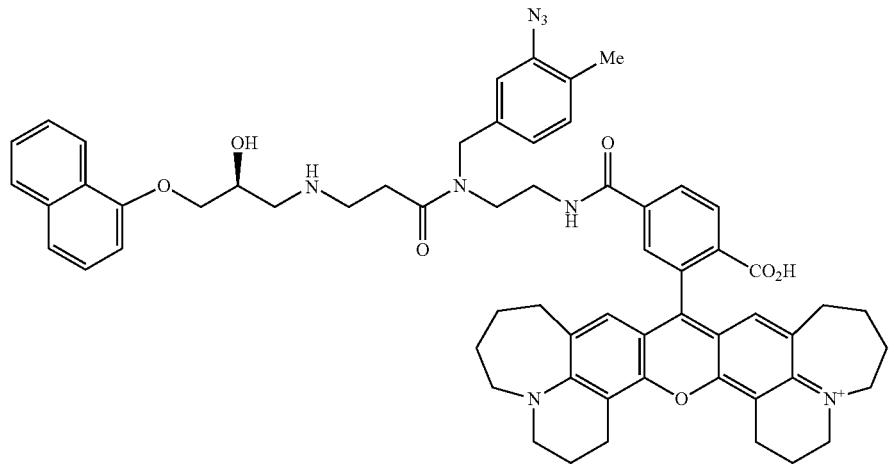
SL-1489
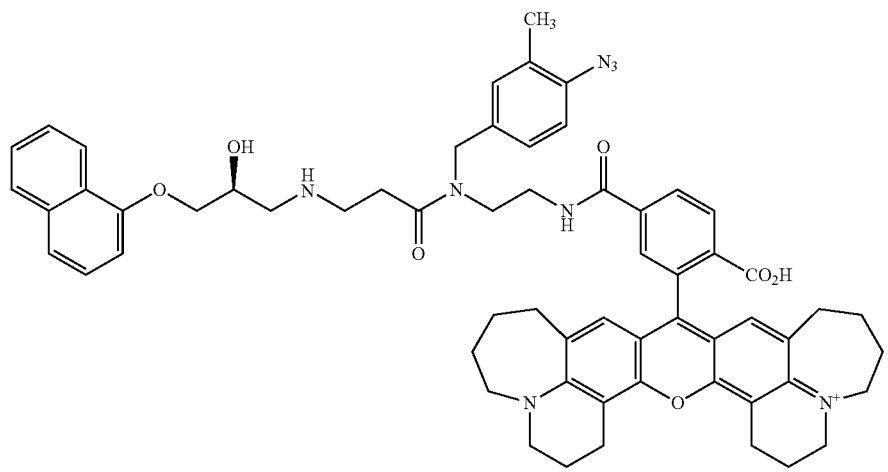
SL-1487
HPLC: 99% purity at 254 nm; ¹H NMR (400 MHz, Methanol-d4, reported for mixture of rotamers) δ 1H NMR (400 MHz, Methanol-d4) δ 8.33 (m, 1H), 8.27-8.15 (m, 1H), 8.06 (m, 1H), 7.84-7.66 (m, 2H), 7.52-7.23 (m, 4H), 7.23-7.00 (m, 3H), 6.82 (m, 1H), 6.65 (m, 1H), 6.60 (s, 0.5H), 6.51 (s, 0.5H), 4.69-4.59 (m, 2H), 4.38 (m, 1H), 4.18 (m, 1H), 4.09 (m, 1H), 3.70 (m, 4H), 3.65-3.35 (m, 11H), 3.20 (m, 1H), 2.95 (m, 5H), 2.86-2.57 (m, 4H), 2.13 (m, 3H), 2.11-1.99 (m, 4H), 1.99-1.87 (m, 4H), 1.82 (s, 4H); HRMS (SI) Calc'd for $C_{57}H_{64}N_7O_7$ [M+]+1021.4971 found 1021.4972.

SL-1600
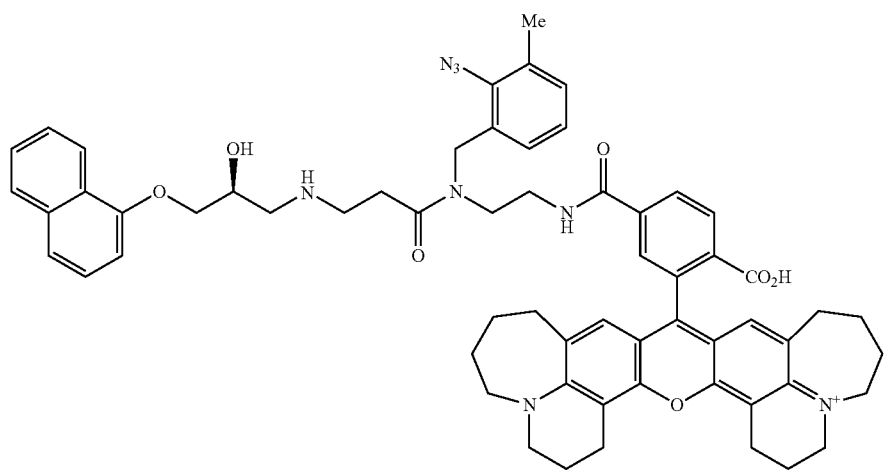
HPLC: 99% purity at 254 nm; $^1$H NMR (400 MHz, Methanol-d4, reported for mixture of rotamers) δ 8.32 (m, 1H), 8.21 (m, 1H), 8.11 (m, 1H), 7.87-7.67 (m, 2H), 7.54-7.41 (m, 1H), 7.38 (m, 2H), 7.33-7.24 (m, 1H), 7.24-7.01 (m, 3H), 6.83 (m, 1H), 6.65 (s, 1H), 6.61 (s, 0.5H), 6.55 (s, 0.5H), 4.71 (m, 2H), 4.39 (m, 1H), 4.18 (m, 1H), 4.10 (m, 1H), 3.78-3.65 (m, 5H), 3.65-3.43 (m, 11H), 3.40 (m, 4H), 3.07-2.84 (m, 5H), 2.79 (m, 4H), 2.40 (m, 3H), 2.06 (m, 4H), 1.93 (m, 4H), 1.82 (m, 4H); HRMS (SI) Calc'd for $C_{57}H_{64}N_7O_7$ [M+]+ 1021.4971 found 1021.4976.
SL-1522
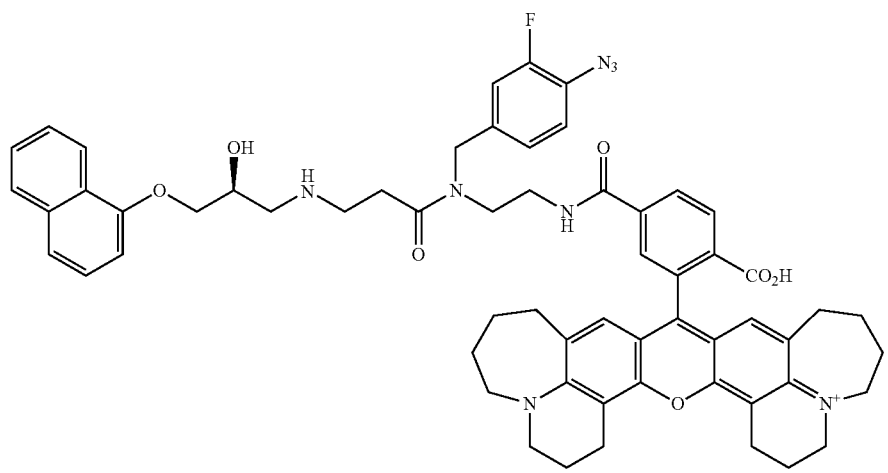
HPLC: 99% purity at 254 nm; $^1$H NMR (400 MHz, Methanol-d4, reported for mixture of rotamers) δ 8.33 (m, 1H), 8.20 (m, 1H), 8.04 (m, 1H), 7.88-7.65 (m, 2H), 7.51-7.23 (m, 4H), 7.23-6.98 (m, 3H), 6.98-6.72 (m, 1H), 6.65 (m, 1H), 6.61 (s, 0.5H), 6.50 (s, 0.5H), 4.71-4.51 (m, 2H), 4.51-4.32 (m, 1H), 4.32-3.96 (m, 2H), 3.84-3.41 (m, 2H), 3.29-3.10 (m, 2H), 2.99 (m, 2H), 2.94-2.86 (m, 2H), 2.85-2.57 (m, 4H), 2.07 (s, 4H), 1.94 (s, 4H), 1.82 (s, 4H); MS (SI) Calc'd for $C_{60}H_{62}FN_8O_7$ [M+]+ 1025.47 found 1026.04.

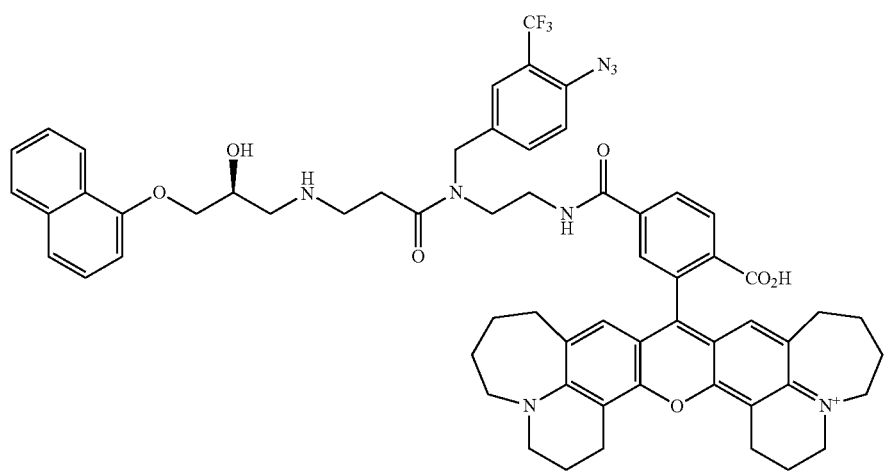
SL-1527
HPLC: 99% purity at 254 nm; ¹H NMR (400 MHz, Methanol-d4, reported for mixture of rotamers) δ 8.33 (m, 1H), 8.27-8.14 (m, 1H), 8.07 (m, 1H), 7.85-7.67 (m, 2H), 7.59 (m, 2H), 7.53-7.41 (m, 2H), 7.37 (m, 2H), 7.34-7.25 (m, 1H), 7.01-6.69 (m, 1H), 6.64 (s, 1H), 6.59 (s, 0.5H), 6.49 (s, 0.5H), 4.69 (s, 2H), 4.38 (m, 1H), 4.29-3.82 (m, 3H), 3.82-3.37 (m, 17H), 3.06-2.86 (m, 5H), 2.86-2.54 (m, 3H), 2.05 (d, J=13.6 Hz, 4H), 1.94 (s, 4H), 1.82 (s, 4H); HRMS (SI) Calc'd for $C_{61}H_{62}F_3N_8O_7$ [M+]+ 1075.4688 found 1075.4684.
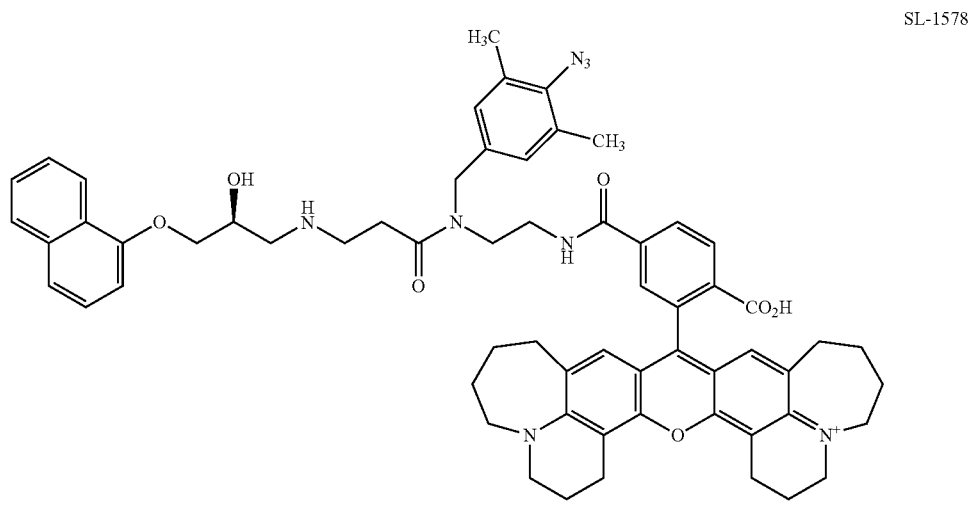 [SMILES: Cc1cc(CN(CCNC(=O)c2ccc(C(=O)O)c(C3=c4cc5c6c(c4Oc4c3cc3c7c4CCCN7CCCC3)CCC[N+]=6CCCC5)c2)C(=O)CCNC[C@H](O)COc2cccc3ccccc23)cc(C)c1N=[N+]=[N-]]
SL-1578
HPLC: 99% purity at 254 nm; ¹H NMR (400 MHz, Methanol-d4, reported for mixture of rotamers) δ 8.39-8.23 (m, 1H), 8.20 (m, 1H), 8.05 (m, 1H), 7.85-7.67 (m, 2H), 7.50-7.41 (m, 1H), 7.41-7.34 (m, 2H), 7.30 (m, 1H), 6.99 (s, 1H), 6.94 (s, 1H), 6.90-6.71 (m, 1H), 6.64 (m, 1H), 6.60 (s, 0.5H), 6.50 (s, 0.5H), 4.70-4.48 (m, 2H), 4.48-4.33 (m, 1H), 4.23-4.13 (m, 1H), 4.09 (m, 1H), 3.81-3.66 (m, 4H), 3.63 (m, 3H), 3.59-3.50 (m, 6H), 3.50-3.35 (m, 4H), 3.27-3.16 (m, 1H), 3.09-2.93 (m, 4H), 2.92-2.64 (m, 5H), 2.29 (m, 6H), 2.15-1.99 (m, 4H), 1.94 (m, 4H), 1.82 (s, 4H); HRMS (SI) Calc'd for $C_{62}H_{67}N_8O_7$ [M+]+ 1035.5127 found 1035.5130.

SL-1553
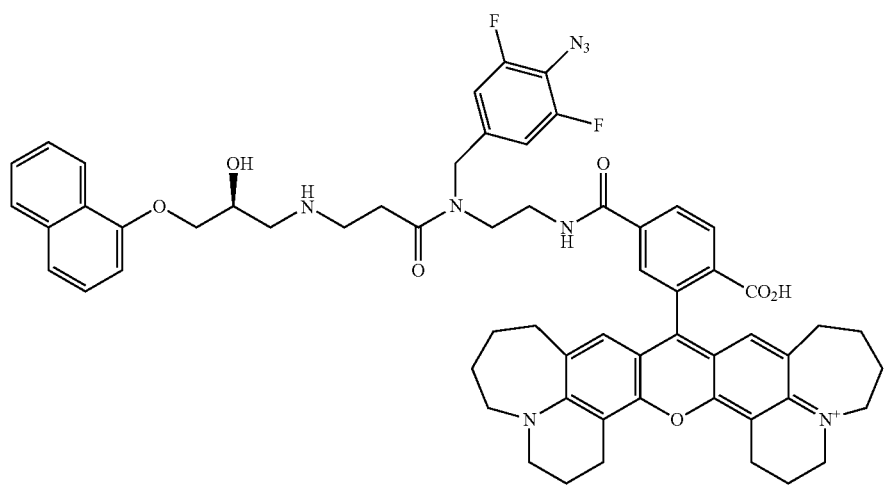
HPLC: 99% purity at 254 nm; $^1$H NMR (400 MHz, Methanol-d4, reported for mixture of rotamers) δ 8.33 (m, 1H), 8.20 (m, 1H), 8.03 (m, 1H), 7.86-7.63 (m, 2H), 7.54-7.19 (m, 4H), 7.00 (m, 2H), 6.93-6.70 (m, 1H), 6.65 (m, 1H), 6.62 (s, 0.5H), 6.49 (s, 0.5H), 4.67-4.48 (m, 2H), 4.38 (m, 1H), 4.24-3.97 (m, 2H), 3.71 (m, 4H), 3.68-3.59 (m, 3H), 3.58-3.51 (m, 5H), 3.51-3.38 (m, 3H), 3.29-3.16 (m, 2H), 3.05-2.92 (m, 4H), 2.92-2.84 (m, 1H), 2.78 (m, 4H), 2.15-2.00 (m, 4H), 1.94 (m, 4H), 1.83 (m, 4H); HRMS (SI) Calc'd for $C_{60}H_{61}F_2N_8O_7$ [M+]+1043.4626 found 1043.4641.
SL-1493
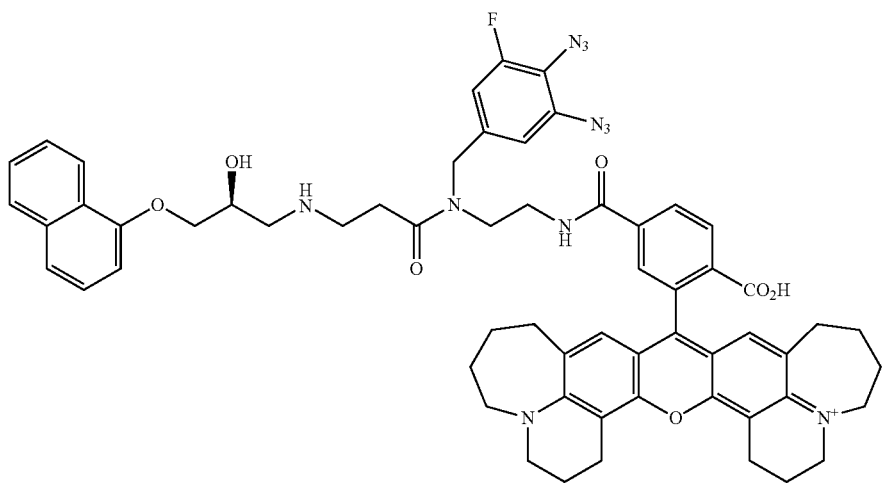
HPLC: 99% purity at 254 nm; $^1$H NMR (400 MHz, Methanol-d4, reported for mixture of rotamers) δ 8.33 (m, 1H), 8.26-8.13 (m, 1H), 8.01 (m, 1H), 7.85-7.62 (m, 2H), 7.51-7.19 (m, 4H), 7.01-6.70 (m, 3H), 6.70-6.44 (m, 2H), 4.70-4.50 (m, 2H), 4.38 (m, 1H), 4.25-4.01 (m, 2H), 3.83-3.58 (m, 8H), 3.58-3.37 (m, 8H), 3.25-3.15 (m, 1H), 2.98 (m, 4H), 2.92 (m, 1H), 2.88-2.66 (m, 4H), 2.08 (m, 4H), 1.94 (s, 4H), 1.83 (m, 4H); HRMS (SI) Calc'd for $C_{60}H_{61}FN_{11}O_7$ [M+]+ 1066.7434 found 1066.4728.

SL-1556
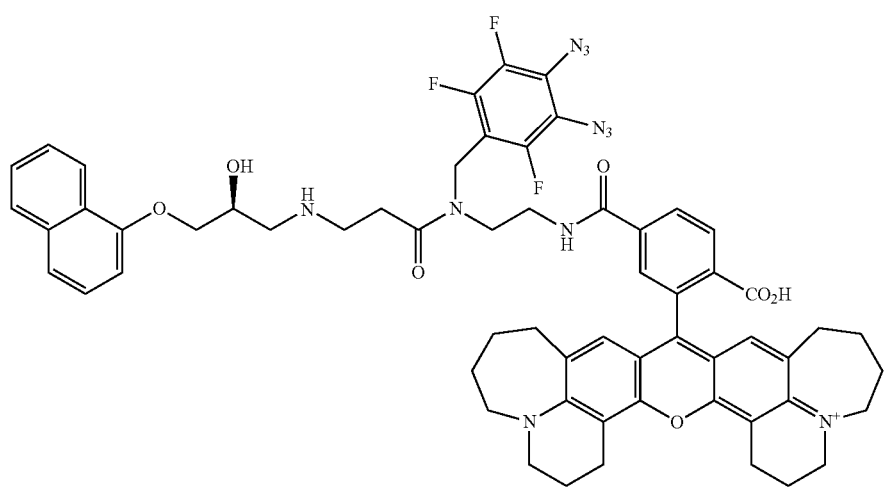
HPLC: 99% purity at 254 nm; $^1$H NMR (400 MHz, Methanol-d4, reported for mixture of rotamers) δ 8.34 (m, 1H), 8.23-7.95 (m, 2H), 7.87 (m, 1H), 7.75 (m, 1H), 7.54-7.35 (m, 2H), 7.35-7.22 (m, 2H), 6.94-6.72 (m, 1H), 6.67 (m, 1H), 6.57 (m, 1H), 4.74 (m, 2H), 4.56-4.25 (m, 1H), 4.21-4.02 (m, 2H), 3.71 (m, 7H), 3.64-3.39 (m, 10H), 3.09 (m, 1H), 3.02-2.85 (m, 4H), 2.85-2.68 (m, 4H), 2.21-2.00 (m, 4H), 2.00-1.90 (m, 4H), 1.83 (s, 4H); HRMS (SI) Calc'd for $C_{60}H_{59}F_4N_8O_7$ [M+]+1079.4437 found 1079.4459.
HPLC: 99% purity at 254 nm; $^1$H NMR (400 MHz, Methanol-d4, reported for mixture of rotamers) δ 8.35 (m, 1H), 8.27-8.16 (m, 1H), 8.09 (m, 1H), 7.91-7.64 (m, 2H), 7.47-7.25 (m, 5H), 6.93-6.84 (m, 1H), 6.84-6.75 (m, 2H), 6.66 (d, J=1.6 Hz, 1H), 6.61 (s, 0.5H), 6.54 (s, 0.5H), 4.64-4.46 (m, 2H), 4.39 (m, 1H), 4.28-4.01 (m, 2H), 3.83-3.67 (m, 4H), 3.67-3.58 (m, 3H), 3.58-3.51 (m, 5H), 3.51-3.37 (m, 4H), 3.19-3.15 (m, 1H), 3.07-2.87 (m, 5H), 2.78 (m, 4H), 2.14-1.99 (m, 4H), 1.93 (m, 4H), 1.82 (m, 4H); HRMS (SI) Calc'd for $C_{60}H_{62}N_{11}O_7$ [M+]+ 1048.4828 found 1048.4824.
SL-1526
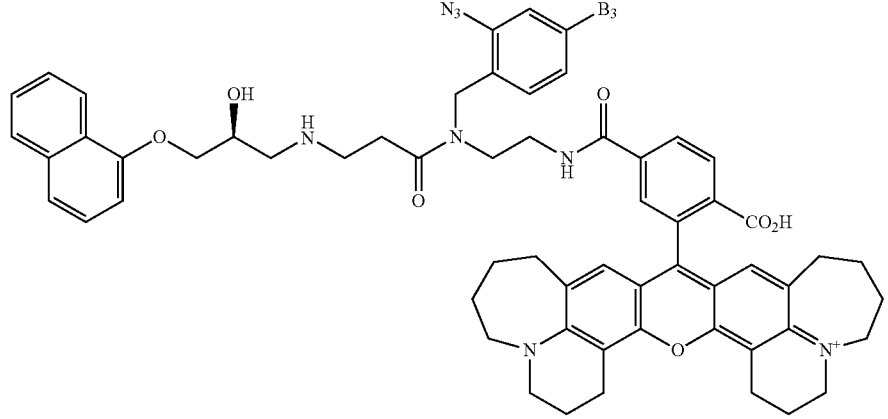

SL-1518
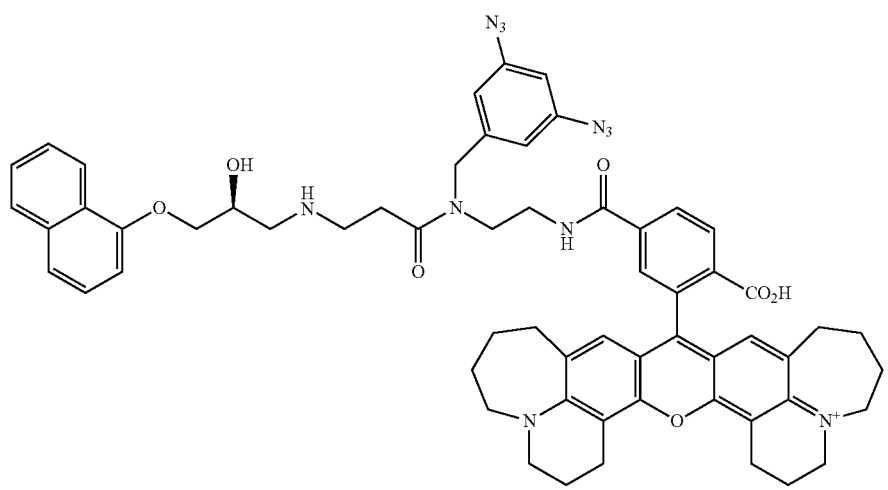
HPLC: 99% purity at 254 nm; $^1$H NMR (400 MHz, Methanol-d4, reported for mixture of rotamers) δ 8.34 (m, 1H), 8.20 (m, 1H), 8.08 (m, 1H), 7.88-7.64 (m, 2H), 7.52-7.41 (m, 1H), 7.41-7.34 (m, 2H), 7.34-7.21 (m, 1H), 6.91-6.69 (m, 3H), 6.69-6.42 (m, 3H), 4.66 (m, 2H), 4.37 (m, 1H), 4.27-4.13 (m, 1H), 4.13-4.00 (m, 1H), 3.71 (m, 4H), 3.63 (m, 3H), 3.58-3.43 (m, 7H), 3.43-3.36 (m, 1H), 3.27-3.15 (m, 2H), 3.08-2.90 (m, 4H), 2.90-2.83 (m, 1H), 2.78 (m, 4H), 2.12-2.04 (m, 4H), 1.94 (m, 4H), 1.84 (m, 4H); MS (SI) Calc'd for $C_{60}H_{62}N_{11}O_7$ [M+]+ 1048.48 found 1048.38.
SL-1566
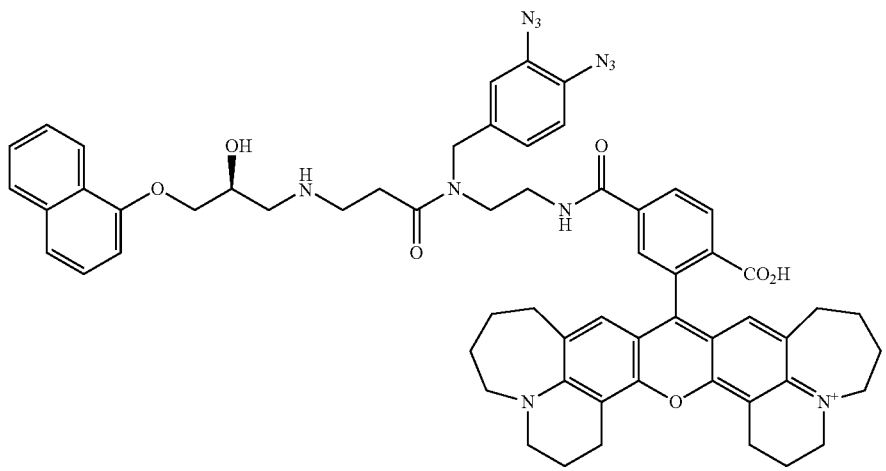
HPLC: 99% purity at 254 nm; $^1$H NMR (400 MHz, Methanol-d4, reported for mixture of rotamers) δ 8.32 (m, 1H), 8.20 (m, 1H), 8.03 (m, 1H), 7.87-7.67 (m, 2H), 7.59-7.41 (m, 1H), 7.41-7.34 (m, 2H), 7.34-7.22 (m, 1H), 7.22-6.99 (m, 3H), 6.92-6.71 (m, 1H), 6.67 (m, 1H), 6.58 (m, 1H), 4.64 (m, 2H), 4.39 (m, 1H), 4.23-4.00 (m, 2H), 3.70 (m, 4H), 3.67-3.59 (m, 3H), 3.59-3.36 (m, 8H), 3.28-3.08 (m, 2H), 2.96 (m, 5H), 2.79 (m, 4H), 2.17-2.00 (m, 4H), 1.94 (m, 4H), 1.82 (m, 4H); HRMS (SI) Calc'd for $C_{60}H_{62}N_{11}O_7$ [M+]+ 1048.4828 found 1048.4827.

SL-1610
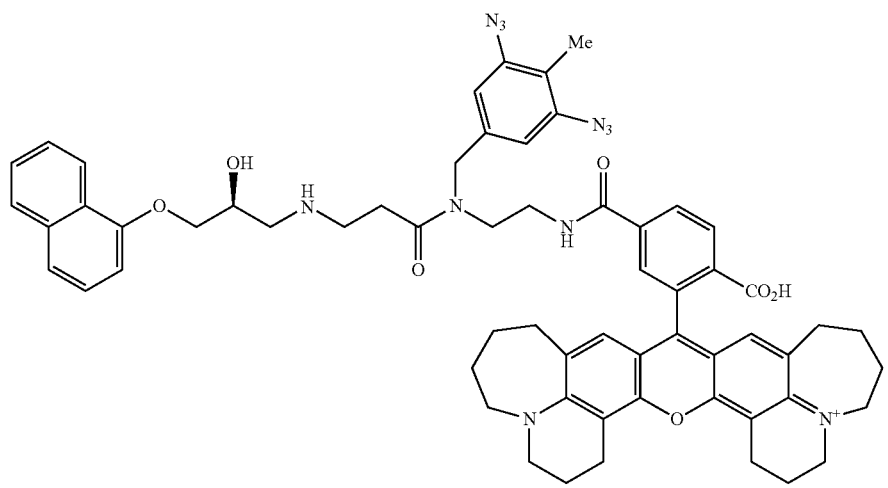
HPLC: 99% purity at 254 nm; $^1$H NMR (400 MHz, Methanol-d4, reported for mixture of rotamers) δ 8.29 (m, 1H), 8.20 (m, 1H), 8.02 (m, 1H), 7.91-7.76 (m, 1H), 7.72 (m, 1H), 7.55-7.41 (m, 1H), 7.41-7.33 (m, 2H), 7.33-7.22 (m, 1H), 6.94 (s, 1H), 6.91-6.74 (m, 2H), 6.67 (m, 1H), 6.59 (m, 1H), 4.68 (m, 2H), 4.50-4.29 (m, 1H), 4.18 (m, 1H), 4.10 (m, 1H), 3.80-3.60 (m, 8H), 3.60-3.45 (m, 6H), 3.45-3.35 (m, 2H), 3.27-3.18 (m, 1H), 3.07-2.86 (m, 5H), 2.86-2.65 (m, 4H), 2.04 (m, 4H), 1.98 (s, 3H), 1.93 (m, 4H), 1.82 (m, 4H); HRMS (SI) Calc'd for $C_{60}H_{62}N_{11}O_7$ [M+]+ 1062.4985 found 1062.4984.
SL-1619
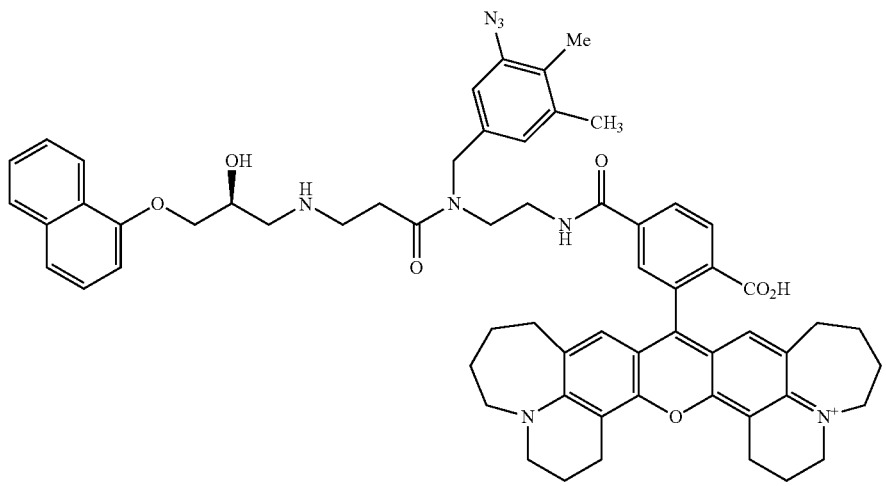
HPLC: 99% purity at 254 nm; $^1$H NMR (400 MHz, Methanol-d4, reported for mixture of rotamers) δ 8.32 (m, 1H), 8.20 (m, 1H), 8.01 (m, 1H), 7.88-7.64 (m, 2H), 7.48-7.40 (m, 1H), 7.40-7.33 (m, 2H), 7.33-7.22 (m, 1H), 7.06-6.90 (m, 2H), 6.90-6.74 (m, 1H), 6.65 (s, 1H), 6.56 (m, 1H), 4.67-4.46 (m, 2H), 4.46-4.30 (m, 1H), 4.27-4.04 (m, 2H), 3.74-3.39 (m, 16H), 2.96 (m, 5H), 2.77 (m, 4H), 2.17 (m, 3H), 2.07 (m, 4H), 1.94 (m, 4H), 1.82 (m, 4H); HRMS (SI) Calc'd for $C_{60}H_{62}N_{11}O_7$ [M+]+ 1062.4985 found 1062.4990.

Synthesis of Cleavable Chloroalkane Photo-Reactive Probes:
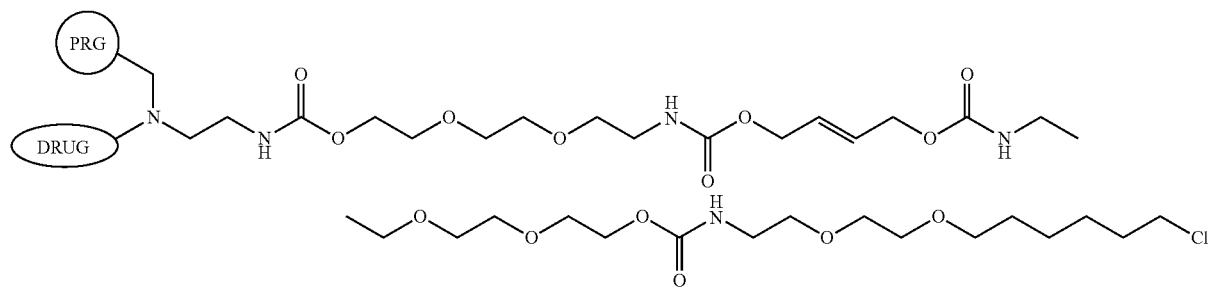
General Structure of Drug-PRG-Chloroalkane Probes
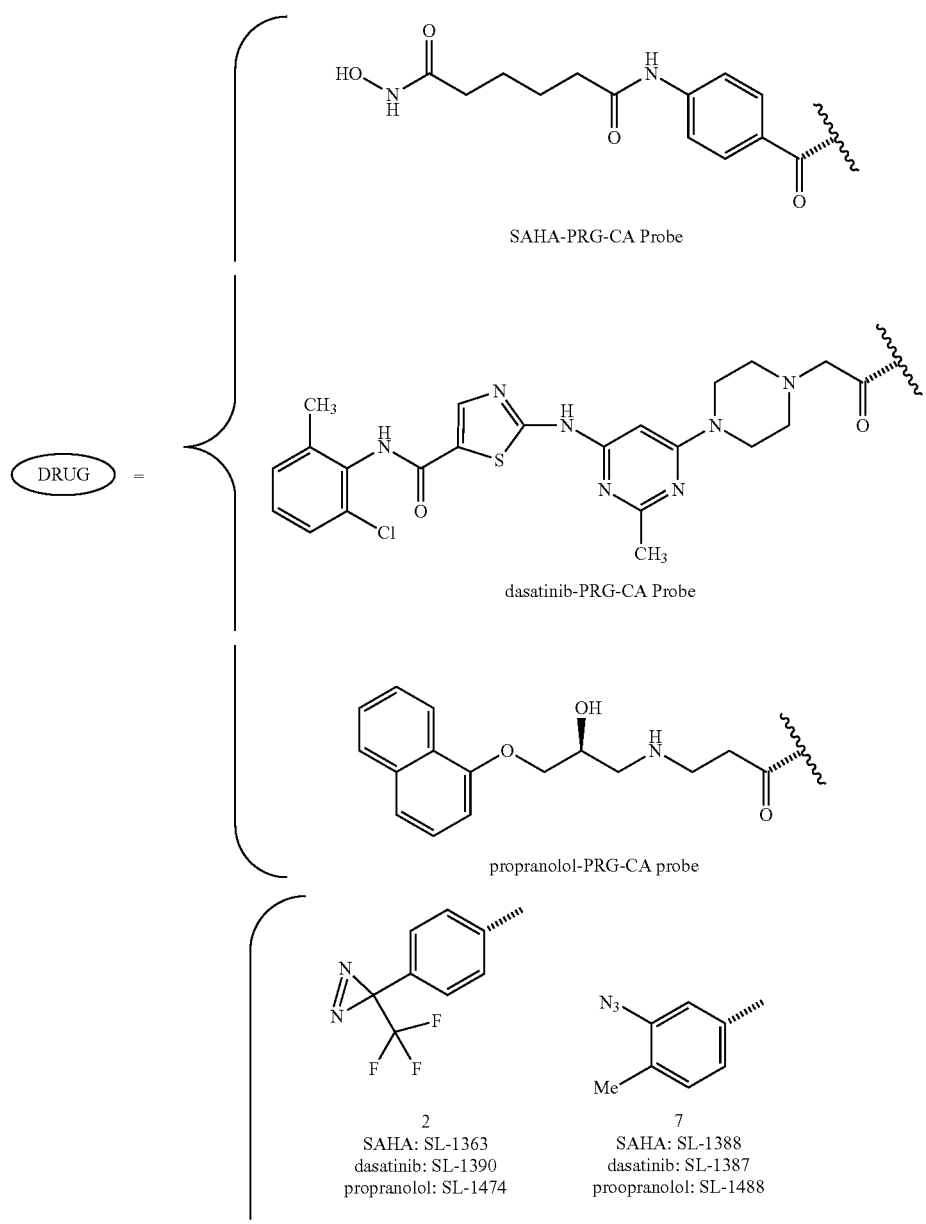
| | |
|---|---|
| 2 | 7 |
| SAHA: SL-1363 | SAHA: SL-1388 |
| dasatinib: SL-1390 | dasatinib: SL-1387 |
| propranolol: SL-1474 | proopranolol: SL-1488 |

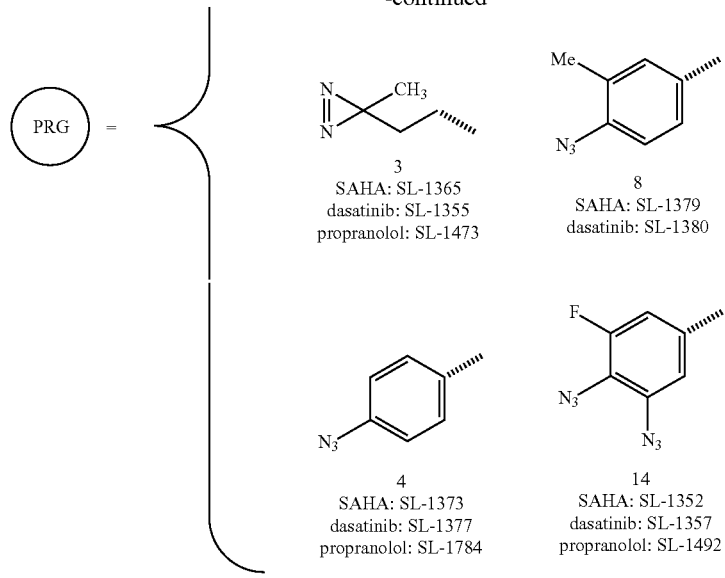
General Scheme for Synthesis of Cleavable Chloroalkane Photo-Reactive Probes:
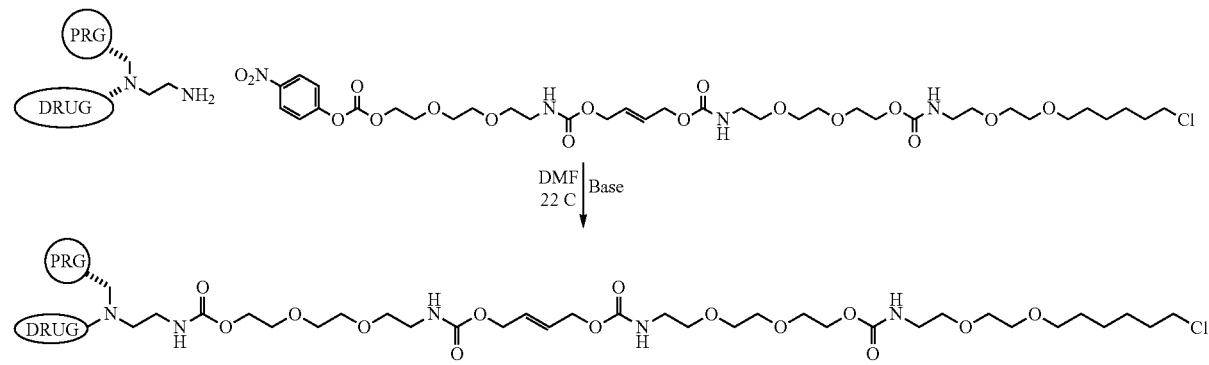
Base = DIPEA for dasatinib and propranolol NMM for SAHA
Exemplary Synthesis of Cleavable Chloroalkane Photo-Reactive Probe:
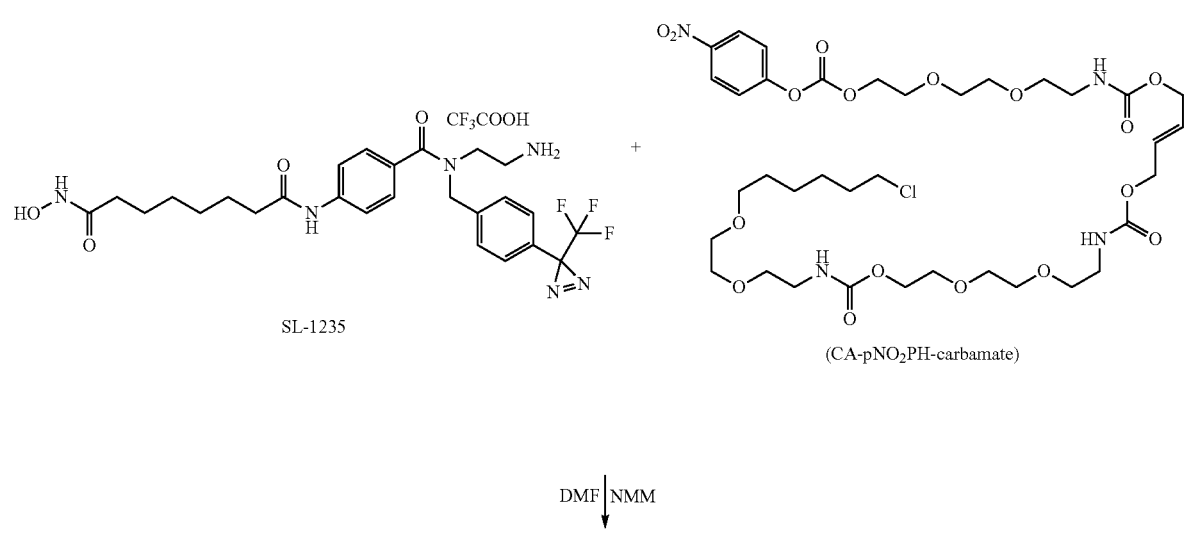

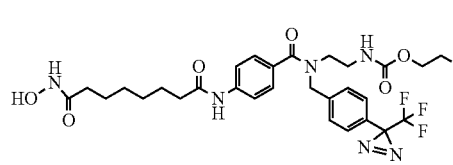
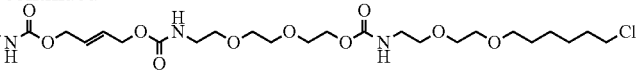

SL-1386

To a solution of SL-1235 (2.5 mg, 3.7 μmol) and NMM (3 μL, 27 μmol) in DMF (6 mL), CA-pNO₂Ph-carbamate (3.2 mg, 3.8 μmol, prepared according to ACS Chem. Biol., 2016, 11, 2608-2617) was added. The resulting solution was stirred at 22° C. for 20 hours at which point HPLC analysis indicated full consumption of the starting material. The reaction mixture was purified by preparative RP HPLC (5→95% MeCN/H₂O buffered with 0.5% TFA) to provide 2.3 mg (48% yield) of conjugate SL-1363 as a clear film. HPLC: 99% purity at 254 nm; ¹H NMR (400 MHz, Methanol-d4, reported for mixture of rotamers) δ 7.64 (m, 2H), 7.50 (s, 1H), 7.39 (m, 2H), 7.27 (m, 3H), 5.84 (m, 2H), 4.66 (m, 1H), 4.52 (m, 4H), 4.29-4.01 (m, 4H), 3.81-3.45 (m, 28H), 3.42 (s, 2H), 3.27 (m, 7H), 2.38 (m, 2H), 2.09 (t, J=7.4 Hz, 2H), 1.86-1.53 (m, 8H), 1.53-0.97 (m, 8H); HRMS (SI) Calc'd for $C_{56}H_{84}CF_3N_9O_{18}$ [M+H]+ 1262.5569, found 1262.5573.

Characterization Data for SAHA-PRG-Chloroalkane Probes:

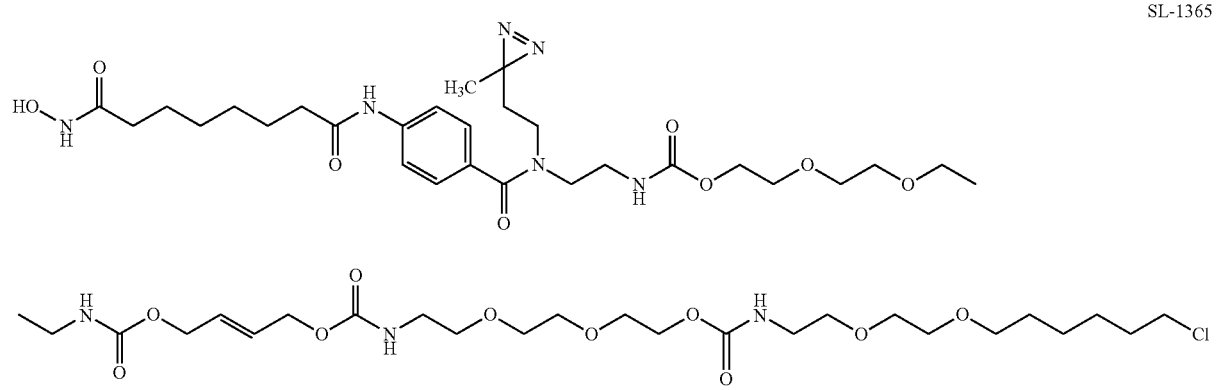

SL-1365

HPLC: 99% purity at 254 nm; ¹H NMR (40 MHz, Methanol-d4, reported for mixture of rotamers) δ 7.67 (d, J=8.1 Hz, 2H), 7.39 (d, J=8.4 Hz, 2H), 5.85 (m, 2H), 4.70-4.41 (m, 4H), 4.37-3.92 (m, 4H), 3.79-3.35 (m, 31H), 3.30-3.22 (m, 6H), 3.15 (m, 1H), 2.39 (t, J=7.4 Hz, 2H), 2.11 (t, J=7.3 Hz, 2H), 1.87-1.51 (m, 10H), 1.51-1.33 (m, 8H); HRMS (SI) Calc'd for $C_{51}H_{51}ClN_9O_{18}$ [M+H]+ 1146.5696, found 1146.5699.

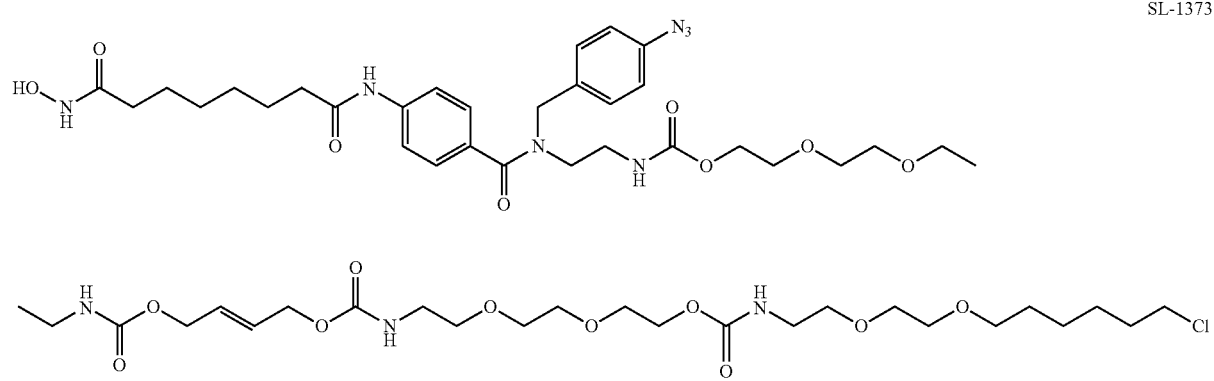

SL-1373

HPLC: 99% purity at 254 nm; 1H NMR (400 MHz, Methanol-d4, reported for mixture of rotamers) δ 7.65 (m, 2H), 7.41 (m, 3H), 7.19 (m, 1H), 7.08 (m, 2H), 5.84 (m, 2H), 4.78 (m, 1H), 4.52 (m, 5H), 4.26-3.94 (m, 4H), 3.80-3.46 (m, 28H), 3.40 (m, 2H), 3.27 (m, 6H), 2.38 (m, 2H), 2.09 (m, 2H), 1.90-1.52 (m, 8H), 1.52-1.18 (m, 8H); HRMS (SI) Calc'd for $C_{54}H_4ClN_{10}O_{18}$ [M+H]+ 1195.57, found 1195.41.

SL-1388

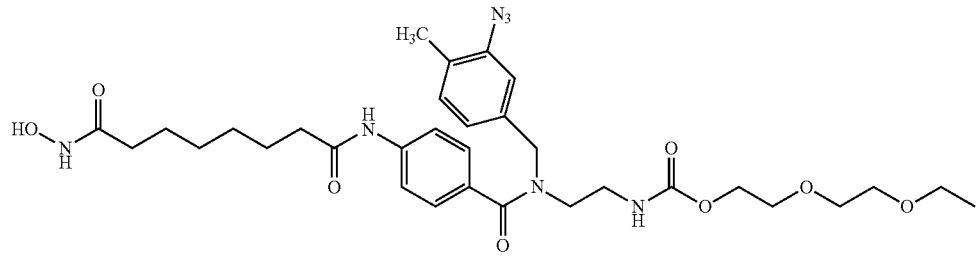

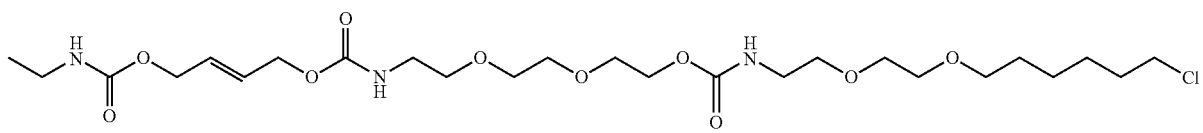

HPLC: 99% purity at 254 nm; 1H NMR (400 MHz, Methanol-d4, reported for mixture of rotamers) δ 7.67 (m, 2H), 7.40 (m, 2H), 7.31-7.01 (m, 2H), 7.01-6.74 (m, 1H), 5.83 (m, 2H), 4.79 (s, 1H), 4.67-4.42 (m, 5H), 4.31-4.03 (m, 4H), 3.79-3.33 (m, 30H), 3.27 (m, 7H), 2.38 (m, 2H), 2.18 (m, 3H), 2.09 (m, 2H), 1.84-1.51 (m, 8H), 1.51-1.18 (m, 8H); HRMS (SI) Calc'd for $C_{55}H_6ClN_{10}O_{18}$ [M+H]+ 1209.5805, found 1209.5814.

SL-1379

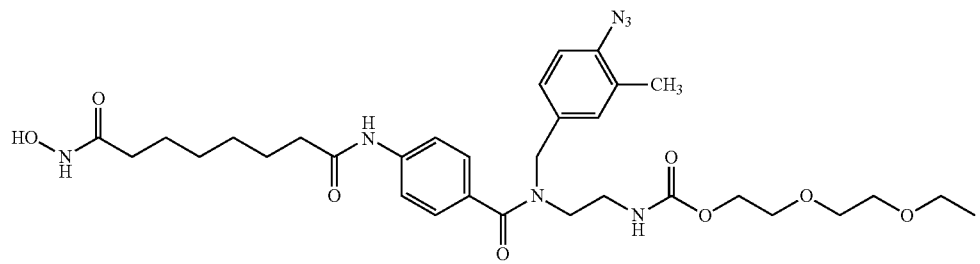

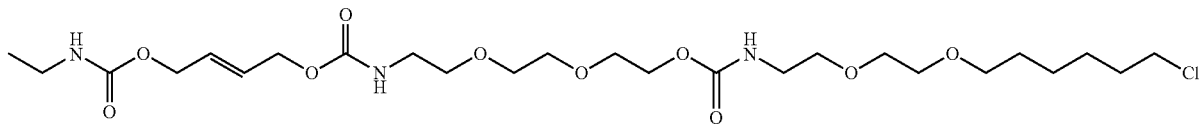

HPLC: 99% purity at 254 nm; $^1$H NMR (400 MHz, Methanol-d4, reported for mixture of rotamers) δ 7.66 (m, 2H), 7.40 (m, 2H), 7.34-6.81 (m, 3H), 5.84 (m, 2H), 4.74 (m, 1H), 4.54 (m, 5H), 4.16 (m, 4H), 3.79-3.44 (m, 28H), 3.40 (s, 2H), 3.27 (m, 5H), 3.20 (s, 1H), 2.38 (m, 2H), 2.34-1.98 (m, 5H), 1.89-1.54 (m, 8H), 1.51-1.34 (m, 8H); HRMS (SI) Calc'd for $C_{55}H_{85}ClN_1NaO_{18}$ [M+Na]+ 1231.5624, found 1231.5594.

SL-1352

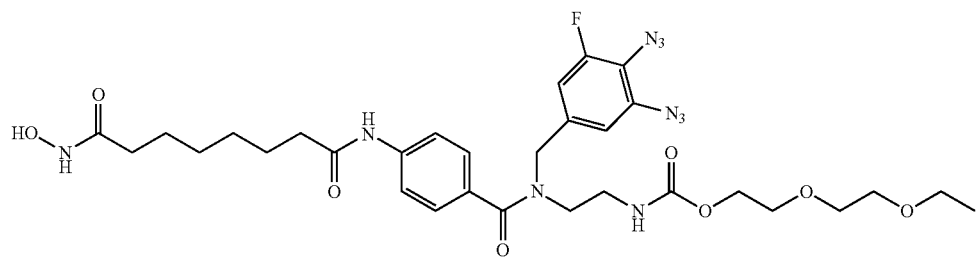

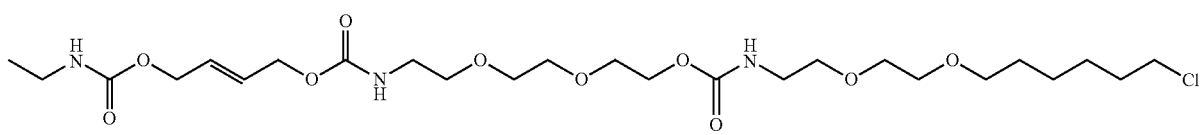

HPLC: 99% purity at 254 nm; ¹H NMR (400 MHz, Methanol-d4, reported for mixture of rotamers) δ 7.69 (m, 2H), 7.56-7.24 (m, 2H), 7.23-6.54 (m, 2H), 5.86 (m, 2H), 4.75 (m, 1H), 4.56 (m, 5H), 4.17 (m, 4H), 3.70 (m, 4H), 3.67-3.56 (m, 15H), 3.52 (m, 11H), 3.31-3.13 (m, 6H), 2.40 (m, 2H), 2.11 (m, 2H), 1.86-1.56 (m, 8H), 1.56-1.34 (m, 8H); HRMS (SI) Calc'd for $C_{54}H_2ClFN_{13}O_{18}$ [M+H]+ 1254.5552, found 1254.5568.

Characterization Data for Dasatinib-PRG-Chloroalkane Probes:

SL-1390

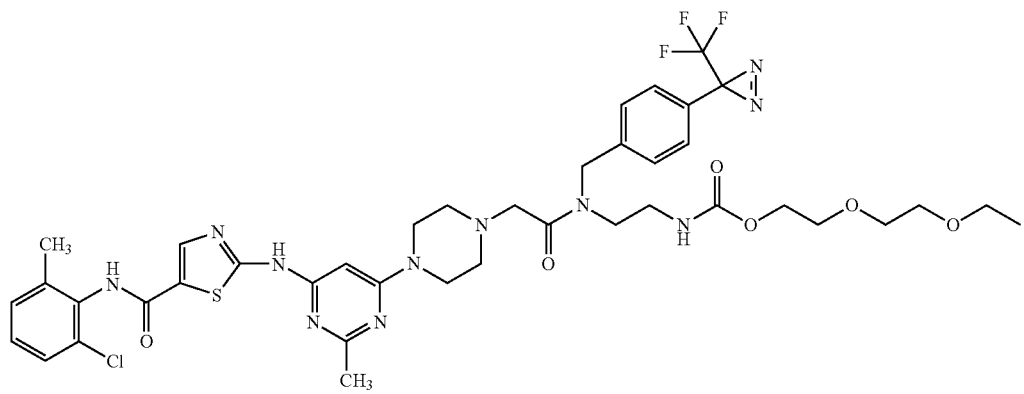

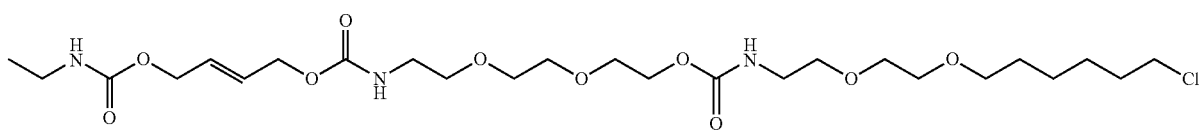

HPLC: 99% purity at 254 nm; ¹H NMR (400 MHz, Methanol-d4, reported for mixture of rotamers) δ 8.18 (m, 1H), 7.46-7.29 (m, 4H), 7.29-7.19 (m, 3H), 6.14 (m, 1H), 5.83 (m, 2H), 4.69 (m, 2H), 4.61-4.26 (m, 6H), 4.17 (m, 4H), 3.86-3.41 (m, 29H), 3.41-3.34 (m, 3H), 3.26 (m, 5H), 2.52 (m, 3H), 2.33 (s, 3H), 1.76 (m, 2H), 1.58 (m, 2H), 1.52-1.35 (m, 4H); HRMS (SI) Calc'd for $C_{54}H_2ClFN_{13}O_{18}$ [M+H]+ 1455.5510, found 1455.5547.

SL-1355
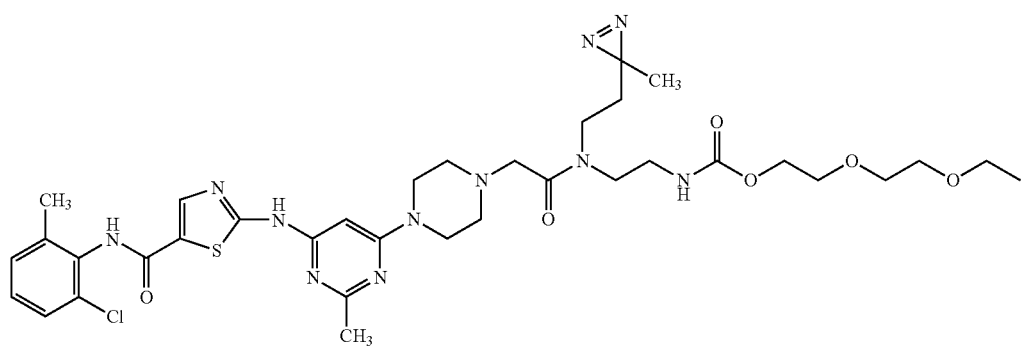
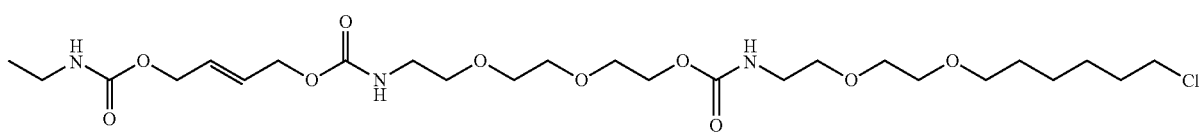
HPLC: 99% purity at 254 nm; $^1$H NMR (400 MHz, Methanol-d4, reported for mixture of rotamers) δ 8.17 (m, 1H), 7.43-7.32 (m, 1H), 7.32-7.09 (m, 2H), 6.15 (m, 1H), 5.84 (m, 2H), 4.53 (m, 4H), 4.28 (m, 2H), 4.17 (m, 4H), 3.82-3.43 (m, 32H), 3.28-3.23 (m, 4H), 2.52 (m, 3H), 2.33 (m, 3H), 1.76 (m, 2H), 1.59 (m, 4H), 1.53-1.34 (m, 4H), 1.17-0.99 (m, 3H); HRMS (SI) Calc'd for $C_{58}H_{89}Cl_2N_{14}O_{16}S$ [M+H]+ 1339.5699, found 1339.5673.
SL-1377
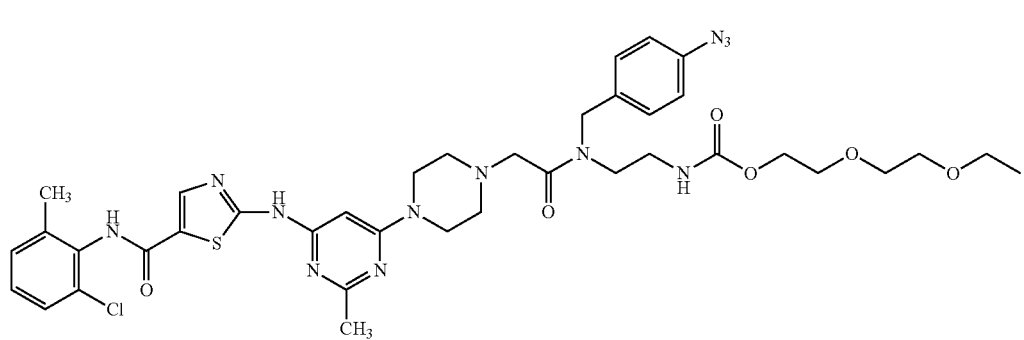
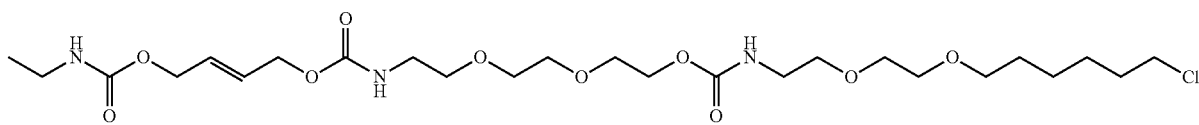
HPLC: 99% purity at 254 nm; $^1$H NMR (400 MHz, Methanol-d4, reported for mixture of rotamers) δ 8.17 (m, 1H), 7.49-7.19 (m, 5H), 7.19-6.90 (m, 2H), 6.14 (m, 1H), 5.83 (m, 2H), 4.68 (m, 1H), 4.59 (m, 1H), 4.55-4.23 (m, 6H), 4.17 (m, 4H), 3.84-3.40 (m, 29H), 3.35 (m, 3H), 3.27 (m, 7H), 2.52 (m, 3H), 2.33 (m, 3H), 1.76 (m 2H), 1.59 (m, 2H), 1.54-1.35 (m, 5H); HRMS (SI) Calc'd for $C_{61}H_{87}Cl_2N_{15}O_{16}S$ [M+2H]2+/2 694.7850, found 694.7846.

SL-1387
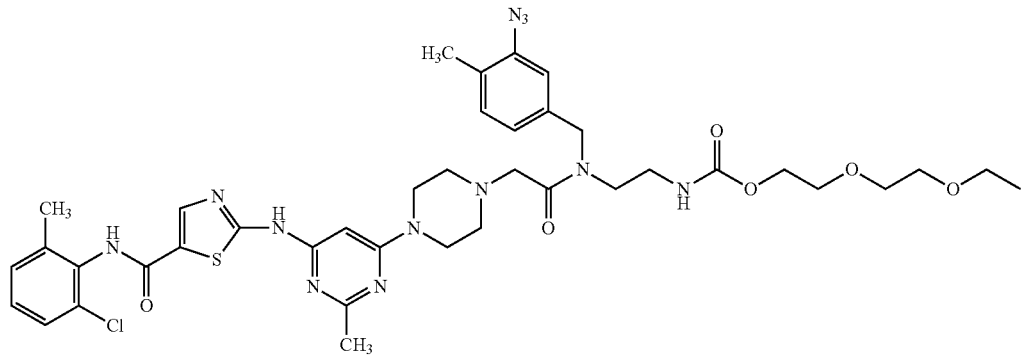
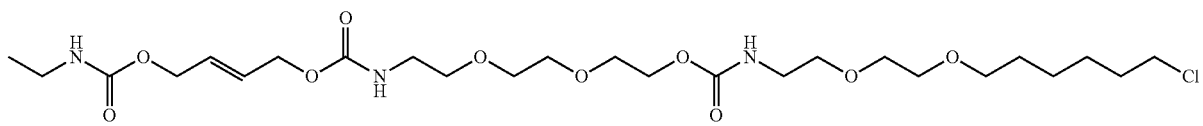
HPLC: 99% purity at 254 nm; ¹H NMR (400 MHz, Methanol-d4, reported for mixture of rotamers) δ 8.18 (m, 1H), 7.36 (m, 1H), 7.31-6.87 (m, 5H), 6.17 (m, 1H), 5.82 (m, 2H), 4.74-4.27 (m, 7H), 4.17 (m, 4H), 3.78-3.40 (m, 31H), 3.40-3.33 (m, 3H), 3.27 (m, 7H), 2.52 (m, 3H), 2.33 (s, 3H), 2.19 (m, 3H), 1.76 (m, 2H), 1.58 (m, 2H), 1.53-1.33 (m, 4H); HRMS (SI) Calc'd for $C_{62}H_{90}Cl_2N_{15}O_{16}S$ [M+2H]2+/2 1402.5782, found 1402.5754.
SL-1351
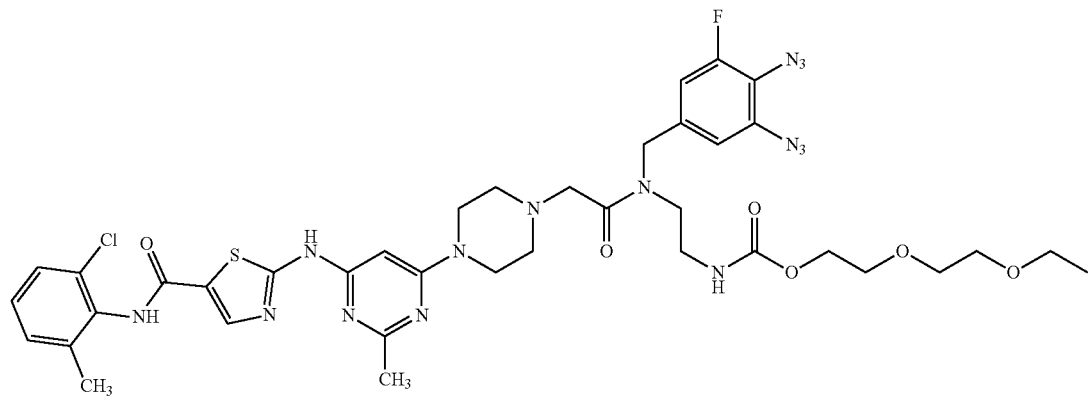
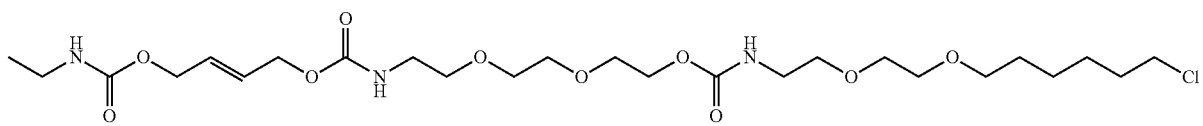
HPLC: 99% purity at 254 nm; ¹H NMR (400 MHz, Methanol-d4, reported for mixture of rotamers) δ 8.18 (s, 1H), 7.36 (m, 1H), 7.30-7.18 (m, 2H), 7.01 (m, 1H), 7.00-6.73 (m, 1H), 6.17 (m, 1H), 5.83 (s, 2H), 4.63-4.27 (m, 7H), 4.27-4.05 (m, 5H), 3.78-3.43 (m, 32H), 3.43-3.35 (m, 3H), 3.27 (m, 6H), 2.52 (m, 3H), 2.33 (s, 3H), 1.87-1.67 (m, 2H), 1.59 (m, 2H), 1.52-1.33 (m, 4H); HRMS (SI) Calc'd for $C_{61}H_5Cl_2FN_{18}O_{16}S$ [M+H]+ 1447.5545, found 1447.5547.

Characterization Data for Propranolol-PRG-Chloroalkane Probes:

SL-1474

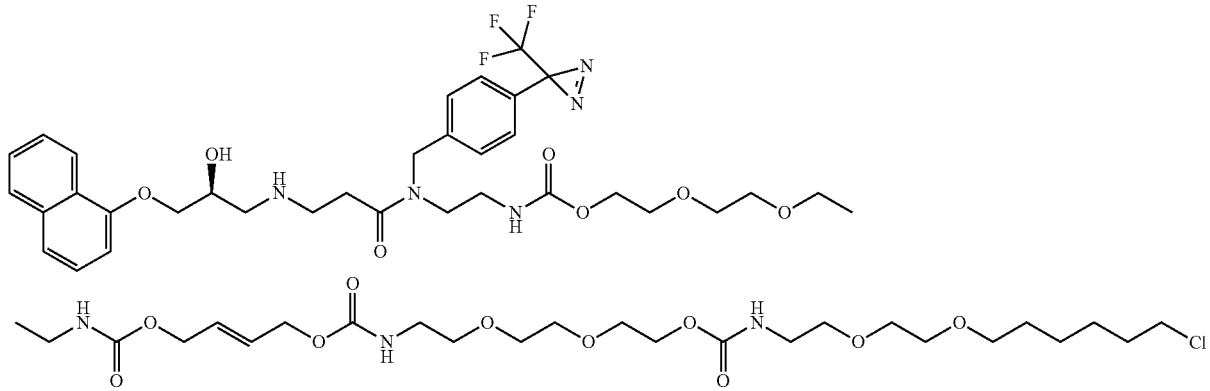

HPLC: 99% purity at 254 nm; $^1$H NMR (400 MHz, Methanol-d4, reported for mixture of rotamers) δ 8.35-8.19 (m, 1H), 7.83 (m, 1H), 7.58-7.42 (m, 3H), 7.42-7.31 (m, 3H), 7.27 (m, 1H), 7.20 (m, 1H), 6.95 (m, 1H), 5.82 (s, 2H), 4.68 (m, 2H), 4.60-4.33 (m, 5H), 4.28 (m, 1H), 4.24-4.06 (m, 5H), 3.85-3.37 (m, 33H), 3.37-3.31 (m, 15H), 3.28-3.18 (m, 5H), 3.04 (m, 1H), 2.84 (m, 1H), 1.85-1.67 (m, 2H), 1.59 (m, 2H), 1.52-1.26 (m, 4H); MS (SI) Calc'd for $C_{57}H_{82}ClF_3N_8O_{17}$ [M+H]+ 1243.55, found 1243.78.

SL-1473

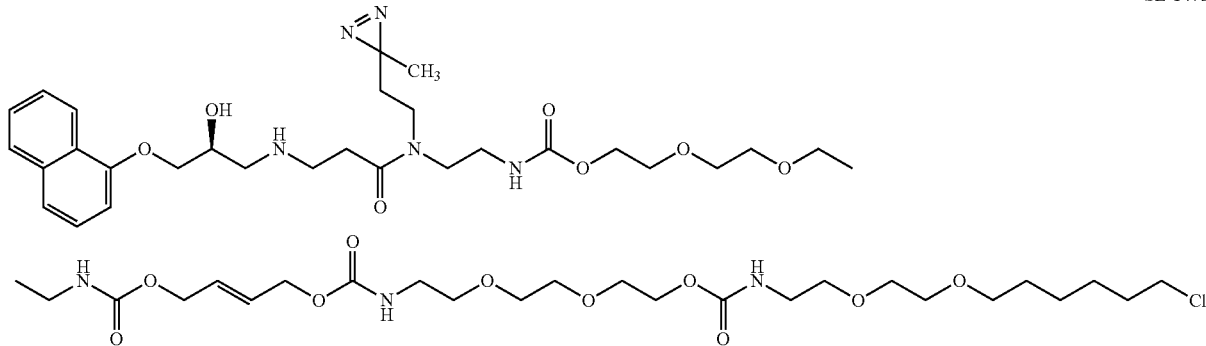

HPLC: 99% purity at 254 nm; $^1$H NMR (400 MHz, Methanol-d4, reported for mixture of rotamers) δ 8.39-8.17 (m, 1H), 7.89-7.69 (m, 1H), 7.58-7.43 (m, 3H), 7.43-7.24 (m, 1H), 6.95 (m, 1H), 5.83 (s, 2H), 4.52 (s, 4H), 4.44 (m, 1H), 4.28 (m, 1H), 4.19 (m, 5H), 3.77-3.34 (m, 39H), 3.28-3.16 (m, 5H), 2.90 (m, 2H), 1.93-1.69 (m, 2H), 1.68-1.33 (m, 9H), 1.06 (s, 1H), 1.02 (s, 2H); MS (SI) Calc'd for $C_{52}H_{84}ClN_8O_{17}$ [M+H]+ 1127.56, found 1227.86.

SL-1484

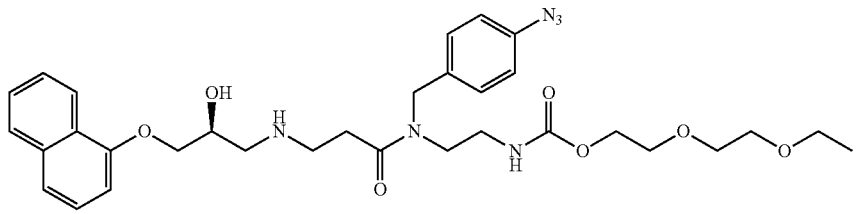

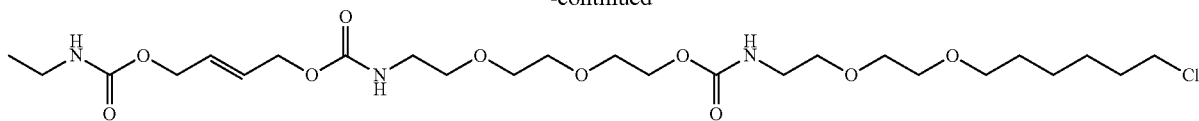
HPLC: 99% purity at 254 nm; ¹H NMR (400 MHz, Methanol-d4, reported for mixture of rotamers) δ 8.43-8.15 (m, 1H), 7.91-7.71 (m, 1H), 7.58-7.43 (m, 3H), 7.43-7.35 (m, 1H), 7.35-7.20 (m, 2H), 7.12-7.04 (m, 1H), 7.04-6.98 (m, 1H), 6.95 (m, 1H), 5.82 (s, 2H), 4.62 (m, 2H), 4.57-4.38 (m, 6H), 4.28 (m, 1H), 4.25-4.08 (m, 5H), 3.78-3.36 (m, 37H), 3.26 (m, 6H), 3.09-2.96 (m, 1H), 2.96-2.83 (m, 1H), 1.82-1.66 (m, 2H), 1.58 (m, 2H), 1.52-1.33 (m, 5H); HRMS (SI) Calc'd for $C_{55}H_{83}ClN_9O_{17}$ [M+H]+ 1176.5590, found 1176.5583.
HPLC: 99% purity at 254 nm; ¹H NMR (400 MHz, Methanol-d4, reported for mixture of
SL-1488
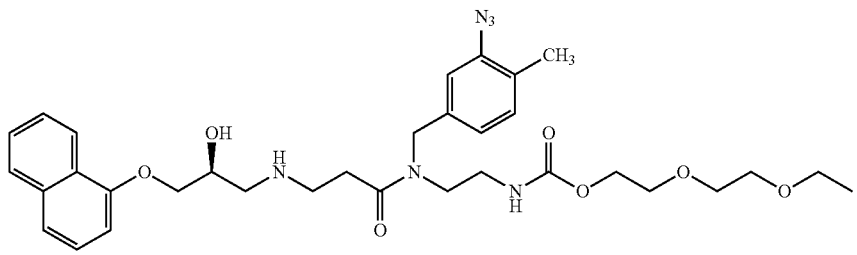
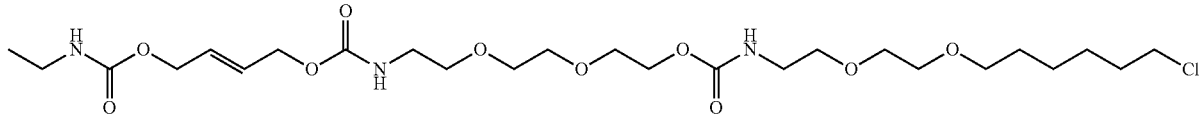
rotamers) δ 8.34-8.14 (m, 1H), 7.88-7.73 (m, 1H), 7.56-7.33 (m, 4H), 7.27-6.82 (m, 4H), 5.82 (m, 2H), 4.63 (m, 2H), 4.58-4.32 (m, 5H), 4.32-4.04 (m, 6H), 3.73-3.36 (m, 32H), 3.29-3.19 (m, 6H), 3.10-2.95 (m, 1H), 2.89 (m, 1H), 2.16 (m, 3H), 1.84-1.67 (m, 2H), 1.58 (m, 2H), 1.50-1.32 (m, 4H); HRMS (SI) Calc'd for $C_{56}H_{85}ClN_9O_{17}$ [M+H]+ 1190.5746, found 1190.5721.
SL-1486
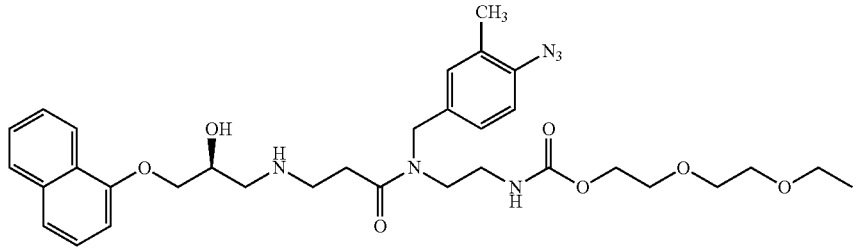
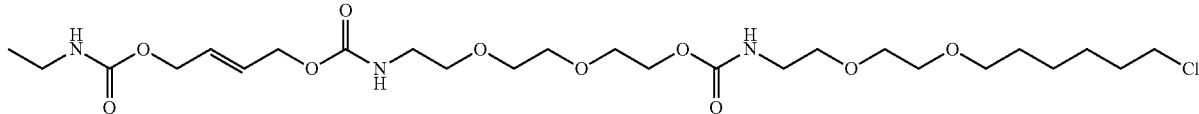

HPLC: 99% purity at 254 nm; $^1$H NMR (400 MHz, Methanol-d4, reported for mixture of rotamers) δ $^1$H NMR (400 MHz, Methanol-d4) δ 8.37-8.10 (m, 1H), 7.90-7.74 (m, 1H), 7.57-7.43 (m, 3H), 7.40 (t, J=7.9 Hz, 1H), 7.21-7.04 (m, 3H), 6.95 (ddd, J=7.7, 3.0, 1.1 Hz, 1H), 5.82 (s, 2H), 4.59 (d, J=7.5 Hz, 2H), 4.55-4.35 (m, 5H), 4.29 (ddd, J=10.6, 5.9, 4.8 Hz, 1H), 4.25-4.07 (m, 5H), 3.74-3.36 (m, 33H), 3.35 (s, 1H), 3.27-3.20 (m, 4H), 3.09-2.97 (m, 1H), 2.97-2.81 (m, 1H), 2.17 (d, J=9.4 Hz, 3H), 1.83-1.68 (m, 2H), 1.58 (p, J=6.7 Hz, 2H), 1.52-1.32 (m, 4H); HRMS (SI) Calc'd for $C_{56}H_{85}ClN_9O_{17}$ [M+H]+ 1190.5746, found 1190.5721.

SL-1492

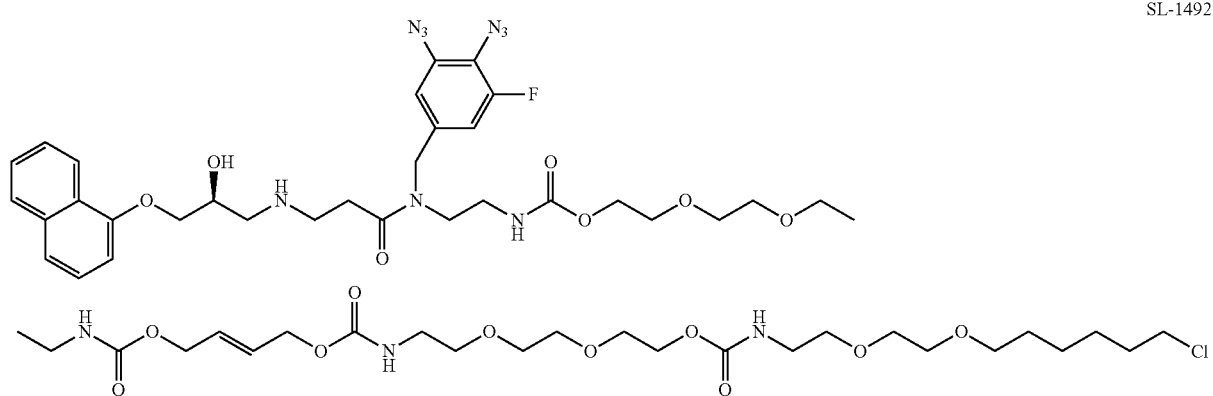

HPLC: 99% purity at 254 nm; $^1$H NMR (400 MHz, Methanol-d4, reported for mixture of rotamers) δ 8.36-8.16 (m, 1H), 7.89-7.73 (m, 1H), 7.51-7.41 (m, 3H), 7.38 (m, 1H), 6.98-6.84 (m, 3H), 5.82 (s, 2H), 4.68-4.36 (m, 7H), 4.36-4.05 (m, 6H), 3.75-3.37 (m, 33H), 3.27 (m, 5H), 3.04 (m, 1H), 2.93-2.75 (m, 1H), 1.83-1.67 (m, 2H), 1.59 (m, 2H), 1.52-1.33 (m, 4H); HRMS (SI) Calc'd for $C_{55}H_1ClFN_{12}O_{17}$ [M+H]+ 1235.5510, found 1235.5523.

Synthesis of SAHA-Dye Tracers:

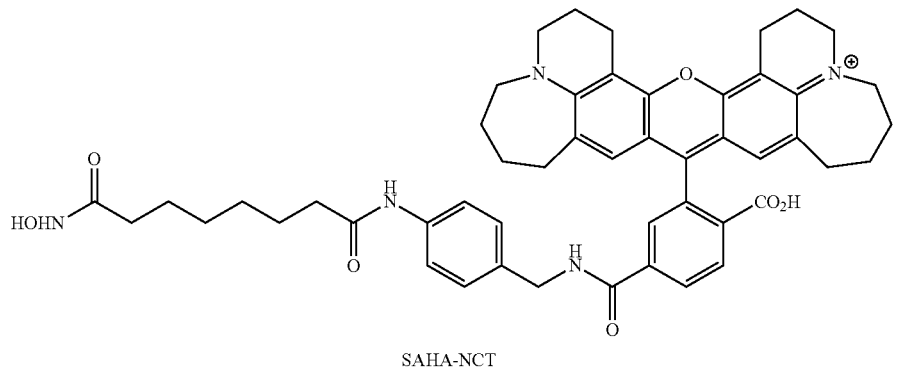

SAHA-NCT

SAHA-NCT was synthesized according to a published protocol in *ACS Chemical Biology*, 2015, 10, 2316-2324

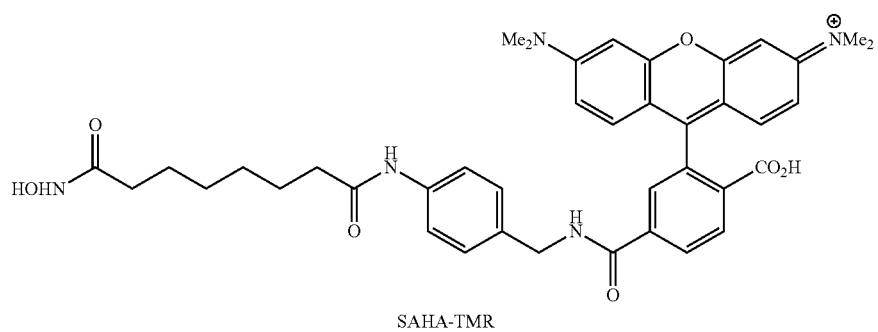

SAHA-TMR

SAHA-TMR was synthesized according to a published protocol in the PCT Int. Appl., 2014093677, 19 Jun. 2014

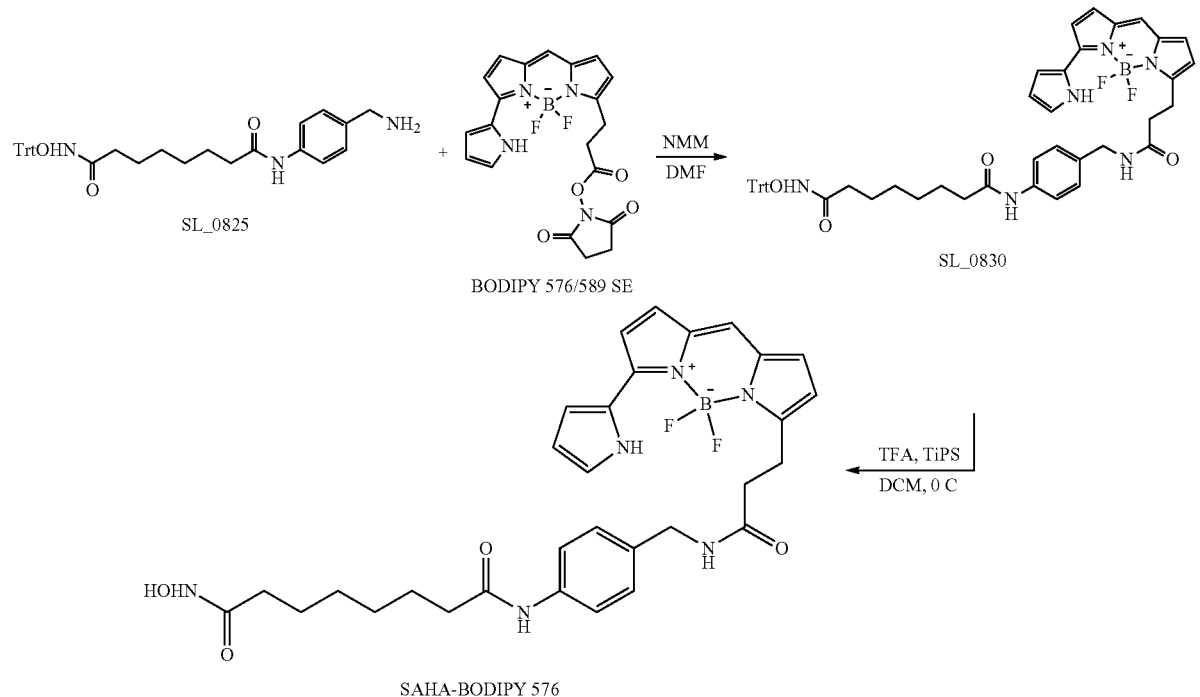

To a solution of SL_0825 (6.0 mg, 11 μmol, prepared according to *ACS Chemical Biology*, 2015, 10, 2316-2324) and NMM (8 μL, 60 μmol) in DMF (4 mL), BODIPY576 SE (4.8 mg, 11 μmol) was added. The resulting solution was allowed to react at 22° C. for 2 hours at which point HPLC analysis indicated full consumption of the starting material. Solvent was removed under vacuum, and the crude residue (SL_0830) used in the next step without further purification. MS (SI) Calc'd for $C_{50}H_{50}BF_2N_6O_4$ [M+H]+ 847.40, found 847.47.

Crude SL_0830 (9.5 mg, 11 μmol) was dissolved in DCM (5 mL), and the stirred solution cooled to 0° C. TiPS (3 drops) was added followed by TFA (1 drop). The resulting solution was left stirred at 0° C. for 3 hours at which point HPLC analysis indicated full consumption of the starting material. The reaction mixture was purified by preparative RP HPLC (5→95% MeCN/H$_2$O buffered with 0.5% TFA) to provide 1.9 mg (28% yield) of SAHA-BODIPY 576 as a purple film. HPLC: 95% purity at 254 nm; $^1$H NMR (300 MHz, Methanol-d4) δ 10.60 (s, 1H), 7.39 (dd, J=8.5, 2.9 Hz, 2H), 7.15-7.06 (m, 6H), 6.91 (t, J=4.9 Hz, 1H), 6.79 (dd, J=7.1, 4.0 Hz, 1H), 6.25 (m, 1H), 6.22-6.03 (m, 1H), 4.23 (d, J=7.6 Hz, 2H), 2.58 (td, J=7.7, 4.2 Hz, 2H), 2.36-2.09 (m, 3H), 1.97 (m, 1H), 1.58 (m, 4H), 1.28 (m, 4H); MS (SI) Calc'd for $C_{31}H_{36}BF_2N_6O_4$ [M+H]+ 605.29, found 605.50.

Synthesis of Propranolol-Dye Tracers:

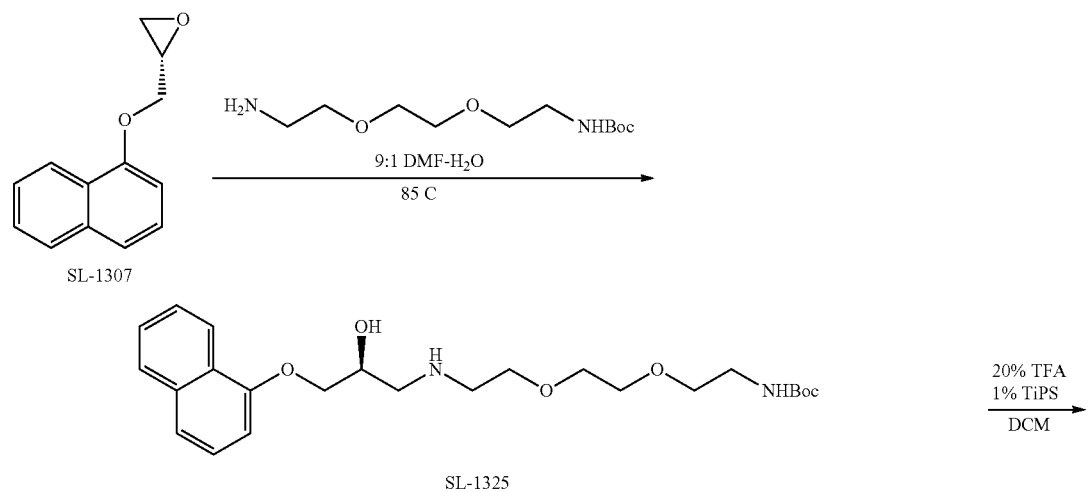

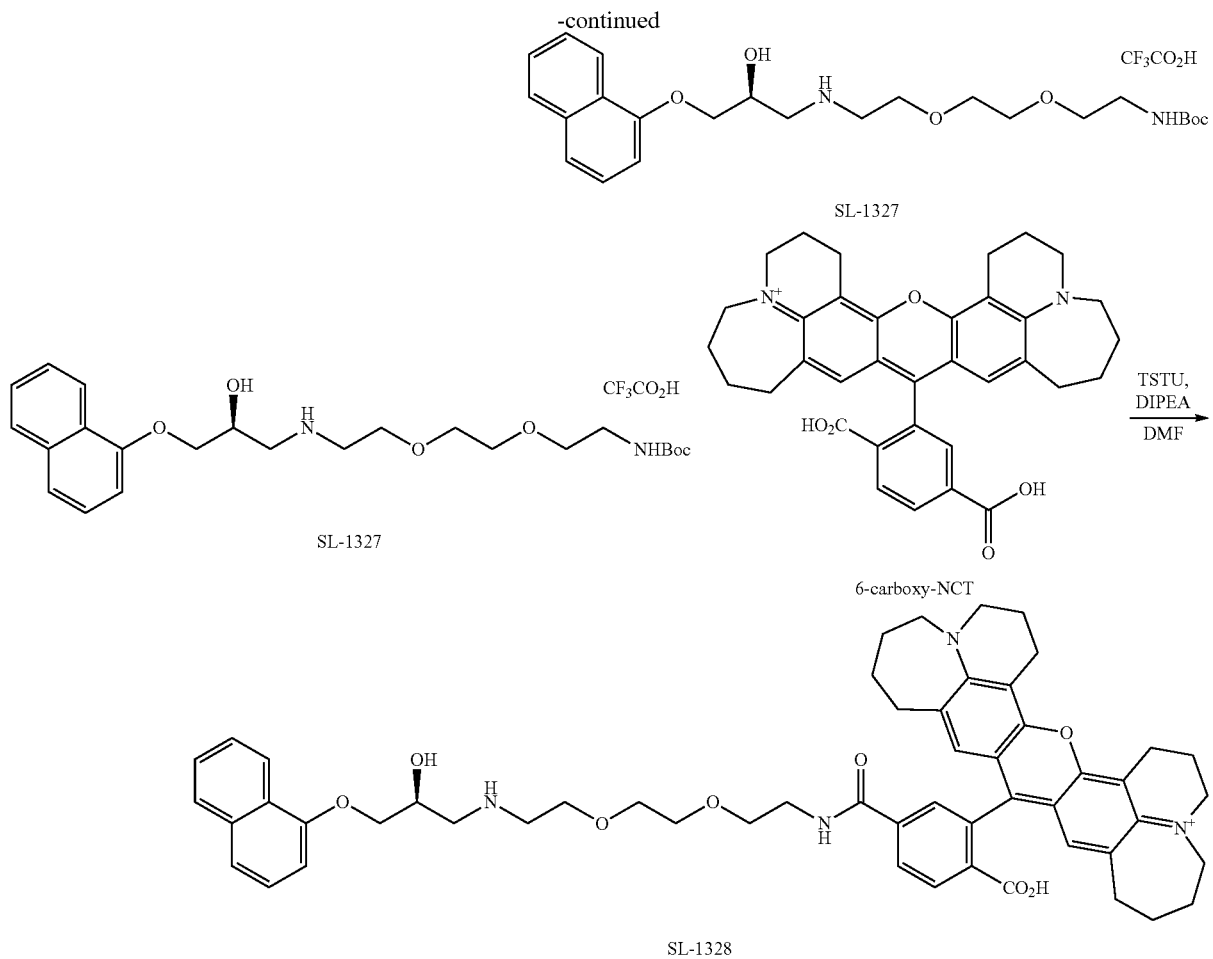

A solution of (S)-2-((naphthalen-1-yloxy)methyl)oxirane (330 mg, 1.65 mmol, prepared according to J. Org. Chem. 1989, 54, 1295-1304) and tert-butyl (2-(2-(2-aminoethoxy)ethoxy)ethyl)carbamate (1.02 g, 4.12 mmol) in 9:1 DMF-water (10 mL) was heated to 85° C. for 21 hours at which point HPLC analysis indicated full consumption of starting material. Volatiles were removed under reduced pressure. The crude residue was purified by silica gel chromatography (0→20% MeOH/DCM) to provide 535 mg (72% yield) of amine SL-1325 as a yellow oil. $^1$H NMR (400 MHz, DMSO-d6) δ 8.39-8.16 (m, 1H), 8.04-7.75 (m, 1H), 7.64-7.48 (m, 2H), 7.46 (d, J=8.3 Hz, 1H), 7.40 (t, J=7.8 Hz, 1H), 6.95 (dd, J=7.6, 1.1 Hz, 1H), 6.76 (t, J=5.7 Hz, 1H), 5.13 (d, J=4.5 Hz, 1H), 4.24-3.89 (m, 3H), 3.55-3.42 (m, 6H), 3.36 (t, J=6.1 Hz, 2H), 3.05 (q, J=6.0 Hz, 2H), 2.88-2.67 (m, 4H), 1.36 (s, 9H); MS (SI) Calc'd for $C_{24}H_{37}N_2O_6$ [M+H]+ 449.27, found 449.64.

To a solution of SL-1325 (313 mg, 698 µmol) in DCM (16 mL), TiPS (200 µL) followed by TFA (4 mL) was added. The resulting solution was stirred at 22° C. for 2 hours at which point HPLC analysis indicated full consumption of starting material. Volatiles were removed under reduced pressure, and crude residue dissolved in 20 mL MeOH, and volatiles removed under vacuum. The crude residue was dried under high vacuum and used in the next step without further purification. $^1$H NMR (400 MHz, DMSO-d6) δ 8.64 (d, J=27.2 Hz, 2H), 8.26 (dd, J=7.9, 1.8 Hz, 1H), 8.04-7.87 (m, 1H), 7.79 (s, 3H), 7.64-7.50 (m, 3H), 7.50-7.29 (m, 1H), 7.06-6.87 (m, 1H), 4.35 (dtd, J=9.9, 5.1, 2.9 Hz, 1H), 4.16 (dp, J=8.6, 4.8 Hz, 2H), 3.73 (ddd, J=6.2, 4.3, 2.2 Hz, 2H), 3.68-3.52 (m, 6H), 3.35 (m, 1H), 3.22 (m, 3H), 2.97 (h, J=5.7 Hz, 2H); MS (SI) Calc'd for $C_{19}H_{29}N_2O_4$[M+H]+ 349.21, found 349.28.

To a solution of 6-carboxy-NCT (10 mg, 18 µmol, prepared according to Org. Lett. 2016, 18, 5316-5319), DIPEA (22 µL, 120 µmol) and TSTU (5.5 mg, 18 µmol) in DMF (5 mL), SL-1327 (10 mg, 18 µmol) was added. The resulting solution was stirred at 22° C. for 2 hours at which point HPLC analysis indicated full consumption of the starting material. The reaction mixture was purified by preparative RP HPLC (5→95% MeCN/H$_2$O buffered with 0.5% TFA) to provide 7 mg (44% yield) of conjugate SL-1328 as a deep blue film. HPLC: 99% purity at 254 nm; $^1$H NMR (400 MHz, Methanol-d4) δ 8.35 (d, J=8.2 Hz, 1H), 8.24-8.02 (m, 2H), 7.87 (d, J=1.8 Hz, 1H), 7.74 (d, J=8.1 Hz, 1H), 7.49-7.36 (m, 2H), 7.36-7.14 (m, 2H), 6.78 (d, J=7.6 Hz, 1H), 6.58 (d, J=2.6 Hz, 2H), 4.41 (dtd, J=10.2, 5.4, 3.0 Hz, 1H), 4.04 (qd, J=9.7, 5.4 Hz, 2H), 3.88-3.75 (m, 2H), 3.75-3.59 (m, 12H), 3.59-3.41 (m, 5H), 3.26 (dd, J=12.7, 10.0 Hz, 3H), 2.94 (dddd, J=25.0, 16.2, 7.2, 4.0 Hz, 4H), 2.78 (dd, J=7.6, 4.3 Hz, 4H), 2.22-1.99 (m, 4H), 1.93 (h, J=6.1, 5.3 Hz, 4H), 1.88-1.69 (m, 4H); HRMS (SI) Calc'd for $C_{57}H_{64}N_7O_7$ [M+]+ 893.4484, found 893.4485.

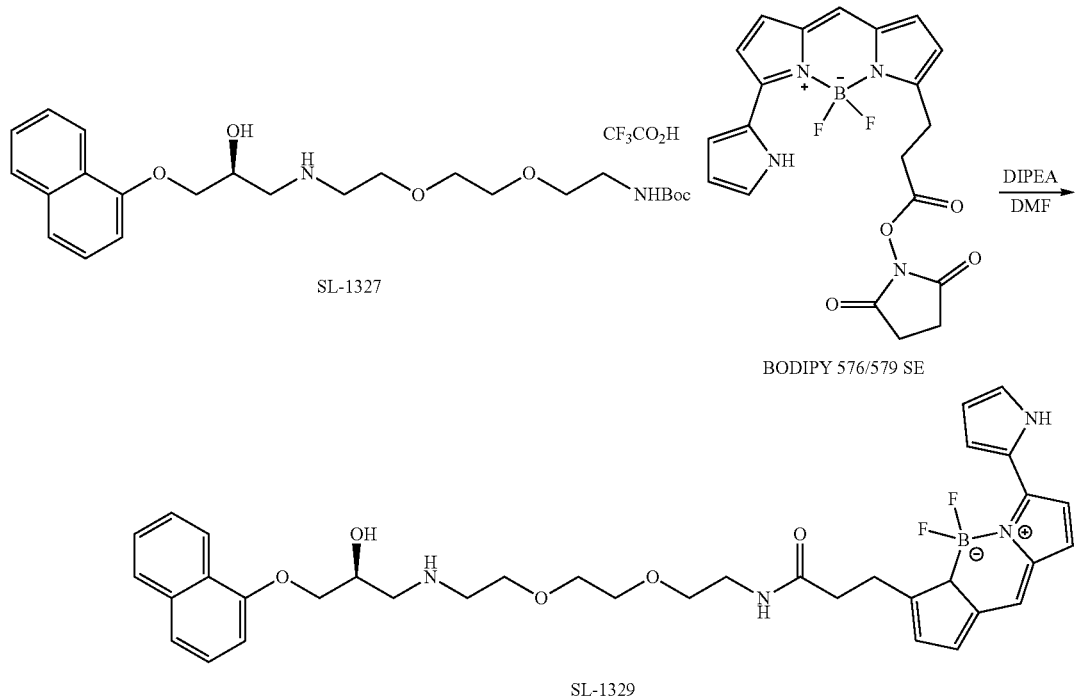

To a solution of SL-1327 (4.1 mg, 7.1 μmol) and DIPEA (9 μL, 50 μmol) in DMF (4 mL), a solution of BODIPY576 SE (3.0 mg, 7.0 μmol) in DMF (4 mL) was added. The resulting solution was allowed to react at 22° C. for 3 hours at which point HPLC analysis indicated full consumption of the starting material. The reaction mixture was purified by preparative RP HPLC (5→95% MeCN/H$_2$O buffered with 0.5% TFA) to provide 4 mg (74% yield) of conjugate SL-1329 as a deep blue film. HPLC: 96% purity at 254 nm; $^1$H NMR (400 MHz, Methanol-d4) δ 8.25 (dd, J=8.2, 1.5 Hz, 1H), 7.81 (dd, J=7.8, 1.5 Hz, 1H), 7.58-7.41 (m, 3H), 7.37 (t, J=7.9 Hz, 1H), 7.24-7.16 (m, 3H), 7.14 (d, J=4.5 Hz, 1H), 6.98 (d, J=4.6 Hz, 1H), 6.88 (dd, J=5.7, 4.2 Hz, 2H), 6.41-6.21 (m, 2H), 4.40 (dtd, J=10.1, 5.2, 3.1 Hz, 1H), 4.17 (dd, J=9.9, 4.9 Hz, 1H), 4.11 (dd, J=9.9, 5.4 Hz, 1H), 3.75 (t, J=5.0 Hz, 2H), 3.69-3.57 (m, 4H), 3.53 (t, J=5.5 Hz, 2H), 3.44-3.34 (m, 3H), 3.29-3.18 (m, 4H), 2.64 (t, J=7.7 Hz, 2H); HRMS (SI) Calc'd for $C_{35}H_{41}BF_2N_5O_5$ [M+H]+ 660.3163, found 660.3158.

Synthesis of Dasatinib-Dye Tracers:

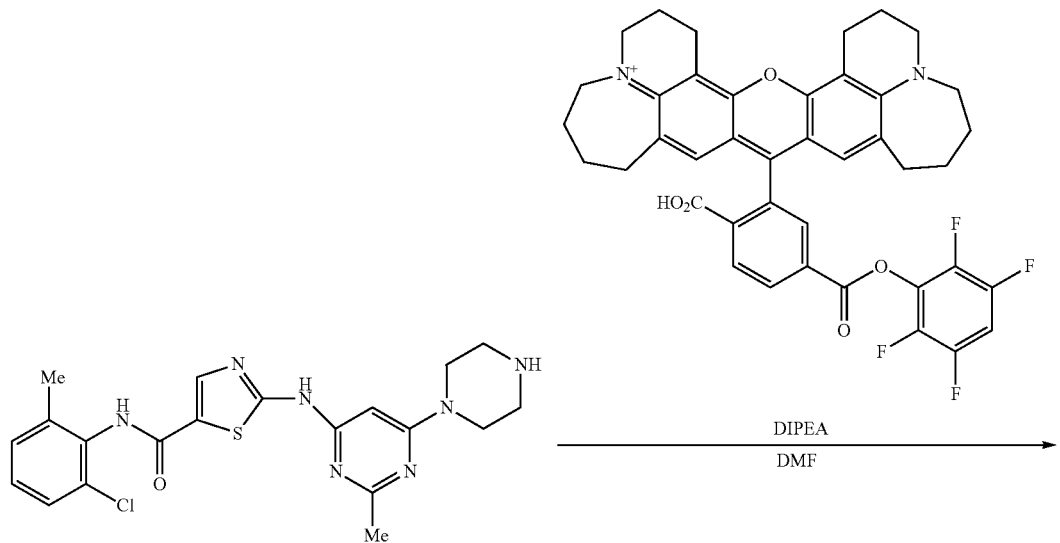

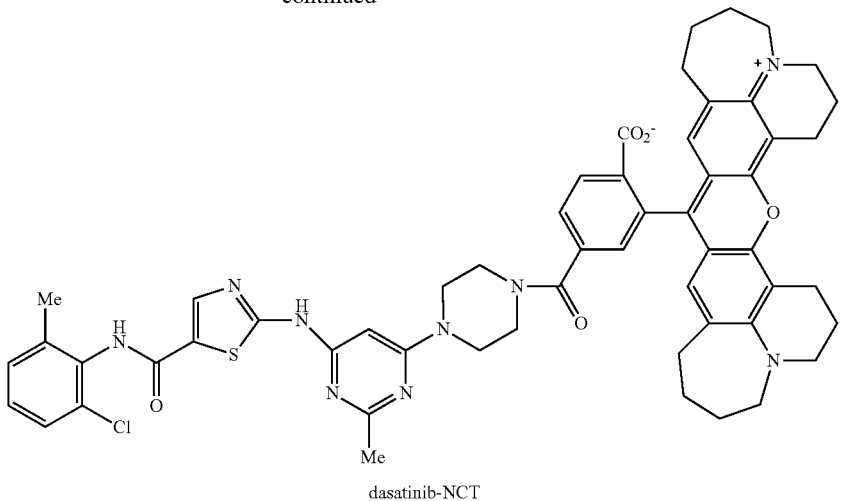

dasatinib-NCT

To a solution of N-Deshydroxyethyl Dasatinib (5 mg, 9 μmol) and DIPEA (4.0 μL, 22 μmol) in DMF (6 mL), NCT-TFP (7 mg, 10 μmol, prepared according to ACS Chem. Biol., 2016, 11, 2608-2617) was added. The resulting solution was stirred at 22° C. for 24 hours at which point HPLC analysis indicated full consumption of the starting material. The reaction mixture was purified by preparative RP HPLC (5→95% MeCN/H$_2$O buffered with 0.5 TFA) to provide 6.5 mg (73 yield) of dasatinib-NCT as a deep blue film. HPLC: 99 purity at 254 nm; HRMS (SI) Calc'd for C$_{55}$H$_{55}$ClN$_9$O$_5$S [M+]+ 988.3730, found 988.3712.

Synthesis of Cleavable Chloroalkane Conjugates:

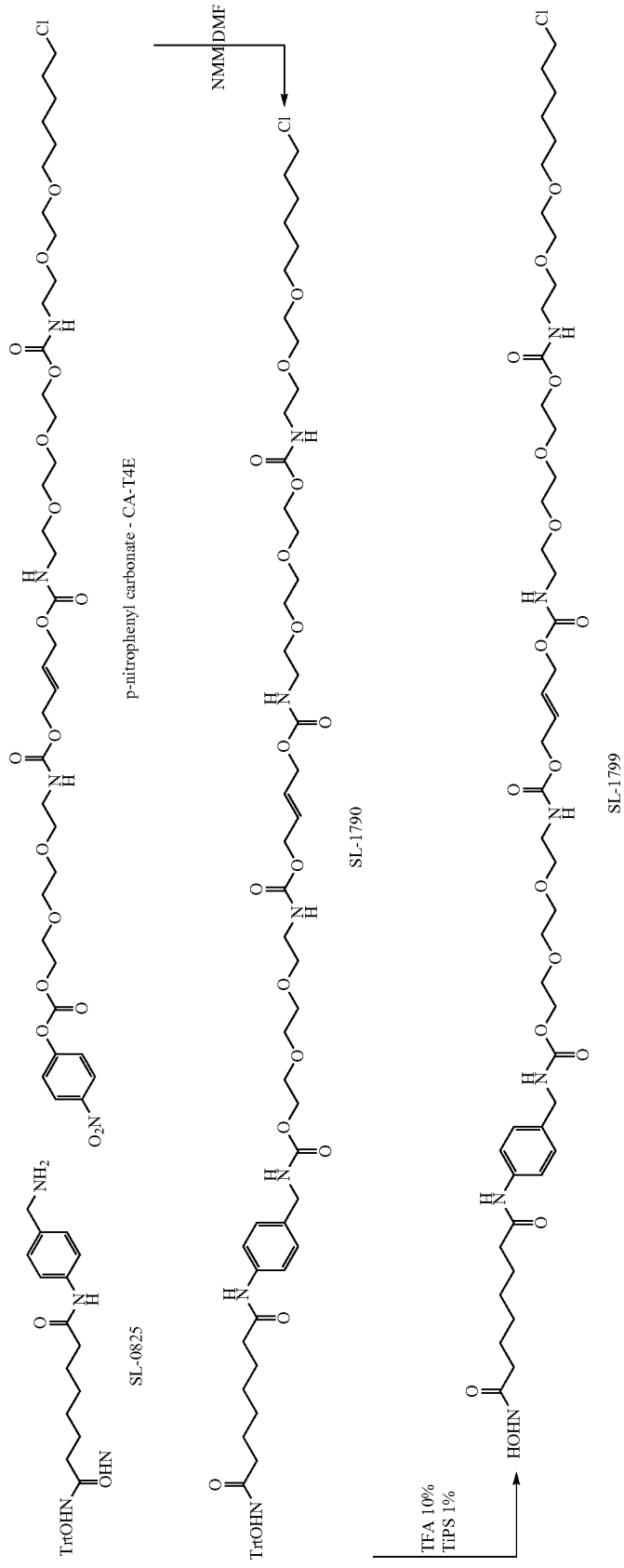

To a solution of SL_0825 (10 mg, 19 μmol, prepared according to *ACS Chemical Biology,* 2015, 10, 2316-2324) and NMM (8 μL, 60 μmol) in DMF (5 mL), p-nitrophenyl carbonate-CA-T4E (16 mg, 19 μmol, prepared according to ACS Chemical Biology 2016, 11, 2608-2617) was added. The resulting solution was stirred at 22° C. for 20 hours at which point HPLC analysis indicated full consumption of starting material. The reaction mixture was purified by preparative RP HPLC (5→95% MeCN/H$_2$O buffered with 0.5% TFA) to provide 16 mg (69% yield) of conjugate SL-1790 as a clear oil. HPLC: 97% purity at 254 nm; MS (SI) Calc'd for $C_{64}H_{90}ClN_6O_{17}$ [M+H]+ 1249.61, found 1249.54.

To a solution of SL-1790 (16 mg, 13 μmol) in DCM (9 mL), TiPS (100 μL) followed by TFA (1 mL) was added. The resulting solution was stirred at 22° C. for 30 minutes at which point HPLC analysis indicated full consumption of starting material. Volatiles were removed under reduced pressure, crude residue dissolved in 5 mL MeOH, and volatiles removed under vacuum. The crude residue was purified by preparative RP HPLC (5→95% MeCN/H$_2$O buffered with 0.5% TFA) to provide 12 mg (90% yield) of conjugate SL-1799 as a white solid. HPLC: 99% purity at 254 nm; $^1$H NMR (400 MHz, Methanol-d4) δ 9.74 (s, 1H), 7.50 (dd, J=8.4, 2.1 Hz, 2H), 7.24 (d, J=8.1 Hz, 2H), 5.84 (s, 2H), 4.52 (s, 4H), 4.24 (s, 2H), 4.20 (t, J=4.7 Hz, 2H), 4.16 (t, J=4.8 Hz, 2H), 3.68 (q, J=5.7 Hz, 4H), 3.62 (d, J=2.0 Hz, 4H), 3.61-3.55 (m, 10H), 3.52 (td, J=6.2, 5.5, 1.8 Hz, 6H), 3.48 (s, 2H), 3.29-3.23 (m, 6H), 2.36 (t, J=7.4 Hz, 2H), 2.10 (s, 1H), 1.84-1.73 (m, 2H), 1.69 (s, 2H), 1.59 (m, 4H), 1.52-1.44 (m, 2H), 1.40 (d, J=5.7 Hz, 6H). MS (SI) Calc'd for $C_{45}H_{76}ClN_6O_{17}$ [M+H]+ 1007.50, found 1007.44.

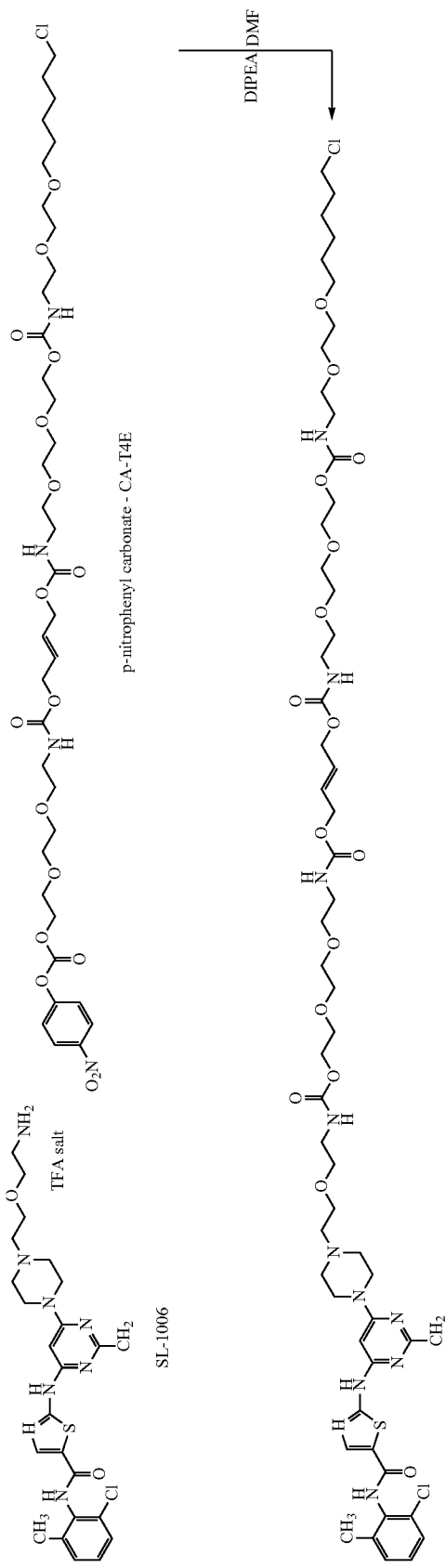

To a solution of SL-1006 (10 mg, 16 μmol, prepared according to, *Cell Chemical Biology* 2018, 25, 206-214) and DIPEA (8 μL, 60 μmol) in DMF (8 mL), p-nitrophenyl carbonate-CA-T4E (16 mg, 19 μmol, prepared according to *ACS Chemical Biology* 2016, 11, 2608-2617) was added. The resulting solution was stirred at 22° C. for 20 hours at which point HPLC analysis indicated full consumption of starting material. The reaction mixture was purified by preparative RP HPLC (5→95% MeCN/H$_2$O buffered with 0.5% TFA) to provide 15 mg (78% yield) of conjugate SL-1118 as a clear oil. HPLC: 99% purity at 254 nm; MS (SI) Calc'd for $C_{54}H_{84}Cl_2N_{11}O_{16}S$ [M+H]+ 1244.52, found 1244.66.

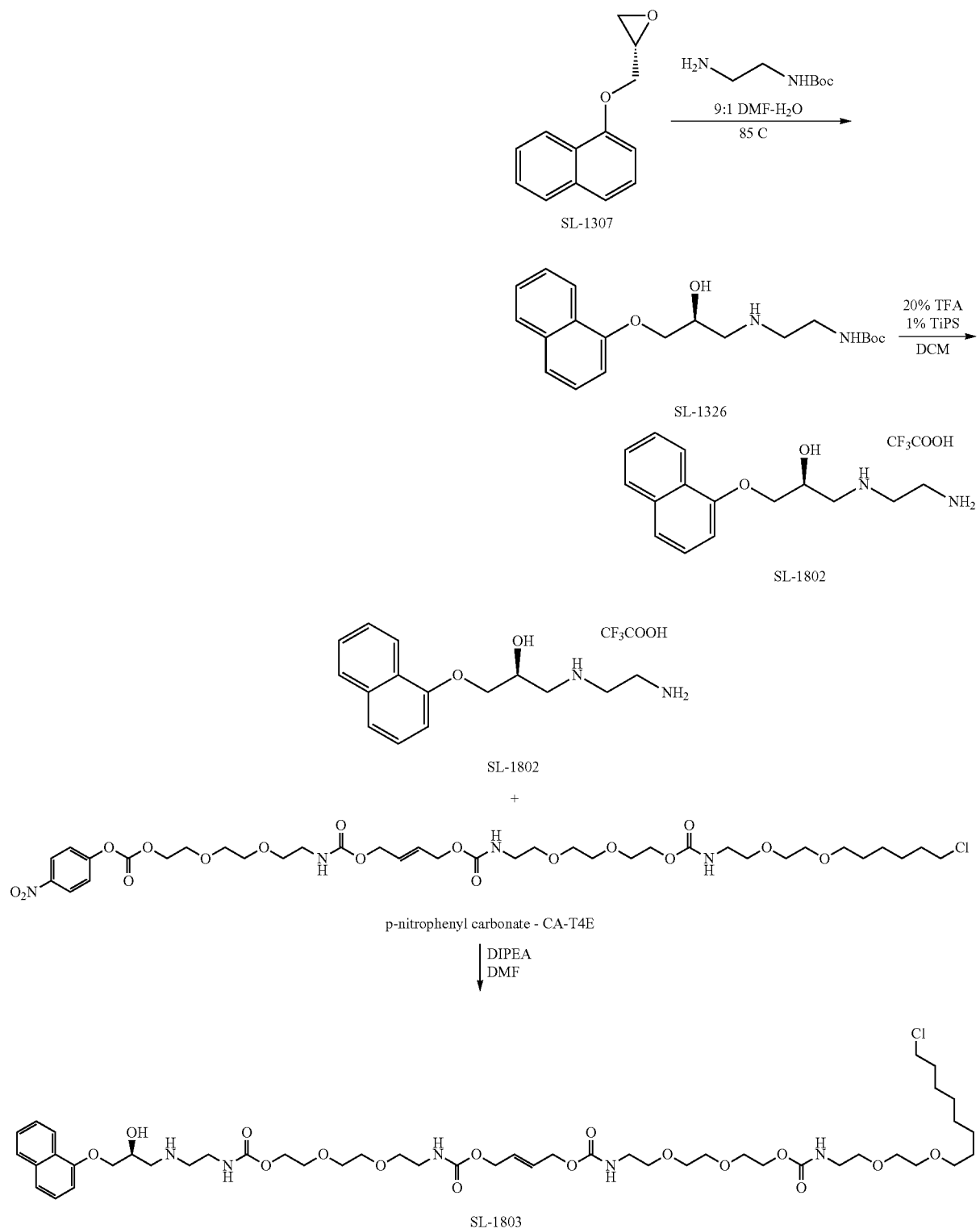

A solution of (S)-2-((naphthalen-1-yloxy)methyl)oxirane (328 mg, 1.64 mmol, prepared according to *J. Org. Chem.* 1989, 54, 1295-1304) and tert-butyl (2-aminoethyl)carbamate (656 mg, 4.10 mmol) in 9:1 DMF-water (10 mL) was heated to 85° C. for 24 hours at which point HPLC analysis indicated full consumption of starting material. The reaction mixture was filtered, and volatiles removed under reduced pressure. The crude residue was purified by silica gel chromatography (0→20% MeOH/DCM) to provide 450 mg (76% yield) of amine SL-1326 as a yellow oil. $^1$H NMR (400 MHz, DMSO-d6) δ 8.24 (dd, J=7.7, 1.9 Hz, 1H), 7.95-7.78 (m, 1H), 7.58-7.45 (m, 3H), 7.40 (t, J=7.9 Hz, 1H), 6.95 (dd, J=7.6, 1.1 Hz, 1H), 6.75 (t, J=5.7 Hz, 1H), 5.09 (d, J=4.6 Hz, 1H), 4.12 (dd, J=9.2, 4.3 Hz, 1H), 4.09-3.96 (m, 2H), 3.02 (q, J=6.2 Hz, 2H), 2.79 (dd, J=11.9, 4.5 Hz, 1H), 2.75-2.65 (m, 1H), 2.61 (t, J=6.5 Hz, 2H), 1.37 (s, 9H); MS (SI) Calc'd for $C_{20}H_{29}N_2O_4$ [M+H]+ 361.21, found 361.76.

To a solution of SL-1326 (16 mg, 44 μmol) in DCM (4 mL), TiPS (50 μL) followed by TFA (1 mL) was added. The resulting solution was stirred at 22° C. for 2 hours at which point HPLC analysis indicated full consumption of starting material. Volatiles were removed under reduced pressure, crude residue dissolved in 5 mL MeOH, and volatiles removed under vacuum. The crude residue was dried under high vacuum and used in the next step without further purification. $^1$H NMR (400 MHz, Methanol-d4) δ 8.38-8.23 (m, 1H), 7.92-7.75 (m, 1H), 7.60-7.44 (m, 3H), 7.40 (t, J=7.9 Hz, 1H), 6.95 (dd, J=7.6, 1.0 Hz, 1H), 4.49 (dtd, J=10.1, 5.2, 3.0 Hz, 1H), 4.27 (dd, J=9.9, 4.9 Hz, 1H), 4.21 (dd, J=9.9, 5.5 Hz, 1H), 3.62-3.47 (m, 3H), 3.47-3.36 (m, 3H); MS (SI) Calc'd for $C_5H_{21}N_2O_2$ [M+H]+ 261.16, found 261.11.

To a solution of SL-1802 (15 mg, 40 μmol) and DIPEA (23 μL, 130 μmol) in DMF (8 mL), p-nitrophenyl carbonate-CA-T4E (11 mg, 13 μmol, prepared according to ACS Chemical Biology 2016, 11, 2608-2617) was added. The resulting solution was stirred at 22° C. for 2 hours at which point HPLC analysis indicated full consumption of starting material. The reaction mixture was purified by preparative RP HPLC (5→95% MeCN/H$_2$O buffered with 0.5% TFA) to provide 9.3 mg (74% yield) of conjugate SL-1803 as a clear oil. HPLC: 99% purity at 254 nm; $^1$H NMR (400 MHz, Methanol-d4) δ 8.38-8.15 (m, 1H), 7.94-7.69 (m, 1H), 7.61-7.44 (m, 3H), 7.39 (t, J=7.9 Hz, 1H), 6.94 (dd, J=7.6, 1.0 Hz, 1H), 5.83 (s, 2H), 4.52 (d, J=2.9 Hz, 4H), 4.43 (dt, J=8.8, 4.1 Hz, 1H), 4.26 (dd, J=9.9, 4.9 Hz, 1H), 4.23-4.05 (m, 5H), 3.67 (q, J=5.0 Hz, 4H), 3.64-3.54 (m, 14H), 3.54-3.40 (m, 12H), 3.28 (m, 8H), 1.88-1.68 (m, 2H), 1.59 (p, J=6.8 Hz, 2H), 1.52-1.32 (m, 4H); HRMS (SI) Calc'd for $C_{45}H_{73}ClN_5O_{16}$ [M+H]+ 974.4735, found 974.4726.

Example 8

Figure 35A:
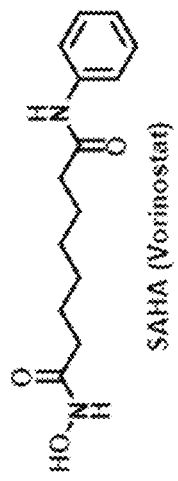
Figure 35B:
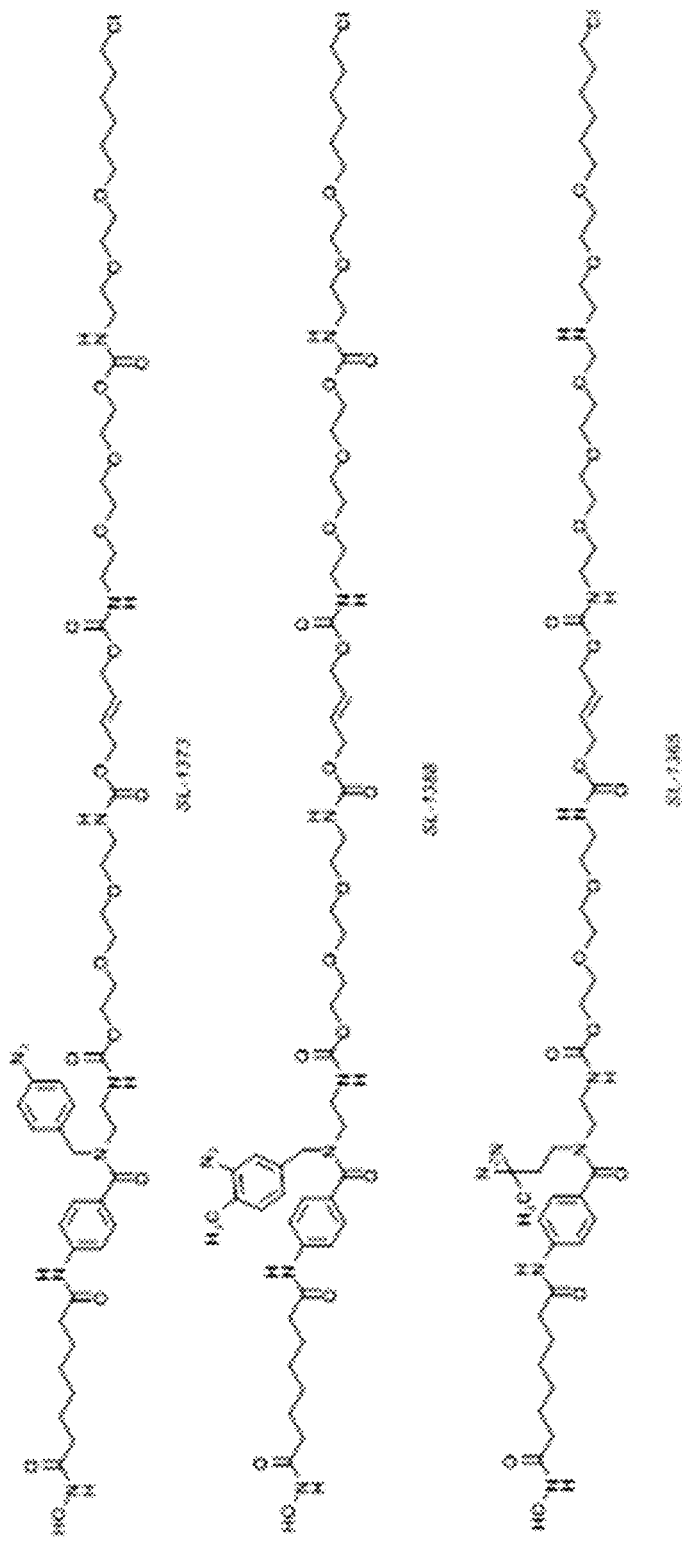

Enrichment experiments conducted during development of embodiments described herein demonstrated enhanced enrichment of endogenous targets for SAHA by 4-phenylazide- and 4-Me-3-4-phenylazide-cleavable chloroalkane probes (SL-1373 and SL-1388 respectively). FIG. 26 provides a schematic illustration of the enrichment workflow. K562 cells were plated in 100 mm dishes at 2×10$^6$ cell/mL and treated in triplicate with a final concentration of 1 μM PRG-cleavable chloroalkane SAHA probe (SL-1373, SL-1388, or SL-1365) in the absence or presence of competing 20 μM SAHA, which served as a control for enrichment specificity. Following 2 hours equilibrium binding, cells were irradiated for 15 minutes. The media was removed, and cells washed with PBS, lysed, and centrifuged at 3000×g for 1 min. Clear lysates were added to 30 μL of settled HaloTag-coated paramagnetic beads and incubated overnight with constant mixing. Following binding, unbound fractions were removed, HaloTag-coated paramagnetic beads were washed 5×, and captured targets were released from the beads by palladium-catalyzed cleavage and subjected to LC-MS/MS analysis. Putative targets identified by the mass spectrometry analysis are defined as those which were enriched at least 4-fold over the control (e.g. +20 μM SAHA) (FIG. 35). This analysis demonstrates enhanced enrichment of relevant SAHA targets by cleavable chloroalkane probes having for a PRG 4-phenylazide or 4-Me-3-phenylazide over diazirine. 4-phenylazide and 4-Me-3-phenylazide cleavable chloroalkane probes enabled enrichment of all the expected HDACs class I/IIB, which are the primary targets of SAHA as well as other proteins associated with them, which are part of megadalton HDACs complexes. In addition, 4-Me-3-phenylazide and especially 4-phenylazide enabled enrichment of SAHA off-targets, many of which bind divalent metal ions. SAHA binds HDACs by chelating to a bound zinc ion and can interact in a similar manner with other metal ion-binding proteins.

Example 9

Figure 36A:
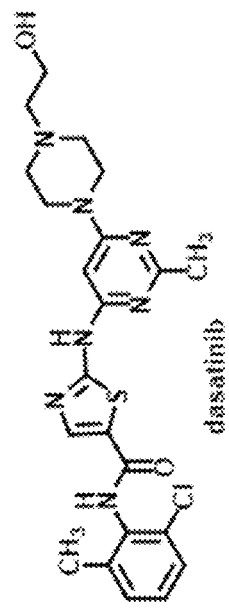
FIGS. 36A-C.
Figure 36B:
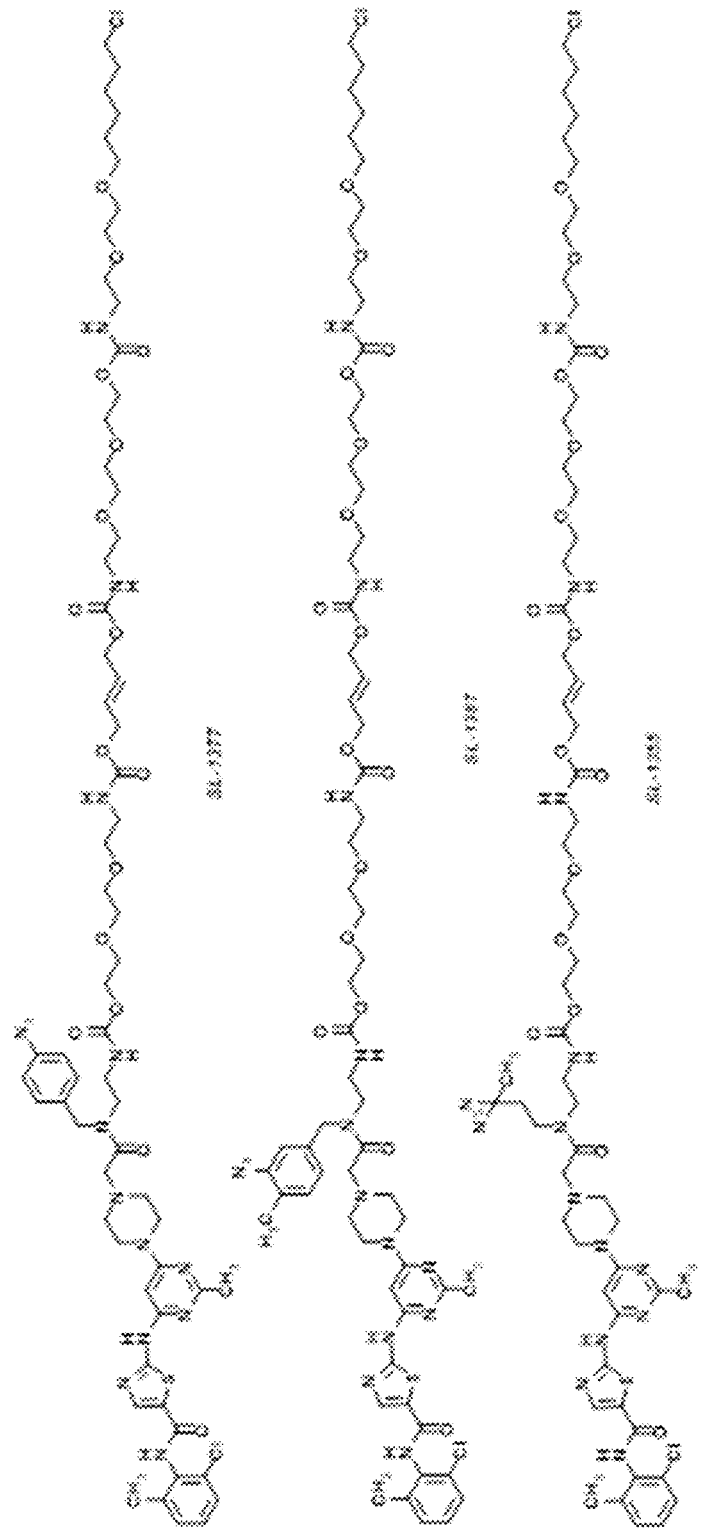
Figure 36C:
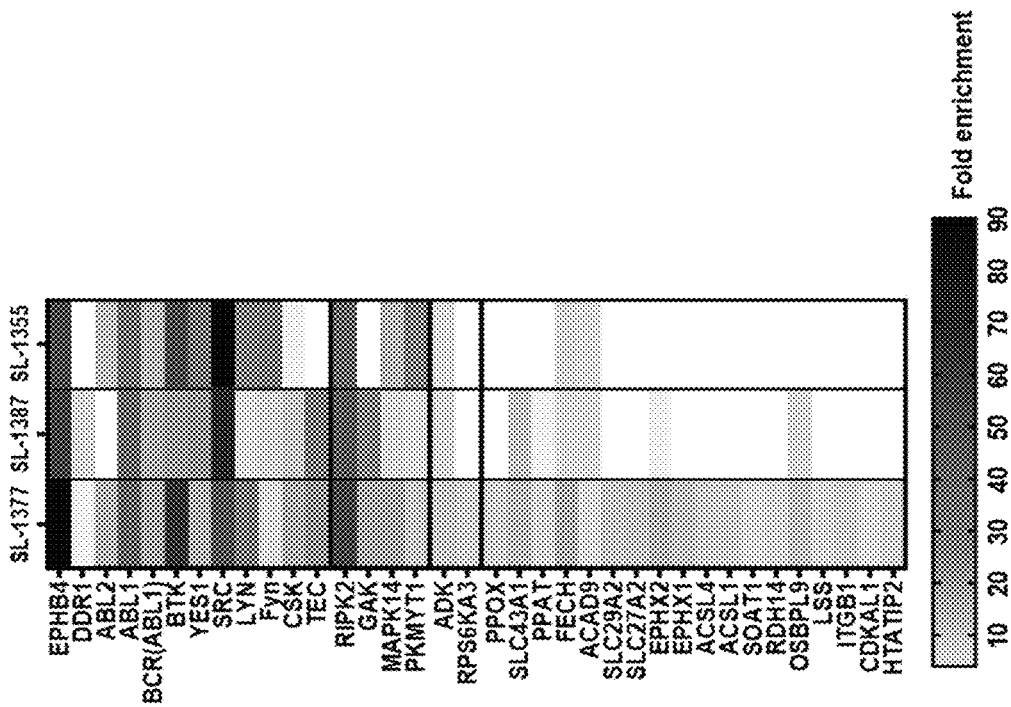

Enrichment experiments conducted during development of embodiments described herein demonstrated enhanced enrichment of endogenous targets for dasatinib by the 4-phenylazide cleavable chloroalkane probe (SL-1377). FIG. 26 provides a schematic illustration of the enrichment workflow. K562 cells were plated in 100 mm dishes at 2×10$^6$ cell/mL and treated in triplicate with a final concentration of 1 μM PRG-cleavable chloroalkane dasatinib probe (SL-1377, SL-1387, or SL-1355) in the absence or presence of competing 20 μM dasatinib, which served as a control for enrichment specificity. Following 2 hours of equilibrium binding, cells were irradiated for 15 minutes. Media was then removed, and cells were washed with PBS, lysed, and centrifuged at 3000×g for 1 min. Clear lysates were added to 30 μL of settled HaloTag-coated paramagnetic beads and incubated overnight with constant mixing. Following binding, unbound fractions were removed, HaloTag-coated paramagnetic beads were washed 5×, and captured targets were released from the beads by palladium-catalyzed cleavage and subjected to LC-MS/MS analysis. Putative targets identified by mass spectrometry analysis are defined as those that were enriched at least 4-fold over the control (e.g. +20 μM dasatinib) (FIG. 36). This analysis demonstrates enhanced enrichment of dasatinib targets and particularly off-targets by a cleavable chloroalkane probe having for a PRG 4-phenylazide (SL-1377). The 4-phenylazide, 4-Me-3-phenylazide, and diazirine cleavable chloroalkane probes (SL-1377, SL-1387, and SL-1355 respectively) enabled enrichment of the expected primary targets including BCR/ABL1, kinases from the Src family, and other kinases. At the same time, 4-phenylazide probe (SL-1377) enabled enhanced enrichment of off-targets, many of which are purine-binding proteins. Dasatinib is a type I kinase inhibitor that occupies kinase ATP binding pocket and can interact in a similar manner with other purine binding proteins.

Example 10

Figure 37A:
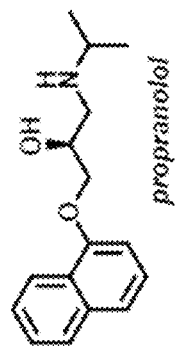
FIGS. 37A-D.
Figure 37B:
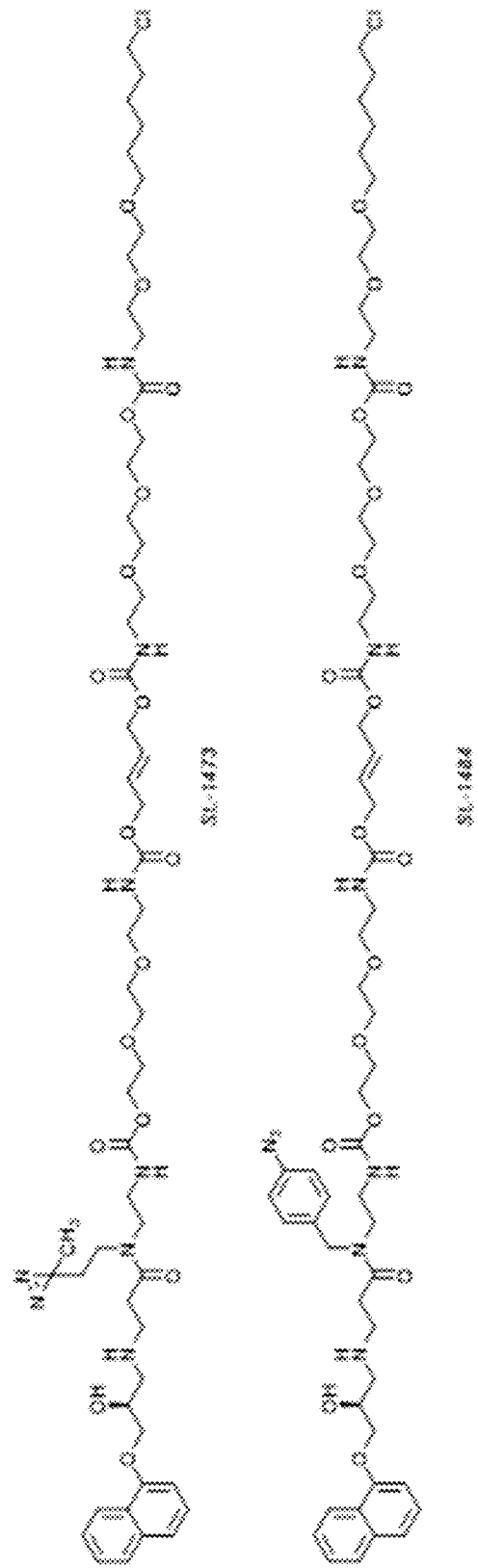
Figure 37C:
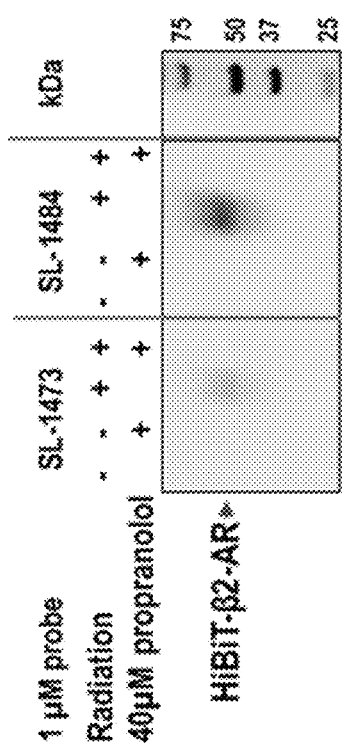
Figure 37D:
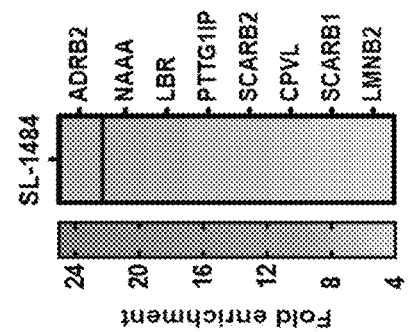

Enrichment experiments conducted during development of embodiments described herein demonstrated enhanced enrichment of endogenous targets for propranolol by the 4-phenylazide cleavable chloroalkane probe (SL-1484). FIG. 26 provides a schematic illustration of the enrichment workflow. Genome-edited PC3 cells expressing a HiBiT-tagged β2-AR were plated in 100 mm dishes at 2×10⁶ cell/mL and treated in triplicate with a final concentration of 1 µM PRG-cleavable chloroalkane propranolol probes in the absence or presence of competing 40 µM propranolol, which served as a control for enrichment specificity. Following a 2 hour equilibrium binding, cells were irradiated for 15 minutes. Media was then removed, and cells were washed with PBS, lysed, and centrifuged at 3000×g for 1 min. Clear lysates were added to 30 µL of settled HaloTag-coated paramagnetic beads and incubated overnight with constant mixing. Following binding, unbound fractions were removed, HaloTag-coated paramagnetic beads were washed 5×, and captured targets were released from the beads by palladium-catalyzed cleavage. The released targets were subjected to a bioluminescence blot analysis (FIG. 37C) and LC-MS/MS analysis (FIG. 37D). The bioluminescence blot analysis, which is reliant on HiBiT/LgBiT complementation, demonstrates the advantage of 4-phenylazide cleavable chloroalkane probe (SL-1484) over a diazirine cleavable chloroalkane probe (SL-1473) for enrichment of 2-AR (GPCR), the primary target of propranolol. LC-MS/MS analysis further demonstrates the capacity of the 4-phenylazide cleavable chloroalkane probe (SL-1484) to enrich and identify 2-AR as well as other putative off-targets most of them are membrane proteins.

REFERENCES

The following references, some of which are cited above are herein incorporated by reference in their entireties.
1. ACS Chem. Biol., 2015, 10 (10), pp 2316-2324
2. ACS Chem. Biol., 2016, 11 (9), pp 2608-2617
3. US20140322794
4. US 20160355523
5. Photo-induced covalent cross-linking for the analysis of biomolecular interactions. Chem. Soc. Rev 2013, 42, 3289
6. Target identification of natural products and bioactive compounds using affinity-based probes. Pan, S; Zhang, H; Wang, C; Yao, S. C; Yao, S. Q. Nat Prod Rep 2016, 33, 612-620.
7. Photoaffinity labeling in target- and binding-site identification. Smith, E; Collins, I. Future Med Chem 2015, 7, 159-183.
8. Development and Leading-Edge Application of Innovative Photoaffinity Labeling. Hatanaka, Y. Chem Pharm Bull (Tokyo) 2015, 63, 1-12.
9. Chemical Reagents in Photoaffinity Labeling. A. Fleming, S. Tetrahedron 1995, 51, 12479-12520.
10. Recent developments and applications of clickable photoprobes in medicinal chemistry and chemical biology. Lapinsky, D. J; Johnson, D. S. Future Med Chem 2015, 7, 2143-2171.
11. Chemical proteomics approaches for identifying the cellular targets of natural products. Wright, M. H; Sieber, S. A. Nat Prod Rep 2016, 33, 681-708

SEQUENCES

WT OgLuc
(SEQ ID NO: 1)
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPDGSL

LFRVTINGVTGWRLCENILA

WT OgLuc Lg
(SEQ ID NO: 2)
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPD

WT OgLuc β9
(SEQ ID NO: 3)
GSLLFRVTIN

WT OgLuc β10
(SEQ ID NO: 4)
GVTGWRLCENILA

NanoLuc
(SEQ ID NO: 5)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTINGVTGWRLCERILA

NanoLuc Lg
(SEQ ID NO: 6)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPD

NanoLuc β9
(SEQ ID NO: 7)
GSLLFRVTINV

NanoLuc β10
(SEQ ID NO: 8)
GVTGWRLCERILA

LgBiT
(SEQ ID NO: 9)
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTIN

SmBiT
(SEQ ID NO: 10)
VTGYRLFEEIL

HiBiT
(SEQ ID NO: 11)
VSGWRLFKKIS

LgTrip (3546)
(SEQ ID NO: 12)
MKHHHHHHVFTLDDFVGDWEQTAAYNLDQVLEQGGVSSLLQNLAVSVTP

IMRIVRSGENALKIDIHVIIPYEGLSADQMAQIEEVFKVVYPVDDHHFK

VILPYGTLVIDGVTPNKLNYFGRPYEGIAVFDGKKITTTGTLWNGNKII

DERLITPD

SmTrip9
(SEQ ID NO: 13)
GSMLFRVTINS

β9/β10 dipeptide
(SEQ ID NO: 14)
GSMLFRVTINSVSGWRLFKKIS

HALOTAG protein
(SEQ ID NO: 15)
MAEIGTGFPFDPHYVEVLGERMHYVDVGPRDGTPVLFLHGNPTSSYVWR

NIIPHVAPTHRCIAPDLIGMGKSDKPDLGYFFDDHVRFMDAFIEALGLE

EVVLVIHDWGSALGFHWAKRNPERVKGIAFMEFIRPIPTWDEWPEFARE

TFQAFRTTDVGRKLIIDQNVFIEGTLPMGVVRPLTEVEMDHYREPFLNP

VDREPLWRFPNELPIAGEPANIVALVEEYMDWLHQSPVPKLLFWGTPGV

LIPPAEAARLAKSLPNCKAVDIGPGLNLLQEDNPDLIGSEIARW

---

The invention claimed is:

1. A composition comprising a PRG/HA probe comprising: a bioactive agent, a photoreactive group (PRG), a linker, and a haloalkane covalently connected in a single compound of the general structure:

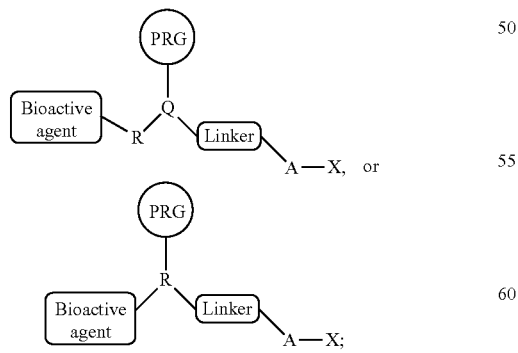

wherein the bioactive agent is a small molecule,
wherein R is a covalent linkage,
wherein A is (CH$_2$)$_n$ and n=4-10, wherein X is a halogen, wherein -A-X is a substrate for a dehalogenase,
wherein the Linker comprises a cleavable moiety flanked on one or both sides by alkylene or heteroalkylene chains, wherein the cleavable moiety is selected from the group consisting of a disulfide, tert-butyl carbamate, silyl ether, diazobenzene, 1,2-diol, and —C(O)OCH$_2$CH=CHCH$_2$OC(O)—, and wherein the alkylene or heteroalkylene chains comprise any suitable combination of functional groups selected from the group consisting of C$_{1-6}$-alkylene, —O—, —(CH$_2$)$_2$O—, and —OC(O)NH— groups,
wherein the PRG is selected from the group consisting of:

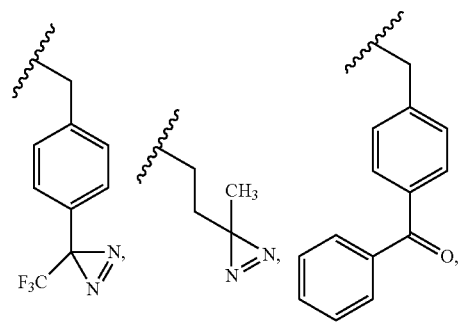

223
-continued

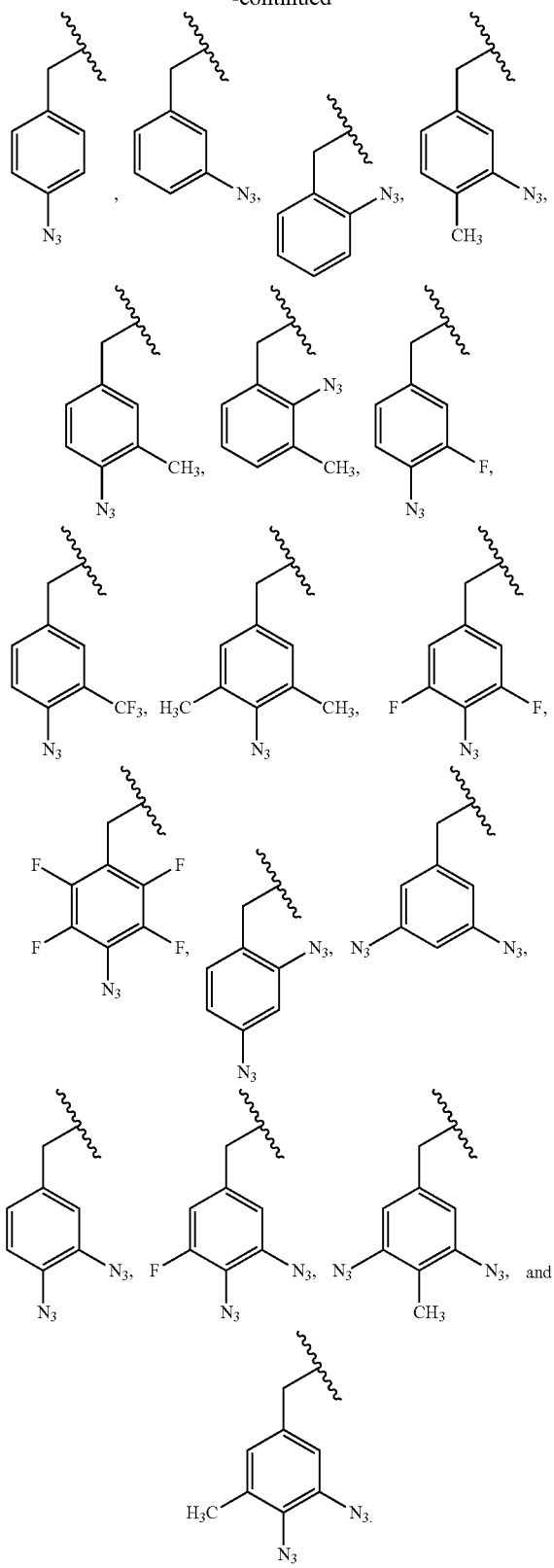

and wherein Q is CH or N.

2. The composition of claim 1, wherein R is —NH—, —C(O)NH—, —OC(O)NH—, N—, C(O)N, OC(O)N, or —N—.

3. The composition of claim 2, wherein R is —$(CH_2)_{0-2}$NH$(CH_2)_{0-2}$—, —$(CH_2)_{0-2}$C(O)NH$(CH_2)_{0-2}$—, —$(CH_2)_{0-2}$OC(O)NH$(CH_2)_{0-2}$—, $(CH_2)_{0-2}$N$(CH_2)_{0-2}$, $(CH_2)_{0-2}$C(O)N$(CH_2)_{0-2}$, $(CH_2)_{0-2}$OC(O)N$(CH_2)_{0-2}$, or —$(CH_2)_{0-2}$O$(CH_2)_{0-2}$—.

4. The composition of claim 1, wherein the PRG is covalently connected to the rest of the compound by a PRG linker moiety.

5. The composition of claim 4, wherein the PRG linker moiety is $(CH_2)_{0-4}$.

6. The composition of claim 1, wherein X is Cl.

7. The composition of claim 6, wherein -A-X is —$(CH_2)_6$Cl.

8. A method of capturing a target molecule comprising:
contacting a sample comprising the target molecule with a PRG/HA probe of claim 1, wherein the bioactive agent is capable of associating with the target molecule;
allowing the bioactive agent to associate with the target molecule; and
irradiating the sample with a wavelength of light that converts the PRG into a reactive form of the PRG, wherein the reactive form of the PRG forms a covalent bond with the target molecule.

9. A method of capturing a cellular target protein comprising:
contacting a cell containing the target protein with a PRG/HA probe of claim 1, wherein the bioactive agent is capable of binding the target protein;
allowing the PRG/HA probe to enter the cell;
allowing the bioactive agent to bind the target protein;
irradiating the cell with a wavelength of UV light that converts the PRG into a reactive form of the PRG, wherein the reactive form of the PRG forms a covalent bond with the target protein;
lysing the cell to form a lysate;
contacting the lysate with a solid-surface-immobilized modified dehalogenase enzyme that forms a covalent bond with a haloalkane substrate upon association therewith;
allowing the modified dehalogenase enzyme to covalently bind the haloalkane of the PRG/HA probe; and
removing the solid surface from the lysate and/or washing non-immobilized components of the lysate from the solid surface.

10. A method of measuring photocrosslinking efficiency of a bioagent-linked PRG, comprising:
contacting sample comprising a target molecule with a PRG/HA probe of claim 1, wherein the bioactive agent is capable of binding the target molecule and wherein the target molecule is tethered to a bioluminescent reporter;
allowing the bioactive agent to bind the target molecule;
irradiating the sample with a wavelength of light that converts the PRG into a reactive form of the PRG, wherein the reactive form of the PRG is capable of forming a covalent bond with the target molecule;
contacting the sample with a BRET reagent comprising the bioactive agent covalently tethered to a fluorophore, wherein the emission spectrum of the bioluminescent reporter overlaps with the excitation spectrum of the fluorophore
contacting the sample with a bioluminescent reporter substrate;
detecting light emission within emission spectra of the bioluminescent reporter and the fluorophore, wherein light emission from the fluorophore is the result of bioluminescence resonance energy transfer (BRET) from the bioluminescent reporter to the fluorophore.

* * * * *

SEQUENCE LISTING

<160> NUMBER OF SEQ ID NOS: 15

<210> SEQ ID NO 1
<211> LENGTH: 170
<212> TYPE: PRT
<213> ORGANISM: Artificial sequence
<220> FEATURE:
<223> OTHER INFORMATION: Synthetic

<400> SEQUENCE: 1

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His Phe Lys Ile Ile Leu His Tyr Gly
            85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
    130                 135                 140

Asn Pro Asp Gly Ser Leu Leu Phe Arg Val Thr Ile Asn Gly Val Thr
145                 150                 155                 160

Gly Trp Arg Leu Cys Glu Asn Ile Leu Ala
            165                 170

<210> SEQ ID NO 2
<211> LENGTH: 147
<212> TYPE: PRT
<213> ORGANISM: Artificial sequence
<220> FEATURE:
<223> OTHER INFORMATION: Synthetic

<400> SEQUENCE: 2

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

```
Gly Glu Asn Gly Leu Lys Ala Asp Ile His Val Ile Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
            115                 120                 125

Thr Gly Thr Leu Trp Asn Gly Asn Lys Ile Tyr Asp Glu Arg Leu Ile
        130                 135                 140

Asn Pro Asp
145

<210> SEQ ID NO 3
<211> LENGTH: 10
<212> TYPE: PRT
<213> ORGANISM: Artificial sequence
<220> FEATURE:
<223> OTHER INFORMATION: Synthetic

<400> SEQUENCE: 3

Gly Ser Leu Leu Phe Arg Val Thr Ile Asn
1               5                   10

<210> SEQ ID NO 4
<211> LENGTH: 13
<212> TYPE: PRT
<213> ORGANISM: Artificial sequence
<220> FEATURE:
<223> OTHER INFORMATION: Synthetic

<400> SEQUENCE: 4

Gly Val Thr Gly Trp Arg Leu Cys Glu Asn Ile Leu Ala
1               5                   10

<210> SEQ ID NO 5
<211> LENGTH: 171
<212> TYPE: PRT
<213> ORGANISM: Artificial sequence
<220> FEATURE:
<223> OTHER INFORMATION: Synthetic

<400> SEQUENCE: 5

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110
```

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
        130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 6
<211> LENGTH: 148
<212> TYPE: PRT
<213> ORGANISM: Artificial sequence
<220> FEATURE:
<223> OTHER INFORMATION: Synthetic

<400> SEQUENCE: 6

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp
145

<210> SEQ ID NO 7
<211> LENGTH: 11
<212> TYPE: PRT
<213> ORGANISM: Artificial sequence
<220> FEATURE:
<223> OTHER INFORMATION: Synthetic

<400> SEQUENCE: 7

Gly Ser Leu Leu Phe Arg Val Thr Ile Asn Val
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic

<400> SEQUENCE: 8

Gly Val Thr Gly Trp Arg Leu Cys Glu Arg Ile Leu Ala
1               5                   10

<210> SEQ ID NO 9
<211> LENGTH: 158
<212> TYPE: PRT
<213> ORGANISM: Artificial sequence
<220> FEATURE:
<223> OTHER INFORMATION: Synthetic

<400> SEQUENCE: 9

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn
145                 150                 155

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10

Val Thr Gly Tyr Arg Leu Phe Glu Glu Ile Leu
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic

<400> SEQUENCE: 11

Val Ser Gly Trp Arg Leu Phe Lys Lys Ile Ser
1               5                   10

<210> SEQ ID NO 12
<211> LENGTH: 155
<212> TYPE: PRT
<213> ORGANISM: Artificial sequence
<220> FEATURE:
<223> OTHER INFORMATION: Synthetic

```
-continued

<400> SEQUENCE: 12

Met Lys His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp
145                 150                 155

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Gly Ser Met Leu Phe Arg Val Thr Ile Asn Ser
1               5                   10

<210> SEQ ID NO 14
<211> LENGTH: 22
<212> TYPE: PRT
<213> ORGANISM: Artificial sequence
<220> FEATURE:
<223> OTHER INFORMATION: Synthetic

<400> SEQUENCE: 14

Gly Ser Met Leu Phe Arg Val Thr Ile Asn Ser Val Ser Gly Trp Arg
1               5                   10                  15

Leu Phe Lys Lys Ile Ser
            20

<210> SEQ ID NO 15
<211> LENGTH: 297
<212> TYPE: PRT
<213> ORGANISM: Artificial sequence
<220> FEATURE:
<223> OTHER INFORMATION: Synthetic

<400> SEQUENCE: 15

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45
```

-continued

```
Arg Asn Ile Ile Pro His Val Ala Pro Thr His Arg Cys Ile Ala Pro
    50              55                  60
Asp Leu Ile Gly Met Gly Lys Ser Asp Lys Pro Asp Leu Gly Tyr Phe
65              70                  75                  80
Phe Asp Asp His Val Arg Phe Met Asp Ala Phe Ile Glu Ala Leu Gly
            85                  90                  95
Leu Glu Glu Val Val Leu Val Ile His Asp Trp Gly Ser Ala Leu Gly
                100                 105                 110
Phe His Trp Ala Lys Arg Asn Pro Glu Arg Val Lys Gly Ile Ala Phe
        115                 120                 125
Met Glu Phe Ile Arg Pro Ile Pro Thr Trp Asp Glu Trp Pro Glu Phe
    130                 135                 140
Ala Arg Glu Thr Phe Gln Ala Phe Arg Thr Thr Asp Val Gly Arg Lys
145                 150                 155                 160
Leu Ile Ile Asp Gln Asn Val Phe Ile Glu Gly Thr Leu Pro Met Gly
                165                 170                 175
Val Val Arg Pro Leu Thr Glu Val Glu Met Asp His Tyr Arg Glu Pro
            180                 185                 190
Phe Leu Asn Pro Val Asp Arg Glu Pro Leu Trp Arg Phe Pro Asn Glu
        195                 200                 205
Leu Pro Ile Ala Gly Glu Pro Ala Asn Ile Val Ala Leu Val Glu Glu
    210                 215                 220
Tyr Met Asp Trp Leu His Gln Ser Pro Val Pro Lys Leu Leu Phe Trp
225                 230                 235                 240
Gly Thr Pro Gly Val Leu Ile Pro Pro Ala Glu Ala Ala Arg Leu Ala
                245                 250                 255
Lys Ser Leu Pro Asn Cys Lys Ala Val Asp Ile Gly Pro Gly Leu Asn
            260                 265                 270
Leu Leu Gln Glu Asp Asn Pro Asp Leu Ile Gly Ser Glu Ile Ala Arg
        275                 280                 285
Trp Leu Ser Thr Leu Glu Ile Ser Gly
290                 295
```